US010716818B2

(12) United States Patent
Suzuki et al.

(10) Patent No.: US 10,716,818 B2
(45) Date of Patent: Jul. 21, 2020

(54) ONCOLYTIC VIROTHERAPY AND IMMUNOTHERAPY

(71) Applicant: Baylor College of Medicine, Houston, TX (US)

(72) Inventors: Masataka Suzuki, Houston, TX (US); Amanda Rosewell Shaw, Pearland, TX (US); Caroline Elaine Porter, Houston, TX (US); Norihiro Watanabe, Houston, TX (US); Malcolm K. Brenner, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/430,347

(22) Filed: Jun. 3, 2019

(65) Prior Publication Data

US 2019/0374589 A1 Dec. 12, 2019

Related U.S. Application Data

(63) Continuation of application No. PCT/US2018/028577, filed on Apr. 20, 2018.

(60) Provisional application No. 62/488,181, filed on Apr. 21, 2017.

(51) Int. Cl.

| | |
|---|---|
| ***A61K 35/17*** | (2015.01) |
| ***A61K 35/761*** | (2015.01) |
| ***A61P 35/00*** | (2006.01) |
| ***C07K 14/725*** | (2006.01) |
| ***C07K 14/705*** | (2006.01) |
| ***C07K 16/32*** | (2006.01) |

(52) U.S. Cl.

CPC ............ *A61K 35/761* (2013.01); *A61K 35/17* (2013.01); *A61P 35/00* (2018.01); *C07K 14/7051* (2013.01); *C07K 14/70521* (2013.01); *C07K 16/32* (2013.01); *C07K 2317/622* (2013.01); *C07K 2317/73* (2013.01); *C07K 2319/03* (2013.01); *C07K 2319/33* (2013.01)

(58) Field of Classification Search

None

See application file for complete search history.

(56) References Cited

FOREIGN PATENT DOCUMENTS

| | | |
|---|---|---|
| WO | WO 2005/086922 A2 | 9/2005 |
| WO | WO 2014/153204 A1 | 9/2014 |

OTHER PUBLICATIONS

Farzad et al. Combinatorial treatment with oncolytic adenovirus and helper-dependent adenovirus augments adenoviral cancer gene therapy. Mol Ther Oncolytics. Dec. 17, 2014;1:14008. (Year: 2014).*

(Continued)

*Primary Examiner* — Michelle S Horning

(74) *Attorney, Agent, or Firm* — Wolf, Greenfield & Sacks, P.C.

(57) ABSTRACT

The present disclosure concerns combination therapy for cancer that utilizes (i) an oncolytic virus; (ii) a virus comprising nucleic acid encoding an immunomodulatory factor, and (iii) at least one cell comprising a chimeric antigen receptor (CAR) specific for a cancer cell antigen. In particular embodiments, the virus comprises nucleic acid encoding an immunomodulatory factor comprises nucleic acid encoding IL-12 and/or antagonist anti-PD-L1 antibody.

10 Claims, 44 Drawing Sheets

Specification includes a Sequence Listing.

(56) References Cited

OTHER PUBLICATIONS

Attwood, T. The Babel of Bioinformatics, Science (2000) vol. 290, No. 5491, pp. 471-473 (Year: 2000).*
Baker et al., Protein Structure Predication and Structural Genomics, Science (2001) vol. 294, No. 5540, pp. 93-96 (Year: 2001).*
Ajina et al., Prospects for combined use of oncolytic viruses and CAR T-cells. J Immunother Cancer. Nov. 21, 2017;5(1):90. doi:10.1186/s40425-017-0294-6.
Barker et al., Adenovirus proteins from both E1B reading frames are required for transformation of rodent cells by viral infection and DNA transfection. Virology. Jan. 1987;156(1):107-21. Erratum in: Virology May 1987;158(1):263.
Butte et al., Programmed death-1 ligand 1 interacts specifically with the B7-1 costimulatory molecule to inhibit T cell responses. Immunity. Jul. 2007;27(1):111-22. Epub Jul. 12, 2007.
Chiocca et al., Oncolytic viruses and their application to cancer immunotherapy. Cancer Immunol Res. Apr. 2014;2(4):295-300. doi:10.1158/2326-6066.CIR-14-0015. Review. Erratum in: Cancer Immunol Res. Jul. 2014;2(7):699.
Economopoulou et al., The emerging role of immunotherapy in head and neck squamous cell carcinoma (HNSCC): anti-tumor immunity and clinical applications. Ann Transl Med. May 2016;4(9):173. doi:10.21037/atm.2016.03.34.
Farzad et al., Combinatorial treatment with oncolytic adenovirus and helper-dependent adenovirus augments adenoviral cancer gene therapy. Mol Ther Oncolytics. Dec. 17, 2014;1:14008. doi:10.1038/mto.2014.8. eCollection 2014.
Fueyo et al., A mutant oncolytic adenovirus targeting the Rb pathway produces anti-glioma effect in vivo. Oncogene. Jan. 6, 2000;19(1):2-12. Erratum in: Oncogene Oct. 12, 2000;19(43):5038.
Gottschalk et al., Harnessing the immune system to potentiate oncolytics. Mol Ther. Feb. 2014;22(2):239-240. doi: 10.1038/mt.2013.295.
Lee et al., Enhanced antitumor effect of oncolytic adenovirus expressing interleukin-12 and B7-1 in an immunocompetent murine model. Clin Cancer Res. Oct. 1, 2006;12(19):5859-68.
Morgenstern, Combining Oncolytic Adenovirus (OncAd) with Tumor Directed, Adenovirus-specific T-cells for the Treatment of Neuroblastoma: Effects of OncAds on Immunosuppressive Myeloid Cells. 2016. Retrieved from https://www.alexslemonade.org/grantee/ari-morgenstern on Aug. 21, 2018.
Nishino et al., Adenovirus-mediated gene therapy specific for small cell lung cancer cells using a Myc-Max binding motif. Int J Cancer. Mar. 15, 2001;91(6):851-6.
Nishio et al., Armed oncolytic virus enhances immune functions of chimeric antigen receptor-modified T cells in solid tumors. Cancer Res. Sep. 15, 2014;74(18):5195-205. doi: 10.1158/0008-5472.CAN-14-0697. Epub Jul. 24, 2014.
Rojas et al., Minimal RB-responsive E1A promoter modification to attain potency, selectivity, and transgene-arming capacity in oncolytic adenoviruses. Mol Ther. Nov. 2010;18(11):1960-71. doi:10.1038/mt.2010.173. Epub Aug. 31, 2010.
Rosewell Shaw et al., Adenovirotherapy Delivering Cytokine and Checkpoint Inhibitor Augments CAR T Cells against Metastatic Head and Neck Cancer. Mol Ther. Nov. 1, 2017;25(11):2440-2451. doi: 10.1016/j.ymthe.2017.09.010. Epub Sep. 14, 2017.
Rosewell Shaw et al., Armed-Ad Gene Therapy Expressing PDL1 Minibody Enhances the Anti-Tumor Effect of Adoptively Transferred Chimeric Antigen Receptor T-Cells for Solid Tumor Treatment. Mol. Ther. May 2016;24(1):S204-S205.
Rosewell Shaw et al., Combinatorial Treatment of "armed" oncolytic adenovirus expressing checkpoint inhibitor and cytokine with chimeric antigen receptor t-cells leads to superior anti-tumor effects inhead and neck cancer. Mol Ther. May 2017;25(5S1):6-7. Abstract 12.
Sun et al., Early transduction produces highly functional chimeric antigen receptor-modified virus-specific T-cells with central memory markers: a Production Assistant for Cell Therapy (PACT) translational application. J Immunother Cancer. Feb. 18, 2015;3:5. doi: 10.1186/s40425-015-0049-1. eCollection 2015.
Tanaka et al., Vaccination Targeting Native Receptors to Enhance the Function and Proliferation of Chimeric Antigen Receptor (CAR)-Modified T Cells. Clin Cancer Res. Jul. 15, 2017;23(14):3499-3509. doi:10.1158/1078-0432.CCR-16-2138. Epub Feb. 9, 2017.
Tanoue et al., Armed Oncolytic Adenovirus-Expressing PD-L1 Mini-Body Enhances Antitumor Effects of Chimeric Antigen Receptor T Cells in Solid Tumors. Cancer Res. Apr. 15, 2017;77(8):2040-2051. doi: 10.1158/0008-5472.CAN-16-1577. Epub Feb. 24, 2017.
Waknine, International Approvals: Procoralan, H101, AP2573. Nov. 21, 2005. Medscape Medical News. Retrieved from http://www.medscape.com/viewarticle/517543_print on Dec. 4, 2017.
International Search Report and Written Opinion for Application No. PCT/US2018/028577, dated Jan. 28, 2019.
International Preliminary Report on Patentability for Application No. PCT/US2018/028577, dated Oct. 31, 2019.
Malekshah et al., Enzyme/Prodrug Systems for Cancer Gene Therapy. Curr Pharmacol Rep. Dec. 2016;2(6):299-308. doi: 10.1007/s40495-016-0073-y. Epub Oct. 19, 2016.

* cited by examiner

SEQUENCE LISTING

```
<160> NUMBER OF SEQ ID NOS: 64

<210> SEQ ID NO 1
<211> LENGTH: 469
<212> TYPE: PRT
<213> ORGANISM: Artificial Sequence
<220> FEATURE:
<223> OTHER INFORMATION: HER2(C5)-CD28TM,ICD-CD3Z CAR

<400> SEQUENCE: 1

Met Thr Arg Ala Met Asp Trp Ile Trp Arg Ile Leu Phe Leu Val Gly
1               5                   10                  15

Ala Ala Thr Gly Ala His Ser Gln Val Gln Leu Gln Glu Ser Gly Pro
            20                  25                  30

Gly Leu Val Lys Pro Ser Glu Thr Leu Ser Leu Thr Cys Thr Val Ser
        35                  40                  45

Gly Gly Ser Ile Ser Ser Ser Ser Tyr Tyr Trp Gly Trp Ile Arg Gln
    50                  55                  60

Pro Pro Gly Lys Gly Leu Glu Trp Ile Gly Ser Ile Tyr Tyr Ser Gly
65                  70                  75                  80

Ser Thr Tyr Tyr Asn Pro Ser Leu Lys Ser Arg Val Thr Ile Ser Val
                85                  90                  95

Asp Thr Ser Lys Asn Gln Phe Ser Leu Lys Leu Ser Ser Val Thr Ala
            100                 105                 110

Ala Asp Thr Ala Val Tyr Tyr Cys Ala Arg Tyr Ala Pro Asp Ser Ser
        115                 120                 125

Gly Tyr Leu Val Ala Phe Asp Ile Trp Gly Gln Gly Thr Met Val Thr
    130                 135                 140

Val Ser Ser Gly Gly Gly Gly Ser Gly Gly Gly Gly Ser Gly Gly Gly
```

-continued

```
145                 150                 155                 160

Gly Ser Gln Thr Val Val Thr Gln Glu Pro Ser Phe Ser Val Ser Pro
                165                 170                 175

Gly Gly Thr Val Thr Leu Thr Cys Gly Leu Ser Ser Gly Ser Val Ser
            180                 185                 190

Thr Gly Tyr Tyr Pro Ser Trp Tyr Gln Gln Thr Pro Gly Gln Ala Pro
        195                 200                 205

Arg Thr Leu Ile Tyr Ser Thr Asn Ser Arg Ser Ser Gly Val Pro Asp
    210                 215                 220

Arg Phe Ser Gly Ser Ile Leu Gly Asn Lys Ala Ala Leu Thr Ile Thr
225                 230                 235                 240

Gly Ala Gln Ala Asp Asp Glu Ser Asp Tyr Tyr Cys Val Leu Tyr Met
                245                 250                 255

Gly Ser Gly Ile Ser Val Phe Gly Gly Gly Thr Lys Leu Thr Val Leu
            260                 265                 270

Gly Ser Glu Pro Lys Ser Cys Asp Lys Thr His Thr Cys Pro Thr Arg
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465


<210> SEQ ID NO 2
<211> LENGTH: 467
<212> TYPE: PRT
<213> ORGANISM: Artificial Sequence
<220> FEATURE:
<223> OTHER INFORMATION: HER2(E4)-CD28TM,ICD-CD3Z CAR

<400> SEQUENCE: 2

Met Thr Arg Ala Met Asp Trp Ile Trp Arg Ile Leu Phe Leu Val Gly
1               5                   10                  15

Ala Ala Thr Gly Ala His Ser Gln Val Gln Leu Gln Gln Trp Gly Ala
            20                  25                  30

Gly Leu Leu Lys Pro Ser Glu Thr Leu Ser Leu Thr Cys Ala Val Tyr
```

```
        35                  40                  45

Gly Gly Ser Phe Ser Gly Tyr Tyr Trp Ser Trp Ile Arg Gln Pro Pro
    50                  55                  60

Gly Lys Gly Leu Glu Trp Ile Gly Glu Ile Asn His Ser Gly Ser Thr
65                  70                  75                  80

Asn Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Thr Ala Asp
            100                 105                 110

Thr Ala Val Tyr Tyr Cys Ala Arg Met Gly Ile Asn Ser Gly Gly Tyr
        115                 120                 125

Leu Tyr Gly Met Asp Val Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Gln Thr Val Val Thr Gln Glu Pro Ser Phe Ser Val Ser Pro Gly Gly
                165                 170                 175

Thr Val Thr Leu Thr Cys Gly Leu Ser Ser Gly Ser Val Ser Thr Ser
            180                 185                 190

Tyr Tyr Pro Ser Trp Tyr Gln Gln Ile Pro Gly Gln Ala Pro Arg Thr
        195                 200                 205

Leu Ile Tyr Thr Thr Asn Ile Arg Ser Ser Gly Val Pro Asp Arg Phe
    210                 215                 220

Gly Gly Ser Ile Leu Gly Asn Lys Ala Ala Leu Thr Ile Thr Gly Ala
225                 230                 235                 240

Gln Ala Glu Asp Glu Ser Asp Tyr Tyr Cys Met Leu Tyr Met Gly Ser
                245                 250                 255

Gly Ile Trp Val Phe Gly Gly Gly Thr Lys Leu Thr Val Leu Gly Ser
            260                 265                 270

Glu Pro Lys Ser Cys Asp Lys Thr His Thr Cys Pro Thr Arg Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Gln Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445

Ser Thr Ala Thr Lys Asp Thr Tyr Asp Ala Leu His Met Gln Ala Leu
    450                 455                 460
```

```
Pro Pro Arg
465


<210> SEQ ID NO 3
<211> LENGTH: 468
<212> TYPE: PRT
<213> ORGANISM: Artificial Sequence
<220> FEATURE:
<223> OTHER INFORMATION: HER2(F1)-CD28TM,ICD-CD3Z CAR

<400> SEQUENCE: 3

Met Thr Arg Ala Met Asp Trp Ile Trp Arg Ile Leu Phe Leu Val Gly
1               5                   10                  15

Ala Ala Thr Gly Ala His Ser Gln Val Gln Leu Val Glu Ser Gly Pro
            20                  25                  30

Gly Leu Val Lys Pro Ser Gly Thr Leu Ser Leu Thr Cys Ala Val Ser
        35                  40                  45

Gly Gly Ser Ile Ser Ser Ser Asn Trp Trp Ser Trp Val Arg Gln Pro
    50                  55                  60

Pro Gly Lys Gly Leu Glu Trp Ile Gly Glu Ile Tyr His Ser Gly Ser
65                  70                  75                  80

Thr Asn Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Met Gly Ala Asn Ser Gly Gly
        115                 120                 125

Tyr Leu Tyr Gly Met Asp Val Trp Gly Gln Gly Thr Thr Val Thr Val
    130                 135                 140

Ser Ser Gly Gly Gly Gly Ser Gly Gly Gly Gly Ser Gly Gly Gly Gly
145                 150                 155                 160

Ser Gln Thr Val Val Thr Gln Glu Pro Ser Phe Ser Val Ser Pro Gly
                165                 170                 175

Gly Thr Val Thr Leu Thr Cys Gly Leu Ser Ser Gly Ser Val Ser Thr
            180                 185                 190

Ser Tyr Tyr Pro Ser Trp Tyr Gln Gln Thr Pro Gly Gln Ala Pro Arg
        195                 200                 205

Thr Leu Ile Tyr Ser Thr Asn Thr Arg Ser Ser Gly Val Pro Asp Arg
    210                 215                 220

Phe Ser Gly Ser Ile Leu Gly Asn Lys Ala Ala Leu Thr Ile Thr Gly
225                 230                 235                 240

Ala Gln Ala Asp Asp Glu Ser Asp Tyr Tyr Cys Val Leu Tyr Met Gly
                245                 250                 255

Ser Gly Ile Trp Val Phe Gly Gly Gly Thr Lys Leu Thr Val Leu Gly
            260                 265                 270

Ser Glu Pro Lys Ser Cys Asp Lys Thr His Thr Cys Pro Thr Arg Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350
```

```
Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Gln Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465


<210> SEQ ID NO 4
<211> LENGTH: 27
<212> TYPE: PRT
<213> ORGANISM: Artificial Sequence
<220> FEATURE:
<223> OTHER INFORMATION: CD28 TMD

<400> SEQUENCE: 4

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 5
<211> LENGTH: 41
<212> TYPE: PRT
<213> ORGANISM: Artificial Sequence
<220> FEATURE:
<223> OTHER INFORMATION: CD28 ICD

<400> SEQUENCE: 5

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 6
<211> LENGTH: 113
<212> TYPE: PRT
<213> ORGANISM: Artificial Sequence
<220> FEATURE:
<223> OTHER INFORMATION: CD3Z ICD

<400> SEQUENCE: 6

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45
```

-continued

Pro Gln Arg Arg Lys Asn Pro Gln Glu Gly Leu Tyr Asn Glu Leu Gln
50 55 60

Lys Asp Lys Met Ala Glu Ala Tyr Ser Glu Ile Gly Met Lys Gly Glu
65 70 75 80

Arg Arg Arg Gly Lys Gly His Asp Gly Leu Tyr Gln Gly Leu Ser Thr
85 90 95

Ala Thr Lys Asp Thr Tyr Asp Ala Leu His Met Gln Ala Leu Pro Pro
100 105 110

Arg

<210> SEQ ID NO 7
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 7

Gly Gly Gly Gly Ser Gly Gly Gly Gly Ser Gly Gly Gly Gly Ser
1 5 10 15

<210> SEQ ID NO 8
<211> LENGTH: 19
<212> TYPE: PRT
<213> ORGANISM: Artificial Sequence
<220> FEATURE:
<223> OTHER INFORMATION: huIgG H leader

<400> SEQUENCE: 8

Met Asp Trp Ile Trp Arg Ile Leu Phe Leu Val Gly Ala Ala Thr Gly
1 5 10 15

Ala His Ser

<210> SEQ ID NO 9
<211> LENGTH: 14
<212> TYPE: PRT
<213> ORGANISM: Artificial Sequence
<220> FEATURE:
<223> OTHER INFORMATION: Hinge

<400> SEQUENCE: 9

Glu Pro Lys Ser Cys Asp Lys Thr His Thr Cys Pro Thr Arg
1 5 10

<210> SEQ ID NO 10
<211> LENGTH: 14
<212> TYPE: PRT
<213> ORGANISM: Artificial Sequence
<220> FEATURE:
<223> OTHER INFORMATION: HER2(C5) LC-CDR1

<400> SEQUENCE: 10

Gly Leu Ser Ser Gly Ser Val Ser Thr Gly Tyr Tyr Pro Ser
1 5 10

<210> SEQ ID NO 11
<211> LENGTH: 7
<212> TYPE: PRT
<213> ORGANISM: Artificial Sequence
<220> FEATURE:
<223> OTHER INFORMATION: HER2(C5) LC-CDR2

<400> SEQUENCE: 11

Ser Thr Asn Ser Arg Ser Ser 1 5

<210> SEQ ID NO 12
<211> LENGTH: 10
<212> TYPE: PRT
<213> ORGANISM: Artificial Sequence
<220> FEATURE:
<223> OTHER INFORMATION: HER2(C5) LC-CDR3

<400> SEQUENCE: 12

Val Leu Tyr Met Gly Ser Gly Ile Ser Val
1 5 10

<210> SEQ ID NO 13
<211> LENGTH: 7
<212> TYPE: PRT
<213> ORGANISM: Artificial Sequence
<220> FEATURE:
<223> OTHER INFORMATION: HER2(C5) HC-CDR1

<400> SEQUENCE: 13

Ser Ser Ser Tyr Tyr Trp Gly
1 5

<210> SEQ ID NO 14
<211> LENGTH: 16
<212> TYPE: PRT
<213> ORGANISM: Artificial Sequence
<220> FEATURE:
<223> OTHER INFORMATION: HER2(C5) HC-CDR2

<400> SEQUENCE: 14

Ser Ile Tyr Tyr Ser Gly Ser Thr Tyr Tyr Asn Pro Ser Leu Lys Ser
1 5 10 15

<210> SEQ ID NO 15
<211> LENGTH: 14
<212> TYPE: PRT
<213> ORGANISM: Artificial Sequence
<220> FEATURE:
<223> OTHER INFORMATION: HER2(C5) HC-CDR3

<400> SEQUENCE: 15

Tyr Ala Pro Asp Ser Ser Gly Tyr Leu Val Ala Phe Asp Ile
1 5 10

<210> SEQ ID NO 16
<211> LENGTH: 112
<212> TYPE: PRT
<213> ORGANISM: Artificial Sequence
<220> FEATURE:
<223> OTHER INFORMATION: HER2(C5) VL

<400> SEQUENCE: 16

Gln Thr Val Val Thr Gln Glu Pro Ser Phe Ser Val Ser Pro Gly Gly
1 5 10 15

Thr Val Thr Leu Thr Cys Gly Leu Ser Ser Gly Ser Val Ser Thr Gly
20 25 30

Tyr Tyr Pro Ser Trp Tyr Gln Gln Thr Pro Gly Gln Ala Pro Arg Thr
35 40 45

Leu Ile Tyr Ser Thr Asn Ser Arg Ser Ser Gly Val Pro Asp Arg Phe
50 55 60

Ser Gly Ser Ile Leu Gly Asn Lys Ala Ala Leu Thr Ile Thr Gly Ala
65 70 75 80

```
Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly Ser
            100                 105                 110


<210> SEQ ID NO 17
<211> LENGTH: 124
<212> TYPE: PRT
<213> ORGANISM: Artificial Sequence
<220> FEATURE:
<223> OTHER INFORMATION: HER2(C5) VH

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Ala Pro Asp Ser Ser Gly Tyr Leu Val Ala Phe Asp
            100                 105                 110

Ile Trp Gly Gln Gly Thr Met Val Thr Val Ser Ser
        115                 120


<210> SEQ ID NO 18
<211> LENGTH: 14
<212> TYPE: PRT
<213> ORGANISM: Artificial Sequence
<220> FEATURE:
<223> OTHER INFORMATION: HER2(E4) LC-CDR1

<400> SEQUENCE: 18

Gly Leu Ser Ser Gly Ser Val Ser Thr Ser Tyr Tyr Pro Ser
1               5                   10


<210> SEQ ID NO 19
<211> LENGTH: 7
<212> TYPE: PRT
<213> ORGANISM: Artificial Sequence
<220> FEATURE:
<223> OTHER INFORMATION: HER2(E4) LC-CDR2

<400> SEQUENCE: 19

Thr Thr Asn Ile Arg Ser Ser
1               5


<210> SEQ ID NO 20
<211> LENGTH: 10
<212> TYPE: PRT
<213> ORGANISM: Artificial Sequence
<220> FEATURE:
<223> OTHER INFORMATION: HER2(E4) LC-CDR3

<400> SEQUENCE: 20

Met Leu Tyr Met Gly Ser Gly Ile Trp Val
1               5                   10
```

<210> SEQ ID NO 21
<211> LENGTH: 6
<212> TYPE: PRT
<213> ORGANISM: Artificial Sequence
<220> FEATURE:
<223> OTHER INFORMATION: HER2(E4) HC-CDR1

<400> SEQUENCE: 21

```
Ser Gly Tyr Tyr Trp Ser
1               5
```

<210> SEQ ID NO 22
<211> LENGTH: 16
<212> TYPE: PRT
<213> ORGANISM: Artificial Sequence
<220> FEATURE:
<223> OTHER INFORMATION: HER2(E4) HC-CDR2

<400> SEQUENCE: 22

```
Glu Ile Asn His Ser Gly Ser Thr Asn Tyr Asn Pro Ser Leu Lys Ser
1               5                   10                  15
```

<210> SEQ ID NO 23
<211> LENGTH: 14
<212> TYPE: PRT
<213> ORGANISM: Artificial Sequence
<220> FEATURE:
<223> OTHER INFORMATION: HER2(E4) HC-CDR3

<400> SEQUENCE: 23

```
Met Gly Ile Asn Ser Gly Gly Tyr Leu Tyr Gly Met Asp Val
1               5                   10
```

<210> SEQ ID NO 24
<211> LENGTH: 112
<212> TYPE: PRT
<213> ORGANISM: Artificial Sequence
<220> FEATURE:
<223> OTHER INFORMATION: HER2(E4) VL

<400> SEQUENCE: 24

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Ile Pro Gly Gln Ala Pro Arg Thr
        35                  40                  45

Leu Ile Tyr Thr Thr Asn Ile Arg Ser Ser Gly Val Pro Asp Arg Phe
    50                  55                  60

Gly Gly Ser Ile Leu Gly Asn Lys Ala Ala Leu Thr Ile Thr Gly Ala
65                  70                  75                  80

Gln Ala Glu Asp Glu Ser Asp Tyr Tyr Cys Met Leu Tyr Met Gly Ser
                85                  90                  95

Gly Ile Trp Val Phe Gly Gly Gly Thr Lys Leu Thr Val Leu Gly Ser
            100                 105                 110
```

<210> SEQ ID NO 25
<211> LENGTH: 122
<212> TYPE: PRT
<213> ORGANISM: Artificial Sequence
<220> FEATURE:
<223> OTHER INFORMATION: HER2(E4) VH

<400> SEQUENCE: 25

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Met Gly Ile Asn Ser Gly Gly Tyr Leu Tyr Gly Met Asp Val Trp
            100                 105                 110

Gly Gln Gly Thr Thr Val Thr Val Ser Ser
        115                 120


<210> SEQ ID NO 26
<211> LENGTH: 14
<212> TYPE: PRT
<213> ORGANISM: Artificial Sequence
<220> FEATURE:
<223> OTHER INFORMATION: HER2(F1) LC-CDR1

<400> SEQUENCE: 26

Gly Leu Ser Ser Gly Ser Val Ser Thr Ser Tyr Tyr Pro Ser
1               5                   10


<210> SEQ ID NO 27
<211> LENGTH: 7
<212> TYPE: PRT
<213> ORGANISM: Artificial Sequence
<220> FEATURE:
<223> OTHER INFORMATION: HER2(F1) LC-CDR2

<400> SEQUENCE: 27

Ser Thr Asn Thr Arg Ser Ser
1               5


<210> SEQ ID NO 28
<211> LENGTH: 10
<212> TYPE: PRT
<213> ORGANISM: Artificial Sequence
<220> FEATURE:
<223> OTHER INFORMATION: HER2(F1) LC-CDR3

<400> SEQUENCE: 28

Val Leu Tyr Met Gly Ser Gly Ile Trp Val
1               5                   10


<210> SEQ ID NO 29
<211> LENGTH: 6
<212> TYPE: PRT
<213> ORGANISM: Artificial Sequence
<220> FEATURE:
<223> OTHER INFORMATION: HER2(F1) HC-CDR1

<400> SEQUENCE: 29

Ser Ser Asn Trp Trp Ser
1               5


<210> SEQ ID NO 30
```

<211> LENGTH: 16
<212> TYPE: PRT
<213> ORGANISM: Artificial Sequence
<220> FEATURE:
<223> OTHER INFORMATION: HER2(F1) HC-CDR2

<400> SEQUENCE: 30

Glu Ile Tyr His Ser Gly Ser Thr Asn Tyr Asn Pro Ser Leu Lys Ser
1 5 10 15

<210> SEQ ID NO 31
<211> LENGTH: 14
<212> TYPE: PRT
<213> ORGANISM: Artificial Sequence
<220> FEATURE:
<223> OTHER INFORMATION: HER2(F1) HC-CDR3

<400> SEQUENCE: 31

Met Gly Ala Asn Ser Gly Gly Tyr Leu Tyr Gly Met Asp Val
1 5 10

<210> SEQ ID NO 32
<211> LENGTH: 112
<212> TYPE: PRT
<213> ORGANISM: Artificial Sequence
<220> FEATURE:
<223> OTHER INFORMATION: HER2(F1) VL

<400> SEQUENCE: 32

Gln Thr Val Val Thr Gln Glu Pro Ser Phe Ser Val Ser Pro Gly Gly
1 5 10 15

Thr Val Thr Leu Thr Cys Gly Leu Ser Ser Gly Ser Val Ser Thr Ser
20 25 30

Tyr Tyr Pro Ser Trp Tyr Gln Gln Thr Pro Gly Gln Ala Pro Arg Thr
35 40 45

Leu Ile Tyr Ser Thr Asn Thr Arg Ser Ser Gly Val Pro Asp Arg Phe
50 55 60

Ser Gly Ser Ile Leu Gly Asn Lys Ala Ala Leu Thr Ile Thr Gly Ala
65 70 75 80

Gln Ala Asp Asp Glu Ser Asp Tyr Tyr Cys Val Leu Tyr Met Gly Ser
85 90 95

Gly Ile Trp Val Phe Gly Gly Gly Thr Lys Leu Thr Val Leu Gly Ser
100 105 110

<210> SEQ ID NO 33
<211> LENGTH: 123
<212> TYPE: PRT
<213> ORGANISM: Artificial Sequence
<220> FEATURE:
<223> OTHER INFORMATION: HER2(F1) VH

<400> SEQUENCE: 33

Gln Val Gln Leu Val Glu Ser Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Thr Ser Lys Asn Gln Phe Ser
65 70 75 80

```
Leu Lys Leu Ser Ser Val Thr Ala Ala Asp Thr Ala Val Tyr Tyr Cys
                85                  90                  95

Ala Arg Met Gly Ala Asn Ser Gly Gly Tyr Leu Tyr Gly Met Asp Val
            100                 105                 110

Trp Gly Gln Gly Thr Thr Val Thr Val Ser Ser
        115                 120
```

<210> SEQ ID NO 34
<211> LENGTH: 281
<212> TYPE: PRT
<213> ORGANISM: Artificial Sequence
<220> FEATURE:
<223> OTHER INFORMATION: Ad2 E1Adelta24

<400> SEQUENCE: 34

```
Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Pro Pro Ser Asp Asp Glu Asp
        115                 120                 125

Glu Glu Gly Glu Glu Phe Val Leu Asp Tyr Val Glu His Pro Gly His
    130                 135                 140

Gly Cys Arg Ser Cys His Tyr His Arg Arg Asn Thr Gly Asp Pro Asp
145                 150                 155                 160

Ile Met Cys Ser Leu Cys Tyr Met Arg Thr Cys Gly Met Phe Val Tyr
                165                 170                 175

Ser Pro Val Ser Glu Pro Glu Pro Glu Pro Glu Pro Glu Pro Glu Pro
            180                 185                 190

Ala Arg Pro Thr Arg Arg Pro Lys Leu Val Pro Ala Ile Leu Arg Arg
        195                 200                 205

Pro Thr Ser Pro Val Ser Arg Glu Cys Asn Ser Ser Thr Asp Ser Cys
    210                 215                 220

Asp Ser Gly Pro Ser Asn Thr Pro Pro Glu Ile His Pro Val Val Pro
225                 230                 235                 240

Leu Cys Pro Ile Lys Pro Val Ala Val Arg Val Gly Gly Arg Arg Gln
                245                 250                 255

Ala Val Glu Cys Ile Glu Asp Leu Leu Asn Glu Ser Gly Gln Pro Leu
            260                 265                 270

Asp Leu Ser Cys Lys Arg Pro Arg Pro
        275                 280
```

<210> SEQ ID NO 35
<211> LENGTH: 536
<212> TYPE: PRT
<213> ORGANISM: Artificial Sequence
<220> FEATURE:
<223> OTHER INFORMATION: huIL-12p70

<400> SEQUENCE: 35

```
Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Val Pro Gly Val Gly Val Pro Gly
                325                 330                 335

Val Gly Ala Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400
```

```
Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser
    530                 535


<210> SEQ ID NO 36
<211> LENGTH: 376
<212> TYPE: PRT
<213> ORGANISM: Artificial Sequence
<220> FEATURE:
<223> OTHER INFORMATION: HSV1 TK

<400> SEQUENCE: 36

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220
```

```
Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Ile Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375


<210> SEQ ID NO 37
<211> LENGTH: 9
<212> TYPE: PRT
<213> ORGANISM: Artificial Sequence
<220> FEATURE:
<223> OTHER INFORMATION: HA tag

<400> SEQUENCE: 37

Tyr Pro Tyr Asp Val Pro Asp Tyr Ala
1               5


<210> SEQ ID NO 38
<211> LENGTH: 534
<212> TYPE: PRT
<213> ORGANISM: Artificial Sequence
<220> FEATURE:
<223> OTHER INFORMATION: PD-L1(H12_gl) minibody

<400> SEQUENCE: 38

Met Asp Trp Ile Trp Arg Ile Leu Phe Leu Val Gly Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Arg Ile Ile Pro Ile Leu Gly Ile Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Gly His Gly Tyr Ser Tyr Gly Ala Phe Asp
        115                 120                 125

Tyr Trp Gly Gln Gly Thr Leu Val Thr Val Ser Ser Gly Gly Gly Gly
```

-continued

```
    130                 135                 140

Ser Gly Gly Gly Gly Ser Gly Gly Gly Gly Ser Gln Ser Val Leu Thr
145                 150                 155                 160

Gln Pro Pro Ser Val Ser Gly Ala Pro Gly Gln Arg Val Thr Ile Ser
                165                 170                 175

Cys Thr Gly Ser Ser Ser Asn Ile Gly Ala Gly Tyr Asp Val His Trp
            180                 185                 190

Tyr Gln Gln Leu Pro Gly Thr Ala Pro Lys Leu Leu Ile Tyr Gly Asn
        195                 200                 205

Ser Asn Arg Pro Ser Gly Val Pro Asp Arg Phe Ser Gly Ser Lys Ser
    210                 215                 220

Gly Thr Ser Ala Ser Leu Ala Ile Thr Gly Leu Gln Ala Glu Asp Glu
225                 230                 235                 240

Ala Asp Tyr Tyr Cys Gln Ser Tyr Asp Ser Ser Leu Ser Gly Ser Tyr
                245                 250                 255

Val Val Phe Gly Gly Gly Thr Lys Leu Thr Val Leu Glu Ala Lys Ser
            260                 265                 270

Cys Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys Gly Gly Gly Gly Ser Tyr Pro Tyr Asp Val Pro Asp
            500                 505                 510

Tyr Ala Gly Tyr Pro Tyr Asp Val Pro Asp Tyr Ala Gly Tyr Pro Tyr
        515                 520                 525

Asp Val Pro Asp Tyr Ala
    530
```

<210> SEQ ID NO 39

<211> LENGTH: 14
<212> TYPE: PRT
<213> ORGANISM: Artificial Sequence
<220> FEATURE:
<223> OTHER INFORMATION: PD-L1(H12_gl) LC-CDR1

<400> SEQUENCE: 39

Thr Gly Ser Ser Ser Asn Ile Gly Ala Gly Tyr Asp Val His
1 5 10

<210> SEQ ID NO 40
<211> LENGTH: 7
<212> TYPE: PRT
<213> ORGANISM: Artificial Sequence
<220> FEATURE:
<223> OTHER INFORMATION: PD-L1(H12_gl) LC-CDR2

<400> SEQUENCE: 40

Gly Asn Ser Asn Arg Pro Ser
1 5

<210> SEQ ID NO 41
<211> LENGTH: 13
<212> TYPE: PRT
<213> ORGANISM: Artificial Sequence
<220> FEATURE:
<223> OTHER INFORMATION: PD-L1(H12_gl) LC-CDR3

<400> SEQUENCE: 41

Gln Ser Tyr Asp Ser Ser Leu Ser Gly Ser Tyr Val Val
1 5 10

<210> SEQ ID NO 42
<211> LENGTH: 5
<212> TYPE: PRT
<213> ORGANISM: Artificial Sequence
<220> FEATURE:
<223> OTHER INFORMATION: PD-L1(H12_gl) HC-CDR1

<400> SEQUENCE: 42

Ser Tyr Ala Ile Ser
1 5

<210> SEQ ID NO 43
<211> LENGTH: 17
<212> TYPE: PRT
<213> ORGANISM: Artificial Sequence
<220> FEATURE:
<223> OTHER INFORMATION: PD-L1(H12_gl) HC-CDR2

<400> SEQUENCE: 43

Arg Ile Ile Pro Ile Leu Gly Ile Ala Asn Tyr Ala Gln Lys Phe Gln
1 5 10 15

Gly

<210> SEQ ID NO 44
<211> LENGTH: 12
<212> TYPE: PRT
<213> ORGANISM: Artificial Sequence
<220> FEATURE:
<223> OTHER INFORMATION: PD-L1(H12_gl) HC-CDR3

<400> SEQUENCE: 44

Ser Gly His Gly Tyr Ser Tyr Gly Ala Phe Asp Tyr
1 5 10

-continued

<210> SEQ ID NO 45
<211> LENGTH: 113
<212> TYPE: PRT
<213> ORGANISM: Artificial Sequence
<220> FEATURE:
<223> OTHER INFORMATION: PD-L1(H12_gl) VL

<400> SEQUENCE: 45

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Tyr Val Val Phe Gly Gly Gly Thr Lys Leu Thr Val
            100                 105                 110

Leu
```

<210> SEQ ID NO 46
<211> LENGTH: 121
<212> TYPE: PRT
<213> ORGANISM: Artificial Sequence
<220> FEATURE:
<223> OTHER INFORMATION: PD-L1(H12_gl) VH

<400> SEQUENCE: 46

```
Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly His Gly Tyr Ser Tyr Gly Ala Phe Asp Tyr Trp Gly
            100                 105                 110

Gln Gly Thr Leu Val Thr Val Ser Ser
        115                 120
```

<210> SEQ ID NO 47
<211> LENGTH: 3750
<212> TYPE: DNA
<213> ORGANISM: Artificial Sequence
<220> FEATURE:
<223> OTHER INFORMATION: HER2(C5)-CD28TM,ICD-CD3Z CAR

<400> SEQUENCE: 47

```
aagttcagat caaggtcagg aacagatgga acagctgaat atgggccaaa caggatatct      60

gtggtaagca gttcctgccc cggctcaggg ccaagaacag atggaacagc tgaatatggg     120
```

```
ccaaacagga tatctgtggt aagcagttcc tgccccggct cagggccaag aacagatggt    180
ccccagatgc ggtccagccc tcagcagttt ctagagaacc atcagatgtt tccagggtgc    240
cccaaggacc tgaaatgacc ctgtgcctta tttgaactaa ccaatcagtt cgcttctcgc    300
ttctgttcgc gcgcttctgc tccccgagct caataaaaga gcccacaacc cctcactcgg    360
cgcgccagtc ctccgattga ctgagtcgcc cgggtacccg tgtatccaat aaaccctctt    420
gcagttgcat ccgacttgtg gtctcgctgt tccttgggag ggtctcctct gagtgattga    480
ctacccgtca gcgggggtct ttcatttggg ggctcgtccg ggatcgggag acccctgccc    540
agggaccacc gacccaccac cgggaggtaa gctggccagc aacttatctg tgtctgtccg    600
attgtctagt gtctatgact gattttatgc gcctgcgtcg gtactagtta gctaactagc    660
tctgtatctg gcggacccgt ggtggaactg acgagttcgg aacacccggc cgcaaccctg    720
ggagacgtcc cagggacttc gggggccgtt tttgtggccc gacctgagtc ctaaaatccc    780
gatcgtttag gactctttgg tgcacccccc ttagaggagg gatatgtggt tctggtagga    840
gacgagaacc taaaacagtt cccgcctccg tctgaatttt tgctttcggt ttgggaccga    900
agccgcgccg cgcgtcttgt ctgctgcagc atcgttctgt gttgtctctg tctgactgtg    960
tttctgtatt tgtctgaaaa tatgggcccg ggctagcctg ttaccactcc cttaagtttg   1020
accttaggtc actggaaaga tgtcgagcgg atcgctcaca accagtcggt agatgtcaag   1080
aagagacgtt gggttacctt ctgctctgca gaatggccaa cctttaacgt cggatggccg   1140
cgagacggca cctttaaccg agacctcatc acccaggtta agatcaaggt cttttcacct   1200
ggcccgcatg gacacccaga ccaggtcccc tacatcgtga cctgggaagc cttggctttt   1260
gacccccctc cctgggtcaa gccctttgta caccctaagc ctccgcctcc tcttcctcca   1320
tccgccccgt ctctccccct tgaacctcct cgttcgaccc cgcctcgatc ctccctttat   1380
ccagccctca ctccttctct aggcgccccc atatggccat atgagatctt atatggggca   1440
cccccgcccc ttgtaaactt ccctgaccct gacatgacaa gagttactaa cagcccctct   1500
ctccaagctc acttacaggc tctctactta gtccagcacg aagtctggag acctctggcg   1560
gcagcctacc aagaacaact ggaccgaccg gtggtacctc acccttaccg agtcggcgac   1620
acagtgtggg tccgccgaca ccagactaag aacctagaac ctcgctggaa aggaccttac   1680
acagtcctgc tgaccacccc caccgccctc aaagtagacg gcatcgcagc ttggatacac   1740
gccgcccacg tgaaggctgc cgaccccggg ggtggaccat gactcgagcc atggattgga   1800
tctggcgcat cctgtttctc gtgggagctg ccacaggcgc ccattctcag gttcagctgc   1860
aagagtctgg ccctggcctg gtcaagccta gcgaaacact gagcctgacc tgtaccgtgt   1920
ctggcggcag catcagcagc agctcttact actggggctg gatcagacag cctcctggca   1980
aaggcctgga atggatcggc tccatctact acagcggcag cacctactac aaccccagcc   2040
tgaagtccag agtgaccatc agcgtggaca ccagcaagaa ccagttctcc ctgaagctga   2100
gcagcgtgac agccgccgat acagccgtgt actactgtgc cagatacgcc cctgatagca   2160
gcggctacct ggtggccttt gatatctggg gccagggcac aatggtcacc gtttctagcg   2220
gaggcggagg ttctggtggc ggaggaagtg gcggcggagg atctcagaca gtggtcacac   2280
aagagcccag cttctccgtg tctcctggcg gaacagtgac cctgacatgt ggccttagct   2340
ctggctctgt gtccaccggc tactacccca gctggtatca gcagacacct ggacaggccc   2400
ctcggacact gatctacagc accaacagca gatccagcgg cgtgcccgat agattcagcg   2460
```

gctctatcct gggcaacaag gccgcactga caatcacagg cgctcaggcc gatgacgaga 2520
gcgactacta ctgcgtgctg tacatgggca gcggcatctc cgtttttggc ggaggcacaa 2580
agctgaccgt gctgggatcc gaaccaaaga gttgcgacaa aacacacacc tgccctacgc 2640
gtttttgggt gctcgtggtg gtgggtggcg tgctcgcttg ctactcactt ctggtgaccg 2700
tagcgtttat catttttttgg gtcaggagca agcgatcccg cctattgcac agcgactaca 2760
tgaacatgac cccccggcgc cccgggccaa cccggaagca ctaccagcca tatgcgcctc 2820
cccgcgattt cgcagcgtat cggtcccggg tcaaattttc acggtccgct gacgccccgg 2880
cctatcaaca gggccagaat cagctgtata atgaattaaa cctcggtaga cgcgaggagt 2940
acgacgtcct cgacaagaga agggggcgcg acccagagat gggaggcaaa ccgcagcgca 3000
ggaagaatcc acaggagggc ctgtacaacg aattacagaa ggacaagatg gcagaggcct 3060
acagcgagat aggaatgaag ggtgaaaggc gtcgtggaaa gggccacgat gggctttacc 3120
agggcctaag tactgccaca aaagatacgt atgacgcgct gcatatgcaa gccctccccc 3180
ccaggtaagc atgcaacctc gatccggatt agtccaattt gttaaagaca ggatatcagt 3240
ggtccaggct ctagttttga ctcaacaata tcaccagctg aagcctatag agtacgagcc 3300
atagataaaa taaaagattt tatttagtct ccagaaaaag gggggaatga aagaccccac 3360
ctgtaggttt ggcaagctag cttaagtaac gccattttgc aaggcatgga aaaatacata 3420
actgagaata gagaagttca gatcaaggtc aggaacagat ggaacagctg aatatgggcc 3480
aaacaggata tctgtggtaa gcagttcctg ccccggctca gggccaagaa cagatggaac 3540
agctgaatat gggccaaaca ggatatctgt ggtaagcagt tcctgccccg gctcagggcc 3600
aagaacagat ggtccccaga tgcggtccag ccctcagcag tttctagaga accatcagat 3660
gtttccaggg tgccccaagg acctgaaatg accctgtgcc ttatttgaac taaccaatca 3720
gttcgcttct cgcttctgtt cgcgcgcttc 3750

<210> SEQ ID NO 48
<211> LENGTH: 3744
<212> TYPE: DNA
<213> ORGANISM: Artificial Sequence
<220> FEATURE:
<223> OTHER INFORMATION: HER2(E4)-CD28TM,ICD-CD3Z CAR

<400> SEQUENCE: 48
aagttcagat caaggtcagg aacagatgga acagctgaat atgggccaaa caggatatct 60
gtggtaagca gttcctgccc cggctcaggg ccaagaacag atggaacagc tgaatatggg 120
ccaaacagga tatctgtggt aagcagttcc tgccccggct cagggccaag aacagatggt 180
ccccagatgc ggtccagccc tcagcagttt ctagagaacc atcagatgtt tccagggtgc 240
cccaaggacc tgaaatgacc ctgtgcctta tttgaactaa ccaatcagtt cgcttctcgc 300
ttctgttcgc gcgcttctgc tccccgagct caataaaaga gcccacaacc cctcactcgg 360
cgcgccagtc ctccgattga ctgagtcgcc cgggtacccg tgtatccaat aaaccctctt 420
gcagttgcat ccgacttgtg gtctcgctgt tccttgggag ggtctcctct gagtgattga 480
ctacccgtca gcgggggtct ttcatttggg ggctcgtccg ggatcgggag acccctgccc 540
agggaccacc gacccaccac cgggaggtaa gctggccagc aacttatctg tgtctgtccg 600
attgtctagt gtctatgact gattttatgc gcctgcgtcg gtactagtta gctaactagc 660
tctgtatctg gcggacccgt ggtggaactg acgagttcgg aacacccggc cgcaaccctg 720
ggagacgtcc cagggacttc gggggccgtt tttgtggccc gacctgagtc ctaaaatccc 780

```
gatcgtttag gactctttgg tgcacccccc ttagaggagg gatatgtggt tctggtagga    840
gacgagaacc taaaacagtt cccgcctccg tctgaatttt tgctttcggt ttgggaccga    900
agccgcgccg cgcgtcttgt ctgctgcagc atcgttctgt gttgtctctg tctgactgtg    960
tttctgtatt tgtctgaaaa tatgggcccg ggctagcctg ttaccactcc cttaagtttg   1020
accttaggtc actggaaaga tgtcgagcgg atcgctcaca accagtcggt agatgtcaag   1080
aagagacgtt gggttacctt ctgctctgca gaatggccaa cctttaacgt cggatggccg   1140
cgagacggca cctttaaccg agacctcatc acccaggtta agatcaaggt cttttcacct   1200
ggcccgcatg gacacccaga ccaggtcccc tacatcgtga cctgggaagc cttggctttt   1260
gacccccctc cctgggtcaa gccctttgta caccctaagc ctccgcctcc tcttcctcca   1320
tccgccccgt ctctcccccct tgaacctcct cgttcgaccc cgcctcgatc ctccctttat   1380
ccagccctca ctccttctct aggcgccccc atatggccat atgagatctt atatggggca   1440
cccccgcccc ttgtaaactt ccctgaccct gacatgacaa gagttactaa cagcccctct   1500
ctccaagctc acttacaggc tctctactta gtccagcacg aagtctggag acctctggcg   1560
gcagcctacc aagaacaact ggaccgaccg gtggtacctc acccttaccg agtcggcgac   1620
acagtgtggg tccgccgaca ccagactaag aacctagaac ctcgctggaa aggaccttac   1680
acagtcctgc tgaccacccc caccgccctc aaagtagacg gcatcgcagc ttggatacac   1740
gccgcccacg tgaaggctgc cgacccccggg ggtggaccat gactcgagcc atggattgga   1800
tctggcgcat cctgtttctc gtgggagctg ccacaggcgc ccattctcag gttcagctgc   1860
aacagtgggg agccggactg ctgaagccta gcgaaacact gagcctgacc tgtgccgtgt   1920
acggcggcag ctttagcggc tactactggt cctggatcag acagcctcct ggcaaaggcc   1980
tggaatggat cggcgagatc aatcacagcg gcagcaccaa ctacaacccc agcctgaagt   2040
ccagagtgac catcagcgtg gacaccagca agaaccagtt ctccctgaag ctgagcagcg   2100
tgaccacagc cgataccgcc gtgtactact gtgcccggat gggcatcaat agcggcggct   2160
acctgtacgg catggatgtg tggggacagg gcaccaccgt gacagtttct agcggaggcg   2220
gaggttctgg tggcggagga agtggcggcg gaggatctca gacagtggtc acacaagagc   2280
ccagcttctc cgtgtctcct ggcggaacag tgaccctgac atgtggcctt agcagcggct   2340
ctgtgtccac cagctactac cctagctggt atcagcagat ccccggacag gcccctcgga   2400
cactgatcta caccaccaac atcagatcca gcggcgtgcc cgatagattc ggcggatcta   2460
tcctgggcaa caaggccgca ctgacaatca caggtgccca ggccgaggac gagtccgact   2520
actactgcat gctgtacatg ggcagcggca tctgggtttt cggcggaggc acaaagctga   2580
ccgttctggg atccgaacca aagagttgcg acaaaacaca cacctgccct acgcgttttt   2640
gggtgctcgt ggtggtgggt ggcgtgctcg cttgctactc acttctggtg accgtagcgt   2700
ttatcatttt ttgggtcagg agcaagcgat cccgcctatt gcacagcgac tacatgaaca   2760
tgaccccccg gcgccccggg ccaacccgga agcactacca gccatatgcg cctccccgcg   2820
atttcgcagc gtatcggtcc cgggtcaaat tttcacggtc cgctgacgcc ccggcctatc   2880
aacagggcca gaatcagctg tataatgaat taaacctcgg tagacgcgag gagtacgacg   2940
tcctcgacaa gagaaggggg cgcgacccag agatgggagg caaaccgcag cgcaggaaga   3000
atccacagga gggcctgtac aacgaattac agaaggacaa gatggcagag gcctacagcg   3060
agataggaat gaagggtgaa aggcgtcgtg gaaagggcca cgatgggctt taccagggcc   3120
```

-continued taagtactgc cacaaaagat acgtatgacg cgctgcatat gcaagccctc ccccccaggt 3180
aagcatgcaa cctcgatccg gattagtcca atttgttaaa gacaggatat cagtggtcca 3240
ggctctagtt ttgactcaac aatatcacca gctgaagcct atagagtacg agccatagat 3300
aaaataaaag attttattta gtctccagaa aaagggggga atgaaagacc ccacctgtag 3360
gtttggcaag ctagcttaag taacgccatt ttgcaaggca tggaaaaata cataactgag 3420
aatagagaag ttcagatcaa ggtcaggaac agatggaaca gctgaatatg ggccaaacag 3480
gatatctgtg gtaagcagtt cctgccccgg ctcagggcca agaacagatg gaacagctga 3540
atatgggcca aacaggatat ctgtggtaag cagttcctgc cccggctcag ggccaagaac 3600
agatggtccc cagatgcggt ccagccctca gcagtttcta gagaaccatc agatgtttcc 3660
agggtgcccc aaggacctga aatgaccctg tgccttattt gaactaacca atcagttcgc 3720
ttctcgcttc tgttcgcgcg cttc 3744

<210> SEQ ID NO 49
<211> LENGTH: 3747
<212> TYPE: DNA
<213> ORGANISM: Artificial Sequence
<220> FEATURE:
<223> OTHER INFORMATION: HER2(F1)-CD28TM,ICD-CD3Z CAR

<400> SEQUENCE: 49
aagttcagat caaggtcagg aacagatgga acagctgaat atgggccaaa caggatatct 60
gtggtaagca gttcctgccc cggctcaggg ccaagaacag atggaacagc tgaatatggg 120
ccaaacagga tatctgtggt aagcagttcc tgccccggct cagggccaag aacagatggt 180
ccccagatgc ggtccagccc tcagcagttt ctagagaacc atcagatgtt tccagggtgc 240
cccaaggacc tgaaatgacc ctgtgcctta tttgaactaa ccaatcagtt cgcttctcgc 300
ttctgttcgc gcgcttctgc tccccgagct caataaaaga gcccacaacc cctcactcgg 360
cgcgccagtc ctccgattga ctgagtcgcc cgggtacccg tgtatccaat aaaccctctt 420
gcagttgcat ccgacttgtg gtctcgctgt tccttgggag ggtctcctct gagtgattga 480
ctacccgtca gcgggggtct ttcatttggg ggctcgtccg ggatcgggag acccctgccc 540
agggaccacc gacccaccac cgggaggtaa gctggccagc aacttatctg tgtctgtccg 600
attgtctagt gtctatgact gattttatgc gcctgcgtcg gtactagtta gctaactagc 660
tctgtatctg gcggacccgt ggtggaactg acgagttcgg aacacccggc cgcaaccctg 720
ggagacgtcc cagggacttc gggggccgtt tttgtggccc gacctgagtc ctaaaatccc 780
gatcgtttag gactctttgg tgcacccccc ttagaggagg gatatgtggt tctggtagga 840
gacgagaacc taaaacagtt cccgcctccg tctgaatttt tgctttcggt ttgggaccga 900
agccgcgccg cgcgtcttgt ctgctgcagc atcgttctgt gttgtctctg tctgactgtg 960
tttctgtatt tgtctgaaaa tatgggcccg ggctagcctg ttaccactcc cttaagtttg 1020
accttaggtc actggaaaga tgtcgagcgg atcgctcaca accagtcggt agatgtcaag 1080
aagagacgtt gggttacctt ctgctctgca gaatggccaa cctttaacgt cggatggccg 1140
cgagacggca cctttaaccg agacctcatc acccaggtta agatcaaggt cttttcacct 1200
ggcccgcatg gacacccaga ccaggtcccc tacatcgtga cctgggaagc cttggctttt 1260
gacccccctc cctgggtcaa gccctttgta caccctaagc ctccgcctcc tcttcctcca 1320
tccgccccgt ctctccccct tgaacctcct cgttcgaccc cgcctcgatc ctccctttat 1380
ccagccctca ctccttctct aggcgccccc atatggccat atgagatctt atatggggca 1440

-continued

```
cccccgcccc ttgtaaactt ccctgaccct gacatgacaa gagttactaa cagcccctct   1500
ctccaagctc acttacaggc tctctactta gtccagcacg aagtctggag acctctggcg   1560
gcagcctacc aagaacaact ggaccgaccg gtggtacctc acccttaccg agtcggcgac   1620
acagtgtggg tccgccgaca ccagactaag aacctagaac ctcgctggaa aggaccttac   1680
acagtcctgc tgaccacccc caccgccctc aaagtagacg gcatcgcagc ttggatacac   1740
gccgcccacg tgaaggctgc cgaccccggg ggtggaccat gactcgagcc atggattgga   1800
tctggcgcat cctgtttctc gtgggagctg ccacaggcgc ccattctcag gttcagctgg   1860
tggaatctgg ccctggcctg gttaagccta gcggcacact gtctctgacc tgtgctgtgt   1920
ctggcggcag catcagcagc agcaattggt ggtcttgggt ccgacagcct cctggcaaag   1980
gcctggaatg gatcggcgag atctaccaca gcggcagcac caactacaac cccagcctga   2040
agtccagagt gaccatcagc gtggacacca gcaagaacca gttctccctg aagctgagca   2100
gcgtgacagc cgccgataca gccgtgtact actgtgccag aatgggagcc aatagcggcg   2160
gctacctgta cggcatggat gtgtggggac agggcaccac cgtgacagtt tctagcggag   2220
gcggaggttc tggtggcgga ggaagtggcg gcggaggatc tcagacagtg gtcacacaag   2280
agcccagctt ctccgtgtct cctggcggaa cagtgaccct gacatgtggc cttagcagcg   2340
gctctgtgtc taccagctac tacccctcct ggtatcagca gacccctgga caggctcccc   2400
ggacactgat ctactccacc aacaccagat ccagcggcgt gcccgataga ttctccggct   2460
ctatcctggg caacaaggcc gcactgacaa tcacaggcgc tcaggccgat gacgagagcg   2520
actactactg cgtgctgtac atgggcagcg gcatctgggt tttcggcgga ggcacaaagc   2580
tgaccgttct gggatccgaa ccaaagagtt gcgacaaaac acacacctgc cctacgcgtt   2640
tttgggtgct cgtggtggtg ggtggcgtgc tcgcttgcta ctcacttctg gtgaccgtag   2700
cgtttatcat tttttgggtc aggagcaagc gatcccgcct attgcacagc gactacatga   2760
acatgacccc ccggcgcccc gggccaaccc ggaagcacta ccagccatat gcgcctcccc   2820
gcgatttcgc agcgtatcgg tcccgggtca aattttcacg gtccgctgac gccccggcct   2880
atcaacaggg ccagaatcag ctgtataatg aattaaacct cggtagacgc gaggagtacg   2940
acgtcctcga caagagaagg gggcgcgacc cagagatggg aggcaaaccg cagcgcagga   3000
agaatccaca ggagggcctg tacaacgaat tacagaagga caagatggca gaggcctaca   3060
gcgagatagg aatgaagggt gaaaggcgtc gtggaaaggg ccacgatggg ctttaccagg   3120
gcctaagtac tgccacaaaa gatacgtatg acgcgctgca tatgcaagcc ctccccccca   3180
ggtaagcatg caacctcgat ccggattagt ccaatttgtt aaagacagga tatcagtggt   3240
ccaggctcta gttttgactc aacaatatca ccagctgaag cctatagagt acgagccata   3300
gataaaataa aagattttat ttagtctcca gaaaaagggg ggaatgaaag accccacctg   3360
taggtttggc aagctagctt aagtaacgcc attttgcaag gcatggaaaa atacataact   3420
gagaatagag aagttcagat caaggtcagg aacagatgga acagctgaat atgggccaaa   3480
caggatatct gtggtaagca gttcctgccc cggctcaggg ccaagaacag atggaacagc   3540
tgaatatggg ccaaacagga tatctgtggt aagcagttcc tgccccggct cagggccaag   3600
aacagatggt ccccagatgc ggtccagccc tcagcagttt ctagagaacc atcagatgtt   3660
tccagggtgc cccaaggacc tgaaatgacc ctgtgcctta tttgaactaa ccaatcagtt   3720
cgcttctcgc ttctgttcgc gcgcttc                                       3747
```

<210> SEQ ID NO 50
<211> LENGTH: 30590
<212> TYPE: DNA
<213> ORGANISM: Artificial Sequence
<220> FEATURE:
<223> OTHER INFORMATION: HDAdIL12p70_TK_aPD-L1

<400> SEQUENCE: 50
aaacatcatc aataatatac cttattttgg attgaagcca atatgataat gaggggggtgg 60 agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020
cagactgtgg atcaaaagtg gtttctggtg cgacttactc tcttgagtat acctgcagtc 1080
ccctttctta agtgtgttaa aaaaaaaggg ggatttcttc aattcgccaa tactctagct 1140
ctccatgtgc tttctaggaa acaagtgtta acccacctta tttgtcaaac ctagctccaa 1200
aggacttttg actccccaca aaccgatgta gctcaagaga gggtatctgt caccagtatg 1260
tatagtgaaa aaagtatccc aagtcccaac agcaattcct aaaaggagtt tatttaaaaa 1320
accacacaca cctgtaaaat aagtatatat cctccaaggt gactagtttt aaaaaaacag 1380
tattggcttt gatgtaaagt actagtgaat atgttagaaa aatctcactg taaccaagtg 1440
aaatgaaagc aagtatggtt tgcagagatt caaagaaaat ataagaaaac ctactgttgc 1500
cactaaaaag aatcatatat taaatatact cacacaatag ctcttcagtc tgataaaatc 1560
tacagtcata ggaatggatc tatcactatt tctattcagt gctttgatgt aatccagcag 1620
gtcagcaaag aatttatagc ccccttgag cacacagagg gctacaatgt gatggcctcc 1680
catctccttc atcacatctc gagcaagacg ttcagtccta cagaaataaa atcaggaatt 1740
taatagaaag tttcatacat taaactttat aacaaacacc tcttagtcat taaacttcca 1800
caccaacctg ggcaatatag tgagacccca tgcctgcaaa aaaaaaaaaa ttagccaggc 1860
atggtagcat gtacctgtag tcccagctac ttgagaggtg aggtgggaaa atcactttag 1920
tgcaggatgt tgaggctgga gtgaactgtg attgtgccac tgcactccag cctggacaat 1980
agagcaagac cttgtctcaa aaaaatgcat taaaaatttt ttttaaatct tccacgtatc 2040
acatcctttg ccctcatgtt tcataaggta aaaaatttga taccttcaaa aaaaccaagc 2100

```
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaatttct aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
```

-continued

```
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
```

-continued

```
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg gggggttct aatttaagaa atgcataatt   7800
ggctatagac agacagttgt ctggaatgaa aatcaatact tttgctataa tcgattactg   7860
aaataatttt actttccagt aaaactggca ttataatttt ttttaatttt taaaacttca   7920
taattttttg ccagactgac ccatgtaaac atacaaatta ctaataatta tgcacgtcac   7980
atctgtaata atggccttca tgtaaacatt tttgtggttt acacataaaa tctctaatta   8040
caaagctata ttatctaaaa ttacagtaag caagaaaatt aatccaagct aagacaatac   8100
ttgcaacatc aattcatcat ctgtgacaag gactgcttaa gtctctttgt ggttaaaaag   8160
gaaaaaaaaa aaaaagacat gttggccaga tgcggtggct cacacctgta atcccagcac   8220
tttgggaggc tgaggtgggc ggatcacccc tggcctgccc aacatggtga aaccccgtct   8280
ctactaaaaa cacaaaaatt agctgggcgt ggtggcgggc gcctgtaatt ccagctactc   8340
gggaggctga ggcaggagaa ttgctagaac ccaggaggca gagattgcag tgagctgaga   8400
ttgcaccatt gcactacagt ctgggcaaca aaagtgaaac tccatcttaa aaaaaaaaag   8460
acaatgttcg tgggtccaaa caagacttaa tggaagtgag tctaaaaatg agctatgtgg   8520
gccaggcgta gtggctccca cctgtaatcc cagcactttg ggaggccgaa gcaggcagat   8580
catgaggtca ggagatggag accatcctgg ccaacacggt gaaatcctgt ctctacaaaa   8640
attagctggg cgtggtggtg cctgcctgta atcccagcta ctcagaaggc tcaggcagga   8700
gaatcgcttg aaccagggag tcggtggcta gagtgagccg agatttgcat cactgcactc   8760
ctgcctggtg acagagcaag actccatctc aaaaaaaaca aacaaaaata aaagataaaa   8820
atgagctatg tgaattaaaa gaggtataac aatagataaa ccatatttta tttaattcct   8880
agtaatgagt aatatttcca aacttctgga atgggcagaa attgctagtt ggcatatttt   8940
taccttttat attcagatac attaaaattc tcaaaaaaaa acacctcaaa gcagatgatc   9000
cgccatctcc ttggataatt tgtgttaact caggataaca gaaaaccaaa attatgagtt   9060
actgatgcaa tattcctaaa tgtaaaaata attaaagcta atagtagatt catcttccaa   9120
tttcatatca gtcttacaaa taaactacat atataacttg cttgccttcc cttctgaggg   9180
```

-continued

```
ataaagctgt tagaagaatt aaaatcagca ttcttgacta ttcaaccaag ggagggataa   9240
attattactc attctaggga catgggctca taactactac atgtgtaagg acatgaattt   9300
acccaatatt acaatttttc cttttattag tgtgtacagt ggaagaatag acatgttcac   9360
tctggacaaa aaaaaaatta tacttatcag ttatcagaag cacaatgctg aagacagtag   9420
ttccataaca atttgaagta tgtgatcgaa ctagtagatt atcttagtag tagtgaatta   9480
ttgtaaatgt tagtaatttg gcagccactg ggcagaaaaa taagaattga ggctcaatat   9540
tgatattaat ggtggtgatt gacacataaa ttttatcaag tctacacaat ataaaattac   9600
agaaaggtag aagagtatac cagtacaact tcaacatatc ttcactacaa gggagtaaaa   9660
tgacatggcc tagttactat ctaatgaact gcagaaaact aaaagaaaac tccaaggcaa   9720
ctcttctctg ctgatctggt tggtcctttt cctacctttt gcaataccca gatacaaaca   9780
atggatagaa aacaaagtag acttgtagta tgcaggtcac agtgctaaat tcacagaaag   9840
aaaccccctga actgaactgc tctatttcct ggtggtcaca aagagtaatt ctggtttaca   9900
cctacagatt gatgtcaatc tacaccctgt tgataacagt gtggccaagg acaaaaaaaa   9960
ggtgctccgt tttaccaatt ctgtaaaaaa ttattggcag ggtaagctcg gctagggcag  10020
gattacattt ctaggactac catccccgaa atttagaaga tattatatcc acataaagca  10080
tatctttcac attaatttgc aaaaatctaa aagctttttc ttagctcaag tgtgtccaag  10140
tttaccctgg cagtttaaaa cgatagttac aagcagcatg ggttgtatca gacacatttg  10200
agggccaatt tcatgtaagt gatattgggc aagttacttc aactatctgt gcctccaagg  10260
tcatactagt gtttatttac ctaaagggta cctgttatgt aactttaggg tgtttacatt  10320
agataatgcc tgcaaaatat ttacttcaac gcctaaaaca tagttaagta ttcaataaat  10380
acctactatt gtcactacta acttaaaagt ttagagatta agagcagaat ctggggtgag  10440
acaaacttag gttcaaatcc tagtattgtt gggtaatctt gggcaagtta cttaacctct  10500
ctgatttgtg taatttaaaa aattagttaa tatacataac agggcttaga agagtatcta  10560
gcacatagca ccatttaagc atttgttatt gctaacatgc aaacaattta agggaaagaa  10620
attttttaaa aaggaagagg gatttgcaaa ctaaaaacaa tgagtatctt atgttcaaag  10680
aaaactaaca aacagccagc tctagcaata attaaattca ctatatactg gggcaggcat  10740
cacaccccaa agctaaaagc gtctacctag gccaggcacg gtggctcatg cctgtaatcc  10800
cagcactttg ggaagcagag gcgggcagat cgcttgagct caggagttca agaccagcct  10860
ggacaacatg gcaaaacacc atctctacaa aaaatacaaa tattaggccg ggcgcagtgg  10920
ctcacgcctg taatcccagc actttgggag gccaaggcgg gtggatcacc tgagatcagg  10980
agttcgagag tagcctggcc aacatggtga aacctcgtct ctattaaaaa tacaaaaaat  11040
tagccaggca tggtggcagg cgcctgtaat cccagctact caggggggatg aggtaggaga  11100
atcgcttgaa cccgggaggc agaggttgca ctgagccgag atcatgccac tgtactccag  11160
cccgggcaac aagagcgaaa ctccatctca aaaaaataaat aaataaataa ataaaataaa  11220
gtacaaatat tagccaggga tggtggtgcg cacctgtagt cccagctact tgggaggctg  11280
aagtgggaga atcccctgag cctggggaga atcacccgag cccgggaagt cgaggctgca  11340
gtgagcagtg attgtgccac tgcactccat cctaggtgac agagtgagac cctgtctcaa  11400
aaaaaagaaa ttggcagaat taagtaagtt gatgtttaga gatgaaaaat caacattttt  11460
tcctcagcaa ctgaataaaa acaacagcca ctaccatttt tttgagtacc tatttgtagc  11520
ctatttttta actggtatta ctcgagagag agagagctag gttcgagaca gagctccttc  11580
```

tcttaataac tgtatgacct agggtatgtc tgttagcctc tctgaggctt caaaggttcc 11640
tcatctgtaa aatggtaata atcataccat tgctacaggg ctgttttgaa gactaattag 11700
gactatgtaa gtaaacatga tgatggctat tattactgtt ccccgccagg ggccatgcaa 11760
gggttgctga ttcacataga ctgtcttata atcctctcaa taactccaag aggtagccag 11820
cacctcagat atacataaaa tgacttaagc ccagagaggt gaagtaagtt gcccacagcc 11880
acacaactag taaatagccc aaacaagctg gattcccagt tagactccgt taatagcact 11940
gctctttacc ttaagtcatt acaatgccta atatgaaata gaatcgcttc tttcttaggg 12000
ttcaagtggt taattattta atgtattcat tcaacaaacc atcatcgagg acctcttaca 12060
agccaagtac tgtgctaagt gctagagtta cggcggtgat tcctgccctt aaaaagtttt 12120
agtgggagaa acaacaggta accaggtcat tgccaaaaca acaaaaataa tcataataaa 12180
gcaggctaaa gcatatttaa ctggccgggg ttttgactat tttagcaagc atgatcagaa 12240
cggttgagga gggaggccag cagcttggcc ggttcaacaa acaagaaaaa accagtgagg 12300
gtggagctaa gataccagag gctgattacg gttaagaatg ttcttgaagg taaggaccag 12360
attctcattt tctatatcct ggggcatcgg tcagcatgga atctggattc tagcacatgt 12420
gaatttcggc ttgaaatgac ctaatgcctt ttccctagtt ccttcgtgtg tcaaatacgc 12480
atggttaccg ctaccagagc tgtagtgggg cttcaatgag gccatgagca tctccataaa 12540
gatgaactac agtgtgtgca aaactaaagg caaaacctgg tccccacacg ccctcccagg 12600
tggtcgcttt ccgtgccgag gcccctccag aggtgccccg agaacctcac catcgcaccc 12660
caaacttcca gggaagggcc tctcccgaga aagcccccac gcccccaccc cgcgccatca 12720
ttcccgaatc tgccctcggc ccctccccgc agcacgctcg caggcggcac atgtcaacca 12780
aaacgccatt tccaccttct cttcccacac gcagtcctct tttcccaggg ctcccccgag 12840
gagggaccca ccccaaaccc cgccattccg tcctccctgc cgccctcgcg tgacgtaaag 12900
ccgaacccgg gaaactggcc gcccccgcct gcggggttcc ctgggcccgg ccgctctaga 12960
actagtggat cccaattgaa ggcctggtct aaatgactcc aaaatcacca cttaattcaa 13020
gagactgatt tccctgagtc aggcccctta aagcagctat ttcaatggga cagggaaaca 13080
accctaggat ctggattaga atcacttggg ggctgccaca cccccagggc tctgatcctg 13140
cccttctccc acacgcacat tcacatactg ctgcagtgac cttccatttc taatgggttc 13200
ctgggccatc tgtcaggtat agggaatgga aaaggggttg gggaggctct gcttcagaaa 13260
gtttgtgtca ggggctccca gagcctccac agatagatag caggggtccc caccctacca 13320
tggcagctat aaatgtgatc aacatttatt ggcctaggat acagcagtta gcaaaatgcc 13380
tgatgtagtt cccactccgt ggaggttgca ggctagctct ttcctaatga gctttacagc 13440
agaagctgtt ttatcgttaa gtgccccaca gagacacttt accaggaggc tgggagagtt 13500
ctccagattt gggagaggcg cagagacagt gtgtgagccg agccctgtct cagcaatcca 13560
cctggaggag ctagagtatc ctcctccctt taccattcag accgagagaa aaagcccagc 13620
ttgtgtgcac cctcgtgggg ttaaggcgag ctgttcctgg tttaaagcct ttcagtattt 13680
gttttgatgt aaggctctgt ggtttggggg ggaacatctg taaacattat tagttgattt 13740
ggggtttgtc tttgatggtt tctatctgca attatcgtca tgtatattta agtgtctgtt 13800
atagaaaacc cacacccact gtcctgtaaa cttttctcag tgtccagact ttctgtaatc 13860
acattttaat tgccacctcg tatttcacct ctacatttga aatctggcgt ctgtttcaag 13920

```
ccagtgtgtt ttttcttcgt tctgtaataa acagccagga gaaaagtgcc tctatgtttt  13980
tatttttcaa gggagtattc agtacctaca aacccaagtc aggaagcctg ctagtggctt  14040
tggttctttc agaggctgct cgatgccttg tgtgtcagaa agaaagattc agcagttttg  14100
catcatggca aagaagcctg ttattttggg gctcagcccc tcattttata gaggatgaaa  14160
cagaggggga tgggaggtca caaagacaac tgccccggga gcaggtgtgg gggagacttg  14220
ccctgagggt ctagacgctc tgcaccaccg tcctgtctcc cttgctgaag accacacatg  14280
cccttctttg accagaccct gccacctgat aggccaggac ctggtaggcg ggtacccagg  14340
tttcatggat ggaaccacat ctccccaaaa gtggggaggt agctactggg atgcacgcct  14400
cccgccatgt gctataggag agcagctgaa gcaacagttg ggatcagatg tagtcacaat  14460
tgaatgcatc atcacattta tccctctaag tggctgggag agttgatatc ctcatcccta  14520
aggtacaaaa tgttccaatt tgatcagtgg ctttcaggag ctgagaaagg catgtgctct  14580
gaggcagagc tgttatgtcc cgcagagcct aaaaatgctc taagaacatg ctccctgcca  14640
aaattctcaa tggctgtgac aagggacaac gatcgaccaa tgggggtgga agcagacctc  14700
cgcagtccag gggccagagc taggacagag gggtcggaga aagagtcatt ttcccaacac  14760
tccagctctt ggccagtcct cacacagtcc cctcctgctt cctgctgaga gagatatcct  14820
cataggtctg ggtaaagtcc ttcagtcagc tttcattccc tgtcaccaac tttgtctctg  14880
ttctccctgc ccgtctcagg cagcactcct caggaaacct ctccaagagc cagcctcact  14940
gcagcgccca ctattgtccc tctgcctcaa gtgtcccatc catgccaggc cccaggcagg  15000
ctgcagcttt ccctcagggc cacaccaaag cacttgggct cagctgtgct gtccccctcc  15060
atcactgagc tcaggggcag caggggtggg gtgccaggag gcccattcac ccttctctgg  15120
ctctgtgttg gacccacctg cccagccact gctgcttaga acctacccgc tgggaaaatg  15180
aagccctccc ggaggggcca cctcaacctg agagcctcac ggatcacagt tgtccccact  15240
cagctctgcc agccctcaga gacccataga taaaagctga gcttggctcg cagagctggt  15300
tccatcttcc attcccagag ggttcaactt cctaccccaa ccacacaggg aacctcaagg  15360
ctgagccagt gtgggctgca gtgcagacca gcttcctgga cacgtcctgc cacctgaccc  15420
caggctggcc tcactgcccc tggcactcct gaccctatcc tcattcctcc tggcagtgcg  15480
tgttctgcca ttccgctttc ccttagctgt cctctcactg tactgtcagc ttctcctttt  15540
ccaggtgccc cccaggggct ttccacatga ccctgtcacc ccacagccca tccagcacca  15600
attccagctc tctgccaccc ttcaaaggag tgacagtgcc ctgcttcacc tcccactcac  15660
ccctcaaccc agagcaatct ggctccagtc ttgcctcctt cccccctaagt actctagtca  15720
cagttccaaa ttcctcctgg tcataaagcc aaatgaagct tcctggtcct cagcggactt  15780
gccacttcag cagtactgga ctctctcctc ccagaaacct gtttcccctt ggctcctgga  15840
gcccacactc tgctggaatc cttctgcctc tctggcctgt agcctggccc tctctcccaa  15900
cctgaggtcc attctctcct gctcctccac aagatgttgc tccttccatt acttcctccc  15960
tctcaaccaa agctccttca ttagctcttt atcttctggt ttcttcccct gggcagacga  16020
atggattcaa gagcctgtgg cccagcagcc cagcactcca ggatctcagc acttcagcat  16080
cccagtaccc tagcatctca ataccccagc accccagcac catagtattc cagcacccca  16140
ttgtccaagc atctcagcac tccagcatcc cagcacccca acactccagc agcccagaat  16200
ctcagcaccc tagcactgca gcatctcagg accccagcac ttcagcatcc cagcacacta  16260
gtactccagc atctcggcac cccagcacct aggcatccca acacccagca ccccagcact  16320
```

taagcatccc accactacag tatctcaaca ctccagcacc ccagcaccat agtgttccag 16380
caccccagca tcccaacacc ccagcactta agcatcccaa cacctcggca tcccaacacc 16440
ccagcactgc agcatctcag caccttagca tcccagtgcc ctagcatctc aatgctccag 16500
cacaccagta ctacagtatt ccagcacccc agcactccag catctcagca ctgcagcact 16560
gcagcactcc agcatcccaa aatcccagca tcccaacacc ccagcagacc agcagaccag 16620
catctcagca ccgcagcatc caaggactat cccagcatcc cagcaaccca gcacctcagc 16680
atcccaacac cccagcattt cagcatggca acaccccagt accccagcac ttcagcaccc 16740
cagtatccca gcatctcagc gacccagtat cacaaaacct cagcatccta gcaccccagc 16800
accccagcac cttagcacct tagcatccca gcatctcagc gcctcagcat cttgatattc 16860
tggctgaggt cagcgtggtg tatctagtca gggtcctaac tttcacttcg cagggaaatg 16920
ctgctggact gggtctcatg ttgggctgaa gctctctaga ccccttgaag acagcataaa 16980
agagcttgga gacgctgggt gtcccccatg gaagagttca ctctcatcct gctttgacaa 17040
cagccttctc tggggtccct cacgggcccc tctttcttac tgcaagtttg tctctgagaa 17100
gactgtgatg cagaagtcac tcagctgcct gtggctcctg aagagctgaa ggtggaggcc 17160
tgtaggcctc cctatgagag gcgcagaaaa aaccatgatt gctagtgggg aggtgctccc 17220
tctacaaccc actccataat ctgcccccgc ccagctctga ggccagcccc aggggaaaat 17280
gccagatccc cagggaggtg tgtgagacct caggggctcc ctcctccctt acagcaggct 17340
caggcccctg gggcctcag ggccaaggtc tgtgggtaag ctactatctc tcacttgtcc 17400
tctagccaca aaagccaggg agatctggca atggacatga ggttctgaag aagcacatat 17460
gactggcttc ctaatgcgtg gttgttcagt gattcaataa acacgcatgg gccaggcatg 17520
gggaaataga caaacatgat ccccaacctc tcccagagtg aactgggagg gaggagtgtt 17580
catccctcag gattacacca gagaaacaaa ccagcaggag atatatatgg ttttgggggg 17640
tcaagaaaga ggaaaaacct ggcaaggcaa gtccaaaatc ataggacagg ctgtcaggaa 17700
gggcagcctg gaacctctca agcaggagct gatgctgcag tccacaggca gaatttcttc 17760
ttcctcgggg aaatctcagc tttgttctta aggcctttca actgattggc tgaggtctgc 17820
cccttccccc acattctcca ggataatctt ccttacttaa agtcaactat taatcacagc 17880
tacaaaatcc cttcacagct acacatagat cagtgtttga ttgacgaaca gcccctacag 17940
cctagccaag ttgacacata aaactaacca tcacaggggg acaaatgatg taaacacatc 18000
aacaaataaa acagtaacaa gttaaggtct atggaaaaaa cacagaaggg gcagagagaa 18060
agaaagcaag aaggagagtc ccagtttgct agggcttgtg ggaagtgggg agcagttctc 18120
tttagctagg atatttggga aaggcatatc tgaaggagtg atatttgagc ttagattaaa 18180
agatgggaag gagcaagcca tgcaaagagc taggatgttc caagcagaga cggaacagca 18240
agtgcaaatg tcaggaggaa tagaaggagg ctggtgggtg gggtccagtg agcaagagga 18300
gggcaggcag gagaggggat ggggaggtgg gcaggcccag accacccagg gccctggaga 18360
ctatcctgat ccaacaaggg aagccttgag tcacttcagt gtccatgtgg agaatggacc 18420
tcagactgaa tgagggaggc agtaaggagg gcctctacct ccagggcttc gccctgtgga 18480
ctgcgcatag acatctccaa ctcagaaagt ctgaaccaaa ctttccatag ttcccccaag 18540
tctgggcatc ctcctactca gtgaaaggca gccatcacac ctccctgccc tgctcccgga 18600
tgccccaaat cctcttggtc tccaagtcca gaacctgaga cttgtccttg atgtttgtct 18660

```
ttccctcacc ctttctgtat tctgggaaga tgggtttttt tcccccagat gaatctgtaa  18720
aacttctgtg atcacaataa aaattctggc agtattattt tctggaacat gacaaagtga  18780
ttcaaaatta tttatctgga agactacaaa acaagaatag ccaggaaatt tctaaaaaga  18840
aagaagaagg aggaggagaa agaaggagga ggaaaaggag gagaagaaga aaagaaaaag  18900
aaccaagaaa gggttctagc tctaccaaat attaaaacat atcatgaagc tatttaaaac  18960
aatatggttg tggatactga aaaagatgtg aataaagtgg aaggaaaata aatagaaatg  19020
cacatgggga ttgagactgt gaaaaaggca gcatctcaca tcagtgaggg atgttcaaca  19080
cctggtgttg ggaaaactgg ctagtcattt aaaccaaaca actgggtcct ctacctcact  19140
cctgacatta agatacattt agatgattca aagagtaaga cagaaaaaat aacacgtgaa  19200
aacactatca gaaaacaacg tgggccaggt gtggtgggtc acgcctgtaa tcccagcact  19260
ttgggaggcc gaggcagaca gatcacctga ggtggggagt tcaagaccag cctgaccaac  19320
atggtgaaat cctgtctcta ctaaaaatac aaaattagct gagcgtggtg gcgcatgcct  19380
gtaatcccag ctactcagga ggccgaggca ggagaatcac ttgaacctgg gaggcagagg  19440
ttgtggtgag ccgagatcac gccattgcac tccagcctgg gcaacaagag tgaaaatcca  19500
tctaaaaaaa aaaaaaaaag ccaaggtgga tatttttata gtatcagggt agatcaagct  19560
tctccaatca tgacatgaaa cccagaaacc ataaaagaaa agaatgataa aattgcccac  19620
gtaaagtaaa aagcttgcac acagaaaaac accatacagg ttacaagatg agcagcaaaa  19680
tcagagaaaa aacattgcaa ttcaggacac acagaggcta ttgttcctaa tatttaaaaa  19740
taaaagtagt ggattgtcta caaaaagatg aagacaagaa tttcagaaaa ccaaatactg  19800
catgttttca cttacaagtg gaagctaaac actgagtaca cgtgtacaca aagaatggaa  19860
ccataggcca ggcaccgtgg ctcacgcctg taatcccagt actttgcgag gccgaagcgg  19920
gcggatcacc tgaggtgagg agttcgagac catcctggcc aacatggtga aacccagtct  19980
ctactaaaaa tacaaaaatt agccgggcgt ggtggtgggt gcctgtaatc ccagctactc  20040
gggaggctgc ggcagtagaa tcgcttgaac cctggaggtg gaccttgcag tgagccgaga  20100
tcgcaccact gcactccagc ctgggcaaca gagtgagact ccatctcaaa aaaaaaaaaa  20160
aggaatagaa caatagacac tggggcctac ttgagggagg agggtgagga tcaaaaacct  20220
gcctatcagg tactatgctt attacctggg tggtgaaata atctgtacac caaaccccag  20280
tgacatgcaa tttaccgatg taacaaacct gcccatgtac ccgctgaacc taaaataaaa  20340
gttggaaaaa aatatagaaa ttttctttgt aatagccaaa aactgcaaac agcccaggtg  20400
tctattagta gaatgcataa acaaactcgg gcatgttcat acaatgtaaa actactcatc  20460
aataaaaagt gatacttctc agcaatgaaa agaaactagc tactgatacc agctacaaca  20520
tggatggatt tcaagtgctt tatgatgaga gcaagaagcc agacacaaaa gtgtctatat  20580
atatatacag tatatatacg tatatataca catatataca gtatatatat acatatacat  20640
gtatatatat actgtatata tactgtatat atatacacag tatatatata catatataca  20700
gtgtatatat actgtgtata tatacatgta tatatactgt gtatatatac atgtatatat  20760
actgtgtata tatacatgta tatatactgt gtatatatac atgtatatat atgtatactg  20820
tatatatact gtatatatat atacacatat atacagtata tatatacagt atatactgta  20880
tatatacagt atatacgtgt atatatacat atatacagta tatatgtaaa tatacatata  20940
tacagtatat atgtaaatat acatatatac atgtatatat atacactata tatatacata  21000
tatagtgtat atatacatat atacatgtat atatttacta tatgattcca tttatataaa  21060
```

gtgccaaaac agtcaaaaat aatctatgtg gaaaaaatca acaaagggat cccccgggct 21120
gcaggaattc gatggcgcgc cgacgtcgca tgcagttagg gataacaggg taatacgacc 21180
atggcatgtc ctctagactc gagcggccgc aataaaatat ctttattttc attacatctg 21240
tgtgttggtt ttttgtgtga atcgtaacta acatacgctc tccatcaaaa caaaacgaaa 21300
caaaacaaac tagcaaaata ggctgtcccc agtgcaagtg caggtgccag aacatttctc 21360
tatcgaagga tctgcgatcg ctccggtgcc cgtcagtggg cagagcgcac atcgcccaca 21420
gtccccgaga agttgggggg aggggtcggc aattgaaccg gtgcctagag aaggtggcgc 21480
ggggtaaact gggaaagtga tgtcgtgtac tggctccgcc tttttcccga gggtggggga 21540
gaaccgtata taagtgcagt agtcgccgtg aacgttcttt ttcgcaacgg gtttgccgcc 21600
agaacacagc tgaagcttcg aggggctcgc atctctcctt cacgcgcccg ccgccctacc 21660
tgaggccgcc atccacgccg gttgagtcgc gttctgccgc ctcccgcctg tggtgcctcc 21720
tgaactgcgt ccgccgtcta ggtaagttta aagctcaggt cgagaccggg cctttgtccg 21780
gcgctccctt ggagcctacc tagactcagc cggctctcca cgctttgcct gaccctgctt 21840
gctcaactct acgtctttgt ttcgttttct gttctgcgcc gttacagatc caagctgtga 21900
ccggcgccta cgtaagtgat atctactaga tttatcaaaa agagtgttga cttgtgagcg 21960
ctcacaattg atacttagat tcatcgagag ggacacgtcg actactaacc ttcttctctt 22020
tcctacagct gagatcaccg gcgaaggagg gccaccatgg gtcaccagca gttggtcatc 22080
tcttggtttt ccctggtttt tctggcatct cccctcgtgg ccatatggga actgaagaaa 22140
gatgtttatg tcgtagaatt ggattggtat ccggatgccc ctggagaaat ggtggtcctc 22200
acctgtgaca cccctgaaga agatggtatc acctggacct tggaccagag cagtgaggtc 22260
ttaggctctg gcaaaaccct gaccatccaa gtcaaagagt ttggagatgc tggccagtac 22320
acctgtcaca aaggaggcga ggttctaagc cattcgctcc tgctgcttca caaaaaggaa 22380
gatggaattt ggtccactga tattttaaag gaccagaaag aacccaaaaa taagaccttt 22440
ctaagatgcg aggccaagaa ttattctgga cgtttcacct gctggtggct gacgacaatc 22500
agtactgatt tgacattcag tgtcaaaagc agcagaggct cttctgaccc ccaaggggtg 22560
acgtgcggag ctgctacact ctctgcagag agagtcagag gggacaacaa ggagtatgag 22620
tactcagtgg agtgccagga ggacagtgcc tgcccagctg ctgaggagag tctgcccatt 22680
gaggtcatgg tggatgccgt tcacaagctc aagtatgaaa actacaccag cagcttcttc 22740
atcagggaca tcatcaaacc tgacccaccc aagaacttgc agctgaagcc attaaagaat 22800
tctcggcagg tggaggtcag ctgggagtac cctgacacct ggagtactcc acattcctac 22860
ttctccctga cattctgcgt tcaggtccag ggcaagagca agagagaaaa gaaagataga 22920
gtcttcacgg acaagacctc agccacggtc atctgccgca aaaatgccag cattagcgtg 22980
cgggcccagg accgctacta tagctcatct tggagcgaat gggcatctgt gccctgcagt 23040
gttcctggag taggggtacc tggggtgggc gccagaaacc tccccgtggc cactccagac 23100
ccaggaatgt tcccatgcct tcaccactcc caaaacctgc tgagggccgt cagcaacatg 23160
ctccagaagg ccagacaaac tctagaattt tacccttgca cttctgaaga gattgatcat 23220
gaagatatca caaaagataa aaccagcaca gtggaggcct gtttaccatt ggaattaacc 23280
aagaatgaga gttgcctaaa ttccagagag acctctttca taactaatgg gagttgcctg 23340
gcctccagaa agacctcttt tatgatggcc ctgtgcctta gtagtattta tgaagacttg 23400

-continued

```
aagatgtacc aggtggagtt caagaccatg aatgcaaagc tgctgatgga tcctaagagg  23460
cagatctttc tagatcaaaa catgctggca gttattgatg agctgatgca ggccctgaat  23520
ttcaacagtg agactgtgcc acaaaaatcc tcccttgaag aaccggattt ttataaaact  23580
aaaatcaagc tctgcatact tcttcatgct ttcagaattc gggcagtgac tattgataga  23640
gtgatgagct atctgaatgc ttcctaaaaa gcgaggtccc tccaaaccgt tgtcattttt  23700
ataaaacttt gaaatgagga aactttgata ggatgtggat taagaactag ggagggggcta  23760
gctcgacatg ataagataca ttgatgagtt tggacaaacc acaactagaa tgcagtgaaa  23820
aaaatgcttt atttgtgaaa tttgtgatgc tattgcttta tttgtgaaat ttgtgatgct  23880
attgctttat ttgtaaccat tataagctgc aataaacaag ttaacaacaa caattgcatt  23940
cattttatgt ttcaggttca gggggaggtg tgggaggttt tttaaagcaa gtaaaacctc  24000
tacaaatgtg gtagatccat ttattagcta ggagtttcag aaaagggggc ctgagtggcc  24060
cctttttca acttaattaa cctgcagggc ctgaaataac ctctgaaaga ggaacttggt  24120
taggtacctt ctgaggctga aagaaccagc tgtggaatgt gtgtcagtta gggtgtggaa  24180
agtccccagg ctccccagca ggcagaagta tgcaaagcat gcatctcaat tagtcagcaa  24240
ccaggtgtgg aaagtcccca ggctccccag caggcagaag tatgcaaagc atgcatctca  24300
attagtcagc aaccatagtc ccactagttt catcaccacc gccaccccc cgcccccccg  24360
ccatctgaaa gggttctagg ggatttgcaa cctctctcgt gtgtttcttc tttccgagaa  24420
gcgccgccac acgagaaagc tggccgcgaa agtcgtgctg gaatcacttc caacgaaacc  24480
ccaggcatag atgggaaagg gtgaagaaca cgttgtcatg gctaccgttt ccccggtcac  24540
ggaataaacg ctctctagga tccggaagta gttccgccgc gacctctcta aaaggatgga  24600
tgtgttctct gcttacattc attggacgtt ttcccttaga ggccaaggcc gcccaggcaa  24660
aggggcggtc ccacgcgtga ggggcccgcg gagccatttg attggagaaa agctgcaaac  24720
cctgaccaat cggaaggagc cacgcttcgg gcatcggtca ccgcacctgg acagctccga  24780
ttggtggact tccgcccccc ctcacgaatc ctcattgggt gccgtgggtg cgtggtgcgg  24840
cgcgattggt gggttcatgt ttcccgtccc ccgcccgcga gaagtggggg tgaaaagcgg  24900
cccgacctgc ttggggtgta gtgggcggac cgcgcggctg gaggtgtgag gatccgaacc  24960
caggggtggg gggtggaggc ggctcctgcg atcgaagggg acttgagact caccggtcgc  25020
acgtcatgaa tctagaacca tggcttcgta ccccggccat cagcacgcgt ctgcgttcga  25080
ccaggctgcg cgttctcgcg gccatagcaa ccgacgtacg gcgttgcgcc ctcgccggca  25140
gcaagaagcc acggaagtcc gcccggagca gaaaatgccc acgctactgc gggtttatat  25200
agacggtccc cacgggatgg ggaaaaccac caccacgcaa ctgctggtgg ccctgggttc  25260
gcgcgacgat atcgtctacg tacccgagcc gatgacttac tggcgggtgc tgggggcttc  25320
cgagacaatc gcgaacatct acaccacaca acaccgcctt gaccagggtg agatatcggc  25380
cggggacgcg gcggtggtaa tgacaagcgc ccagataaca atgggcatgc cttatgccgt  25440
gaccgacgcc gttctggctc ctcatatcgg gggggaggct gggagctcac atgccccgcc  25500
cccggccctc accctcatct tcgaccgcca tcccatcgcc gccctcctgt gctacccggc  25560
cgcgcgatac cttatgggca gcatgacccc ccaggccgtg ctggcgttcg tggccctcat  25620
cccgccgacc ttgcccggca caaacatcgt gttgggggcc cttccggagg acagacacat  25680
cgaccgcctg gccaaacgcc agcgccccgg cgagcggctt gacctggcta tgctggccgc  25740
gattcgccgc gtttacgggc tgcttgccaa tacggtgcgg tatctgcagg gcggcgggtc  25800
```

```
gtggcgggag gattggggac agctttcggg gacggccgtg ccgccccagg gtgccgagcc  25860
ccagagcaac gcgggcccac gaccccatat cggggacacg ttatttaccc tgtttcgggc  25920
ccccgagttg ctggccccca acggcgacct gtacaacgtg tttgcctggg ccttggacgt  25980
cttggccaaa cgcctccgtc ccatgcacgt ctttatcctg gattacgacc aatcgcccgc  26040
cggctgccgg gacgccctgc tgcaacttac ctccgggatg atccagaccc acgtcaccac  26100
cccaggctcc ataccgacga tctgcgacct ggcgcgcacg tttgcccggg agatggggga  26160
ggctaactga gtatacccta ggattatccc taatacctgc caccccactc ttaatcagtg  26220
gtggaagaac ggtctcagaa ctgtttgttt caattggcca tttaagttta gtagtaaaag  26280
actggttaat gataacaatg catcgtaaaa ccttcagaag gaaaggagaa tgttttgtgg  26340
accactttgg ttttcttttt tgcgtgtggc agttttaagt tattagtttt taaaatcagt  26400
actttttaat ggaaacaact tgaccaaaaa tttgtcacag aattttgaga cccattaaaa  26460
aagttaaatg agaaacctgt gtgttccttt ggtcaacacc gagacattta ggtgaaagac  26520
atctaattct ggttttacga atctggaaac ttcttgaaaa tgtaattctt gagttaacac  26580
ttctgggtgg agaatagggt tgttttcccc ccacataatt ggaaggggaa ggaatatcat  26640
ttaaagctat gggagggttt ctttgattac aacactggag agaaatgcag catgttgctg  26700
attgcctgtc actaaaacag gccaaaaact gagtccttgg gttgcataga aagctgcctg  26760
caggcgttac ataacttacg gtaaatggcc cgcctggctg accgcccaac gacccccgcc  26820
cattgacgtc aataatgacg tatgttccca tagtaacgcc aatagggact ttccattgac  26880
gtcaatgggt ggagtattta cggtaaactg cccacttggc agtacatcaa gtgtatcata  26940
tgccaagtac gccccctatt gacgtcaatg acggtaaatg gcccgcctgg cattatgccc  27000
agtacatgac cttatgggac tttcctactt ggcagtacat ctacgtatta gtcatcgcta  27060
ttaccatgat gatgcggttt tggcagtaca tcaatgggcg tggatagcgg tttgactcac  27120
ggggatttcc aagtctccac cccattgacg tcaatgggag tttgttttga ctagttaccg  27180
gcggaaacgg tctcgggttg agaggtcacc cgagggacag gcagctgctg aaccaatagg  27240
accggcgcac agggcggatg ctgcccctca ttggcggccg ttgagagtga ccaagagcca  27300
atgagtcagc ccggggggcg tagcagtgac gtaagttgcg gaggaggccg cttcgaatcg  27360
gcagcggcca gcttggtggc atggaccaat cagcgtcctc caacgaggag cgccttcgcc  27420
aatcggaggc ctccacgacg gggctggggg gagggtatat aagccgagtc ggcggcggcg  27480
cgctccacac gggccgagac cacagcgacg ggagcgtctg cctctgcggg gccgagaggt  27540
aagcgccgcg gcctgccctt tccaggccaa ctcggagccc gtctcgtggc tccgcctgat  27600
cgggggctcc tgtcgccctc agatcggtcg gaacgccgtc gcgctccggg actacaagcc  27660
tgttgctggg cccggagact gccgaaggac cgctgagcac tgtcctcagc gccggcacca  27720
tggattggat ctggcggatc ctgttccttg tgggagctgc cacaggcgcc cattctgaag  27780
ttcagctggt tcagtctggc gccgaagtga agaaacctgg cgcctctgtg aaggtgtcct  27840
gcaaagcttc tggcggcacc ttcagcagct acgccatctc ttgggttcga caggcccctg  27900
gacaaggcct ggaatggatg ggcagaatca tccccatcct gggaatcgcc aactacgccc  27960
agaaattcca gggcagagtg accatcaccg ccgacaagag cacaagcacc gcctacatgg  28020
aactgagcag cctgagaagc gaggacaccg ccgtgtacta ctgtgccaga agcggccacg  28080
gctacagcta cggcgccttt gattattggg gccagggcac cctggtcacc gtttctagcg  28140
```

-continued

```
gaggcggagg tagtggtggc ggaggttcag gcggcggagg atctcaatct gtgctgacac  28200
agcctccaag cgtgtcaggt gctcctggcc agagagtgac aatcagctgt acaggcagca  28260
gcagcaacat cggagccggc tatgacgtgc actggtatca gcagctgcct ggcacagccc  28320
ctaaactgct gatctacggc aacagcaaca gacccagcgg cgtgcccgat agattttccg  28380
gctctaagag cggcacaagc gccagcctgg ctattactgg actgcaggcc gaggacgagg  28440
ccgactacta ctgtcagagc tacgacagca gcctgtccgg cagctacgtt gtgtttggcg  28500
gcggaacaaa gctgaccgtg ctggaagcca agagctgcga caagacccac acctgtcctc  28560
catgtcctgc tccagaactg ctcggcggac cttccgtgtt cctgtttcct ccaaagccta  28620
aggacaccct gatgatcagc agaacccctg aagtgacctg cgtggtggtg gatgtgtccc  28680
acgaggaccc agaagtgaag ttcaattggt acgtggacgg cgtggaagtg cacaacgcca  28740
agaccaagcc tagagaggaa cagtacaaca gcacctacag agtggtgtcc gtgctgacag  28800
tgctgcacca ggattggctg aacggcaaag agtacaagtg caaggtgtcc aacaaggccc  28860
tgcctgctcc tatcgagaaa accatcagca aggccaaggg ccagcctagg gaaccccagg  28920
tttacacact gccacctagc agggacgagc tgaccaagaa tcaggtgtcc ctgacctgcc  28980
tggtcaaggg cttctaccct tccgatatcg ccgtggaatg ggagagcaat ggccagccag  29040
agaacaacta caagacaacc cctcctgtgc tggacagcga cggctcattc ttcctgtact  29100
ccaagctgac tgtggacaag agccggtggc agcagggcaa tgtgttcagc tgtagcgtga  29160
tgcacgaggc cctgcacaac cactacacac agaagtccct gtctctgagc cccggaaaag  29220
gtggcggtgg ctcttaccct tacgacgtgc cagattacgc cggctatccc tacgatgtgc  29280
ctgactatgc tggctacccc tatgacgtcc ccgactacgc ttaactagct acggaattcc  29340
ggctagctgg ccagacatga taagatacat tgatgagttt ggacaaacca caactagaat  29400
gcagtgaaaa aaatgcttta tttgtgaaat ttgtgatgct attgctttat ttgtaaccat  29460
tataagctgc aataaacaag ttaacaacaa caattgcatt cattttatgt ttcaggttca  29520
gggggaggtg tgggaggttt tttaaagcaa gtaaaacctc tacaaatgtg gtatggaaat  29580
gttaattaac tagccatgac caaaatccct taacgtgagt tttcgttcca ctgagcgtca  29640
gaccccgtag aaaagatcaa aggatcttct tgagatcctt tttttctgcg cgtaatctgc  29700
tgcttgcaaa caaaaaaacc accgctacca gcggtggttt gtttgccgga tcaagagcta  29760
ccaactcttt ttccgaaggt aactggcttc agcagagcgc agataccaaa tactgttctt  29820
ctagtgtagc cgtagttagg ccaccacttc aagaactctg tagcaccgcc tacatacctc  29880
gctctgctaa tcctgttacc agtggctgct gccagtggcg ataagtcgtg tcttaccggg  29940
ttggactcaa gacgatagtt accggataag gcgcagcggt cgggctgaac ggggggttcg  30000
tgcacacagc ccagcttgga gcgaacgacc tacaccgaac tgagatacct acagcgtgag  30060
ctatgagaaa gcgccacgct tcccgaaggg agaaaggcgg acaggtatcc ggtaagcggc  30120
agggtcggaa caggagagcg cacgagggag cttccagggg gaaacgcctg gtatctttat  30180
agtcctgtcg ggtttcgcca cctctgactt gagcgtcgat ttttgtgatg ctcgtcaggg  30240
gggcggagcc tatggaaaaa cgccagcaac gcggcctttt tacggttcct ggccttttgc  30300
tggccttttg ctcagggttc gaaatcgata agcttggatc cggagagctc ccaacgcgtc  30360
ggctagctag tagggataac agggtaataa gcgtcgacgg cgcgccccta ggggccggcc  30420
ttaattaaat caagcttatc gataccgtcg aacctcgagg gggggcatca ctccgcccta  30480
aaacctacgt cacccgcccc gttcccacgc cccgcgccac gtcacaaact ccaccccctc  30540
```

attatcatat tggcttcaat ccaaaataag gtatattatt gatgatgttt 30590

<210> SEQ ID NO 51
<211> LENGTH: 39752
<212> TYPE: DNA
<213> ORGANISM: Artificial Sequence
<220> FEATURE:
<223> OTHER INFORMATION: ICOSTAT
<220> FEATURE:
<221> NAME/KEY: misc_feature
<222> LOCATION: (5915)..(5917)
<223> OTHER INFORMATION: n is a, c, g, or t
<220> FEATURE:
<221> NAME/KEY: misc_feature
<222> LOCATION: (32912)..(32912)
<223> OTHER INFORMATION: n is a, c, g, or t
<220> FEATURE:
<221> NAME/KEY: misc_feature
<222> LOCATION: (34601)..(34601)
<223> OTHER INFORMATION: n is a, c, g, or t
<220> FEATURE:
<221> NAME/KEY: misc_feature
<222> LOCATION: (38163)..(38168)
<223> OTHER INFORMATION: n is a, c, g, or t

<400> SEQUENCE: 51
taacatcatc aattatacct tccattttgg attgaagcca atatgataat gagggggtgg 60
agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
tacgtcggcg gctcgtggct cttccgggaa aaggattctc ggaaagtggt tcgagtacgt 480
cggcggctcg tggctcttcc gggaaaagga ttctcggaaa gtggttcgaa gtacgtcgac 540
cacaaacccc gcccagcgtc ttgtcattgg cgtcgacgct gtacggggtc aaagttggcg 600
ttttattatt atagtcagct gacgtgtagt gtatttatac ccggtgagtt cctcaagagg 660
ccactcttga gtgccagcga gtagagtttt ctcctccgag ccgctccgac accgggactg 720
aaaatgagac atattatctg ccacggaggt gttattaccg aagaaatggc cgccagtctt 780
ttggaccagc tgatcgaaga ggtactggct gataatcttc cacctcctag ccattttgaa 840
ccacctaccc ttcacgaact gtatgattta gacgtgacgg cccccgaaga tcccaacgag 900
gaggcggttt cgcagatttt tcccgactct gtaatgttgg cggtgcagga agggattgac 960
ttactcactt ttccgccggc gcccggttct ccggagccgc ctcacctttc ccggcagccc 1020
gagcagccgg agcagagagc cttgggtccg gtttctatgc caaaccttgt accggaggtg 1080
atcgatccac ccagtgacga cgaggatgaa gagggtgagg agtttgtgtt agattatgtg 1140
gagcaccccg ggcacggttg caggtcttgt cattatcacc ggaggaatac gggggaccca 1200
gatattatgt gttcgctttg ctatatgagg acctgtggca tgtttgtcta cagtaagtga 1260
aaattatggg cagtgggtga tagagtggtg ggtttggtgt ggtaattttt tttttaattt 1320
ttacagtttt gtggtttaaa gaattttgta ttgtgatttt tttaaaaggt cctgtgtctg 1380
aacctgagcc tgagcccgag ccagaaccgg agcctgcaag acctacccgc cgtcctaaaa 1440
tggcgcctgc tatcctgaga cgcccgacat cacctgtgtc tagagaatgc aatagtagta 1500

-continued

```
cggatagctg tgactccggt ccttctaaca cacctcctga gatacacccg gtggtcccgc   1560
tgtgccccat taaaccagtt gccgtgagag ttggtgggcg tcgccaggct gtggaatgta   1620
tcgaggactt gcttaacgag cctgggcaac ctttggactt gagctgtaaa cgccccaggc   1680
cataaggtgt aaacctgtga ttgcgtgtgt ggttaacgcc tttgtttgct gaatgagttg   1740
atgtaagttt aataaagggt gagataatgt ttaacttgca tggcgtgtta aatggggcgg   1800
ggcttaaagg gtatataatg cgccgtgggc taatcttggt tacatctgac ctcatggagg   1860
cttgggagtg tttggaagat ttttctgctg tgcgtaactt gctggaacag agctctaaca   1920
gtacctcttg gttttggagg tttctgtggg gctcatccca ggcaaagtta gtctgcagaa   1980
ttaaggagga ttacaagtgg gaatttgaag agcttttgaa atcctgtggt gagctgtttg   2040
attctttgaa tctgggtcac caggcgcttt tccaagagaa ggtcatcaag actttggatt   2100
tttccacacc ggggcgcgct gcggctgctg ttgctttttt gagttttata aaggataaat   2160
ggagcgaaga aacccatctg agcggggggt acctgctgga ttttctggcc atgcatctgt   2220
ggagagcggt tgtgagacac aagaatcgcc tgctactgtt gtcttccgtc cgcccggcga   2280
taataccgac ggaggagcag cagcagcagc aggaggaagc caggcggcgg cggcaggagc   2340
agagcccatg gaacccgaga gccggcctgg accctcggga atgaatgttg tacaggtggc   2400
tgaactgtat ccagaactga gacgcatttt gacaattaca gaggatgggc aggggctaaa   2460
gggggtaaag agggagcggg gggcttgtga ggctacagag gaggctagga atctagcttt   2520
tagcttaatg accagacacc gtcctgagtg tattactttt caacagatca aggataattg   2580
cgctaatgag cttgatctgc tggcgcagaa gtattccata gagcagctga ccacttactg   2640
gctgcagcca ggggatgatt ttgaggaggc tattagggta tatgcaaagg tggcacttag   2700
gccagattgc aagtacaaga tcagcaaact tgtaaatatc aggaattgtt gctacatttc   2760
tgggaacggg gccgaggtgg agatagatac ggaggatagg gtggccttta gatgtagcat   2820
gataaatatg tggccggggg tgcttggcat ggacggggtg gttattatga atgtaaggtt   2880
tactggcccc aattttagcg gtacggtttt cctggccaat accaacctta tcctacacgg   2940
tgtaagcttc tatgggttta acaatacctg tgtggaagcc tggaccgatg taagggttcg   3000
gggctgtgcc ttttactgct gctggaaggg ggtggtgtgt cgccccaaaa gcagggcttc   3060
aattaagaaa tgcctctttg aaaggtgtac cttgggtatc ctgtctgagg gtaactccag   3120
ggtgcgccac aatgtggcct ccgactgtgg ttgcttcatg ctagtgaaaa gcgtggctgt   3180
gattaagcat aacatggtat gtggcaactg cgaggacagg gcctctcaga tgctgacctg   3240
ctcggacggc aactgtcacc tgctgaagac cattcacgta gccagccact ctcgcaaggc   3300
ctggccagtg tttgagcata acatactgac ccgctgttcc ttgcatttgg gtaacaggag   3360
gggggtgttc ctaccttacc aatgcaattt gagtcacact aagatattgc ttgagcccga   3420
gagcatgtcc aaggtgaacc tgaacggggt gtttgacatg accatgaaga tctggaaggt   3480
gctgaggtac gatgagaccc gcaccaggtg cagaccctgc gagtgtggcg gtaaacatat   3540
taggaaccag cctgtgatgc tggatgtgac cgaggagctg aggcccgatc acttggtgct   3600
ggcctgcacc cgcgctgagt ttggctctag cgatgaagat acagattgag gtactgaaat   3660
gtgtgggcgt ggcttaaggg tgggaaagaa tatataaggt gggggtctta tgtagttttg   3720
tatctgtttt gcagcagccg ccgccgccat gagcaccaac tcgtttgatg gaagcattgt   3780
gagctcatat ttgacaacgc gcatgccccc atgggccggg gtgcgtcaga atgtgatggg   3840
ctccagcatt gatggtcgcc ccgtcctgcc cgcaaactct actaccttga cctacgagac   3900
```

```
cgtgtctgga acgccgttgg agactgcagc ctccgccgcc gcttcagccg ctgcagccac   3960
cgcccgcggg attgtgactg actttgcttt cctgagcccg cttgcaagca gtgcagcttc   4020
ccgttcatcc gcccgcgatg acaagttgac ggctcttttg gcacaattgg attctttgac   4080
ccgggaactt aatgtcgttt ctcagcagct gttggatctg cgccagcagg tttctgccct   4140
gaaggcttcc tcccctccca atgcggttta aaacataaat aaaaaaccag actctgtttg   4200
gatttggatc aagcaagtgt cttgctgtct ttatttaggg gttttgcgcg cgcggtaggc   4260
ccgggaccag cggtctcggt cgttgagggt cctgtgtatt ttttccagga cgtggtaaag   4320
gtgactctgg atgttcagat acatgggcat aagcccgtct ctggggtgga ggtagcacca   4380
ctgcagagct tcatgctgcg gggtggtgtt gtagatgatc cagtcgtagc aggagcgctg   4440
ggcgtggtgc ctaaaaatgt ctttcagtag caagctgatt gccaggggca ggcccttggt   4500
gtaagtgttt acaaagcggt taagctggga tgggtgcata cgtggggata tgagatgcat   4560
cttggactgt atttttaggt tggctatgtt cccagccata tccctccggg gattcatgtt   4620
gtgcagaacc accagcacag tgtatccggt gcacttggga aatttgtcat gtagcttaga   4680
aggaaatgcg tggaagaact tggagacgcc cttgtgacct ccaagatttt ccatgcattc   4740
gtccataatg atggcaatgg gcccacgggc ggcggcctgg gcgaagatat ttctgggatc   4800
actaacgtca tagttgtgtt ccaggatgag atcgtcatag gccattttta caaagcgcgg   4860
gcggagggtg ccagactgcg gtataatggt tccatccggc ccaggggcgt agttaccctc   4920
acagatttgc atttcccacg ctttgagttc agatgggggg atcatgtcta cctgcggggc   4980
gatgaagaaa acggtttccg ggtaggggga gatcagctgg gaagaaagca ggttcctgag   5040
cagctgcgac ttaccgcagc cggtgggccc gtaaatcaca cctattaccg ggtgcaactg   5100
gtagttaaga gagctgcagc tgccgtcatc cctgagcagg ggggccactt cgttaagcat   5160
gtccctgact cgcatgtttt ccctgaccaa atccgccaga aggcgctcgc cgcccagcga   5220
tagcagttct tgcaaggaag caaagttttt caacggtttg agaccgtccg ccgtaggcat   5280
gcttttgagc gtttgaccaa gcagttccag gcggtcccac agctcggtca cctgctctac   5340
ggcatctcga tccagcatat ctcctcgttt cgcgggttgg ggcggctttc gctgtacggc   5400
agtagtcggt gctcgtccag acgggccagg gtcatgtctt tccacgggcg cagggtcctc   5460
gtcagcgtag tctgggtcac ggtgaagggg tgcgctccgg gctgcgcgct ggccagggtg   5520
cgcttgaggc tggtcctgct ggtgctgaag cgctgccggt cttcgccctg cgcgtcggcc   5580
aggtagcatt tgaccatggt gtcatagtcc agcccctccg cggcgtggcc cttggcgcgc   5640
agcttgccct tggaggaggc gccgcacgag gggcagtgca gacttttgag ggcgtagagc   5700
ttgggcgcga gaaataccga ttccggggag taggcatccg cgccgcaggc cccgcagacg   5760
gtctcgcatt ccacgagcca ggtgagctct ggccgttcgg ggtcaaaaac caggtttccc   5820
ccatgctttt tgatgcgttt cttacctctg gtttccatga gccggtgtcc acgctcggtg   5880
acgaaaaggc tgtccgtgtc cccgtataca gactnnngtt ttgagaggcc tgtcctcgag   5940
cggtgttccg cggtcctcct cgtatagaaa ctcggaccac tctgagacaa aggctcgcgt   6000
ccaggccagc acgaaggagg ctaagtggga ggggtagcgg tcgttgtcca ctagggggtc   6060
cactcgctcc agggtgtgaa gacacatgtc gccctcttcg gcatcaagga aggtgattgg   6120
tttgtaggtg taggccacgt gaccgggtgt tcctgaaggg gggctataaa agggggtggg   6180
ggcgcgttcg tcctcactct cttccgcatc gctgtctgcg agggccagct gttggggtga   6240
```

-continued

```
gtactccctc tgaaaagcgg gcatgacttc tgcgctaaga ttgtcagttt ccaaaaacga   6300
ggaggatttg atattcacct ggcccgcggt gatgcctttg agggtggccg catccatctg   6360
gtcagaaaag acaatctttt tgttgtcaag cttggtggca aacgacccgt agagggcgtt   6420
ggacagcaac ttggcgatgg agcgcagggt ttggtttttg tcgcgatcgg cgcgctcctt   6480
ggccgcgatg tttagctgca cgtattcgcg cgcaacgcac cgccattcgg gaaagacggt   6540
ggtgcgctcg tcgggcacca ggtgcacgcg ccaaccgcgg ttgtgcaggg tgacaaggtc   6600
aacgctggtg gctacctctc cgcgtaggcg ctcgttggtc cagcagaggc ggccgccctt   6660
gcgcgagcag aatggcggta gggggtctag ctgcgtctcg tccggggggt ctgcgtccac   6720
ggtaaagacc ccgggcagca ggcgcgcgtc gaagtagtct atcttgcatc cttgcaagtc   6780
tagcgcctgc tgccatgcgc gggcggcaag cgcgcgctcg tatgggttga gtgggggacc   6840
ccatggcatg gggtgggtga gcgcggaggc gtacatgccg caaatgtcgt aaacgtagag   6900
gggctctctg agtattccaa gatatgtagg gtagcatctt ccaccgcgga tgctggcgcg   6960
cacgtaatcg tatagttcgt gcgagggagc gaggaggtcg ggaccgaggt tgctacgggc   7020
gggctgctct gctcggaaga ctatctgcct gaagatggca tgtgagttgg atgatatggt   7080
tggacgctgg aagacgttga agctggcgtc tgtgagacct accgcgtcac gcacgaagga   7140
ggcgtaggag tcgcgcagct tgttgaccag ctcggcggtg acctgcacgt ctagggcgca   7200
gtagtccagg gtttccttga tgatgtcata cttatcctgt ccctttttttt tccacagctc   7260
gcggttgagg acaaactctt cgcggtcttt ccagtactct tggatcggaa acccgtcggc   7320
ctccgaacgg taagagccta gcatgtagaa ctggttgacg gcctggtagg cgcagcatcc   7380
cttttctacg ggtagcgcgt atgcctgcgc ggccttccgg agcgaggtgt gggtgagcgc   7440
aaaggtgtcc ctgaccatga ctttgaggta ctggtatttg aagtcagtgt cgtcgcatcc   7500
gccctgctcc cagagcaaaa agtccgtgcg ctttttggaa cgcggatttg gcagggcgaa   7560
ggtgacatcg ttgaagagta tctttcccgc gcgaggcata aagttgcgtg tgatgcggaa   7620
gggtcccggc acctcggaac ggttgttaat tacctgggcg gcgagcacga tctcgtcaaa   7680
gccgttgatg ttgtggccca caatgtaaag ttccaagaag cgcgggatgc ccttgatgga   7740
aggcaatttt ttaagttcct cgtaggtgag ctcttcaggg gagctgagcc cgtgctctga   7800
aagggcccag tctgcaagat gagggttgga agcgacgaat gagctccaca ggtcacgggc   7860
cattagcatt tgcaggtggt cgcgaaaggt cctaaactgg cgacctatgg ccattttttc   7920
tggggtgatg cagtagaagg taagcgggtc ttgttcccag cggtcccatc caaggttcgc   7980
ggctaggtct cgcgcggcag tcactagagg ctcatctccg ccgaacttca tgaccagcat   8040
gaagggcacg agctgcttcc caaaggcccc catccaagta taggtctcta catcgtaggt   8100
gacaaagaga cgctcggtgc gaggatgcga gccgatcggg aagaactgga tctcccgcca   8160
ccaattggag gagtggctat tgatgtggtg aaagtagaag tccctgcgac gggccgaaca   8220
ctcgtgctgg cttttgtaaa aacgtgcgca gtactggcag cggtgcacgg gctgtacatc   8280
ctgcacgagg ttgacctgac gaccgcgcac aaggaagcag agtgggaatt tgagcccctc   8340
gcctggcggg tttggctggt ggtcttctac ttcggctgct tgtccttgac cgtctggctg   8400
ctcgagggga gttacggtgg atcggaccac cacgccgcgc gagcccaaag tccagatgtc   8460
cgcgcgcggc ggtcggagct tgatgacaac atcgcgcaga tgggagctgt ccatggtctg   8520
gagctcccgc ggcgtcaggt caggcgggag ctcctgcagg tttacctcgc atagacgggt   8580
cagggcgcgg gctagatcca ggtgatacct aatttccagg ggctggttgg tggcggcgtc   8640
```

-continued

```
gatggcttgc aagaggccgc atccccgcgg cgcgactacg gtaccgcgcg gcgggcggtg   8700
ggccgcgggg gtgtccttgg atgatgcatc taaaagcggt gacgcgggcg agcccccgga   8760
ggtagggggg gctccggacc cgccgggaga gggggcaggg gcacgtcggc gccgcgcgcg   8820
ggcaggagct ggtgctgcgc gcgtaggttg ctggcgaacg cgacgacgcg gcggttgatc   8880
tcctgaatct ggcgcctctg cgtgaagacg acgggcccgg tgagcttgag cctgaaagag   8940
agttcgacag aatcaatttc ggtgtcgttg acggcggcct ggcgcaaaat ctcctgcacg   9000
tctcctgagt tgtcttgata ggcgatctcg gccatgaact gctcgatctc ttcctcctgg   9060
agatctccgc gtccggctcg ctccacggtg gcggcgaggt cgttggaaat gcgggccatg   9120
agctgcgaga aggcgttgag gcctccctcg ttccagacgc ggctgtagac cacgccccct   9180
tcggcatcgc gggcgcgcat gaccacctgc gcgagattga gctccacgtg ccgggcgaag   9240
acggcgtagt ttcgcaggcg ctgaaagagg tagttgaggg tggtggcggt gtgttctgcc   9300
acgaagaagt acataaccca gcgtcgcaac gtggattcgt tgatatcccc caaggcctca   9360
aggcgctcca tggcctcgta gaagtccacg gcgaagttga aaaactggga gttgcgcgcc   9420
gacacggtta actcctcctc cagaagacgg atgagctcgg cgacagtgtc gcgcacctcg   9480
cgctcaaagg ctacaggggc ctcttcttct tcttcaatct cctcttccat aagggcctcc   9540
ccttcttctt cttctggcgg cggtggggga gggggacac ggcggcgacg acggcgcacc   9600
gggaggcggt cgacaaagcg ctcgatcatc tccccgcggc gacggcgcat ggtctcggtg   9660
acggcgcggc cgttctcgcg gggcgcagt tggaagacgc cgcccgtcat gtcccggtta   9720
tgggttggcg gggggctgcc atgcggcagg gatacggcgc taacgatgca tctcaacaat   9780
tgttgtgtag gtactccgcc gccgagggac ctgagcgagt ccgcatcgac cggatcggaa   9840
aacctctcga gaaaggcgtc taaccagtca cagtcgcaag gtaggctgag caccgtggcg   9900
ggcggcagcg ggcggcggtc ggggttgttt ctggcggagg tgctgctgat gatgtaatta   9960
aagtaggcgg tcttgagacg gcggatggtc gacagaagca ccatgtcctt gggtccggcc  10020
tgctgaatgc gcaggcggtc ggccatgccc caggcttcgt tttgacatcg gcgcaggtct  10080
ttgtagtagt cttgcatgag cctttctacc ggcacttctt cttctccttc ctcttgtcct  10140
gcatctcttg catctatcgc tgcggcggcg gcggagtttg gccgtaggtg gcgccctctt  10200
cctcccatgc gtgtgacccc gaagcccctc atcggctgaa gcagggctag gtcggcgaca  10260
acgcgctcgg ctaatatggc ctgctgcacc tgcgtgaggg tagactggaa gtcatccatg  10320
tccacaaagc ggtggtatgc gcccgtgttg atggtgtaag tgcagttggc cataacggac  10380
cagttaacgg tctggtgacc cggctgcgag agctcggtgt acctgagacg cgagtaagcc  10440
ctcgagtcaa atacgtagtc gttgcaagtc cgcaccaggt actggtatcc caccaaaaag  10500
tgcggcggcg gctggcggta gaggggccag cgtagggtgg ccggggctcc gggggcgaga  10560
tcttccaaca taaggcgatg atatccgtag atgtacctgg acatccaggt gatgccggcg  10620
gcggtggtgg aggcgcgcgg aaagtcgcgg acgcggttcc agatgttgcg cagcggcaaa  10680
aagtgctcca tggtcgggac gctctggccg gtcaggcgcg cgcaatcgtt gacgctctac  10740
cgtgcaaaag gagagcctgt aagcgggcac tcttccgtgg tctggtggat aaattcgcaa  10800
gggtatcatg gcggacgacc ggggttcgag ccccgtatcc ggccgtccgc cgtgatccat  10860
gcggttaccg cccgcgtgtc gaacccaggt gtgcgacgtc agacaacggg ggagtgctcc  10920
ttttggcttc cttccaggcg cggcggctgc tgcgctagct tttttggcca ctggccgcgc  10980
```

gcagcgtaag cggttaggct ggaaagcgaa agcattaagt ggctcgctcc ctgtagccgg 11040
agggttattt tccaagggtt gagtcgcggg acccccggtt cgagtctcgg accggccgga 11100
ctgcggcgaa cgggggtttg cctccccgtc atgcaagacc ccgcttgcaa attcctccgg 11160
aaacagggac gagccccttt tttgcttttc ccagatgcat ccggtgctgc ggcagatgcg 11220
ccccccctcct cagcagcggc aagagcaaga gcagcggcag acatgcaggg caccctcccc 11280
tcctcctacc gcgtcaggag gggcgacatc cgcggttgac gcggcagcag atggtgatta 11340
cgaacccccg cggcgccggg cccggcacta cctggacttg gaggagggcg agggcctggc 11400
gcggctagga gcgccctctc ctgagcggta cccaagggtg cagctgaagc gtgatacgcg 11460
tgaggcgtac gtgccgcggc agaacctgtt tcgcgaccgc gagggagagg agcccgagga 11520
gatgcgggat cgaaagttcc acgcagggcg cgagctgcgg catggcctga atcgcgagcg 11580
gttgctgcgc gaggaggact ttgagcccga cgcgcgaacc gggattagtc ccgcgcgcgc 11640
acacgtggcg gccgccgacc tggtaaccgc atacgagcag acggtgaacc aggagattaa 11700
ctttcaaaaa agctttaaca accacgtgcg tacgcttgtg gcgcgcgagg aggtggctat 11760
aggactgatg catctgtggg actttgtaag cgcgctggag caaaacccaa atagcaagcc 11820
gctcatggcg cagctgttcc ttatagtgca gcacagcagg gacaacgagg cattcaggga 11880
tgcgctgcta aacatagtag agcccgaggg ccgctggctg ctcgatttga taaacatcct 11940
gcagagcata gtggtgcagg agcgcagctt gagcctggct gacaaggtgg ccgccatcaa 12000
ctattccatg cttagcctgg gcaagtttta cgcccgcaag atataccata ccccttacgt 12060
tcccatagac aaggaggtaa agatcgaggg gttctacatg cgcatggcgc tgaaggtgct 12120
taccttgagc gacgacctgg gcgtttatcg caacgagcgc atccacaagg ccgtgagcgt 12180
gagccggcgg cgcgagctca gcgaccgcga gctgatgcac agcctgcaaa gggccctggc 12240
tggcacgggc agcggcgata gagaggccga gtcctacttt gacgcgggcg ctgacctgcg 12300
ctgggcccca agccgacgcg ccctggaggc agctggggcc ggacctgggc tggcggtggc 12360
acccgcgcgc gctggcaacg tcggcggcgt ggaggaatat gacgaggacg atgagtacga 12420
gccagaggac ggcgagtact aagcggtgat gtttctgatc agatgatgca agacgcaacg 12480
gacccggcgg tgcgggcggc gctgcagagc cagccgtccg gccttaactc cacggacgac 12540
tggcgccagg tcatggaccg catcatgtcg ctgactgcgc gcaatcctga cgcgttccgg 12600
cagcagccgc aggccaaccg gctctccgca attctggaag cggtggtccc ggcgcgcgca 12660
aaccccacgc acgagaaggt gctggcgatc gtaaacgcgc tggccgaaaa cagggccatc 12720
cggcccgacg aggccggcct ggtctacgac gcgctgcttc agcgcgtggc tcgttacaac 12780
agcggcaacg tgcagaccaa cctggaccgg ctggtggggg atgtgcgcga ggccgtggcg 12840
cagcgtgagc gcgcgcagca gcagggcaac ctgggctcca tggttgcact aaacgccttc 12900
ctgagtacac agcccgccaa cgtgccgcgg ggacaggagg actacaccaa ctttgtgagc 12960
gcactgcggc taatggtgac tgagacaccg caaagtgagg tgtaccagtc tgggccagac 13020
tatttttttcc agaccagtag acaaggcctg cagaccgtaa acctgagcca ggctttcaaa 13080
aacttgcagg ggctgtgggg ggtgcgggct cccacaggcg accgcgcgac cgtgtctagc 13140
ttgctgacgc ccaactcgcg cctgttgctg ctgctaatag cgcccttcac ggacagtggc 13200
agcgtgtccc gggacacata cctaggtcac ttgctgacac tgtaccgcga ggccataggt 13260
caggcgcatg tggacgagca tactttccag gagattacaa gtgtcagccg cgcgctgggg 13320
caggaggaca cgggcagcct ggaggcaacc ctaaactacc tgctgaccaa ccggcggcag 13380
aagatcccct cgttgcacag tttaaacagc gaggaggagc gcattttgcg ctacgtgcag 13440
cagagcgtga gccttaacct gatgcgcgac ggggtaacgc ccagcgtggc gctggacatg 13500
accgcgcgca acatggaacc gggcatgtat gcctcaaacc ggccgtttat caaccgccta 13560
atggactact tgcatcgcgc ggccgccgtg aaccccgagt atttcaccaa tgccatcttg 13620
aacccgcact ggctaccgcc ccctggtttc tacaccgggg gattcgaggt gcccgagggt 13680
aacgatggat tcctctggga cgacatagac gacagcgtgt tttccccgca accgcagacc 13740
ctgctagagt tgcaacagcg cgagcaggca gaggcggcgc tgcgaaagga aagcttccgc 13800
aggccaagca gcttgtccga tctaggcgct gcggccccgc ggtcagatgc tagtagccca 13860
tttccaagct tgatagggtc tcttaccagc actcgcacca cccgcccgcg cctgctgggc 13920
gaggaggagt acctaaacaa ctcgctgctg cagccgcagc gcgaaaaaaa cctgcctccg 13980
gcatttccca acaacgggat agagagccta gtggacaaga tgagtagatg gaagacgtac 14040
gcgcaggagc acagggacgt gccaggcccg cgcccgccca cccgtcgtca aaggcacgac 14100
cgtcagcggg gtctggtgtg ggaggacgat gactcggcag acgacagcag cgtcctggat 14160
ttgggaggga gtggcaaccc gtttgcgcac cttcgcccca ggctggggag aatgttttaa 14220
aaaaaaaaaa gcatgatgca aaataaaaaa ctcaccaagg ccatggcacc gagcgttggt 14280
tttcttgtat tccccttagt atgcggcgcg cggcgatgta tgaggaaggt cctcctccct 14340
cctacgagag tgtggtgagc gcggcgccag tggcggcggc gctgggttct cccttcgatg 14400
ctcccctgga cccgccgttt gtgcctccgc ggtacctgcg gcctaccggg gggagaaaca 14460
gcatccgtta ctctgagttg gcacccctat tcgacaccac ccgtgtgtac ctggtggaca 14520
acaagtcaac ggatgtggca tccctgaact accagaacga ccacagcaac tttctgacca 14580
cggtcattca aaacaatgac tacagcccgg gggaggcaag cacacagacc atcaatcttg 14640
acgaccggtc gcactggggc ggcgacctga aaaccatcct gcataccaac atgccaaatg 14700
tgaacgagtt catgtttacc aataagttta aggcgcgggt gatggtgtcg cgcttgccta 14760
ctaaggacaa tcaggtggag ctgaaatacg agtgggtgga gttcacgctg cccgagggca 14820
actactccga gaccatgacc atagacctta tgaacaacgc gatcgtggag cactacttga 14880
aagtgggcag acagaacggg gttctggaaa gcgacatcgg ggtaaagttt gacacccgca 14940
acttcagact ggggtttgac cccgtcactg gtcttgtcat gcctggggta tatacaaacg 15000
aagccttcca tccagacatc attttgctgc caggatgcgg ggtggacttc acccacagcc 15060
gcctgagcaa cttgttgggc atccgcaagc ggcaaccctt ccaggagggc tttaggatca 15120
cctacgatga tctggagggt ggtaacattc ccgcactgtt ggatgtggac gcctaccagg 15180
cgagcttgaa agatgacacc gaacagggcg ggggtggcgc aggcggcagc aacagcagtg 15240
gcagcggcgc ggaagagaac tccaacgcgg cagccgcggc aatgcagccg gtggaggaca 15300
tgaacgatca tgccattcgc ggcgacacct ttgccacacg ggctgaggag aagcgcgctg 15360
aggccgaagc agcggccgaa gctgccgccc ccgctgcgca acccgaggtc gagaagcctc 15420
agaagaaacc ggtgatcaaa cccctgacag aggacagcaa gaaacgcagt tacaacctaa 15480
taagcaatga cagcaccttc acccagtacc gcagctggta ccttgcatac aactacggcg 15540
accctcagac cggaatccgc tcatggaccc tgctttgcac tcctgacgta acctgcggct 15600
cggagcaggt ctactggtcg ttgccagaca tgatgcaaga ccccgtgacc ttccgctcca 15660
cgcgccagat cagcaacttt ccggtggtgg gcgccgagct gttgcccgtg cactccaaga 15720

-continued

```
gcttctacaa cgaccaggcc gtctactccc aactcatccg ccagtttacc tctctgaccc  15780
acgtgttcaa tcgctttccc gagaaccaga ttttggcgcg cccgccagcc cccaccatca  15840
ccaccgtcag tgaaaacgtt cctgctctca cagatcacgg gacgctaccg ctgcgcaaca  15900
gcatcggagg agtccagcga gtgaccatta ctgacgccag acgccgcacc tgcccctacg  15960
tttacaaggc cctgggcata gtctcgccgc gcgtcctatc gagccgcact ttttgagcaa  16020
gcatgtccat ccttatatcg cccagcaata acacaggctg gggcctgcgc ttcccaagca  16080
agatgtttgg cggggccaag aagcgctccg accaacaccc agtgcgcgtg cgcgggcact  16140
accgcgcgcc ctggggcgcg cacaaacgcg gccgcactgg gcgcaccacc gtcgatgacg  16200
ccatcgacgc ggtggtggag gaggcgcgca actacacgcc cacgccgcca ccagtgtcca  16260
cagtggacgc ggccattcag accgtggtgc gcggagcccg gcgctatgct aaaatgaaga  16320
gacggcggag gcgcgtagca cgtcgccacc gccgccgacc cggcactgcc gcccaacgcg  16380
cggcggcggc cctgcttaac cgcgcacgtc gcaccggccg acgggcggcc atgcgggccg  16440
ctcgaaggct ggccgcgggt attgtcactg tgccccccag gtccaggcga cgagcggccg  16500
ccgcagcagc cgcggccatt agtgctatga ctcagggtcg caggggcaac gtgtattggg  16560
tgcgcgactc ggttagcggc ctgcgcgtgc ccgtgcgcac ccgcccccg cgcaactaga  16620
ttgcaagaaa aaactactta gactcgtact gttgtatgta tccagcggcg gcggcgcgca  16680
acgaagctat gtccaagcgc aaaatcaaag aagagatgct ccaggtcatc gcgccggaga  16740
tctatggccc cccgaagaag gaagagcagg attacaagcc ccgaaagcta aagcgggtca  16800
aaaagaaaaa gaaagatgat gatgatgaac ttgacgacga ggtggaactg ctgcacgcta  16860
ccgcgcccag gcgacgggta cagtggaaag gtcgacgcgt aaaacgtgtt ttgcgacccg  16920
gcaccaccgt agtctttacg cccggtgagc gctccacccg cacctacaag cgcgtgtatg  16980
atgaggtgta cggcgacgag gacctgcttg agcaggccaa cgagcgcctc ggggagtttg  17040
cctacggaaa gcggcataag gacatgctgg cgttgccgct ggacgagggc aacccaacac  17100
ctagcctaaa gcccgtaaca ctgcagcagg tgctgcccgc gcttgcaccg tccgaagaaa  17160
agcgcggcct aaagcgcgag tctggtgact tggcacccac cgtgcagctg atggtaccca  17220
agcgccagcg actggaagat gtcttggaaa aaatgaccgt ggaacctggg ctggagcccg  17280
aggtccgcgt gcggccaatc aagcaggtgg cgccgggact gggcgtgcag accgtggacg  17340
ttcagatacc cactaccagt agcaccagta ttgccaccgc cacagagggc atggagacac  17400
aaacgtcccc ggttgcctca gcggtggcgg atgccgcggt gcaggcggtc gctgcggccg  17460
cgtccaagac ctctacggag gtgcaaacgg acccgtggat gtttcgcgtt tcagcccccc  17520
ggcgcccgcg cggttcgagg aagtacggcg ccgccagcgc gctactgccc gaatatgccc  17580
tacatccttc cattgcgcct acccccggct atcgtggcta cacctaccgc cccagaagac  17640
gagcaactac ccgacgccga accaccactg gaacccgccg ccgccgtcgc cgtcgccagc  17700
ccgtgctggc cccgatttcc gtgcgcaggg tggctcgcga aggaggcagg accctggtgc  17760
tgccaacagc gcgctaccac cccagcatcg tttaaaagcc ggtctttgtg gttcttgcag  17820
atatggccct cacctgccgc ctccgtttcc cggtgccggg attccgagga agaatgcacc  17880
gtaggagggg catggccggc cacggcctga cgggcggcat gcgtcgtgcg caccaccggc  17940
ggcggcgcgc gtcgcaccgt cgcatgcgcg gcggtatcct gcccctcctt attccactga  18000
tcgccgcggc gattggcgcc gtgcccggaa ttgcatccgt ggccttgcag gcgcagagac  18060
actgattaaa aacaagttgc atgtggaaaa atcaaaataa aaagtctgga ctctcacgct  18120
```

cgcttggtcc tgtaactatt ttgtagaatg gaagacatca actttgcgtc tctggccccg 18180
cgacacggct cgcgcccgtt catgggaaac tggcaagata tcggcaccag caatatgagc 18240
ggtggcgcct tcagctgggg ctcgctgtgg agcggcatta aaaatttcgg ttccaccgtt 18300
aagaactatg gcagcaaggc ctggaacagc agcacaggcc agatgctgag ggataagttg 18360
aaagagcaaa atttccaaca aaaggtggta gatggcctgg cctctggcat tagcggggtg 18420
gtggacctgg ccaaccaggc agtgcaaaat aagattaaca gtaagcttga tccccgccct 18480
cccgtagagg agcctccacc ggccgtggag acagtgtctc cagaggggcg tggcgaaaag 18540
cgtccgcgcc ccgacaggga agaaactctg gtgacgcaaa tagacgagcc tccctcgtac 18600
gaggaggcac taaagcaagg cctgcccacc acccgtccca tcgcgcccat ggctaccgga 18660
gtgctgggcc agcacacacc cgtaacgctg gacctgcctc cccccgccga cacccagcag 18720
aaacctgtgc tgccaggccc gaccgccgtt gttgtaaccc gtcctagccg cgcgtccctg 18780
cgccgcgccg ccagcggtcc gcgatcgttg cggcccgtag ccagtggcaa ctggcaaagc 18840
acactgaaca gcatcgtggg tctgggggtg caatccctga agcgccgacg atgcttctga 18900
atagctaacg tgtcgtatgt gtgtcatgta tgcgtccatg tcgccgccag aggagctgct 18960
gagccgccgc gcgcccgctt tccaagatgg ctaccccttc gatgatgccg cagtggtctt 19020
acatgcacat ctcgggccag gacgcctcgg agtacctgag ccccgggctg gtgcagtttg 19080
cccgcgccac cgagacgtac ttcagcctga ataacaagtt tagaaacccc acggtggcgc 19140
ctacgcacga cgtgaccaca gaccggtccc agcgtttgac gctgcggttc atccctgtgg 19200
accgtgagga tactgcgtac tcgtacaagg cgcggttcac cctagctgtg ggtgataacc 19260
gtgtgctgga catggcttcc acgtactttg acatccgcgg cgtgctggac aggggcccta 19320
cttttaagcc ctactctggc actgcctaca acgccctggc tcccaagggt gccccaaatc 19380
cttgcgaatg ggatgaagct gctactgctc ttgaaataaa cctagaagaa gaggacgatg 19440
acaacgaaga cgaagtagac gagcaagctg agcagcaaaa aactcacgta tttgggcagg 19500
cgccttattc tggtataaat attacaaagg agggtattca aataggtgtc gaaggtcaaa 19560
cacctaaata tgccgataaa acatttcaac ctgaacctca aataggagaa tctcagtggt 19620
acgaaactga aattaatcat gcagctggga gagtccttaa aaagactacc ccaatgaaac 19680
catgttacgg ttcatatgca aaacccacaa atgaaaatgg agggcaaggc attcttgtaa 19740
agcaacaaaa tggaaagcta gaaagtcaag tggaaatgca atttttctca actactgagg 19800
cgaccgcagg caatggtgat aacttgactc ctaaagtggt attgtacagt gaagatgtag 19860
atatagaaac cccagacact catatttctt acatgcccac tattaaggaa ggtaactcac 19920
gagaactaat gggccaacaa tctatgccca acaggcctaa ttacattgct tttagggaca 19980
attttattgg tctaatgtat tacaacagca cgggtaatat gggtgttctg gcgggccaag 20040
catcgcagtt gaatgctgtt gtagatttgc aagacagaaa cacagagctt tcataccagc 20100
ttttgcttga ttccattggt gatagaacca ggtacttttc tatgtggaat caggctgttg 20160
acagctatga tccagatgtt agaattattg aaaatcatgg aactgaagat gaacttccaa 20220
attactgctt tccactggga ggtgtgatta atacagagac tcttaccaag gtaaaaccta 20280
aaacaggtca ggaaaatgga tgggaaaaag atgctacaga attttcagat aaaaatgaaa 20340
taagagttgg aaataatttt gccatggaaa tcaatctaaa tgccaacctg tggagaaatt 20400
tcctgtactc caacatagcg ctgtatttgc ccgacaagct aaagtacagt ccttccaacg 20460

```
taaaaatttc tgataaccca aacacctacg actacatgaa caagcgagtg gtggctcccg  20520
ggttagtgga ctgctacatt aaccttggag cacgctggtc ccttgactat atggacaacg  20580
tcaacccatt taaccaccac cgcaatgctg gcctgcgcta ccgctcaatg ttgctgggca  20640
atggtcgcta tgtgcccttc cacatccagg tgcctcagaa gttctttgcc attaaaaacc  20700
tccttctcct gccgggctca tacacctacg agtggaactt caggaaggat gttaacatgg  20760
ttctgcagag ctccctagga aatgacctaa gggttgacgg agccagcatt aagtttgata  20820
gcatttgcct ttacgccacc ttcttcccca tggcccacaa caccgcctcc acgcttgagg  20880
ccatgcttag aaacgacacc aacgaccagt cctttaacga ctatctctcc gccgccaaca  20940
tgctctaccc tatacccgcc aacgctacca acgtgcccat atccatcccc tcccgcaact  21000
gggcggcttt ccgcggctgg gccttcacgc gccttaagac taaggaaacc ccatcactgg  21060
gctcgggcta cgacccttat tacacctact ctggctctat accctaccta gatggaacct  21120
tttacctcaa ccacaccttt aagaaggtgg ccattacctt tgactcttct gtcagctggc  21180
ctggcaatga ccgcctgctt acccccaacg agtttgaaat taagcgctca gttgacgggg  21240
agggttacaa cgttgcccag tgtaacatga ccaaagactg gttcctggta caaatgctag  21300
ctaactacaa cattggctac cagggcttct atatcccaga gagctacaag gaccgcatgt  21360
actccttctt tagaaacttc cagcccatga gccgtcaggt ggtggatgat actaaataca  21420
aggactacca acaggtgggc atcctacacc aacacaacaa ctctggattt gttggctacc  21480
ttgcccccac catgcgcgaa ggacaggcct accctgctaa cttcccctat ccgcttatag  21540
gcaagaccgc agttgacagc attacccaga aaaagtttct ttgcgatcgc accctttggc  21600
gcatcccatt ctccagtaac tttatgtcca tgggcgcact cacagacctg ggccaaaacc  21660
ttctctacgc caactccgcc cacgcgctag acatgacttt tgaggtggat cccatggacg  21720
agcccaccct tctttatgtt ttgtttgaag tctttgacgt ggtccgtgtg caccggccgc  21780
accgcggcgt catcgaaacc gtgtacctgc gcacgccctt ctcggccggc aacgccacaa  21840
cataaagaag caagcaacat caacaacagc tgccgccatg ggctccagtg agcaggaact  21900
gaaagccatt gtcaaagatc ttggttgtgg gccatatttt ttgggcacct atgacaagcg  21960
ctttccaggc tttgtttctc cacacaagct cgcctgcgcc atagtcaata cggccggtcg  22020
cgagactggg ggcgtacact ggatggcctt tgcctggaac ccgcactcaa aaacatgcta  22080
cctctttgag ccctttggct tttctgacca gcgactcaag caggtttacc agtttgagta  22140
cgagtcactc ctgcgccgta gcgccattgc ttcttccccc gaccgctgta taacgctgga  22200
aaagtccacc caaagcgtac aggggcccaa ctcggccgcc tgtggactat tctgctgcat  22260
gtttctccac gcctttgcca actggcccca aactcccatg gatcacaacc ccaccatgaa  22320
ccttattacc ggggtaccca actccatgct caacagtccc caggtacagc ccaccctgcg  22380
tcgcaaccag gaacagctct acagcttcct ggagcgccac tcgccctact tccgcagcca  22440
cagtgcgcag attaggagcg ccacttcttt ttgtcacttg aaaaacatgt aaaaataatg  22500
tactagagac actttcaata aaggcaaatg cttttatttg tacactctcg ggtgattatt  22560
tacccccacc cttgccgtct gcgccgttta aaaatcaaag ggttctgccc gcgcatcgct  22620
atgcgccact ggcagggaca cgttgcgata ctggtgttta gtgctccact taaactcagg  22680
cacaaccatc cgcggcagct cggtgaagtt ttcactccac aggctgcgca ccatcaccaa  22740
cgcgtttagc aggtcgggcg ccgatatctt gaagtcgcag ttggggcctc cgccctgcgc  22800
gcgcgagttg cgatacacag ggttgcagca ctggaacact atcagcgccg ggtggtgcac  22860
```

```
gctggccagc acgctcttgt cggagatcag atccgcgtcc aggtcctccg cgttgctcag  22920
ggcgaacgga gtcaactttg gtagctgcct tcccaaaaag ggcgcgtgcc caggctttga  22980
gttgcactcg caccgtagtg gcatcaaaag gtgaccgtgc ccggtctggg cgttaggata  23040
cagcgcctgc ataaaagcct tgatctgctt aaaagccacc tgagcctttg cgccttcaga  23100
gaagaacatg ccgcaagact tgccggaaaa ctgattggcc ggacaggccg cgtcgtgcac  23160
gcagcacctt gcgtcggtgt tggagatctg caccacattt cggccccacc ggttcttcac  23220
gatcttggcc ttgctagact gctccttcag cgcgcgctgc ccgttttcgc tcgtcacatc  23280
catttcaatc acgtgctcct tatttatcat aatgcttccg tgtagacact taagctcgcc  23340
ttcgatctca gcgcagcggt gcagccacaa cgcgcagccc gtgggctcgt gatgcttgta  23400
ggtcacctct gcaaacgact gcaggtacgc ctgcaggaat cgccccatca tcgtcacaaa  23460
ggtcttgttg ctggtgaagg tcagctgcaa cccgcggtgc tcctcgttca gccaggtctt  23520
gcatacggcc gccagagctt ccacttggtc aggcagtagt ttgaagttcg cctttagatc  23580
gttatccacg tggtacttgt ccatcagcgc gcgcgcagcc tccatgccct tctcccacgc  23640
agacacgatc ggcacactca gcgggttcat caccgtaatt tcactttccg cttcgctggg  23700
ctcttcctct tcctcttgcg tccgcatacc acgcgccact gggtcgtctt cattcagccg  23760
ccgcactgtg cgcttacctc ctttgccatg cttgattagc accggtgggt tgctgaaacc  23820
caccatttgt agcgccacat cttctctttc ttcctcgctg tccacgatta cctctggtga  23880
tggcgggcgc tcgggcttgg gagaagggcg cttctttttc ttcttgggcg caatggccaa  23940
atccgccgcc gaggtcgatg gccgcgggct gggtgtgcgc ggcaccagcg cgtcttgtga  24000
tgagtcttcc tcgtcctcgg actcgatacg ccgcctcatc cgcttttttg ggggcgcccg  24060
gggaggcggc ggcgacgggg acggggacga cacgtcctcc atggttgggg gacgtcgcgc  24120
cgcaccgcgt ccgcgctcgg gggtggtttc gcgctgctcc tcttcccgac tggccatttc  24180
cttctcctat aggcagaaaa agatcatgga gtcagtcgag aagaaggaca gcctaaccgc  24240
cccctctgag ttcgccacca ccgcctccac cgatgccgcc aacgcgccta ccaccttccc  24300
cgtcgaggca cccccgcttg aggaggagga agtgattatc gagcaggacc caggttttgt  24360
aagcgaagac gacgaggacc gctcagtacc aacagaggat aaaaagcaag accaggacaa  24420
cgcagaggca aacgaggaac aagtcgggcg gggggacgaa aggcatggcg actacctaga  24480
tgtgggagac gacgtgctgt tgaagcatct gcagcgccag tgcgccatta tctgcgacgc  24540
gttgcaagag cgcagcgatg tgcccctcgc catagcggat gtcagccttg cctacgaacg  24600
ccacctattc tcaccgcgcg taccccccaa acgccaagaa aacggcacat gcgagcccaa  24660
cccgcgcctc aacttctacc ccgtatttgc cgtgccagag gtgcttgcca cctatcacat  24720
ctttttccaa aactgcaaga taccccctatc ctgccgtgcc aaccgcagcc gagcggacaa  24780
gcagctggcc ttgcggcagg gcgctgtcat acctgatatc gcctcgctca acgaagtgcc  24840
aaaaatcttt gagggtcttg gacgcgacga gaagcgcgcg gcaaacgctc tgcaacagga  24900
aaacagcgaa aatgaaagtc actctggagt gttggtggaa ctcgagggtg acaacgcgcg  24960
cctagccgta ctaaaacgca gcatcgaggt cacccacttt gcctacccgg cacttaacct  25020
accccccaag gtcatgagca cagtcatgag tgagctgatc gtgcgccgtg cgcagcccct  25080
ggagagggat gcaaatttgc aagaacaaac agaggagggc ctacccgcag ttggcgacga  25140
gcagctagcg cgctggcttc aaacgcgcga gcctgccgac ttggaggagc gacgcaaact  25200
```

-continued

```
aatgatggcc gcagtgctcg ttaccgtgga gcttgagtgc atgcagcggt tctttgctga  25260
cccggagatg cagcgcaagc tagaggaaac attgcactac acctttcgac agggctacgt  25320
acgccaggcc tgcaagatct ccaacgtgga gctctgcaac ctggtctcct accttggaat  25380
tttgcacgaa aaccgccttg ggcaaaacgt gcttcattcc acgctcaagg gcgaggcgcg  25440
ccgcgactac gtccgcgact gcgtttactt atttctatgc tacacctggc agacggccat  25500
gggcgtttgg cagcagtgct tggaggagtg caacctcaag gagctgcaga aactgctaaa  25560
gcaaaacttg aaggacctat ggacggcctt caacgagcgc tccgtggccg cgcacctggc  25620
ggacatcatt ttccccgaac gcctgcttaa aaccctgcaa cagggtctgc cagacttcac  25680
cagtcaaagc atgttgcaga actttaggaa ctttatccta gagcgctcag gaatcttgcc  25740
cgccacctgc tgtgcacttc ctagcgactt tgtgcccatt aagtaccgcg aatgccctcc  25800
gccgctttgg ggccactgct accttctgca gctagccaac taccttgcct accactctga  25860
cataatggaa gacgtgagcg gtgacggtct actggagtgt cactgtcgct gcaacctatg  25920
caccccgcac cgctccctgg tttgcaattc gcagctgctt aacgaaagtc aaattatcgg  25980
tacctttgag ctgcagggtc cctcgcctga cgaaaagtcc gcggctccgg ggttgaaact  26040
cactccgggg ctgtggacgt cggcttacct tcgcaaattt gtacctgagg actaccacgc  26100
ccacgagatt aggttctacg aagaccaatc ccgcccgcca aatgcggagc ttaccgcctg  26160
cgtcattacc cagggccaca ttcttggcca attgcaagcc atcaacaaag cccgccaaga  26220
gtttctgcta cgaaagggac ggggggttta cttggacccc cagtccggcg aggagctcaa  26280
cccaatcccc ccgccgccgc agccctatca gcagcagccg cgggcccttg cttcccagga  26340
tggcacccaa aaagaagctg cagctgccgc cgccacccac ggacgaggag gaatactggg  26400
acagtcaggc agaggaggtt ttggacgagg aggaggagga catgatggaa gactgggaga  26460
gcctagacga ggaagcttcc gaggtcgaag aggtgtcaga cgaaacaccg tcaccctcgg  26520
tcgcattccc ctcgccggcg ccccagaaat cggcaaccgg ttccagcatg gctacaacct  26580
ccgctcctca ggcgccgccg gcactgcccg ttcgccgacc caaccgtaga tgggacacca  26640
ctggaaccag ggccggtaag tccaagcagc cgccgccgtt agcccaagag caacaacagc  26700
gccaaggcta ccgctcatgg cgcgggcaca agaacgccat agttgcttgc ttgcaagact  26760
gtgggggcaa catctccttc gcccgccgct ttcttctcta ccatcacggc gtggccttcc  26820
cccgtaacat cctgcattac taccgtcatc tctacagccc atactgcacc ggcggcagcg  26880
gcagcggcag caacagcagc ggccacacag aagcaaaggc gaccggatag caagactctg  26940
acaaagccca agaaatccac agcggcggca gcagcaggag gaggagcgct gcgtctggcg  27000
cccaacgaac ccgtatcgac ccgcgagctt agaaacagga tttttcccac tctgtatgct  27060
atatttcaac agagcagggg ccaagaacaa gagctgaaaa taaaaaacag gtctctgcga  27120
tccctcaccc gcagctgcct gtatcacaaa agcgaagatc agcttcggcg cacgctggaa  27180
gacgcggagg ctctcttcag taaatactgc gcgctgactc ttaaggacta gtttcgcgcc  27240
ctttctcaaa tttaagcgcg aaaactacgt catctccagc ggccacaccc ggcgccagca  27300
cctgtcgtca gcgccattat gagcaaggaa attcccacgc cctacatgtg gagttaccag  27360
ccacaaatgg gacttgcggc tggagctgcc caagactact caacccgaat aaactacatg  27420
agcgcgggac cccacatgat atcccgggtc aacggaatcc gcgcccaccg aaaccgaatt  27480
ctcttggaac aggcggctat taccaccaca cctcgtaata accttaatcc ccgtagttgg  27540
cccgctgccc tggtgtacca ggaaagtccc gctcccacca ctgtggtact tcccagagac  27600
```

-continued

```
gcccaggccg aagttcagat gactaactca ggggcgcagc ttgcgggcgg ctttcgtcac  27660
agggtgcggt cgcccgggca gggtataact cacctgacaa tcagagggcg aggtattcag  27720
ctcaacgacg agtcggtgag ctcctcgctt ggtctccgtc cggacgggac atttcagatc  27780
ggcggcgccg gccgctcttc attcacgcct cgtcaggcaa tcctaactct gcagacctcg  27840
tcctctgagc cgcgctctgg aggcattgga actctgcaat ttattgagga gtttgtgcca  27900
tcggtctact ttaacccctt ctcgggacct cccggccact atccggatca atttattcct  27960
aactttgacg cggtaaagga ctcggcggat ggctacgact gaatgttaag tggagaggca  28020
gagcaactgc gcctgaaaca cctggtccac tgtcgccgcc acaagtgctt tgcccgcgac  28080
tccggtgagt tttgctactt tgaattgccc gaggatcata tcgagggccc ggcgcacggc  28140
gtccggctta ccgcccaggg agagcttgcc cgtagcctga ttcgggagtt tacccagcgc  28200
cccctgctag ttgagcggga caggggaccc tgtgttctca ctgtgatttg caactgtcct  28260
aaccctggat tacatcaaga tctttgttgc catctctgtg ctgagtataa taaatacaga  28320
aattaaaata tactggggct cctatcgcca tcctgtaaac gccaccgtct tcacccgccc  28380
aagcaaacca aggcgaacct tacctggtac ttttaacatc tctccctctg tgatttacaa  28440
cagtttcaac ccagacggag tgagtctacg agagaacctc tccgagctca gctactccat  28500
cagaaaaaac accaccctcc ttacctgccg ggaacgtacg acctagggat aacagggtaa  28560
taagcaattg actctatgtg ggatatgctc cagcgctaca accttgaagt caggcttcct  28620
ggatgtcagc atctgacttt ggccagcacc tgtcccgcgg atttgttcca gtccaactac  28680
agcgacccac cctaacagag atgaccaaca caaccaacgc ggccgccgct accggactta  28740
catctaccac aaatacaccc caagtttctg cctttgtcaa taactgggat aacttgggca  28800
tgtggtggtt ctccatagcg cttatgtttg tatgccttat tattatgtgg ctcatctgct  28860
gcctaaagcg caaacgcgcc cgaccaccca tctatagtcc catcattgtg ctacacccaa  28920
acaatgatgg aatccataga ttggacggac tgaaacacat gttcttttct cttacagtat  28980
gattaaatga gacatgattc ctcgagtttt tatattactg acccttgttg cgcttttttg  29040
tgcgtgctcc acattggctg cggtttctca catcgaagta gactgcattc cagccttcac  29100
agtctatttg ctttacggat ttgtcaccct cacgctcatc tgcagcctca tcactgtggt  29160
catcgccttt atccagtgca ttgactgggt ctgtgtgcgc tttgcatatc tcagacacca  29220
tccccagtac agggacagga ctatagctga gcttcttaga attctttaat tatgaaattt  29280
actgtgactt ttctgctgat tatttgcacc ctatctgcgt tttgttcccc gacctccaag  29340
cctcaaagac atatatcatg cagattcact cgtatatgga atattccaag ttgctacaat  29400
gaaaaaagcg atctttccga agcctggtta tatgcaatca tctctgttat ggtgttctgc  29460
agtaccatct tagccctagc tatatatccc taccttgaca ttggctggaa acgaatagat  29520
gccatgaacc acccaacttt ccccgcgccc gctatgcttc cactgcaaca agttgttgcc  29580
ggcggctttg tcccagccaa tcagcctcgc cccacttctc ccaccccac tgaaatcagc  29640
tactttaatc taacaggagg agatgactga caccctagat ctagaaatgg acggaattat  29700
tacagagcag cgcctgctag aaagacgcag ggcagcggcc gagcaacagc gcatgaatca  29760
agagctccaa gacatggtta acttgcacca gtgcaaaagg ggtatctttt gtctggtaaa  29820
gcaggccaaa gtcacctacg acagtaatac caccggacac cgccttagct acaagttgcc  29880
aaccaagcgt cagaaattgg tggtcatggt gggagaaaag cccattacca taactcagca  29940
```

```
ctcggtagaa accgaaggct gcattcactc accttgtcaa ggacctgagg atctctgcac  30000
ccttattaag accctgtgcg gtctcaaaga tcttattccc tttaactaat aaaaaaaaat  30060
aataaagcat cacttactta aaatcagtta gcaaatttct gtccagttta ttcagcagca  30120
cctccttgcc ctcctcccag ctctggtatt gcagcttcct cctggctgca aactttctcc  30180
acaatctaaa tggaatgtca gtttcctcct gttcctgtcc atccgcaccc actatcttca  30240
tgttgttgca gatgaagcgc gcaagaccgt ctgaagatac cttcaacccc gtgtatccat  30300
atgacacgga aaccggtcct ccaactgtgc cttttcttac tcctcccttt gtatccccca  30360
atgggtttca agagagtccc cctggggtac tctctttgcg cctatccgaa cctctagtta  30420
cctccaatgg catgcttgcg ctcaaaatgg gcaacggcct ctctctggac gaggccggca  30480
accttacctc ccaaaatgta accactgtga gcccacctct caaaaaaacc aagtcaaaca  30540
taaacctgga aatatctgca cccctcacag ttacctcaga agccctaact gtggctgccg  30600
ccgcacctct aatggtcgcg ggcaacacac tcaccatgca atcacaggcc ccgctaaccg  30660
tgcacgactc caaacttagc attgccaccc aaggacccct cacagtgtca gaaggaaagc  30720
tagccctgca aacatcaggc cccctcacca ccaccgatag cagtaccctt actatcactg  30780
cctcaccccc tctaactact gccactggta gcttgggcat tgacttgaaa gagcccattt  30840
atacacaaaa tggaaaacta ggactaaagt acggggctcc tttgcatgta acagacgacc  30900
taaacacttt gaccgtagca actggtccag gtgtgactat taataatact tccttgcaaa  30960
ctaaagttac tggagccttg ggttttgatt cacaaggcaa tatgcaactt aatgtagcag  31020
gaggactaag gattgattct caaaacagac gccttatact tgatgttagt tatccgtttg  31080
atgctcaaaa ccaactaaat ctaagactag gacagggccc tctttttata aactcagccc  31140
acaacttgga tattaactac aacaaaggcc tttacttgtt tacagcttca aacaattcca  31200
aaaagcttga ggttaaccta agcactgcca aggggttgat gtttgacgct acagccatag  31260
ccattaatgc aggagatggg cttgaatttg gttcacctaa tgcaccaaac acaaatcccc  31320
tcaaaacaaa aattggccat ggcctagaat ttgattcaaa caaggctatg gttcctaaac  31380
taggaactgg ccttagtttt gacagcacag gtgccattac agtaggaaac aaaaataatg  31440
ataagctaac cctatggaca ggtccaaaac cagaagccaa ctgcataatt gaatacggga  31500
aacaaaaccc agatagcaaa ctaactttaa tccttgtaaa aaatggagga attgttaatg  31560
gatatgtaac gctaatggga gcctcagact acgttaacac cttatttaaa aacaaaaatg  31620
tctccattaa tgtagaacta tactttgatg ccactggtca tatattacca gactcatctt  31680
ctcttaaaac agatctagaa ctaaaataca agcaaaccgc tgactttagt gcaagaggtt  31740
ttatgccaag tactacagcg tatccatttg tccttcctaa tgcgggaaca cataatgaaa  31800
attatatttt tggtcaatgc tactacaaag caagcgatgg tgcccttttt ccgttggaag  31860
ttactgttat gcttaataaa cgcctgccag atagtcgcac atcctatgtt atgacttttt  31920
tatggtcctt gaatgctggt ctagctccag aaactactca ggcaaccctc ataacctccc  31980
catttacctt ttcctatatt agagaagatg actaataaac tctaaagaat cgtttgtgtt  32040
atgtttcaac gtgtttattt ttcaattgca gaaaatttca agtcattttt cattcagtag  32100
tatagcccca ccaccacata gcttatacag atcaccgtac cttaatcaaa ctcacagaac  32160
cctagtattc aacctgccac ctccctccca acacacagag tacacagtcc tttctccccg  32220
gctggcctta aaaagcatca tatcatgggt aacagacata ttcttaggtg ttatattcca  32280
cacggtttcc tgtcgagcca aacgctcatc aagtgatatt aataaactcc ccgggcagct  32340
```

cacttaagtt catgtcgctg tccagctgct gagccacagg ctgctgtcca acttgcggtt 32400
gcttaacggg cggcgaagga gaagtccacg cctacatggg gggagagtca taatcgtgca 32460
tcaggatagg gcggtggtgc tgcagcagcg cgcgaataaa ctgctgccgc cgccgctccg 32520
tcctgcagga atacaacatg gcagtggtct cctcagcgat gattcgcacc gcccgcagca 32580
taaggcgctt gtcctccggg cacagcagcg caccctgatc tcacttaaat cagcacagta 32640
actgcagcac agcaccacaa tattgttcaa aatcccacag tgcaaggcgc tgtatccaaa 32700
gctcatggcg gggaccacag aacccacgtg gccatcatac cacaagcgca ggtagattaa 32760
gtggcgaccc ctcataaaca cgctggacat aaacattacc tcttttggca tgttgtaatt 32820
caccacctcc cggtaccata taaacctctg attaaacatg gcgccatcca ccaccatcct 32880
aaaccagctg gccaaaacct gccccgccgg gntatacact gcagggaacc gggacttgga 32940
caatgacaag tgggagagcc caggactcgt aaccatggat catcatgctc gtcatgatat 33000
caatgttggc acaacacagg cacacgtgca tacacttcct caggattaca agctcctccc 33060
gcgttagaac catatcccag ggaacaaccc attcctgaat cagcgtaaat cccacactgc 33120
agggaagacc tcgcacgtaa ctcacgttgt gcattgtcaa agtgttacat tcgggcagca 33180
gcggatgatc ctccagtatg gtagcgcggg tttctgtctc aaaaggaggt agacgatccc 33240
tactgtacgg agtgcgccga gacaaccgag atcgtgttgg tcgtagtgtc atgccaaatg 33300
gaacgccgga cgtagtcata tttcctgaag caaaaccagg tgcgggcgtg acaaacagat 33360
ctgcgtctcc ggtctcgccg cttagatcgc tctgtgtagt agttgtagta tatccactct 33420
ctcaaagcat ccaggcgccc cctggcttcg ggttctatgt aaactccttc atgcgccgct 33480
gccctgataa catccaccac cgcagaataa gccacaccca gccaacctac acattcgttc 33540
tgcgagtcac acacgggagg agcgggaaga gctggaagaa ccatgttttt tttttttattc 33600 caaaagatta tccaaaacct caaaatgaag atctattaag tgaacgcgct cccctccggt 33660
ggcgtggtca aactctacag ccaaagaaca gataatggca tttgtaagat gttgcacaat 33720
ggcttccaaa aggcaaacgg ccctcacgtc caagtggacg taaaggctaa acccttcagg 33780
gtgaatctcc tctataaaca ttccagcacc ttcaaccatg cccaaataat tctcatctcg 33840
ccaccttctc aatatatctc taagcaaatc ccgaatattt aagtccgggc cattgtaaaa 33900
aatttggctc cagagcgccc tccaccttca gcctcaagca gcgaatcatg attgcaaaaa 33960
ttcaggttcc tcacagacct gtataagatt caaaagcgga acattaacaa aaataccgcg 34020
atcccgtagg tcccttcgca gggccagctg aacataatcg tgcaggtctg cacggaccag 34080
cgcggccact tccccgccag gaaccatgac aaaagaaccc acactgatta tgacacgcat 34140
actcggagct atgctaacca gcgtagcccc gatgtaagct tgttgcatgg gcggcgatat 34200
aaaatgcaag gtgctgctca aaaaatcagg caaagcctcg cgcaaaaaag aaagcacatc 34260
gtagtcatgc tcatgcagat aaaggcaggt aagctccgga accaccacag aaaaagacac 34320
catttttctc tcaaacatgt ctgcgggttt ctgcataaac acaaaataaa ataacaaaaa 34380
aacatttaaa cattagaagc ctgtcttaca acaggaaaaa caacccttat aagcataaga 34440
cggactacgg ccatgccggc gtgaccgtaa aaaaactggt caccgtgatt aaaaagcacc 34500
accgacagct cctcggtcag tccggagtca taatgtaaga ctcggtaaac acatcaggtt 34560
gattcacatc ggtcagtgtt aaaaagcgac cgaaatagcc ngggggaata caatacccgc 34620
aggcgtagag acaacattac agcccccata ggaggtataa caaaattaat aggagagaaa 34680

-continued

```
aacacataaa cacctgaaaa accctcctgc ctaggcaaaa tagcaccctc ccgctccaga  34740
acaacataca gcgcttccac agcggcagcc ataacagtca gccttaccag taaaaaagaa  34800
aacctattaa aaaaacacca ctcgacacgg caccagctca atcagtcaca gtgtaaaaaa  34860
gggccaagtg cagagcgagt atatatagga ctaaaaaatg acggtaacgg ttaaagtcca  34920
caaaaaacac ccagaaaacc gcacgcgaac ctacgcccag aaacgaaagc caaaaaaccc  34980
acaacttcct caaatcgtca cttccgtttt cccacgttac gtcacttccc attttaagaa  35040
aactacaatt cccaacacat acaagttact ccgccctaaa acctacgtca cccgccccgt  35100
tcccacgccc cgcgccacgt cacaaactcc accccctcat tatcatattg gcttcaatcc  35160
aaaataaggt atattattga tgatgttaat taacatgcat ggatcctcgt ctcgacgatg  35220
cccttgagag ccttcaaccc agtcagctcc ttccggtggg cgcggggcat gactatcgtc  35280
gccgcactta tgactgtctt ctttatcatg caactcgtag gacaggtgcc ggcagcgctc  35340
tgggtcattt tcggcgagga ccgctttcgc tggagcgcga cgatgatcgg cctgtcgctt  35400
gcggtattcg gaatcttgca cgccctcgct caagccttcg tcactggtcc cgccaccaaa  35460
cgtttcggcg agaagcaggc cattatcgcc ggcatggcgg ccgacgcgct gggctacgtc  35520
ttgctggcgt tcgcgacgcg aggctggatg gccttcccca ttatgattct tctcgcttcc  35580
ggcggcatcg ggatgcccgc gttgcaggcc atgctgtcca ggcaggtaga tgacgaccat  35640
cagggacagc ttcaaggatc gctcgcggct cttaccagcc taacttcgat cactggaccg  35700
ctgatcgtca cggcgattta tgccgcctcg gcgagcacat ggaacgggtt ggcatggatt  35760
gtaggcgccg ccctatacct tgtctgcctc cccgcgttgc gtcgcggtgc atggagccgg  35820
gccacctcga cctgaatgga agccggcggc acctcgctaa cggattcacc actccaagaa  35880
ttggagccaa tcaattcttg cggagaactg tgaatgcgca aaccaaccct tggcagaaca  35940
tatccatcgc gtccgccatc tccagcagcc gcacgcggcg catctcgggc agcgttgggt  36000
cctggccacg ggtgcgcatg atcgtgctcc tgtcgttgag gacccggcta ggctggcggg  36060
gttgccttac tggttagcag aatgaatcac cgatacgcga gcgaacgtga agcgactgct  36120
gctgcaaaac gtctgcgacc tgagcaacaa catgaatggt cttcggtttc cgtgtttcgt  36180
aaagtctgga aacgcggaag tcagcgccct gcaccattat gttccggatc tgcatcgcag  36240
gatgctgctg gctaccctgt ggaacaccta catctgtatt aacgaagcgc tggcattgac  36300
cctgagtgat ttttctctgg tcccgccgca tccataccgc cagttgttta ccctcacaac  36360
gttccagtaa ccgggcatgt tcatcatcag taacccgtat cgtgagcatc ctctctcgtt  36420
tcatcggtat cattaccccc atgaacagaa attccccctt acacggaggc atcaagtgac  36480
caaacaggaa aaaaccgccc ttaacatggc ccgctttatc agaagccaga cattaacgct  36540
tctggagaaa ctcaacgagc tggacgcgga tgaacaggca gacatctgtg aatcgcttca  36600
cgaccacgct gatgagcttt accgcagctg cctcgcgcgt ttcggtgatg acggtgaaaa  36660
cctctgacac atgcagctcc cggagacggt cacagcttgt ctgtaagcgg atgccgggag  36720
cagacaagcc cgtcagggcg cgtcagcggg tgttggcggg tgtcggggcg cagccatgac  36780
ccagtcacgt agcgatagcg gagtgtatac tggcttaact atgcggcatc agagcagatt  36840
gtactgagag tgcaccatat gcggtgtgaa ataccgcaca gatgcgtaag gagaaaatac  36900
cgcatcaggc gctcttccgc ttcctcgctc actgactcgc tgcgctcggt cgttcggctg  36960
cggcgagcgg tatcagctca ctcaaaggcg gtaatacggt tatccacaga atcaggggat  37020
aacgcaggaa agaacatgtg agcaaaaggc cagcaaaagg ccaggaaccg taaaaaggcc  37080
```

```
gcgttgctgg cgtttttcca taggctccgc cccccctgacg agcatcacaa aaatcgacgc  37140
tcaagtcaga ggtggcgaaa cccgacagga ctataaagat accaggcgtt tccccctgga  37200
agctccctcg tgcgctctcc tgttccgacc ctgccgctta ccggatacct gtccgccttt  37260
ctcccttcgg gaagcgtggc gctttctcaa tgctcacgct gtaggtatct cagttcggtg  37320
taggtcgttc gctccaagct gggctgtgtg cacgaacccc ccgttcagcc cgaccgctgc  37380
gccttatccg gtaactatcg tcttgagtcc aacccggtaa gacacgactt atcgccactg  37440
gcagcagcca ctggtaacag gattagcaga gcgaggtatg taggcggtgc tacagagttc  37500
ttgaagtggt ggcctaacta cggctacact agaaggacag tatttggtat ctgcgctctg  37560
ctgaagccag ttaccttcgg aaaaagagtt ggtagctctt gatccggcaa acaaaccacc  37620
gctggtagcg gtggtttttt tgtttgcaag cagcagatta cgcgcagaaa aaaaggatct  37680
caagaagatc ctttgatctt ttctacgggg tctgacgctc agtggaacga aaactcacgt  37740
taagggattt tggtcatgag attatcaaaa aggatcttca cctagatcct tttaaattaa  37800
aaatgaagtt ttaaatcaat ctaaagtata tatgagtaaa cttggtctga cagttaccaa  37860
tgcttaatca gtgaggcacc tatctcagcg atctgtctat ttcgttcatc catagttgcc  37920
tgactccccg tcgtgtagat aactacgata cgggagggct taccatctgg ccccagtgct  37980
gcaatgatac cgcgagaccc acgctcaccg gctccagatt tatcagcaat aaaccagcca  38040
gccggaaggg ccgagcgcag aagtggtcct gcaactttat ccgcctccat ccagtctatt  38100
aattgttgcc gggaagctag agtaagtagt tcgccagtta atagtttgcg caacgttggt  38160
tgnnnnnnaa aaaggatctt cacctagatc cttttcacgt agaaagccag tccgcagaaa  38220
cggtgctgac cccggatgaa tgtcagctac tgggctatct ggacaaggga aaacgcaagc  38280
gcaaagagaa agcaggtagc ttgcagtggg cttacatggc gatagctaga ctgggcggtt  38340
ttatggacag caagcgaacc ggaattgcca gctggggcgc cctctggtaa ggttgggaag  38400
ccctgcaaag taaactggat ggctttctcg ccgccaagga tctgatggcg caggggatca  38460
agctctgatc aagagacagg atgaggatcg tttcgcatga ttgaacaaga tggattgcac  38520
gcaggttctc cggccgcttg ggtggagagg ctattcggct atgactgggc acaacagaca  38580
atcggctgct ctgatgccgc cgtgttccgg ctgtcagcgc aggggcgccc ggttcttttt  38640
gtcaagaccg acctgtccgg tgccctgaat gaactgcaag acgaggcagc gcggctatcg  38700
tggctggcca cgacgggcgt tccttgcgca gctgtgctcg acgttgtcac tgaagcggga  38760
agggactggc tgctattggg cgaagtgccg gggcaggatc tcctgtcatc tcaccttgct  38820
cctgccgaga aagtatccat catggctgat gcaatgcggc ggctgcatac gcttgatccg  38880
gctacctgcc cattcgacca ccaagcgaaa catcgcatcg agcgagcacg tactcggatg  38940
gaagccggtc ttgtcgatca ggatgatctg gacgaagagc atcaggggct cgcgccagcc  39000
gaactgttcg ccaggctcaa ggcgagcatg cccgacggcg aggatctcgt cgtgacccat  39060
ggcgatgcct gcttgccgaa tatcatggtg gaaaatggcc gcttttctgg attcatcgac  39120
tgtggccggc tgggtgtggc ggaccgctat caggacatag cgttggctac ccgtgatatt  39180
gctgaagagc ttggcggcga atgggctgac cgcttcctcg tgctttacgg tatcgccgct  39240
cccgattcgc agcgcatcgc cttctatcgc cttcttgacg agttcttctg aattttgtta  39300
aaatttttgt taaatcagct catttttaa ccaataggcc gaaatcggca acatccctta  39360
taaatcaaaa gaatagaccg cgatagggtt gagtgttgtt ccagtttgga acaagagtcc  39420
```

actattaaag aacgtggact ccaacgtcaa agggcgaaaa accgtctatc agggcgatgg 39480
cccactacgt gaaccatcac ccaaatcaag ttttttgcgg tcgaggtgcc gtaaagctct 39540
aaatcggaac cctaaaggga gcccccgatt tagagcttga cggggaaagc cggcgaacgt 39600
ggcgagaaag gaagggaaga aagcgaaagg agcgggcgct agggcgctgg caagtgtagc 39660
ggtcacgctg cgcgtaacca ccacacccgc gcgcttaatg cgccgctaca gggcgcgtcc 39720
attcgccatt caggatcgaa ttaattctta at 39752

<210> SEQ ID NO 52
<211> LENGTH: 8
<212> TYPE: PRT
<213> ORGANISM: Artificial Sequence
<220> FEATURE:
<223> OTHER INFORMATION: Amino acids 121-128 of Ad E1A protein

<400> SEQUENCE: 52

Leu Thr Cys His Glu Ala Cys Phe
1 5

<210> SEQ ID NO 53
<211> LENGTH: 9
<212> TYPE: PRT
<213> ORGANISM: Artificial Sequence
<220> FEATURE:
<223> OTHER INFORMATION: STAT1 binding site (1)

<400> SEQUENCE: 53

Thr Thr Cys Cys Gly Gly Gly Ala Ala
1 5

<210> SEQ ID NO 54
<211> LENGTH: 9
<212> TYPE: PRT
<213> ORGANISM: Artificial Sequence
<220> FEATURE:
<223> OTHER INFORMATION: STAT1 binding site (2)

<400> SEQUENCE: 54

Thr Thr Cys Thr Cys Gly Gly Ala Ala
1 5

<210> SEQ ID NO 55
<211> LENGTH: 35010
<212> TYPE: DNA
<213> ORGANISM: Artificial Sequence
<220> FEATURE:
<223> OTHER INFORMATION: Ad5/3Ad2E1Adelta24

<400> SEQUENCE: 55
taacatcatc aataatatac cttattttgg attgaagcca atatgataat gaggggggtgg 60 agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttattatta tagtcagctg acgtgtagtg tatttatacc 480
cggtgagttc ctcaagaggc cactcttgag tgccagcgag tagagttttc tcctccgagc 540

-continued

```
cgctccgaca ccgggactga aaatgagaca tattatctgc cacggaggtg ttattaccga    600
agaaatggcc gccagtcttt tggaccagct gatcgaagag gtactggctg ataatcttcc    660
acctcctagc cattttgaac cacctaccct tcacgaactg tatgatttag acgtgacggc    720
ccccgaagat cccaacgagg aggcggtttc gcagattttt cccgagtctg taatgttggc    780
ggtgcaggaa gggattgact tattcacttt tccgccggcg cccggttctc cggagccgcc    840
tcacctttcc cggcagcccg agcagccgga gcagagagcc ttgggtccgg tttctatgcc    900
aaaccttgtg ccggaggtga tcgatccacc cagtgacgac gaggatgaag agggtgagga    960
gtttgtgtta gattatgtgg agcaccccgg gcacggttgc aggtcttgtc attatcaccg   1020
gaggaatacg ggggacccag atattatgtg ttcgctttgc tatatgagga cctgtggcat   1080
gtttgtctac agtaagtgaa aattatgggc agtcggtgat agagtggtgg gtttggtgtg   1140
gtaatttttt tttaattttt acagttttgt ggtttaaaga attttgtatt gtgatttttt   1200
aaaaggtcct gtgtctgaac ctgagcctga gcccgagcca gaaccggagc ctgcaagacc   1260
tacccggcgt cctaaattgg tgcctgctat cctgagacgc ccgacatcac ctgtgtctag   1320
agaatgcaat agtagtacgg atagctgtga ctccggtcct tctaacacac ctcctgagat   1380
acacccggtg gtcccgctgt gccccattaa accagttgcc gtgagagttg gtgggcgtcg   1440
ccaggctgtg gaatgtatcg aggacttgct taacgagtct gggcaacctt tggacttgag   1500
ctgtaaacgc cccaggccat aaggtgtaaa cctgtgattg cgtgtgtggt taacgccttt   1560
gtttgctgaa tgagttgatg taagtttaat aaagggtgag ataatgttta acttgcatgg   1620
cgtgttaaat ggggcggggc ttaaagggta tataatgcgc cgtgggctaa tcttggttac   1680
atctgacctc atggaggctt gggagtgttt ggaagatttt tctgctgtgc gtaacttgct   1740
ggaacagagc tctaacagta cctcttggtt ttggaggttt ctgtggggct catcccaggc   1800
aaagttagtc tgcagaatta aggaggatta caagtgggaa tttgaagagc ttttgaaatc   1860
ctgtggtgag ctgtttgatt ctttgaatct gggtcaccag gcgcttttcc aagagaaggt   1920
catcaagact ttggattttt ccacaccggg gcgcgctgcg gctgctgttg ctttttgag   1980
ttttataaag gataaatgga gcgaagaaac ccatctgagc ggggggtacc tgctggattt   2040
tctggccatg catctgtgga gagcggttgt gagacacaag aatcgcctgc tactgttgtc   2100
ttccgtccgc ccggcgataa taccgacgga ggagcagcag cagcagcagg aggaagccag   2160
gcggcggcgg caggagcaga gcccatggaa cccgagagcc ggcctggacc ctcgggaatg   2220
aatgttgttc aggtggctga actgtatcca gaactgagac gcattttgac aattacagag   2280
gatgggcagg ggctaaaggg ggtaaagagg gagcgggggg cttgtgaggc tacagaggag   2340
gctaggaatc tagcttttag cttaatgacc agacaccgtc ctgagtgtat tacttttcaa   2400
cagatcaagg ataattgcgc taatgagctt gatctgctgg cgcagaagta ttccatagag   2460
cagctgacca cttactggct gcagccaggg gatgattttg aggaggctat tagggtatat   2520
gcaaaggtgg cacttaggcc agattgcaag tacaagatca gcaaacttgt aaatatcagg   2580
aattgttgct acatttctgg gaacggggcc gaggtggaga tagatacgga ggatagggtg   2640
gcctttagat gtagcatgat aaatatgtgg ccgggggtgc ttggcatgga cggggtggtt   2700
attatgaatg taaggtttac tggccccaat tttagcggta cggttttcct ggccaatacc   2760
aaccttatcc tacacggtgt aagcttctat gggtttaaca atacctgtgt ggaagcctgg   2820
accgatgtaa gggttcgggg ctgtgccttt tactgctgct ggaagggggt ggtgtgtcgc   2880
cccaaaagca gggcttcaat taagaaatgc ctctttgaaa ggtgtacctt gggtatcctg   2940
```

```
tctgagggta actccagggt gcgccacaat gtggcctccg actgtggttg cttcatgcta   3000
gtgaaaagcg tggctgtgat taagcataac atggtatgtg gcaactgcga ggacagggcc   3060
tctcagatgc tgacctgctc ggacggcaac tgtcaccttc tgaagaccat tcacgtagcc   3120
agccactctc gcaaggcctg gccagtgttt gagcataaca tactgacccg ctgttccttg   3180
catttgggta acaggagggg ggtgttccta ccttaccaat gcaatttgag tcacactaag   3240
atattgcttg agcccgagag catgtccaag gtgaacctga acggggtgtt tgacatgacc   3300
atgaagatct ggaaggtgct gaggtacgat gagacccgca ccaggtgcag accctgcgag   3360
tgtggcggta aacatattag gaaccagcct gtgatgctgg atgtgaccga ggagctgagg   3420
cccgatcact tggtgctggc ctgcacccgc gctgagtttg gctctagcga tgaagataca   3480
gattgaggta ctgaaatgtg tgggcgtggc ttaagggtgg gaaagaatat ataaggtggg   3540
ggtcttatgt agttttgtat ctgttttgca gcagccgccg ccgccatgag caccaactcg   3600
tttgatggaa gcattgtgag ctcatatttg acaacgcgca tgcccccatg ggccggggtg   3660
cgtcagaatg tgatgggctc cagcattgat ggtcgccccg tcctgcccgc aaactctact   3720
accttgacct acgagaccgt gtctggaacg ccgttggaga ctgcagcctc cgccgccgct   3780
tcagccgctg cagccaccgc ccgcgggatt gtgactgact ttgctttcct gagcccgctt   3840
gcaagcagtg cagcttcccg ttcatccgcc cgcgatgaca agttgacggc tcttttggca   3900
caattggatt ctttgacccg ggaacttaat gtcgtttctc agcagctgtt ggatctgcgc   3960
cagcaggttt ctgccctgaa ggcttcctcc cctcccaatg cggtttaaaa cataaataaa   4020
aaaccagact ctgtttggat ttggatcaag caagtgtctt gctgtcttta tttaggggtt   4080
ttgcgcgcgc ggtaggcccg ggaccagcgg tctcggtcgt tgagggtcct gtgtattttt   4140
tccaggacgt ggtaaaggtg actctggatg ttcagataca tgggcataag cccgtctctg   4200
gggtggaggt agcaccactg cagagcttca tgctgcgggg tggtgttgta gatgatccag   4260
tcgtagcagg agcgctgggc gtggtgccta aaaatgtctt tcagtagcaa gctgattgcc   4320
aggggcaggc ccttggtgta agtgtttaca aagcggttaa gctgggatgg gtgcatacgt   4380
ggggatatga gatgcatctt ggactgtatt tttaggttgg ctatgttccc agccatatcc   4440
ctccggggat tcatgttgtg cagaaccacc agcacagtgt atccggtgca cttgggaaat   4500
ttgtcatgta gcttagaagg aaatgcgtgg aagaacttgg agacgccctt gtgacctcca   4560
agattttcca tgcattcgtc cataatgatg gcaatgggcc cacgggcggc ggcctgggcg   4620
aagatatttc tgggatcact aacgtcatag ttgtgttcca ggatgagatc gtcataggcc   4680
atttttacaa agcgcgggcg gagggtgcca gactgcggta taatggttcc atccggccca   4740
ggggcgtagt taccctcaca gatttgcatt tcccacgctt tgagttcaga tgggggggatc   4800
atgtctacct gcggggcgat gaagaaaacg gtttccgggg taggggagat cagctgggaa   4860
gaaagcaggt tcctgagcag ctgcgactta ccgcagccgg tgggcccgta aatcacacct   4920
attaccgggt gcaactggta gttaagagag ctgcagctgc cgtcatccct gagcaggggg   4980
gccacttcgt taagcatgtc cctgactcgc atgttttccc tgaccaaatc cgccagaagg   5040
cgctcgccgc ccagcgatag cagttcttgc aaggaagcaa agtttttcaa cggtttgaga   5100
ccgtccgccg taggcatgct tttgagcgtt tgaccaagca gttccaggcg gtcccacagc   5160
tcggttacct gctctacggc atctcgatcc agcatatctc ctcgtttcgc gggttggggc   5220
ggctttcgct gtacggcagt agtcggtgct cgtccagacg ggccagggtc atgtctttcc   5280
```

acgggcgcag ggtcctcgtc agcgtagtct gggtcacggt gaaggggtgc gctccgggct 5340
gcgcgctggc cagggtgcgc ttgaggctgg tcctgctggt gctgaagcgc tgccggtctt 5400
cgccctgcgc gtcggccagg tagcatttga ccatggtgtc atagtccagc ccctccgcgg 5460
cgtggccctt ggcgcgcagc ttgcccttgg aggaggcgcc gcacgagggg cagtgcagac 5520
ttttgagggc gtagagcttg ggcgcgagaa ataccgattc cggggagtag gcatccgcgc 5580
cgcaggcccc gcagacggtc tcgcattcca cgagccaggt gagctctggc cgttcggggt 5640
caaaaaccag gtttccccca tgctttttga tgcgtttctt acctctggtt tccatgagcc 5700
ggtgtccacg ctcggtgacg aaaaggctgt ccgtgtcccc gtatacagac ttgagaggcc 5760
tgtcctcgag cggtgttccg cggtcctcct cgtatagaaa ctcggaccac tctgagacaa 5820
aggctcgcgt ccaggccagc acgaaggagg ctaagtggga ggggtagcgg tcgttgtcca 5880
ctagggggtc cactcgctcc agggtgtgaa gacacatgtc gccctcttcg gcatcaagga 5940
aggtgattgg tttgtaggtg taggccacgt gaccgggtgt tcctgaaggg gggctataaa 6000
agggggtggg ggcgcgttcg tcctcactct cttccgcatc gctgtctgcg agggccagct 6060
gttggggtga gtactccctc tgaaaagcgg gcatgacttc tgcgctaaga ttgtcagttt 6120
ccaaaaacga ggaggatttg atattcacct ggcccgcggt gatgcctttg agggtggccg 6180
catccatctg gtcagaaaag acaatctttt tgttgtcaag cttggtggca aacgacccgt 6240
agagggcgtt ggacagcaac ttggcgatgg agcgcagggt ttggtttttg tcgcgatcgg 6300
cgcgctcctt ggccgcgatg tttagctgca cgtattcgcg cgcaacgcac cgccattcgg 6360
gaaagacggt ggtgcgctcg tcgggcacca ggtgcacgcg ccaaccgcgg ttgtgcaggg 6420
tgacaaggtc aacgctggtg gctacctctc cgcgtaggcg ctcgttggtc cagcagaggc 6480
ggccgccctt gcgcgagcag aatggcggta gggggtctag ctgcgtctcg tccgggggt 6540 ctgcgtccac ggtaaagacc ccgggcagca ggcgcgcgtc gaagtagtct atcttgcatc 6600
cttgcaagtc tagcgcctgc tgccatgcgc gggcggcaag cgcgcgctcg tatgggttga 6660
gtgggggacc ccatggcatg gggtgggtga gcgcggaggc gtacatgccg caaatgtcgt 6720
aaacgtagag gggctctctg agtattccaa gatatgtagg gtagcatctt ccaccgcgga 6780
tgctggcgcg cacgtaatcg tatagttcgt gcgagggagc gaggaggtcg ggaccgaggt 6840
tgctacgggc gggctgctct gctcggaaga ctatctgcct gaagatggca tgtgagttgg 6900
atgatatggt tggacgctgg aagacgttga agctggcgtc tgtgagacct accgcgtcac 6960
gcacgaagga ggcgtaggag tcgcgcagct tgttgaccag ctcggcggtg acctgcacgt 7020
ctagggcgca gtagtccagg gtttccttga tgatgtcata cttatcctgt cccttttttt 7080
tccacagctc gcggttgagg acaaactctt cgcggtcttt ccagtactct tggatcggaa 7140
acccgtcggc ctccgaacgg taagagccta gcatgtagaa ctggttgacg gcctggtagg 7200
cgcagcatcc cttttctacg ggtagcgcgt atgcctgcgc ggccttccgg agcgaggtgt 7260
gggtgagcgc aaaggtgtcc ctgaccatga ctttgaggta ctggtatttg aagtcagtgt 7320
cgtcgcatcc gccctgctcc cagagcaaaa agtccgtgcg ctttttggaa cgcggatttg 7380
gcagggcgaa ggtgacatcg ttgaagagta tctttcccgc gcgaggcata aagttgcgtg 7440
tgatgcggaa gggtcccggc acctcggaac ggttgttaat tacctgggcg gcgagcacga 7500
tctcgtcaaa gccgttgatg ttgtggccca caatgtaaag ttccaagaag cgcgggatgc 7560
ccttgatgga aggcaatttt ttaagttcct cgtaggtgag ctcttcaggg gagctgagcc 7620
cgtgctctga aagggcccag tctgcaagat gagggttgga agcgacgaat gagctccaca 7680
ggtcacgggc cattagcatt tgcaggtggt cgcgaaaggt cctaaactgg cgacctatgg 7740
ccattttttc tggggtgatg cagtagaagg taagcgggtc ttgttcccag cggtcccatc 7800
caaggttcgc ggctaggtct cgcgcggcag tcactagagg ctcatctccg ccgaacttca 7860
tgaccagcat gaagggcacg agctgcttcc caaaggcccc catccaagta taggtctcta 7920
catcgtaggt gacaaagaga cgctcggtgc gaggatgcga gccgatcggg aagaactgga 7980
tctcccgcca ccaattggag gagtggctat tgatgtggtg aaagtagaag tccctgcgac 8040
gggccgaaca ctcgtgctgg cttttgtaaa aacgtgcgca gtactggcag cggtgcacgg 8100
gctgtacatc ctgcacgagg ttgacctgac gaccgcgcac aaggaagcag agtgggaatt 8160
tgagcccctc gcctggcggg tttggctggt ggtcttctac ttcggctgct tgtccttgac 8220
cgtctggctg ctcgagggga gttacggtgg atcggaccac cacgccgcgc gagcccaaag 8280
tccagatgtc cgcgcgcggc ggtcggagct tgatgacaac atcgcgcaga tgggagctgt 8340
ccatggtctg gagctcccgc ggcgtcaggt caggcgggag ctcctgcagg tttacctcgc 8400
atagacgggt cagggcgcgg gctagatcca ggtgatacct aatttccagg ggctggttgg 8460
tggcggcgtc gatggcttgc aagaggccgc atccccgcgg cgcgactacg gtaccgcgcg 8520
gcgggcggtg ggccgcgggg gtgtccttgg atgatgcatc taaaagcggt gacgcgggcg 8580
agcccccgga ggtagggggg gctccggacc cgccgggaga gggggcaggg gcacgtcggc 8640
gccgcgcgcg ggcaggagct ggtgctgcgc gcgtaggttg ctggcgaacg cgacgacgcg 8700
gcggttgatc tcctgaatct ggcgcctctg cgtgaagacg acgggcccgg tgagcttgag 8760
cctgaaagag agttcgacag aatcaatttc ggtgtcgttg acggcggcct ggcgcaaaat 8820
ctcctgcacg tctcctgagt tgtcttgata ggcgatctcg gccatgaact gctcgatctc 8880
ttcctcctgg agatctccgc gtccggctcg ctccacggtg gcggcgaggt cgttggaaat 8940
gcgggccatg agctgcgaga aggcgttgag gcctccctcg ttccagacgc ggctgtagac 9000
cacgcccccct tcggcatcgc gggcgcgcat gaccacctgc gcgagattga gctccacgtg 9060
ccgggcgaag acggcgtagt ttcgcaggcg ctgaaagagg tagttgaggg tggtggcggt 9120
gtgttctgcc acgaagaagt acataaccca gcgtcgcaac gtggattcgt tgatatcccc 9180
caaggcctca aggcgctcca tggcctcgta gaagtccacg gcgaagttga aaaactggga 9240
gttgcgcgcc gacacggtta actcctcctc cagaagacgg atgagctcgg cgacagtgtc 9300
gcgcacctcg cgctcaaagg ctacaggggc ctcttcttct tcttcaatct cctcttccat 9360
aagggcctcc ccttcttctt cttctggcgg cggtggggga gggggacac ggcggcgacg 9420
acggcgcacc gggaggcggt cgacaaagcg ctcgatcatc tccccgcggc gacggcgcat 9480
ggtctcggtg acggcgcggc cgttctcgcg gggggcgcagt tggaagacgc cgcccgtcat 9540
gtcccggtta tgggttggcg gggggctgcc atgcggcagg gatacggcgc taacgatgca 9600
tctcaacaat tgttgtgtag gtactccgcc gccgagggac ctgagcgagt ccgcatcgac 9660
cggatcggaa aacctctcga gaaaggcgtc taaccagtca cagtcgcaag gtaggctgag 9720
caccgtggcg ggcggcagcg ggcggcggtc ggggttgttt ctggcggagg tgctgctgat 9780
gatgtaatta aagtaggcgg tcttgagacg gcggatggtc gacagaagca ccatgtcctt 9840
gggtccggcc tgctgaatgc gcaggcggtc ggccatgccc caggcttcgt tttgacatcg 9900
gcgcaggtct ttgtagtagt cttgcatgag cctttctacc ggcacttctt cttctccttc 9960
ctcttgtcct gcatctcttg catctatcgc tgcggcggcg gcggagtttg gccgtaggtg 10020

```
gcgccctctt cctcccatgc gtgtgacccc gaagcccctc atcggctgaa gcagggctag  10080
gtcggcgaca acgcgctcgg ctaatatggc ctgctgcacc tgcgtgaggg tagactggaa  10140
gtcatccatg tccacaaagc ggtggtatgc gcccgtgttg atggtgtaag tgcagttggc  10200
cataacggac cagttaacgg tctggtgacc cggctgcgag agctcggtgt acctgagacg  10260
cgagtaagcc ctcgagtcaa atacgtagtc gttgcaagtc cgcaccaggt actggtatcc  10320
caccaaaaag tgcggcggcg gctggcggta gaggggccag cgtagggtgg ccggggctcc  10380
gggggcgaga tcttccaaca taaggcgatg atatccgtag atgtacctgg acatccaggt  10440
gatgccggcg gcggtggtgg aggcgcgcgg aaagtcgcgg acgcggttcc agatgttgcg  10500
cagcggcaaa aagtgctcca tggtcgggac gctctggccg gtcaggcgcg cgcaatcgtt  10560
gacgctctag accgtgcaaa aggagagcct gtaagcgggc actcttccgt ggtctggtgg  10620
ataaattcgc aagggtatca tggcggacga ccggggttcg agccccgtat ccggccgtcc  10680
gccgtgatcc atgcggttac cgcccgcgtg tcgaacccag gtgtgcgacg tcagacaacg  10740
ggggagtgct ccttttggct tccttccagg cgcggcggct gctgcgctag cttttttggc  10800
cactggccgc gcgcagcgta agcggttagg ctggaaagcg aaagcattaa gtggctcgct  10860
ccctgtagcc ggagggttat ttttccaaggg ttgagtcgcg ggacccccgg ttcgagtctc  10920
ggaccggccg gactgcggcg aacgggggtt tgcctccccg tcatgcaaga ccccgcttgc  10980
aaattcctcc ggaaacaggg acgagcccct tttttgcttt tcccagatgc atccggtgct  11040
gcggcagatg cgcccccctc ctcagcagcg gcaagagcaa gagcagcggc agacatgcag  11100
ggcaccctcc cctcctccta ccgcgtcagg aggggcgaca tccgcggttg acgcggcagc  11160
agatggtgat tacgaacccc cgcggcgccg ggcccggcac tacctggact tggaggaggg  11220
cgagggcctg gcgcggctag gagcgccctc tcctgagcgg tacccaaggg tgcagctgaa  11280
gcgtgatacg cgtgaggcgt acgtgccgcg gcagaacctg tttcgcgacc gcgagggaga  11340
ggagcccgag gagatgcggg atcgaaagtt ccacgcaggg cgcgagctgc ggcatggcct  11400
gaatcgcgag cggttgctgc gcgaggagga ctttgagccc gacgcgcgaa ccgggattag  11460
tcccgcgcgc gcacacgtgg cggccgccga cctggtaacc gcatacgagc agacggtgaa  11520
ccaggagatt aactttcaaa aaagctttaa caaccacgtg cgtacgcttg tggcgcgcga  11580
ggaggtggct ataggactga tgcatctgtg ggactttgta agcgcgctgg agcaaaaccc  11640
aaatagcaag ccgctcatgg cgcagctgtt ccttatagtg cagcacagca gggacaacga  11700
ggcattcagg gatgcgctgc taaacatagt agagcccgag ggccgctggc tgctcgattt  11760
gataaacatc ctgcagagca tagtggtgca ggagcgcagc ttgagcctgg ctgacaaggt  11820
ggccgccatc aactattcca tgcttagcct gggcaagttt tacgcccgca agatatacca  11880
taccccttac gttcccatag acaaggaggt aaagatcgag gggttctaca tgcgcatggc  11940
gctgaaggtg cttaccttga gcgacgacct gggcgtttat cgcaacgagc gcatccacaa  12000
ggccgtgagc gtgagccggc ggcgcgagct cagcgaccgc gagctgatgc acagcctgca  12060
aagggccctg gctggcacgg gcagcggcga tagagaggcc gagtcctact ttgacgcggg  12120
cgctgacctg cgctgggccc caagccgacg cgccctggag gcagctgggg ccggacctgg  12180
gctggcggtg gcacccgcgc gcgctggcaa cgtcggcggc gtggaggaat atgacgagga  12240
cgatgagtac gagccagagg acggcgagta ctaagcggtg atgtttctga tcagatgatg  12300
caagacgcaa cggacccggc ggtgcgggcg gcgctgcaga gccagccgtc cggccttaac  12360
tccacggacg actggcgcca ggtcatggac cgcatcatgt cgctgactgc gcgcaatcct  12420
```

-continued

```
gacgcgttcc ggcagcagcc gcaggccaac cggctctccg caattctgga agcggtggtc  12480
ccggcgcgcg caaaccccac gcacgagaag gtgctggcga tcgtaaacgc gctggccgaa  12540
aacagggcca tccggcccga cgaggccggc ctggtctacg acgcgctgct tcagcgcgtg  12600
gctcgttaca acagcggcaa cgtgcagacc aacctggacc ggctggtggg ggatgtgcgc  12660
gaggccgtgg cgcagcgtga gcgcgcgcag cagcagggca acctgggctc catggttgca  12720
ctaaacgcct tcctgagtac acagcccgcc aacgtgccgc ggggacagga ggactacacc  12780
aactttgtga gcgcactgcg gctaatggtg actgagacac cgcaaagtga ggtgtaccag  12840
tctgggccag actatttttt ccagaccagt agacaaggcc tgcagaccgt aaacctgagc  12900
caggctttca aaaacttgca ggggctgtgg ggggtgcggg ctcccacagg cgaccgcgcg  12960
accgtgtcta gcttgctgac gcccaactcg cgcctgttgc tgctgctaat agcgcccttc  13020
acggacagtg gcagcgtgtc ccgggacaca tacctaggtc acttgctgac actgtaccgc  13080
gaggccatag gtcaggcgca tgtggacgag catactttcc aggagattac aagtgtcagc  13140
cgcgcgctgg ggcaggagga cacgggcagc ctggaggcaa ccctaaacta cctgctgacc  13200
aaccggcggc agaagatccc ctcgttgcac agtttaaaca gcgaggagga gcgcattttg  13260
cgctacgtgc agcagagcgt gagccttaac ctgatgcgcg acggggtaac gcccagcgtg  13320
gcgctggaca tgaccgcgcg caacatggaa ccgggcatgt atgcctcaaa ccggccgttt  13380
atcaaccgcc taatggacta cttgcatcgc gcggccgccg tgaaccccga gtatttcacc  13440
aatgccatct tgaacccgca ctggctaccg ccccctggtt tctacaccgg gggattcgag  13500
gtgcccgagg gtaacgatgg attcctctgg gacgacatag acgacagcgt gttttccccg  13560
caaccgcaga ccctgctaga gttgcaacag cgcgagcagg cagaggcggc gctgcgaaag  13620
gaaagcttcc gcaggccaag cagcttgtcc gatctaggcg ctgcggcccc gcggtcagat  13680
gctagtagcc catttccaag cttgataggg tctcttacca gcactcgcac cacccgcccg  13740
cgcctgctgg gcgaggagga gtacctaaac aactcgctgc tgcagccgca gcgcgaaaaa  13800
aacctgcctc cggcatttcc caacaacggg atagagagcc tagtggacaa gatgagtaga  13860
tggaagacgt acgcgcagga gcacagggac gtgccaggcc cgcgcccgcc cacccgtcgt  13920
caaaggcacg accgtcagcg gggtctggtg tgggaggacg atgactcggc agacgacagc  13980
agcgtcctgg atttgggagg gagtggcaac ccgtttgcgc accttcgccc caggctgggg  14040
agaatgtttt aaaaaaaaaa aagcatgatg caaaataaaa aactcaccaa ggccatggca  14100
ccgagcgttg gttttcttgt attcccctta gtatgcggcg cgcggcgatg tatgaggaag  14160
gtcctcctcc ctcctacgag agtgtggtga gcgcggcgcc agtggcggcg gcgctgggtt  14220
ctcccttcga tgctcccctg gacccgccgt ttgtgcctcc gcggtacctg cggcctaccg  14280
gggggagaaa cagcatccgt tactctgagt tggcacccct attcgacacc acccgtgtgt  14340
acctggtgga caacaagtca acggatgtgg catccctgaa ctaccagaac gaccacagca  14400
actttctgac cacggtcatt caaaacaatg actacagccc gggggaggca agcacacaga  14460
ccatcaatct tgacgaccgg tcgcactggg gcggcgacct gaaaaccatc ctgcatacca  14520
acatgccaaa tgtgaacgag ttcatgttta ccaataagtt taaggcgcgg gtgatggtgt  14580
cgcgcttgcc tactaaggac aatcaggtgg agctgaaata cgagtgggtg gagttcacgc  14640
tgcccgaggg caactactcc gagaccatga ccatagacct tatgaacaac gcgatcgtgg  14700
agcactactt gaaagtgggc agacagaacg gggttctgga aagcgacatc ggggtaaagt  14760
```

-continued

```
ttgacacccg caacttcaga ctggggtttg accccgtcac tggtcttgtc atgcctgggg  14820
tatatacaaa cgaagccttc catccagaca tcattttgct gccaggatgc ggggtggact  14880
tcacccacag ccgcctgagc aacttgttgg gcatccgcaa gcggcaaccc ttccaggagg  14940
gctttaggat cacctacgat gatctggagg gtggtaacat tcccgcactg ttggatgtgg  15000
acgcctacca ggcgagcttg aaagatgaca ccgaacaggg cgggggtggc gcaggcggca  15060
gcaacagcag tggcagcggc gcggaagaga actccaacgc ggcagccgcg gcaatgcagc  15120
cggtggagga catgaacgat catgccattc gcggcgacac ctttgccaca cgggctgagg  15180
agaagcgcgc tgaggccgaa gcagcggccg aagctgccgc ccccgctgcg caacccgagg  15240
tcgagaagcc tcagaagaaa ccggtgatca aacccctgac agaggacagc aagaaacgca  15300
gttacaacct aataagcaat gacagcacct tcacccagta ccgcagctgg taccttgcat  15360
acaactacgg cgaccctcag accggaatcc gctcatggac cctgctttgc actcctgacg  15420
taacctgcgg ctcggagcag gtctactggt cgttgccaga catgatgcaa gaccccgtga  15480
ccttccgctc cacgcgccag atcagcaact ttccggtggt gggcgccgag ctgttgcccg  15540
tgcactccaa gagcttctac aacgaccagg ccgtctactc ccaactcatc cgccagttta  15600
cctctctgac ccacgtgttc aatcgctttc ccgagaacca gattttggcg cgcccgccag  15660
cccccaccat caccaccgtc agtgaaaacg ttcctgctct cacagatcac gggacgctac  15720
cgctgcgcaa cagcatcgga ggagtccagc gagtgaccat tactgacgcc agacgccgca  15780
cctgccccta cgtttacaag gccctgggca tagtctcgcc gcgcgtccta tcgagccgca  15840
ctttttgagc aagcatgtcc atccttatat cgcccagcaa taacacaggc tggggcctgc  15900
gcttcccaag caagatgttt ggcggggcca agaagcgctc cgaccaacac ccagtgcgcg  15960
tgcgcgggca ctaccgcgcg ccctggggcg cgcacaaacg cggccgcact gggcgcacca  16020
ccgtcgatga cgccatcgac gcggtggtgg aggaggcgcg caactacacg cccacgccgc  16080
caccagtgtc cacagtggac gcggccattc agaccgtggt gcgcggagcc cggcgctatg  16140
ctaaaatgaa gagacggcgg aggcgcgtag cacgtcgcca ccgccgccga cccggcactg  16200
ccgcccaacg cgcggcggcg gccctgctta accgcgcacg tcgcaccggc cgacgggcgg  16260
ccatgcgggc cgctcgaagg ctggccgcgg gtattgtcac tgtgcccccc aggtccaggc  16320
gacgagcggc cgccgcagca gccgcggcca ttagtgctat gactcagggt cgcaggggca  16380
acgtgtattg ggtgcgcgac tcggttagcg gcctgcgcgt gcccgtgcgc acccgccccc  16440
cgcgcaacta gattgcaaga aaaaactact tagactcgta ctgttgtatg tatccagcgg  16500
cggcggcgcg caacgaagct atgtccaagc gcaaaatcaa agaagagatg ctccaggtca  16560
tcgcgccgga gatctatggc cccccgaaga aggaagagca ggattacaag ccccgaaagc  16620
taaagcgggt caaaaagaaa aagaaagatg atgatgatga acttgacgac gaggtggaac  16680
tgctgcacgc taccgcgccc aggcgacggg tacagtggaa aggtcgacgc gtaaaacgtg  16740
ttttgcgacc cggcaccacc gtagtcttta cgcccggtga gcgctccacc cgcacctaca  16800
agcgcgtgta tgatgaggtg tacggcgacg aggacctgct tgagcaggcc aacgagcgcc  16860
tcggggagtt tgcctacgga aagcggcata aggacatgct ggcgttgccg ctggacgagg  16920
gcaacccaac acctagccta aagcccgtaa cactgcagca ggtgctgccc gcgcttgcac  16980
cgtccgaaga aaagcgcggc ctaaagcgcg agtctggtga cttggcaccc accgtgcagc  17040
tgatggtacc caagcgccag cgactggaag atgtcttgga aaaaatgacc gtggaacctg  17100
ggctggagcc cgaggtccgc gtgcggccaa tcaagcaggt ggcgccggga ctgggcgtgc  17160
```

```
agaccgtgga cgttcagata cccactacca gtagcaccag tattgccacc gccacagagg  17220
gcatggagac acaaacgtcc ccggttgcct cagcggtggc ggatgccgcg gtgcaggcgg  17280
tcgctgcggc cgcgtccaag acctctacgg aggtgcaaac ggacccgtgg atgtttcgcg  17340
tttcagcccc ccggcgcccg cgcggttcga ggaagtacgg cgccgccagc gcgctactgc  17400
ccgaatatgc cctacatcct tccattgcgc ctacccccgg ctatcgtggc tacacctacc  17460
gccccagaag acgagcaact acccgacgcc gaaccaccac tggaacccgc cgccgccgtc  17520
gccgtcgcca gcccgtgctg gccccgattt ccgtgcgcag ggtggctcgc gaaggaggca  17580
ggaccctggt gctgccaaca gcgcgctacc accccagcat cgtttaaaag ccggtctttg  17640
tggttcttgc agatatggcc ctcacctgcc gcctccgttt cccggtgccg ggattccgag  17700
gaagaatgca ccgtaggagg ggcatggccg gccacggcct gacgggcggc atgcgtcgtg  17760
cgcaccaccg gcggcggcgc gcgtcgcacc gtcgcatgcg cggcggtatc ctgcccctcc  17820
ttattccact gatcgccgcg gcgattggcg ccgtgcccgg aattgcatcc gtggccttgc  17880
aggcgcagag acactgatta aaaacaagtt gcatgtggaa aaatcaaaat aaaaagtctg  17940
gactctcacg ctcgcttggt cctgtaacta ttttgtagaa tggaagacat caactttgcg  18000
tctctggccc cgcgacacgg ctcgcgcccg ttcatgggaa actggcaaga tatcggcacc  18060
agcaatatga gcggtggcgc cttcagctgg ggctcgctgt ggagcggcat taaaaatttc  18120
ggttccaccg ttaagaacta tggcagcaag gcctggaaca gcagcacagg ccagatgctg  18180
agggataagt tgaaagagca aaatttccaa caaaaggtgg tagatggcct ggcctctggc  18240
attagcgggg tggtggacct ggccaaccag gcagtgcaaa ataagattaa cagtaagctt  18300
gatccccgcc ctcccgtaga ggagcctcca ccggccgtgg agacagtgtc tccagagggg  18360
cgtggcgaaa agcgtccgcg ccccgacagg gaagaaactc tggtgacgca aatagacgag  18420
cctccctcgt acgaggaggc actaaagcaa ggcctgccca ccacccgtcc catcgcgccc  18480
atggctaccg gagtgctggg ccagcacaca cccgtaacgc tggacctgcc tccccccgcc  18540
gacacccagc agaaacctgt gctgccaggc ccgaccgccg ttgttgtaac ccgtcctagc  18600
cgcgcgtccc tgcgccgcgc cgccagcggt ccgcgatcgt tgcggcccgt agccagtggc  18660
aactggcaaa gcacactgaa cagcatcgtg ggtctggggg tgcaatccct gaagcgccga  18720
cgatgcttct gaatagctaa cgtgtcgtat gtgtgtcatg tatgcgtcca tgtcgccgcc  18780
agaggagctg ctgagccgcc gcgcgcccgc tttccaagat ggctacccct tcgatgatgc  18840
cgcagtggtc ttacatgcac atctcgggcc aggacgcctc ggagtacctg agccccgggc  18900
tggtgcagtt tgcccgcgcc accgagacgt acttcagcct gaataacaag tttagaaacc  18960
ccacggtggc gcctacgcac gacgtgacca cagaccggtc ccagcgtttg acgctgcggt  19020
tcatccctgt ggaccgtgag gatactgcgt actcgtacaa ggcgcggttc accctagctg  19080
tgggtgataa ccgtgtgctg gacatggctt ccacgtactt tgacatccgc ggcgtgctgg  19140
acaggggccc tacttttaag ccctactctg gcactgccta caacgccctg gctcccaagg  19200
gtgccccaaa tccttgcgaa tgggatgaag ctgctactgc tcttgaaata aacctagaag  19260
aagaggacga tgacaacgaa gacgaagtag acgagcaagc tgagcagcaa aaaactcacg  19320
tatttgggca ggcgccttat tctggtataa atattacaaa ggagggtatt caaataggtg  19380
tcgaaggtca aacacctaaa tatgccgata aaacatttca acctgaacct caaataggag  19440
aatctcagtg gtacgaaact gaaattaatc atgcagctgg gagagtcctt aaaaagacta  19500
```

```
ccccaatgaa accatgttac ggttcatatg caaaacccac aaatgaaaat ggagggcaag  19560
gcattcttgt aaagcaacaa aatggaaagc tagaaagtca agtggaaatg caatttttct  19620
caactactga ggcgaccgca ggcaatggtg ataacttgac tcctaaagtg gtattgtaca  19680
gtgaagatgt agatatagaa accccagaca ctcatatttc ttacatgccc actattaagg  19740
aaggtaactc acgagaacta atgggccaac aatctatgcc caacaggcct aattacattg  19800
cttttaggga caattttatt ggtctaatgt attacaacag cacgggtaat atgggtgttc  19860
tggcgggcca agcatcgcag ttgaatgctg ttgtagattt gcaagacaga aacacagagc  19920
tttcatacca gcttttgctt gattccattg gtgatagaac caggtacttt tctatgtgga  19980
atcaggctgt tgacagctat gatccagatg ttagaattat tgaaaatcat ggaactgaag  20040
atgaacttcc aaattactgc tttccactgg gaggtgtgat taatacagag actcttacca  20100
aggtaaaacc taaaacaggt caggaaaatg gatgggaaaa agatgctaca gaattttcag  20160
ataaaaatga aataagagtt ggaaataatt ttgccatgga aatcaatcta aatgccaacc  20220
tgtggagaaa tttcctgtac tccaacatag cgctgtattt gcccgacaag ctaaagtaca  20280
gtccttccaa cgtaaaaatt tctgataacc caaacaccta cgactacatg aacaagcgag  20340
tggtggctcc cgggttagtg gactgctaca ttaaccttgg agcacgctgg tcccttgact  20400
atatggacaa cgtcaaccca tttaaccacc accgcaatgc tggcctgcgc taccgctcaa  20460
tgttgctggg caatggtcgc tatgtgccct tccacatcca ggtgcctcag aagttctttg  20520
ccattaaaaa cctccttctc ctgccgggct catacaccta cgagtggaac ttcaggaagg  20580
atgttaacat ggttctgcag agctccctag gaaatgacct aagggttgac ggagccagca  20640
ttaagtttga tagcatttgc ctttacgcca ccttcttccc catggcccac aacaccgcct  20700
ccacgcttga ggccatgctt agaaacgaca ccaacgacca gtcctttaac gactatctct  20760
ccgccgccaa catgctctac cctatacccg ccaacgctac caacgtgccc atatccatcc  20820
cctcccgcaa ctgggcggct ttccgcggct gggccttcac gcgccttaag actaaggaaa  20880
ccccatcact gggctcgggc tacgaccctt attacaccta ctctggctct ataccctacc  20940
tagatggaac cttttacctc aaccacacct ttaagaaggt ggccattacc tttgactctt  21000
ctgtcagctg gcctggcaat gaccgcctgc ttacccccaa cgagtttgaa attaagcgct  21060
cagttgacgg ggagggttac aacgttgccc agtgtaacat gaccaaagac tggttcctgg  21120
tacaaatgct agctaactac aacattggct accagggctt ctatatccca gagagctaca  21180
aggaccgcat gtactccttc tttagaaact tccagcccat gagccgtcag gtggtggatg  21240
atactaaata caaggactac caacaggtgg gcatcctaca ccaacacaac aactctggat  21300
ttgttggcta ccttgccccc accatgcgcg aaggacaggc ctaccctgct aacttcccct  21360
atccgcttat aggcaagacc gcagttgaca gcattaccca gaaaaagttt ctttgcgatc  21420
gcaccctttg gcgcatccca ttctccagta actttatgtc catgggcgca ctcacagacc  21480
tgggccaaaa ccttctctac gccaactccg cccacgcgct agacatgact tttgaggtgg  21540
atcccatgga cgagcccacc cttctttatg ttttgtttga agtctttgac gtggtccgtg  21600
tgcaccggcc gcaccgcggc gtcatcgaaa ccgtgtacct gcgcacgccc ttctcggccg  21660
gcaacgccac aacataaaga agcaagcaac atcaacaaca gctgccgcca tgggctccag  21720
tgagcaggaa ctgaaagcca ttgtcaaaga tcttggttgt gggccatatt ttttgggcac  21780
ctatgacaag cgctttccag gctttgtttc tccacacaag ctcgcctgcg ccatagtcaa  21840
tacggccggt cgcgagactg gggcgtaca ctggatggcc tttgcctgga acccgcactc  21900
```

aaaaacatgc tacctctttg agccctttgg cttttctgac cagcgactca agcaggttta 21960
ccagtttgag tacgagtcac tcctgcgccg tagcgccatt gcttcttccc ccgaccgctg 22020
tataacgctg gaaaagtcca cccaaagcgt acaggggccc aactcggccg cctgtggact 22080
attctgctgc atgtttctcc acgcctttgc caactggccc caaactccca tggatcacaa 22140
ccccaccatg aaccttatta ccggggtacc caactccatg ctcaacagtc cccaggtaca 22200
gcccaccctg cgtcgcaacc aggaacagct ctacagcttc ctggagcgcc actcgcccta 22260
cttccgcagc cacagtgcgc agattaggag cgccacttct ttttgtcact tgaaaaacat 22320
gtaaaaataa tgtactagag acactttcaa taaaggcaaa tgcttttatt tgtacactct 22380
cgggtgatta tttaccccca cccttgccgt ctgcgccgtt taaaaatcaa aggggttctg 22440
ccgcgcatcg ctatgcgcca ctggcaggga cacgttgcga tactggtgtt tagtgctcca 22500
cttaaactca ggcacaacca tccgcggcag ctcggtgaag ttttcactcc acaggctgcg 22560
caccatcacc aacgcgttta gcaggtcggg cgccgatatc ttgaagtcgc agttggggcc 22620
tccgccctgc gcgcgcgagt tgcgatacac agggttgcag cactggaaca ctatcagcgc 22680
cgggtggtgc acgctggcca gcacgctctt gtcggagatc agatccgcgt ccaggtcctc 22740
cgcgttgctc agggcgaacg gagtcaactt tggtagctgc cttcccaaaa agggcgcgtg 22800
cccaggcttt gagttgcact cgcaccgtag tggcatcaaa aggtgaccgt gcccggtctg 22860
ggcgttagga tacagcgcct gcataaaagc cttgatctgc ttaaaagcca cctgagcctt 22920
tgcgccttca gagaagaaca tgccgcaaga cttgccggaa aactgattgg ccggacaggc 22980
cgcgtcgtgc acgcagcacc ttgcgtcggt gttggagatc tgcaccacat ttcggcccca 23040
ccggttcttc acgatcttgg ccttgctaga ctgctccttc agcgcgcgct gcccgttttc 23100
gctcgtcaca tccatttcaa tcacgtgctc cttatttatc ataatgcttc cgtgtagaca 23160
cttaagctcg ccttcgatct cagcgcagcg gtgcagccac aacgcgcagc ccgtgggctc 23220
gtgatgcttg taggtcacct ctgcaaacga ctgcaggtac gcctgcagga atcgccccat 23280
catcgtcaca aaggtcttgt tgctggtgaa ggtcagctgc aacccgcggt gctcctcgtt 23340
cagccaggtc ttgcatacgg ccgccagagc ttccacttgg tcaggcagta gtttgaagtt 23400
cgcctttaga tcgttatcca cgtggtactt gtccatcagc gcgcgcgcag cctccatgcc 23460
cttctcccac gcagacacga tcggcacact cagcgggttc atcaccgtaa tttcactttc 23520
cgcttcgctg ggctcttcct cttcctcttg cgtccgcata ccacgcgcca ctgggtcgtc 23580
ttcattcagc cgccgcactg tgcgcttacc tcctttgcca tgcttgatta gcaccggtgg 23640
gttgctgaaa cccaccattt gtagcgccac atcttctctt tcttcctcgc tgtccacgat 23700
tacctctggt gatggcgggc gctcgggctt gggagaaggg cgcttctttt tcttcttggg 23760
cgcaatggcc aaatccgccg ccgaggtcga tggccgcggg ctgggtgtgc gcggcaccag 23820
cgcgtcttgt gatgagtctt cctcgtcctc ggactcgata cgccgcctca tccgcttttt 23880
tgggggcgcc cggggaggcg gcggcgacgg ggacggggac gacacgtcct ccatggttgg 23940
gggacgtcgc gccgcaccgc gtccgcgctc gggggtggtt tcgcgctgct cctcttcccg 24000
actggccatt tccttctcct ataggcagaa aaagatcatg gagtcagtcg agaagaagga 24060
cagcctaacc gccccctctg agttcgccac caccgcctcc accgatgccg ccaacgcgcc 24120
taccaccttc cccgtcgagg cacccccgct tgaggaggag gaagtgatta tcgagcagga 24180
cccaggtttt gtaagcgaag acgacgagga ccgctcagta ccaacagagg ataaaaagca 24240

-continued

```
agaccaggac aacgcagagg caaacgagga acaagtcggg cgggggggacg aaaggcatgg  24300
cgactaccta gatgtgggag acgacgtgct gttgaagcat ctgcagcgcc agtgcgccat  24360
tatctgcgac gcgttgcaag agcgcagcga tgtgcccctc gccatagcgg atgtcagcct  24420
tgcctacgaa cgccacctat tctcaccgcg cgtacccccc aaacgccaag aaaacggcac  24480
atgcgagccc aacccgcgcc tcaacttcta ccccgtattt gccgtgccag aggtgcttgc  24540
cacctatcac atctttttcc aaaactgcaa gataccccta tcctgccgtg ccaaccgcag  24600
ccgagcggac aagcagctgg ccttgcggca gggcgctgtc atacctgata tcgcctcgct  24660
caacgaagtg ccaaaaatct ttgagggtct tggacgcgac gagaagcgcg cggcaaacgc  24720
tctgcaacag gaaaacagcg aaaatgaaag tcactctgga gtgttggtgg aactcgaggg  24780
tgacaacgcg cgcctagccg tactaaaacg cagcatcgag gtcacccact ttgcctaccc  24840
ggcacttaac ctacccccca aggtcatgag cacagtcatg agtgagctga tcgtgcgccg  24900
tgcgcagccc ctggagaggg atgcaaattt gcaagaacaa acagaggagg gcctacccgc  24960
agttggcgac gagcagctag cgcgctggct tcaaacgcgc gagcctgccg acttggagga  25020
gcgacgcaaa ctaatgatgg ccgcagtgct cgttaccgtg gagcttgagt gcatgcagcg  25080
gttctttgct gacccggaga tgcagcgcaa gctagaggaa acattgcact acacctttcg  25140
acagggctac gtacgccagg cctgcaagat ctccaacgtg gagctctgca acctggtctc  25200
ctaccttgga attttgcacg aaaaccgcct tgggcaaaac gtgcttcatt ccacgctcaa  25260
gggcgaggcg cgccgcgact acgtccgcga ctgcgtttac ttatttctat gctacacctg  25320
gcagacggcc atgggcgttt ggcagcagtg cttggaggag tgcaacctca aggagctgca  25380
gaaactgcta aagcaaaact tgaaggacct atggacggcc ttcaacgagc gctccgtggc  25440
cgcgcacctg gcggacatca ttttccccga acgcctgctt aaaaccctgc aacagggtct  25500
gccagacttc accagtcaaa gcatgttgca gaactttagg aactttatcc tagagcgctc  25560
aggaatcttg cccgccacct gctgtgcact tcctagcgac tttgtgccca ttaagtaccg  25620
cgaatgccct ccgccgcttt ggggccactg ctaccttctg cagctagcca actaccttgc  25680
ctaccactct gacataatgg aagacgtgag cggtgacggt ctactggagt gtcactgtcg  25740
ctgcaaccta tgcaccccgc accgctccct ggtttgcaat tcgcagctgc ttaacgaaag  25800
tcaaattatc ggtacctttg agctgcaggg tccctcgcct gacgaaaagt ccgcggctcc  25860
ggggttgaaa ctcactccgg ggctgtggac gtcggcttac cttcgcaaat ttgtacctga  25920
ggactaccac gcccacgaga ttaggttcta cgaagaccaa tcccgcccgc caaatgcgga  25980
gcttaccgcc tgcgtcatta cccagggcca cattcttggc caattgcaag ccatcaacaa  26040
agcccgccaa gagtttctgc tacgaaaggg acgggggggtt tacttggacc cccagtccgg  26100
cgaggagctc aacccaatcc ccccgccgcc gcagccctat cagcagcagc cgcgggccct  26160
tgcttcccag gatggcaccc aaaaagaagc tgcagctgcc gccgccaccc acggacgagg  26220
aggaatactg ggacagtcag gcagaggagg ttttggacga ggaggaggag gacatgatgg  26280
aagactggga gagcctagac gaggaagctt ccgaggtcga agaggtgtca gacgaaacac  26340
cgtcaccctc ggtcgcattc ccctcgccgg cgccccagaa atcggcaacc ggttccagca  26400
tggctacaac ctccgctcct caggcgccgc cggcactgcc cgttcgccga cccaaccgta  26460
gatgggacac cactggaacc agggccggta agtccaagca gccgccgccg ttagcccaag  26520
agcaacaaca gcgccaaggc taccgctcat ggcgcgggca caagaacgcc atagttgctt  26580
gcttgcaaga ctgtgggggc aacatctcct tcgcccgccg ctttcttctc taccatcacg  26640
```

gcgtggcctt cccccgtaac atcctgcatt actaccgtca tctctacagc ccatactgca 26700
ccggcggcag cggcagcggc agcaacagca gcggccacac agaagcaaag gcgaccggat 26760
agcaagactc tgacaaagcc caagaaatcc acagcggcgg cagcagcagg aggaggagcg 26820
ctgcgtctgg cgcccaacga acccgtatcg acccgcgagc ttagaaacag gatttttccc 26880
actctgtatg ctatatttca acagagcagg ggccaagaac aagagctgaa aataaaaaac 26940
aggtctctgc gatccctcac ccgcagctgc ctgtatcaca aaagcgaaga tcagcttcgg 27000
cgcacgctgg aagacgcgga ggctctcttc agtaaatact gcgcgctgac tcttaaggac 27060
tagtttcgcg ccctttctca aatttaagcg cgaaaactac gtcatctcca gcggccacac 27120
ccggcgccag cacctgtcgt cagcgccatt atgagcaagg aaattcccac gccctacatg 27180
tggagttacc agccacaaat gggacttgcg gctggagctg cccaagacta ctcaacccga 27240
ataaactaca tgagcgcggg accccacatg atatcccggg tcaacggaat ccgcgcccac 27300
cgaaaccgaa ttctcttgga acaggcggct attaccacca cacctcgtaa taaccttaat 27360
ccccgtagtt ggcccgctgc cctggtgtac caggaaagtc ccgctcccac cactgtggta 27420
cttcccagag acgcccaggc cgaagttcag atgactaact caggggcgca gcttgcgggc 27480
ggctttcgtc acagggtgcg gtcgcccggg cagggtataa ctcacctgac aatcagaggg 27540
cgaggtattc agctcaacga cgagtcggtg agctcctcgc ttggtctccg tccggacggg 27600
acatttcaga tcggcggcgc cggccgctct tcattcacgc ctcgtcaggc aatcctaact 27660
ctgcagacct cgtcctctga gccgcgctct ggaggcattg gaactctgca atttattgag 27720
gagtttgtgc catcggtcta ctttaacccc ttctcgggac ctcccggcca ctatccggat 27780
caatttattc ctaactttga cgcggtaaag gactcggcgg atggctacga ctgaatgtta 27840
agtggagagg cagagcaact gcgcctgaaa cacctggtcc actgtcgccg ccacaagtgc 27900
tttgcccgcg actccggtga gttttgctac tttgaattgc ccgaggatca tatcgagggc 27960
ccggcgcacg gcgtccggct taccgcccag ggagagcttg cccgtagcct gattcgggag 28020
tttacccagc gcccccctgct agttgagcgg gacaggggac cctgtgttct cactgtgatt 28080
tgcaactgtc ctaaccctgg attacatcaa gatctttgtt gccatctctg tgctgagtat 28140
aataaataca gaaattaaaa tatactgggg ctcctatcgc catcctgtaa acgccaccgt 28200
cttcacccgc ccaagcaaac caaggcgaac cttacctggt acttttaaca tctctccctc 28260
tgtgatttac aacagtttca acccagacgg agtgagtcta cgagagaacc tctccgagct 28320
cagctactcc atcagaaaaa acaccaccct ccttacctgc cgggaacgta cgacctaggg 28380
ataacagggt aataagcaat tgactctatg tgggatatgc tccagcgcta caaccttgaa 28440
gtcaggcttc ctggatgtca gcatctgact ttggccagca cctgtcccgc ggatttgttc 28500
cagtccaact acagcgaccc accctaacag agatgaccaa cacaaccaac gcggccgccg 28560
ctaccggact tacatctacc acaaatacac cccaagtttc tgcctttgtc aataactggg 28620
ataacttggg catgtggtgg ttctccatag cgcttatgtt tgtatgcctt attattatgt 28680
ggctcatctg ctgcctaaag cgcaaacgcg cccgaccacc catctatagt cccatcattg 28740
tgctacaccc aaacaatgat ggaatccata gattggacgg actgaaacac atgttctttt 28800
ctcttacagt atgattaaat gagacatgat tcctcgagtt tttatattac tgacccttgt 28860
tgcgcttttt tgtgcgtgct ccacattggc tgcggtttct cacatcgaag tagactgcat 28920
tccagccttc acagtctatt tgctttacgg atttgtcacc ctcacgctca tctgcagcct 28980
catcactgtg gtcatcgcct ttatccagtg cattgactgg gtctgtgtgc gctttgcata 29040
tctcagacac catccccagt acagggacag gactatagct gagcttctta gaattcttta 29100
attatgaaat ttactgtgac ttttctgctg attatttgca ccctatctgc gttttgttcc 29160
ccgacctcca agcctcaaag acatatatca tgcagattca ctcgtatatg gaatattcca 29220
agttgctaca atgaaaaaag cgatctttcc gaagcctggt tatatgcaat catctctgtt 29280
atggtgttct gcagtaccat cttagcccta gctatatatc cctaccttga cattggctgg 29340
aaacgaatag atgccatgaa ccacccaact ttccccgcgc ccgctatgct tccactgcaa 29400
caagttgttg ccggcggctt tgtcccagcc aatcagcctc gccccacttc tcccaccccc 29460
actgaaatca gctactttaa tctaacagga ggagatgact gacaccctag atctagaaat 29520
ggacggaatt attacagagc agcgcctgct agaaagacgc agggcagcgg ccgagcaaca 29580
gcgcatgaat caagagctcc aagacatggt taacttgcac cagtgcaaaa ggggtatctt 29640
ttgtctggta aagcaggcca aagtcaccta cgacagtaat accaccggac accgccttag 29700
ctacaagttg ccaaccaagc gtcagaaatt ggtggtcatg gtgggagaaa agcccattac 29760
cataactcag cactcggtag aaaccgaagg ctgcattcac tcaccttgtc aaggacctga 29820
ggatctctgc acccttatta agaccctgtg cggtctcaaa gatcttattc cctttaacta 29880
ataaaaaaaa ataataaagc atcacttact taaaatcagt tagcaaattt ctgtccagtt 29940
tattcagcag cacctccttg ccctcctccc agctctggta ttgcagcttc ctcctggctg 30000
caaactttct ccacaatcta aatggaatgt cagtttcctc ctgttcctgt ccatccgcac 30060
ccactatctt catgttgttg cagatgaagc gcgcaagacc gtctgaagat accttcaacc 30120
ccgtgtatcc atatgacacg gaaaccggtc ctccaactgt gccttttctt actcctccct 30180
ttgtatcccc caatgggttt caagagagtc cccctggggt actctctttg cgcctatccg 30240
aacctctagt tacctccaat ggcatgcttg cgctcaaaat gggcaacggc ctctctctgg 30300
acgaggccgg caaccttacc tcccaaaatg taaccactgt gagcccacct ctcaaaaaaa 30360
ccaagtcaaa cataaacctg gaaatatctg cacccctcac agttacctca gaagccctaa 30420
ctgtggctgc cgccgcacct ctaatggtcg cgggcaacac actcaccatg caatcacagg 30480
ccccgctaac cgtgcacgac tccaaactta gcattgccac ccaaggaccc ctcacagtgt 30540
cagaaggaaa gctagccctg caaacatcag gcccccctcac caccaccgat agcagtaccc 30600
ttactatcac tgcctcaccc cctctaacta ctgccactgg tagcttgggc attgacttga 30660
aagagcccat ttatacacaa aatggaaaac taggactaaa gtacggggct cctttgcatg 30720
taacagacga cctaaacact ttgaccgtag caactggtcc aggtgtgact attaataata 30780
cttccttgca aactaaagtt actggagcct tgggttttga ttcacaaggc aatatgcaac 30840
ttaatgtagc aggaggacta aggattgatt ctcaaaacag acgccttata cttgatgtta 30900
gttatccgtt tgatgctcaa aaccaactaa atctaagact aggacagggc cctcttttta 30960
taaactcagc ccacaacttg gatattaact acaacaaagg cctttacttg tttacagctt 31020
caaacaattc caaaaagctt gaggttaacc taagcactgc caaggggttg atgtttgacg 31080
ctacagccat agccattaat gcaggagatg ggcttgaatt tggttcacct aatgcaccaa 31140
acacaaatcc cctcaaaaca aaaattggcc atggcctaga atttgattca aacaaggcta 31200
tggttcctaa actaggaact ggccttagtt ttgacagcac aggtgccatt acagtaggaa 31260
acaaaaataa tgataagcta accctatgga caggtccaaa accagaagcc aactgcataa 31320
ttgaatacgg gaaacaaaac ccagatagca aactaacttt aatccttgta aaaaatggag 31380

-continued

```
gaattgttaa tggatatgta acgctaatgg gagcctcaga ctacgttaac accttattta  31440
aaaacaaaaa tgtctccatt aatgtagaac tatactttga tgccactggt catatattac  31500
cagactcatc ttctcttaaa acagatctag aactaaaata caagcaaacc gctgacttta  31560
gtgcaagagg ttttatgcca agtactacag cgtatccatt tgtccttcct aatgcgggaa  31620
cacataatga aaattatatt tttggtcaat gctactacaa agcaagcgat ggtgcccttt  31680
ttccgttgga agttactgtt atgcttaata aacgcctgcc agatagtcgc acatcctatg  31740
ttatgacttt tttatggtcc ttgaatgctg gtctagctcc agaaactact caggcaaccc  31800
tcataacctc cccatttacc ttttcctata ttagagaaga tgactaataa actctaaaga  31860
atcgtttgtg ttatgtttca acgtgtttat ttttcaattg cagaaaattt caagtcattt  31920
ttcattcagt agtatagccc caccaccaca tagcttatac agatcaccgt accttaatca  31980
aactcacaga accctagtat tcaacctgcc acctccctcc caacacacag agtacacagt  32040
cctttctccc cggctggcct taaaaagcat catatcatgg gtaacagaca tattcttagg  32100
tgttatattc cacacggttt cctgtcgagc caaacgctca tcagtgatat taataaactc  32160
cccgggcagc tcacttaagt tcatgtcgct gtccagctgc tgagccacag gctgctgtcc  32220
aacttgcggt tgcttaacgg gcggcgaagg agaagtccac gcctacatgg gggtagagtc  32280
ataatcgtgc atcaggatag ggcggtggtg ctgcagcagc gcgcgaataa actgctgccg  32340
ccgccgctcc gtcctgcagg aatacaacat ggcagtggtc tcctcagcga tgattcgcac  32400
cgcccgcagc ataaggcgcc ttgtcctccg ggcacagcag cgcaccctga tctcacttaa  32460
atcagcacag taactgcagc acagcaccac aatattgttc aaaatcccac agtgcaaggc  32520
gctgtatcca aagctcatgg cggggaccac agaacccacg tggccatcat accacaagcg  32580
caggtagatt aagtggcgac ccctcataaa cacgctggac ataaacatta cctcttttgg  32640
catgttgtaa ttcaccacct cccggtacca tataaacctc tgattaaaca tggcgccatc  32700
caccaccatc ctaaaccagc tggccaaaac ctgcccgccg gctatacact gcagggaacc  32760
gggactggaa caatgacagt ggagagccca ggactcgtaa ccatggatca tcatgctcgt  32820
catgatatca atgttggcac aacacaggca cacgtgcata cacttcctca ggattacaag  32880
ctcctcccgc gttagaacca tatcccaggg aacaacccat tcctgaatca gcgtaaatcc  32940
cacactgcag ggaagacctc gcacgtaact cacgttgtgc attgtcaaag tgttacattc  33000
gggcagcagc ggatgatcct ccagtatggt agcgcgggtt tctgtctcaa aaggaggtag  33060
acgatcccta ctgtacggag tgcgccgaga caaccgagat cgtgttggtc gtagtgtcat  33120
gccaaatgga acgccggacg tagtcatatt tcctgaagca aaaccaggtg cgggcgtgac  33180
aaacagatct gcgtctccgg tctcgccgct tagatcgctc tgtgtagtag ttgtagtata  33240
tccactctct caaagcatcc aggcgccccc tggcttcggg ttctatgtaa actccttcat  33300
gcgccgctgc cctgataaca tccaccaccg cagaataagc cacacccagc caacctacac  33360
attcgttctg cgagtcacac acgggaggag cgggaagagc tggaagaacc atgttttttt  33420
ttttattcca aaagattatc caaaacctca aaatgaagat ctattaagtg aacgcgctcc  33480
cctccggtgg cgtggtcaaa ctctacagcc aaagaacaga taatggcatt tgtaagatgt  33540
tgcacaatgg cttccaaaag gcaaacggcc ctcacgtcca agtggacgta aaggctaaac  33600
ccttcagggt gaatctcctc tataaacatt ccagcacctt caaccatgcc caaataattc  33660
tcatctcgcc accttctcaa tatatctcta agcaaatccc gaatattaag tccggccatt  33720
```

-continued

```
gtaaaaatct gctccagagc gccctccacc ttcagcctca agcagcgaat catgattgca  33780

aaaattcagg ttcctcacag acctgtataa gattcaaaag cggaacatta acaaaaatac  33840

cgcgatcccg taggtccctt cgcagggcca gctgaacata atcgtgcagg tctgcacgga  33900

ccagcgcggc cacttccccg ccaggaacct tgacaaaaga acccacactg attatgacac  33960

gcatactcgg agctatgcta accagcgtag ccccgatgta agctttgttg catgggcggc  34020

gatataaaat gcaaggtgct gctcaaaaaa tcaggcaaag cctcgcgcaa aaaagaaagc  34080

acatcgtagt catgctcatg cagataaagg caggtaagct ccggaaccac cacagaaaaa  34140

gacaccattt ttctctcaaa catgtctgcg ggtttctgca taaacacaaa ataaaataac  34200

aaaaaaacat ttaaacatta gaagcctgtc ttacaacagg aaaaacaacc cttataagca  34260

taagacggac tacggccatg ccggcgtgac cgtaaaaaaa ctggtcaccg tgattaaaaa  34320

gcaccaccga cagctcctcg gtcatgtccg gagtcataat gtaagactcg gtaaacacat  34380

caggttgatt catcggtcag tgctaaaaag cgaccgaaat agcccggggg aatacatacc  34440

cgcaggcgta gagacaacat tacagccccc ataggaggta taacaaaatt aataggagag  34500

aaaaacacat aaacacctga aaaaccctcc tgcctaggca aaatagcacc ctcccgctcc  34560

agaacaacat acagcgcttc acagcggcag cctaacagtc agccttacca gtaaaaaaga  34620

aaacctatta aaaaaacacc actcgacacg gcaccagctc aatcagtcac agtgtaaaaa  34680

agggccaagt gcagagcgag tatatatagg actaaaaaat gacgtaacgg ttaaagtcca  34740

caaaaaacac ccagaaaacc gcacgcgaac ctacgcccag aaacgaaagc caaaaaaccc  34800

acaacttcct caaatcgtca cttccgtttt cccacgttac gtaacttccc attttaagaa  34860

aactacaatt cccaacacat acaagttact ccgccctaaa acctacgtca cccgccccgt  34920

tcccacgccc cgcgccacgt cacaaactcc accccctcat tatcatattg gcttcaatcc  34980

aaaataaggt atattattga tgatgttaat                                    35010
```

<210> SEQ ID NO 56
<211> LENGTH: 464
<212> TYPE: PRT
<213> ORGANISM: Artificial Sequence
<220> FEATURE:
<223> OTHER INFORMATION: HER2(A3)-CD28TM,ICD-CD3Z CAR

<400> SEQUENCE: 56

```
Met Thr Arg Ala Met Asp Trp Ile Trp Arg Ile Leu Phe Leu Val Gly
1               5                   10                  15

Ala Ala Thr Gly Ala His Ser Glu Val Gln Leu Val Gln Ser Gly Thr
            20                  25                  30

Glu Val Lys Lys Pro Gly Ala Ser Val Arg Val Ser Cys Lys Ser Ser
        35                  40                  45

Gly Tyr Thr Phe Thr Ser Tyr Tyr Ile His Trp Val Arg Gln Ala Pro
    50                  55                  60

Gly Gln Gly Leu Glu Trp Met Ala Ile Ile Asn Pro Gly Asn Gly Asp
65                  70                  75                  80

Thr Asn Tyr Ala Gln Arg Phe Gln Gly Arg Val Thr Met Thr Arg Asp
                85                  90                  95

Thr Ser Thr Ser Thr Val Tyr Met Glu Leu Arg Ser Leu Arg Ser Asp
            100                 105                 110

Asp Thr Ala Val Tyr Phe Cys Ala Arg Glu Ile Ala Ser Tyr Ser Gly
        115                 120                 125

Ser Tyr Tyr Asp Tyr Trp Gly Gln Gly Thr Leu Val Thr Val Ser Ser
```

```
    130                 135                 140

Gly Gly Gly Gly Ser Gly Gly Gly Gly Ser Gly Gly Gly Gly Ser Gln
145                 150                 155                 160

Ala Val Val Leu Gln Glu Pro Ser Leu Ser Val Ser Pro Gly Gly Thr
                165                 170                 175

Val Thr Leu Thr Cys Gly Leu Ser Ser Gly Ser Val Ser Thr Gly His
            180                 185                 190

Tyr Ala Ser Trp Tyr Gln Gln Thr Pro Gly Gln Ala Pro Arg Thr Leu
        195                 200                 205

Phe Tyr Asn Thr Asn Thr Arg Ser Ser Gly Val Pro Asp Arg Phe Ser
    210                 215                 220

Gly Ser Ile Val Gly Asn Lys Ala Ala Leu Thr Ile Thr Gly Ala Gln
225                 230                 235                 240

Ala Asp Asp Glu Ser Asp Tyr Tyr Cys Val Leu Tyr Val Gly Asp Gly
                245                 250                 255

Ile Trp Val Phe Gly Gly Gly Thr Lys Leu Thr Val Leu Glu Pro Lys
            260                 265                 270

Ser Cys Asp Lys Thr His Thr Cys Pro Thr Arg Phe Trp Val Leu Val
        275                 280                 285

Val Val Gly Gly Val Leu Ala Cys Tyr Ser Leu Leu Val Thr Val Ala
    290                 295                 300

Phe Ile Ile Phe Trp Val Arg Ser Lys Arg Ser Arg Leu Leu His Ser
305                 310                 315                 320

Asp Tyr Met Asn Met Thr Pro Arg Arg Pro Gly Pro Thr Arg Lys His
                325                 330                 335

Tyr Gln Pro Tyr Ala Pro Pro Arg Asp Phe Ala Ala Tyr Arg Ser Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Gln Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460


<210> SEQ ID NO 57
<211> LENGTH: 14
<212> TYPE: PRT
<213> ORGANISM: Artificial Sequence
<220> FEATURE:
<223> OTHER INFORMATION: HER2(A3) LC-CDR1

<400> SEQUENCE: 57

Gly Leu Ser Ser Gly Ser Val Ser Thr Gly His Tyr Ala Ser
1               5                   10


<210> SEQ ID NO 58
<211> LENGTH: 7
<212> TYPE: PRT
```

```
<213> ORGANISM: Artificial Sequence
<220> FEATURE:
<223> OTHER INFORMATION: HER2(A3) LC-CDR2

<400> SEQUENCE: 58

Asn Thr Asn Thr Arg Ser Ser
1               5


<210> SEQ ID NO 59
<211> LENGTH: 10
<212> TYPE: PRT
<213> ORGANISM: Artificial Sequence
<220> FEATURE:
<223> OTHER INFORMATION: HER2(A3) LC-CDR3

<400> SEQUENCE: 59

Val Leu Tyr Val Gly Asp Gly Ile Trp Val
1               5                   10


<210> SEQ ID NO 60
<211> LENGTH: 10
<212> TYPE: PRT
<213> ORGANISM: Artificial Sequence
<220> FEATURE:
<223> OTHER INFORMATION: HER2(A3) HC-CDR1

<400> SEQUENCE: 60

Ser Tyr Tyr Ile His Trp Val Arg Gln Ala
1               5                   10


<210> SEQ ID NO 61
<211> LENGTH: 17
<212> TYPE: PRT
<213> ORGANISM: Artificial Sequence
<220> FEATURE:
<223> OTHER INFORMATION: HER2(A3) HC-CDR2

<400> SEQUENCE: 61

Ile Ile Asn Pro Gly Asn Gly Asp Thr Asn Tyr Ala Gln Arg Phe Gln
1               5                   10                  15

Gly


<210> SEQ ID NO 62
<211> LENGTH: 12
<212> TYPE: PRT
<213> ORGANISM: Artificial Sequence
<220> FEATURE:
<223> OTHER INFORMATION: HER2(A3) HC-CDR3

<400> SEQUENCE: 62

Glu Ile Ala Ser Tyr Ser Gly Ser Tyr Tyr Asp Tyr
1               5                   10


<210> SEQ ID NO 63
<211> LENGTH: 110
<212> TYPE: PRT
<213> ORGANISM: Artificial Sequence
<220> FEATURE:
<223> OTHER INFORMATION: HER2(A3) VL

<400> SEQUENCE: 63

Gln Ala Val Val Leu Gln Glu Pro Ser Leu Ser Val Ser Pro Gly Gly
1               5                   10                  15

Thr Val Thr Leu Thr Cys Gly Leu Ser Ser Gly Ser Val Ser Thr Gly
            20                  25                  30
```

-continued

```
His Tyr Ala Ser Trp Tyr Gln Gln Thr Pro Gly Gln Ala Pro Arg Thr
        35                  40                  45

Leu Phe Tyr Asn Thr Asn Thr Arg Ser Ser Gly Val Pro Asp Arg Phe
    50                  55                  60

Ser Gly Ser Ile Val Gly Asn Lys Ala Ala Leu Thr Ile Thr Gly Ala
65                  70                  75                  80

Gln Ala Asp Asp Glu Ser Asp Tyr Tyr Cys Val Leu Tyr Val Gly Asp
                85                  90                  95

Gly Ile Trp Val Phe Gly Gly Gly Thr Lys Leu Thr Val Leu
            100                 105                 110


<210> SEQ ID NO 64
<211> LENGTH: 121
<212> TYPE: PRT
<213> ORGANISM: Artificial Sequence
<220> FEATURE:
<223> OTHER INFORMATION: HER2(A3) VH

<400> SEQUENCE: 64

Glu Val Gln Leu Val Gln Ser Gly Thr Glu Val Lys Lys Pro Gly Ala
1               5                   10                  15

Ser Val Arg Val Ser Cys Lys Ser Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Ala Ile Ile Asn Pro Gly Asn Gly Asp Thr Asn Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Arg Ser Leu Arg Ser Asp Asp Thr Ala Val Tyr Phe Cys
                85                  90                  95

Ala Arg Glu Ile Ala Ser Tyr Ser Gly Ser Tyr Tyr Asp Tyr Trp Gly
            100                 105                 110

Gln Gly Thr Leu Val Thr Val Ser Ser
        115                 120
```

ONCOLYTIC VIROTHERAPY AND IMMUNOTHERAPY

CROSS REFERENCE TO RELATED APPLICATIONS

This application is a continuation of PCT Application No. PCT/US2018/028577, filed Apr. 20, 2018, entitled "ONCOLYTIC VIROTHERAPY AND IMMUNOTHERAPY", which claims priority to U.S. Provisional Application No. 62/488,181, filed Apr. 21, 2017, the disclosures of which are hereby incorporated by reference in their entireties.

TECHNICAL FIELD

The present disclosure relates at least to the fields of cell biology, molecular biology, immunology, virology, and medicine, including cancer therapy. In particular embodiments the disclosure relates to combination treatments involving the use of oncolytic virotherapy and immunotherapy.

BACKGROUND

Oncolytic Virotherapy for Squamous Cell Carcinoma of the Head and Neck (HNSCC)

HNSCC is the sixth leading cancer by incidence worldwide. Treatment of locally advanced, recurrent and metastatic HNSCC is often limited by an unfavorable efficacy to toxicity ratio and median survival for patients with metastatic disease remains less than one year (Zandberg and Strome, Oral Oncology (2014) 50: 627-632). Since HNSCC is a locoregional disease that presents at or close to the surface of the body, it is amenable to initial intratumoral injection of adenoviral vectors (Ads) to prompt a locoregional and even a systemic anti-tumor immune response (Liu et al., Nature Clinical Practice Oncology (2007) 4: 101-117). Several clinical trials of conditionally-replicating Ads (OncAds) or replication-deficient Ads encoding a therapeutic transgene have demonstrated the safety and feasibility of Ad gene therapy for HNSCC, but failed to show improved overall survival since intensive local treatment, even when combined with chemo/radiotherapy, did not prevent metastasis to distant sites (Liu et al., supra). OncAds are generally administered intratumorally, and poorly re-target to metastasized tumors (Koksi et al., Molecular Therapy: The Journal of the American Society of Gene Therapy (2015) 23:1641-1652).

OncAd with Helper-Dependent Ad (HDAd) Expressing Immunomodulatory Molecules

Adenoviral-based vectors (Ads) can infect a range of malignant cells and express high levels of lytic antigens and immunogenic transgenes, making them attractive as agents for cancer gene therapy (Cerullo et al., Advances in Cancer Research (2012) 115, 265-318). OncAds selectively replicate in cancer cells and are commonly used Ad-based vectors in clinical trials for cancer gene therapy. However, OncAds have a limited coding capacity for transgenes (~1.5 kb). Helper-dependent Ads (HDAds) are devoid of viral coding sequences, enabling a cargo capacity of up to 34 kb for insertion of multiple transgenes in a single vector (Suzuki et al., Human Gene Therapy (2010) 21; 120-126). Since HDAd vector DNA encodes packaging signals, the OncAd replication machinery acts in trans to replicate and package both OncAd and HDAd within infected tumor cells, leading to multiple cycles of production and release of both the oncolytic virus and the transgenes encoded by the HDAd (combinatorial adenoviral vectors: CAd-VEC; Farzad et al., Molecular Therapy—Oncolytics (2014) 1, 14008).

CAR T-Cell Therapy

The use of T-cells as agents for cancer therapy has recently been facilitated by the expression of cancer cell antigen-directed chimeric antigen receptors (CARs; reviewed in Kershaw et al., Nature (2013) 13: 525-541). CAR-modified T-cells have shown promise for the treatment of hematological malignancies (Garfall et al., The New England Journal of Medicine (2015) 373:1040-1047), but have been less effective in treating solid tumors, which may in part be a consequence of the highly immunosuppressive nature of the solid tumor microenvironment (Quail et al., Nature Medicine (2013) 19:1423-1437). Due to immunosuppressive mechanisms at tumor site CAR T-cells fail to expand and persist long term despite the expression of one or two costimulatory endodomains. The present disclosure provides a solution to a long-felt need for effective cancer therapies, including combinatorial cancer therapies.

BRIEF SUMMARY

In one aspect, the present disclosure provides a method of treating a cancer, comprising administering to a subject:

(i) an oncolytic virus;

(ii) a virus comprising nucleic acid encoding an immunomodulatory factor; and (iii) at least one cell comprising a chimeric antigen receptor (CAR) specific for a cancer cell antigen.

Also provided is a combination of (i) an oncolytic virus, (ii) a virus comprising nucleic acid encoding an immunomodulatory factor, and (iii) at least one cell comprising a chimeric antigen receptor (CAR) specific for a cancer cell antigen, for use in a method of treating a cancer.

Also provided is the use of (i) an oncolytic virus, (ii) a virus comprising nucleic acid encoding an immunomodulatory factor, and (iii) at least one cell comprising a chimeric antigen receptor (CAR) specific for a cancer cell antigen, in the manufacture of a medicament for use in a method of treating a cancer.

Also provided is a method of treating a cancer, comprising administering to a subject:

(i) an oncolytic virus; and (ii) at least one cell comprising a chimeric antigen receptor (CAR) specific for a cancer cell antigen.

Also provided is a combination of (i) an oncolytic virus, and (ii) at least one cell comprising a chimeric antigen receptor (CAR) specific for a cancer cell antigen, for use in a method of treating a cancer.

Also provided is the use of (i) an oncolytic virus, and (ii) at least one cell comprising a chimeric antigen receptor (CAR) specific for a cancer cell antigen, in the manufacture of a medicament for use in a method of treating a cancer.

In some embodiments the cell comprising a CAR is specific for the oncolytic virus.

Also provided is a method of treating a cancer, comprising administering to a subject:

(i) an oncolytic virus; and (ii) at least one immune cell specific for the oncolytic virus.

Also provided is a combination of (i) an oncolytic virus, and (ii) at least one immune cell specific for the oncolytic virus, for use in a method of treating a cancer.

Also provided is the use of (i) an oncolytic virus, and (ii) at least one immune cell specific for the oncolytic virus, in the manufacture of a medicament for use in a method of treating a cancer.

In some embodiments, the oncolytic virus is an oncolytic adenovirus (OncAd). In some embodiments, the oncolytic virus is derived from adenovirus 5 (Ad5). In some embodiments, the oncolytic virus encodes an E1A protein which displays reduced binding to Rb protein as compared to E1A protein encoded by Ad5. In some embodiments, the oncolytic virus encodes an E1A protein lacking the amino acid sequence LTCHEACF (SEQ ID NO:52). In some embodiments, the oncolytic virus encodes an E1A protein comprising, or consisting of or consisting essentially of, the amino acid sequence SEQ ID NO:34. In some embodiments, the oncolytic virus comprises nucleic acid having one or more binding sites for one or more transcription factors. In some embodiments, the oncolytic virus comprises nucleic acid having one or more binding sites for STAT1.

In some embodiments, the virus comprising nucleic acid encoding an immunomodulatory factor is a helper-dependent adenovirus (HDAd). In some embodiments, the immunomodulatory factor is selected from: an agonist of an effector immune response or antagonist of an immunoregulatory response. In some embodiments, the virus comprising nucleic acid encoding an immunomodulatory factor comprises nucleic acid encoding IL-12 and/or antagonist anti-PD-L1 antibody. In some embodiments, the virus comprising nucleic acid encoding an immunomodulatory factor comprises nucleic acid encoding an enzyme capable of catalysing conversion of a non-toxic factor to a cytotoxic form. In some embodiments, the enzyme is selected from: thymidine kinase, cytosine deaminase, nitroreductase, cytochrome P450, carboxypeptidase G2, purine nucleoside phosphorylase, horseradish peroxidase and carboxylesterase. In some embodiments, the virus comprising nucleic acid encoding an immunomodulatory factor comprises nucleic acid encoding a thymidine kinase.

In some embodiments, the at least one cell comprising a CAR specific for a cancer cell antigen is a T cell. In some embodiments, the CAR comprises an antigen binding domain capable of specific binding to HER2. In some embodiments, the CAR comprises an antigen binding domain comprising:

a VL domain comprising:
- LC-CRD1: SEQ ID NO:10;
- LC-CRD2: SEQ ID NO:11;
- LC-CRD3: SEQ ID NO:12;

and a VH domain comprising:
- HC-CRD1: SEQ ID NO:13;
- HC-CRD2: SEQ ID NO:14;
- HC-CRD3: SEQ ID NO:15;

or a VL domain comprising:
- LC-CRD1: SEQ ID NO:18;
- LC-CRD2: SEQ ID NO:19;
- LC-CRD3: SEQ ID NO:20;

and a VH domain comprising:
- HC-CRD1: SEQ ID NO:21;
- HC-CRD2: SEQ ID NO:22;
- HC-CRD3: SEQ ID NO:23;

or a VL domain comprising:
- LC-CRD1: SEQ ID NO:26;
- LC-CRD2: SEQ ID NO:27;
- LC-CRD3: SEQ ID NO:28;

and a VH domain comprising:
- HC-CRD1: SEQ ID NO:29;
- HC-CRD2: SEQ ID NO:30;
- HC-CRD3: SEQ ID NO:31;

or a VL domain comprising:
- LC-CRD1: SEQ ID NO:57;
- LC-CRD2: SEQ ID NO:58;
- LC-CRD3: SEQ ID NO:59;

and a VH domain comprising:
- HC-CRD1: SEQ ID NO:60;
- HC-CRD2: SEQ ID NO:61;
- HC-CRD3: SEQ ID NO:62.

In some embodiments, the CAR comprises an antigen binding domain comprising:

a VL comprising, or consisting of or consisting essentially of, an amino acid sequence having at least 75%, 80%, 85%, 90%, 95% or greater sequence identity to SEQ ID NO:16 and a VH comprising, or consisting of or consisting essentially of, an amino acid sequence having at least 75%, 80%, 85%, 90%, 95% or greater sequence identity to SEQ ID NO:17;

or a VL comprising, or consisting of or consisting essentially of, an amino acid sequence having at least 75%, 80%, 85%, 90%, 95% or greater sequence identity to SEQ ID NO:24 and a VH comprising, or consisting of or consisting essentially of, an amino acid sequence having at least 75%, 80%, 85%, 90%, 95% or greater sequence identity to SEQ ID NO:25;

or a VL comprising, or consisting of or consisting essentially of, an amino acid sequence having at least 75%, 80%, 85%, 90%, 95% or greater sequence identity to SEQ ID NO:32 and a VH comprising, or consisting of or consisting essentially of, an amino acid sequence having at least 75%, 80%, 85%, 90%, 95% or greater sequence identity to SEQ ID NO:33;

or a VL comprising, or consisting of, an amino acid sequence having at least 75% sequence identity to SEQ ID NO:63 and a VH comprising, or consisting of, an amino acid sequence having at least 75% sequence identity to SEQ ID NO:64.

In some embodiments, the method additionally comprises:

(a) isolating at least one cell from a subject, and in specific embodiments the cell is an immune cell;
(b) modifying the at least one cell to express or comprise a CAR specific for a cancer cell antigen, or a nucleic acid encoding a CAR specific for a cancer cell antigen,
(c) optionally expanding the modified at least one cell, and;
(d) administering the modified at least one cell to a subject; in specific embodiments the modified cell upon administration is provided to the subject with one or more other agents for cancer therapy.

In some embodiments, the method of treating a cancer comprises:

(a) isolating at least one cell from a subject;
(b) modifying the at least one cell to express or comprise a CAR specific for a cancer cell antigen, or a nucleic acid encoding a CAR specific for a cancer cell antigen,
(c) optionally expanding the modified at least one cell, and;
(d) administering the modified at least one cell to a subject.

In some embodiments, the method of treating a cancer comprises:

(a) isolating immune cells from a subject;
(b) generating or expanding a population of immune cells specific for an oncolytic virus by a method comprising:

stimulating the immune cells by culture in the presence of antigen presenting cells (APCs) presenting a peptide of the oncolytic virus, and;

(c) administering at least one immune cell specific for the oncolytic virus to a subject.

In some embodiments, the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

The present disclosure also provides an oncolytic adenovirus (OncAd) encoding an EIA protein comprising, or consisting of or consisting essentially of, the amino acid sequence SEQ ID NO:34.

The present disclosure also provides an oncolytic adenovirus (OncAd) comprising nucleic acid having one or more binding sites for STAT1. In some embodiments, the OncAd comprises a nucleic acid sequence having at least 60%, 65%, 70%, 75%, 80%, 85%, 90%, 95% or greater sequence identity to SEQ ID NO:51 or an equivalent sequence as a result of codon degeneracy.

Also provided is an OncAd comprising a nucleic acid sequence having at least 60%, 65%, 70%, 75%, 80%, 85%, 90%, 95% or greater sequence identity to SEQ ID NO:55 or an equivalent sequence as a result of codon degeneracy. In some embodiments the OncAd encodes an EIA protein comprising, or consisting of or consisting essentially of, the amino acid sequence SEQ ID NO:34.

The present disclosure also provides a helper-dependent adenovirus (HDAd) comprising nucleic acid encoding IL-12 and/or antagonist anti-PD-L1 antibody. In some embodiments the HDAd additionally comprises nucleic acid encoding an enzyme capable of catalysing conversion of a non-toxic factor to a cytotoxic form. In some embodiments the enzyme is selected from: thymidine kinase, cytosine deaminase, nitroreductase, cytochrome P450, carboxypeptidase G2, purine nucleoside phosphorylase, horseradish peroxidase and carboxylesterase.

In some embodiments, the HDAd additionally comprises nucleic acid encoding a thymidine kinase. In cases wherein the HDAd nucleic acid encodes IL-12 and anti-PD-L1 antibody, the respective expression sequences may or may not be regulated by the same regulatory sequence. In such cases wherein the HDAd nucleic acid encodes both IL-12 and anti-PD-L1 antibody, the positioning on the HDAd nucleic acid may be of any suitable configuration, such as in a 5' to 3' direction the nucleic acid region encoding IL-12 being either upstream or downstream of the nucleic acid region encoding anti-PD-L1 antibody.

The present disclosure also provides a chimeric antigen receptor (CAR) comprising an antigen binding domain comprising:

a VL domain comprising:
LC-CRD1: SEQ ID NO:10;
LC-CRD2: SEQ ID NO:11;
LC-CRD3: SEQ ID NO:12;
and a VH domain comprising:
HC-CRD1: SEQ ID NO:13;
HC-CRD2: SEQ ID NO:14;
HC-CRD3: SEQ ID NO:15;

or a VL domain comprising:
LC-CRD1: SEQ ID NO:18;
LC-CRD2: SEQ ID NO:19;
LC-CRD3: SEQ ID NO:20;
and a VH domain comprising:
HC-CRD1: SEQ ID NO:21;
HC-CRD2: SEQ ID NO:22;
HC-CRD3: SEQ ID NO:23;

or a VL domain comprising:
LC-CRD1: SEQ ID NO:26;
LC-CRD2: SEQ ID NO:27;
LC-CRD3: SEQ ID NO:28;
and a VH domain comprising:
HC-CRD1: SEQ ID NO:29;
HC-CRD2: SEQ ID NO:30;
HC-CRD3: SEQ ID NO:31;

or a VL domain comprising:
LC-CRD1: SEQ ID NO:57;
LC-CRD2: SEQ ID NO:58;
LC-CRD3: SEQ ID NO:59;
and a VH domain comprising:
HC-CRD1: SEQ ID NO:60;
HC-CRD2: SEQ ID NO:61;
HC-CRD3: SEQ ID NO:62.

In some embodiments, the CAR comprises an antigen binding domain comprising:

a VL comprising, or consisting of or consisting essentially of, an amino acid sequence having at least 75%, 80%, 85%, 90%, 95% or greater sequence identity to SEQ ID NO:16 and a VH comprising, or consisting of or consisting essentially of, an amino acid sequence having at least 75%, 80%, 85%, 90%, 95% or greater sequence identity to SEQ ID NO:17;

or a VL comprising, or consisting of, an amino acid sequence having at least 75%, 80%, 85%, 90%, 95% or greater sequence identity to SEQ ID NO:24 and a VH comprising, or consisting of or consisting essentially of, an amino acid sequence having at least 75%, 80%, 85%, 90%, 95% or greater sequence identity to SEQ ID NO:25;

or a VL comprising, or consisting of, an amino acid sequence having at least 75%, 80%, 85%, 90%, 95% or greater sequence identity to SEQ ID NO:32 and a VH comprising, or consisting of or consisting essentially of, an amino acid sequence having at least 75%, 80%, 85%, 90%, 95% sequence identity to SEQ ID NO:33;

or a VL comprising, or consisting of, an amino acid sequence having at least 75%, 80%, 85%, 90%, 95% or greater sequence identity to SEQ ID NO:63 and a VH comprising, or consisting of or consisting essentially of, an amino acid sequence having at least 75%, 80%, 85%, 90%, 95% sequence identity to SEQ ID NO:64.

The present disclosure also provides a nucleic acid, or a plurality of nucleic acids, optionally isolated, encoding the oncolytic adenovirus (OncAd), the helper-dependent adenovirus (HDAd), or the chimeric antigen receptor (CAR) according to the present disclosure.

The present disclosure also provides a cell comprising the oncolytic adenovirus (OncAd), the helper-dependent adenovirus (HDAd), the chimeric antigen receptor (CAR), or the nucleic acid or plurality of nucleic acids according to the present disclosure.

The present disclosure also provides a pharmaceutical composition comprising the oncolytic adenovirus (OncAd), the helper-dependent adenovirus (HDAd), the chimeric antigen receptor (CAR); the nucleic acid or plurality of nucleic acids or the cell according to the present disclosure may be associated with or comprised in a pharmaceutically acceptable carrier, diluent, excipient or adjuvant.

The present disclosure also provides a method of treating cancer comprising administering to a subject the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure.

The present disclosure also provides the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure for use in a method of treating a cancer.

The present disclosure also provides the use of the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure in the manufacture of a medicament for treating a cancer.

In some embodiments in accordance with various aspects of the present disclosure, the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

The present disclosure also provides a kit of parts comprising a predetermined quantity of the oncolytic adenovirus (OncAd), the helper-dependent adenovirus (HDAd), the chimeric antigen receptor (CAR), the nucleic acid or plurality of nucleic acids, the cell or the pharmaceutical composition according to the present disclosure.

DETAILED DESCRIPTION

The present disclosure is concerned with the combined use of multiple therapeutic agents for the treatment of cancer. In particular, (i) oncolytic virus, (ii) virus providing immunomodulatory factor(s) and (iii) CAR-bearing immune cells (such as T cells) specific for a cancer cell antigen are used in combination as a cancer therapy. The therapeutic agents are combined to provide an improved treatment effect as compared to the effect seen when any one of the agents is used alone. In certain embodiments, at least two of the three therapeutic agents act in an additive manner to treat the cancer, whereas in other embodiments at least two of the three different therapeutic agents act synergisitically to treat the cancer.

Without wishing to be bound by any particular theory, the improved treatment effect is thought to be achieved by combining the advantageous features of oncolytic virotherapy (e.g. effective treatment of solid tumours) and CAR-T cell therapy (e.g. effective treatment of diffuse/metastatic cancer), in conjunction with providing a favourable immune environment for CAR-T cell proliferation and activity.

Oncolytic Virus

The present disclosure employs oncolytic virus. Oncolytic viruses and their use to treat cancer is reviewed, for example, in Chiocca and Rabkin Cancer Immunol Res (2014) 2(4): 295-300, which is hereby incorporated by reference in its entirety.

Oncolytic viruses replicate in, and cause lysis of, cancer cells. Often they are selective for cancer cells over non-cancerous cells; for example, oncolytic viruses commonly replicate in dividing cells in preference to non-dividing cells. Oncolytic viruses are therefore useful to selectively kill cancer cells and destroy tumours, without causing substantial damage to normal, non-cancerous cells/tissue.

Oncolytic virotherapy is associated with several advantages features. Oncolytic viruses often target several oncogenic pathways and use multiple mechanisms for cytotoxicity, minimising the chances of resistance arising. As noted above, because oncolytic viruses replicate selectively in tumours and are non-pathogenic they display minimal toxicity. Virus dose in the tumour also increases over time due to replication of the virus, and the oncolytic viruses can also be manipulated genetically to improve safety, e.g. by engineering sensitivity to a drug.

There are two main classes of oncolytic virus:

(i) viruses that naturally replicate preferentially in cancer cells, and which are non-pathogenic in humans often due to elevated sensitivity to innate antiviral signalling or dependence on oncogenic signalling pathways, including autonomous parvoviruses, myxoma virus (MYXV; poxvirus), Newcastle disease virus (NDV; paramyxovirus), reovirus, and Seneca valley virus (SW; picomavirus); and (ii) viruses that are genetically-manipulated, e.g. with mutations/deletions in genes required for replication in normal, but not cancer cells, including adenovirus (Ad), herpes simplex virus (HSV), vaccinia virus (VV), and vesicular stomatitis virus (VSV; rhabdovirus); or viruses that are genetically-manipulated for use as vaccine vectors including measles virus (MV; paramyxovirus), poliovirus (PV; picomavirus), and W (poxvirus).

Genetic manipulation can include insertion/alteration of functional sequences to provide enhanced selectivity for cancer cells, safety, and/or to modify virus tropism.

For example, oncolytic virus may by genetically engineered to introduce tissue-specific internal ribosome entry sites (IRESs) only permitting viral translation in target cells, and/or to introduce miRNAs/miRNA response elements (MREs); differential miRNA expression between healthy cells or certain tissues vs. tumor cells allows viruses to be detargeted from healthy cells/tissues. Oncolytic virus may also by engineered to place transcription of the viral genome under the control of a cell- or tissue-specific regulatory region, such as promoter/enhancers (e.g. tumour cell-specific promoter). In some embodiments, the oncolytic virus according to the present disclosure may comprise one or more modifications for such purpose.

Virus may also be modified for transductional targeting, e.g. through modification of virus receptors/coat proteins to target tumour cells and/or detarget healthy cells/tissues.

Oncolytic viruses may be administered in such a way as to minimise anti-oncolytic virus responses (e.g. neutralisation by anti-virus antibodies) in the subject and sequestration in the liver, and to maximise tumour delivery, as described in Chiocca and Rabkin, supra. For example, oncolytic virus may be administered in a cell carrier, e.g. in mesenchymal stromal cells, myeloid-derived suppresser cells (MDSCs), neural stem cells, T cells, cytokine-induced killer cells, or irradiated tumor cells, or can be coated in nanoparticles.

In some embodiments, the oncolytic virus of the present disclosure is, or is derived from, an adenovirus (Ad), herpes simplex virus (HSV), vaccinia virus (VV), vesicular stomatitis virus (VSV); autonomous parvovirus, myxoma virus (MYXV), Newcastle disease virus (NDV), reovirus, Seneca valley virus (SVV) morbillivirus virus, retrovirus, influenza virus, Sindbis virus (SINV) or poxvirus, as examples. In some embodiments, the oncolytic virus is not vaccinia virus. In some embodiments, the oncolytic virus is not vaccinia virus JX-594.

As used herein, an oncolytic virus which is "derived from" a reference virus comprises a nucleic acid sequence or amino acid sequence which is possessed by the reference virus. In some embodiments an oncolytic virus which is "derived from" a reference virus comprises one or more genes possessed by the reference virus. In some embodiments an oncolytic virus which is "derived from" encodes one or more proteins encoded by the reference virus.

In some embodiments, an oncolytic virus which is derived from a reference virus may comprise nucleic acid sequence encoding one or more functional elements of the reference virus. A "functional element" may e.g. be a transcriptional regulator (e.g. a promoter/enhancer), a regulator of post-transcriptional processing, a translational regulator, a regulator of post-transcriptional processing, a response element, a repeat sequence, or a viral protein. In some embodiments, an oncolytic virus which is derived from a reference virus may comprise one or more genes of, or proteins encoded by, the reference virus.

In some embodiments the oncolytic virus of the present disclosure is, or is derived from, an adenovirus (OncAd). OncAds are reviewed e.g. in Larson et al., Oncotarget. (2015) 6(24): 19976-19989, which is hereby incorporated by reference in its entirety.

In some embodiments the OncAd is, or is derived from, a species A, B, C, D, E, F or G human adenovirus (i.e. HAdV-A, HAdV-B, HAdV-C, HAdV-D, HAdV-E, HAdV-F or HAdV-G). In some embodiments the OncAd is, or is derived from, a species C human adenovirus. In some embodiments the OncAd is, or is derived from, Ad5, Ad2, Ad1, Ad6 or Ad57.

In some embodiments the OncAd is a conditionally replicating adenovirus (or CRAd).

In some embodiments the OncAd has reduced ability to infect, replicate in and/or lyse non-cancerous cells (as compared to the ability to infect/replicate in and/or lyse equivalent cancerous cells), for example as a consequence of a genetic modification of the adenovirus from which the OncAd is derived.

In some embodiments the oncolytic virus comprises a modification to one or more protein encoding sequences. In some embodiments, the modification alters the production or activity of the encoded protein. In some embodiments, the modification is a truncation or deletion of the protein.

In some embodiments, the OncAd comprises modification to an adenovirus early protein. In some embodiments, the modification is to the region encoding EIA protein. In some embodiments, the OncAd encodes an E1A protein having reduced ability to bind to Rb protein as compared to wild-type EIA protein (e.g. E1A encoded by the adenovirus from which the OncAd is derived). In some embodiments the OncAd encodes an EIA protein lacking the amino acid sequence LTCHEACF (SEQ ID NO:52). An example of an OncAd comprising encodes an E1A protein lacking the amino acid sequence LTCHEACF (SEQ ID NO:52) is Onc5/3Ad2E1Δ24 shown in SEQ ID NO:55.

In some embodiments the oncolytic virus encodes an EIA protein comprising, or consisting of or consisting essentially of, an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:34.

In some embodiments, the oncolytic virus comprises a nucleic acid sequence providing one or more binding sites for one or more transcription factors. In some embodiments, the transcription factor is an activating transcription factor (i.e. a transcriptional activator). The one or more binding sites for one or more transcription factors are preferably provided upstream of (i.e. 5' to) to nucleic acid sequence encoding one or more functional elements (e.g. viral proteins).

In some embodiments, the transcription factor is a transcription factor having increased expression, or increased activity, in cancerous cells as compared to comparable non-cancerous cells (e.g. non-cancerous cells derived from the same tissue/cell type).

Herein, "expression" may refer to gene expression or protein expression. Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry. ELISA, ELISPOT, or reporter-based methods.

An example of an OncAd comprising one or more binding sites for one or more transcription factors is ICOVIR15 described in Rojas et al. 2010 Mol Ther 18 1960-1971, which is hereby incorporated by reference its entirety. ICOVIR15 comprises 8 binding sites for the transcription factor E2F.

In some embodiments the oncolytic virus comprises one or more binding sites for a transcription factor whose gene or protein expression, or activity in a cell, is upregulated in response to a factor produced or expressed by an immune cell. In some embodiments, a factor produced or expressed by an immune cell may at least one cytokine/chemokine produced by, or a protein expressed at the cell surface of, an effector immune cell, e.g. CD8+ cytotoxic T lymphocyte (CTL), CD4+T helper 1 ($T_H1$) cell, natural killer (NK) cell or natural killer T (NKT) cell.

In some embodiments, the oncolytic virus of the present disclosure comprises one or more binding sites for a STAT transcription factor. In some embodiments, the oncolytic virus comprises one or more binding sites for a STAT1. An ICOSTAT OncAd described herein possesses 8 binding sites for STAT1, and STAT1 is known to be upregulated by IFNγ. In particular embodiments, ICOSTAT is a particularly effective treatment for a cancer because the host's immune response to the cancer cells will promote the replication of the oncolytic virus in situ.

In some embodiments, the oncolytic virus comprises more than one binding site for a STAT1, e.g. at least 2, 3, 4, 5, 6, 7, 8, 9, or 10 binding sites for STAT1. In some embodiments, a binding site for STAT1 may comprise or consist of or consist essentially of the sequence TTCCGGGAA (SEQ ID NO:53), or TTCTCGGAA (SEQ ID NO:54). In some embodiments, the oncolytic virus of the present disclosure comprises one or more copies of the sequence TTCCGGGAA (SEQ ID NO:53) or TTCTCGGAA (SEQ ID NO:54).

In some embodiments the oncolytic virus according to the present disclosure comprises, or consists of, or consists essentially of, a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 88%, 89%, 90%, 87%, 88%, 89%, 90%, 91%, 92%, 93%, 94%, 95%, 96%, 97%, 98%, 99% or having 100% sequence identity to SEQ ID NO:51 or an equivalent sequence as a result of codon degeneracy.

In some embodiments the oncolytic virus according to the present disclosure comprises, or consists of, or consists essentially of, a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:55 or an equivalent sequence as a result of codon degeneracy.

In some embodiments the oncolytic virus according to the present disclosure encodes the same proteins as the proteins encoded by an oncolytic virus comprising, consisting of, or consisting essentially of, the nucleic acid shown in SEQ ID NO:55. In some embodiments the oncolytic virus according to the present disclosure encodes the same proteins as the proteins encoded by an oncolytic virus comprising, consisting of, or consisting essentially of, the nucleic acid shown in SEQ ID NO:51.

Virus Comprising Nucleic Acid Encoding an Immunomodulatory Factor

The present disclosure employs a virus comprising nucleic acid encoding an immunomodulatory factor. The virus acts as a vector for delivering the immunomodulatory factor. In certain embodiments, the virus comprises nucleic acid encoding more than one immunomodulatory factor(s).

Any virus capable of introducing the nucleic acid encoding an immunomodulatory factor into a cell (e.g. a primary human immune cell) may be used. Suitable viruses include gammaretrovirus (e.g. murine Leukemia virus (MLV)-derived vectors), lentivirus, adenovirus, adeno-associated virus, vaccinia virus and herpesvirus, e.g. as described in Maus et al., Annu Rev Immunol (2014) 32:189-225 or Morgan and Boyerinas, Biomedicines 2016 4, 9, which are both hereby incorporated by reference in its entirety. In some embodiments, the virus comprising nucleic acid encoding an immunomodulatory factor is, or is derived from, an adenovirus, lentivirus, retrovirus, or herpesvirus.

In some embodiments, the virus comprising nucleic acid encoding at least one immunomodulatory factor is an oncolytic virus comprising nucleic acid encoding at least one immunomodulatory factor.

An immunomodulatory factor(s) encoded by the virus comprising nucleic acid encoding the immunomodulatory factor(s) according to the present disclosure are preferably selected to facilitate the immune response to a cancer in a subject, in particular the cell-mediated immune response. In one embodiment, the immunomodulatory factor(s) provide favourable conditions for the activation, recruitment, proliferation, activity and/or survival of effector immune cells (e.g. CTLs, $T_H1$ cells, NK cells or NKT cells).

In some embodiments, the immunomodulatory factor may be an agonist of an effector immune response, e.g. a cytokine or chemokine promoting activation, recruitment, proliferation, activity and/or survival of effector immune cells (e.g. IL-2, IL-7, IL-17, IL-12, IL-21, IL-15, MIP-1α or RANTES), agonist antibody for a costimulatory receptor (e.g. 4-1 BB, OX40, CD28, CD27. ICOS, CD30 or GITR), or ligand for a costimulatory receptor (e.g. 4-1 BBL, OX40L, CD80, CD86. CD70, ICOSL, CD30L or GITRL). In some embodiments, the agonist of an effector immune response may be an antagonist of an immune checkpoint inhibitor, or an antagonist of ligand for immune checkpoint inhibitor, e.g. antagonist antibody to PD-L1, PD-L2, PD-1, CTLA-4, LAG-3, TIM-3, Gal-9, TIGIT, VISTA or BTLA, or an antagonist of a cytokine/chemokine which is an antagonist of an effector immune response, e.g. TGFβ (i.e. antagonist anti-TGFβ antibody or soluble/decoy TGFβ receptor). In some embodiments, an agonist of an effector immune response may be a molecule for engaging and co-opting bystander effector immune cells such as T cells and NK cells.

In some embodiments, the immunomodulatory factor may be an antagonist of an immunoregulatory response, e.g. an antagonist of a cytokine/chemokine promoting activation, recruitment, proliferation, activity and/or survival of immunoregulatory cells such as regulatory T cells (Tregs) and/or myeloid-derived suppressor cells (MDSCs), e.g. CCL9, CXCL10, CCL20, CCL22.

In some embodiments the virus comprising nucleic acid encoding an immunomodulatory factor may additionally comprise nucleic acid encoding further functional sequence (s). For example, the virus may comprise nucleic acid encoding a protein(s) for reducing growth/proliferation/survival of infected cells, or protein(s) for rendering infected cells sensitive to treatment with a given agent, or protein(s) for disrupting tumour structure (e.g. enzymes for digesting tumour matrix) to facilitate immune cell infiltration.

In some embodiments the virus comprising nucleic acid encoding an immunomodulatory factor additionally comprises nucleic acid encoding an enzyme capable of catalysing conversion of a non-toxic factor to a cytotoxic form. The enzyme may catalyse conversion of a non-toxic prodrug into its active, cytotoxic form.

Enzyme/prodrug systems are well known in the art and include those described in Malekshah et al. Curr Pharmacol Rep. (2016) 2(6): 299-308 which is hereby incorporated by reference in its entirety. Examples of non-toxic prodrugs, their active cytotoxic forms and enzymes capable of catalysing conversion of the non-toxic prodrugs to their active cytotoxic forms are shown in FIG. 2 of Malekshah et al.

In some embodiments the virus comprising nucleic acid encoding an immunomodulatory factor additionally comprises nucleic acid encoding a thymidine kinase, cytosine deaminase, nitroreductase, cytochrome P450, carboxypeptidase G2, purine nucleoside phosphorylase, horseradish peroxidase and/or carboxylesterase.

For example, the virus may comprise nucleic acid encoding thymidine kinase for rendering cells expressing the virus sensitive to treatment with ganciclovir (GCV), aciclovir (ACV) and/or valaciclovir. The virus may comprise nucleic acid encoding cytosine deaminase for rendering cells expressing the virus sensitive to treatment with 5-fluorocytosine (5-FC), which is converted by cytosine deaminase to 5-fluorouracil (5-FU). The virus may comprise nucleic acid encoding nitroreductase for rendering cells expressing the virus sensitive to treatment with CB1954, nitro-CBI-DEI and/or PR-104A. The virus may comprise nucleic acid encoding cytochrome P450 for rendering cells expressing the virus sensitive to treatment with oxazaphosphorine (e.g. cyclophosphamide or ifosfamide). The virus may comprise nucleic acid encoding carboxypeptidase G2 for rendering cells expressing the virus sensitive to treatment with nitrogen mustard based drugs (e.g. CMDA or ZD2767P). The virus may comprise nucleic acid encoding purine nucleoside phosphorylase for rendering cells expressing the virus sensitive to treatment with 6-methylpurine 2-deoxyriboside and/or fludarabine (e.g. 6-methylpurine-2'-deoxyriboside (MeP-dR), 2-F-2'-deoxyadenosine (F-dAdo) or arabinofuranosyl-2-F-adenine monophosphate (F-araAMP). The virus may comprise nucleic acid encoding horseradish peroxidase for rendering cells expressing the virus sensitive to treatment with indole-3-acetic acid (IAA). The virus may comprise nucleic acid encoding carboxylesterase for rendering cells expressing the virus sensitive to treatment with irinotecan.

In some embodiments the virus may comprise nucleic acid encoding antagonist of a growth factor.

In some embodiments, the virus may be a helper-dependent adenovirus (HDAd). HDAds are reviewed, for example, in Rosewell et al., J Genet Syndr Gene Ther (2011) Suppl 5:001, which is hereby incorporated by reference in its entirety.

HDAds are devoid of viral protein coding sequences, and therefore possess a large capacity (up to 37 Kb) for transduction of a coding sequence of interest. HDAds are non-integrating, and are able to efficiently transduce a wide variety of cell types independently of the cell cycle, and mediate long-term transgene expression without chronic toxicity.

HDAds comprise only the cis acting viral elements required for genomic replication (inverted terminal repeats (ITRs)) and encapsidation (ψ), and are therefore dependent on helper virus for propagation. When a cell is infected with both the helper virus and the HDAd, the helper virus replication machinery acts in trans to replicate and package HDAd.

In particular embodiments of the present disclosure, the oncolytic virus is an OncAd and the virus comprising nucleic acid encoding an immunomodulatory factor is a HDAd, and the OncAd and HDAd are able to co-infect and replicate in cells of a cancer.

Dependence of the HDAd on help from the OncAd provides highly localised expression of the immunomodulatory factor(s). That is, because the HDAd is only able to propagate in cells co-infected with the OncAd, and in turn because the OncAd is selective for replication in cancerous cells, expression of the factor(s) encoded by the HDAd is restricted to cancerous cells/tissue, minimising side effects.

Furthermore, because the OncAd and HDAd efficiently target and infect tumour cells, expression of the immunomodulatory factor(s) in those cells can change the normally immunosuppressive tumour microenvironment to provide conditions promoting the activation, recruitment (i.e. tumour penetration/infiltration), proliferation, activity and/or survival of effector immune cells.

In particular, in the context of the present disclosure wherein the methods of treatment employ the use of CAR-T cells, expression of the immunomodulatory factor(s) encoded by the HDAd provide for enhanced activation, recruitment, proliferation, activity and/or survival of the CAR-T cells.

In particular embodiments herein the virus comprising nucleic acid encoding an immunomodulatory factor is a HDAd comprising nucleic acid encoding IL-12p70, HSV-1 thymidine kinase and an antagonist anti-PD-L1 minibody.

In some embodiments, the virus comprising nucleic acid encoding an immunomodulatory factor according to the present disclosure encodes IL-12. In some embodiments the virus comprising nucleic acid encoding an immunomodulatory factor comprises nucleic acid encoding an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:35.

In some embodiments, the virus comprising nucleic acid encoding an immunomodulatory factor according to the present disclosure encodes an antagonist of PD-1/PD-L1 signalling. In some embodiments the antagonist of PD-1/PD-L1 signalling is an anti-PD-L1 antibody.

In some embodiments the anti-PD-L1 antibody comprises an antigen binding domain comprising a VL domain comprising:

LC-CRD1: SEQ ID NO:39;
LC-CRD2: SEQ ID NO:40;
LC-CRD3: SEQ ID NO:41;

and a VH domain comprising:

HC-CRD1: SEQ ID NO:42;
HC-CRD2: SEQ ID NO:43;
HC-CRD3: SEQ ID NO:44.

In some embodiments the anti-PD-L1 antibody comprises a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:45 and a VH comprising, or consisting of or consisting essentially of, an amino acid sequence having at least 75%, 76%, 77%, 78%, 79%, 80%, 83%, 84%, 83%, 85%, 86%, 87%, 88%, 89%, 90%, 91%, 9%, 93%, 94%, 95%, 96%, 97%, 98%, 99% or having 100% sequence identity to SEQ ID NO:46.

In some embodiments the virus comprising nucleic acid encoding an immunomodulatory factor comprises nucleic acid encoding an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:38.

In some embodiments, the virus comprising nucleic acid encoding an immunomodulatory factor according to the present disclosure comprises an amino acid sequence encoding a thymidine kinase. In some embodiments the virus comprising nucleic acid encoding an immunomodulatory factor comprises nucleic acid encoding an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:36.

In some embodiments, the virus comprising nucleic acid encoding an immunomodulatory factor according to the present disclosure comprises, or consists of or consist essentially of, a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:50 or an equivalent sequence as a result of codon degeneracy.

Chimeric Antigen Receptors (CARs) and CAR-Expressing Cells

The present disclosure employs immune cells comprising a chimeric antigen receptor (CAR).

Chimeric Antigen Receptors (CARs) are recombinant receptors that provide both antigen-binding and immune cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signaling region. An optional hinge region may provide separation between the antigen-binding region and cell membrane anchor region, and may act as a flexible linker.

The antigen-binding region of a CAR may be based on the antigen-binding region of an antibody which is specific for the antigen to which the CAR is targeted, or other agent capable of binding to the target. For example, the antigen-binding domain of a CAR may comprise amino acid sequences for the complementarity-determining regions (CDRs) or complete light chain and heavy chain variable region amino acid sequences of an antibody which binds specifically to the target protein. Antigen-binding domains of CARs may target antigen based on other protein:protein interaction, such as ligand:receptor binding; for example an IL-13Rα2-targeted CAR has been developed using an antigen-binding domain based on IL-13 (see e.g. Kahlon et al. 2004 Cancer Res 64(24): 9160-9166).

The CAR of the present disclosure comprises an antigen-binding region specific for a cancer cell antigen. The antigen binding region of the CAR may be provided with any suitable format, e.g. scFv, Fab, etc. In some embodiments, the antigen binding region of the CAR comprises or consists of a cancer cell antigen binding scFv.

A cancer cell antigen is an antigen which is expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response.

In some embodiments, the antigen is expressed at the cell surface of the cancer cell (i.e. the cancer cell antigen is a cancer cell surface antigen). In some embodiments, the part of the antigen which is bound by the bispecific antigen binding polypeptide of the present disclosure is displayed on the external surface of the cancer cell (i.e. is extracellular). In some embodiments, the antigen is anchored to the cell membrane, e.g. via a transmembrane domain or other membrane anchor (e.g. a lipid anchor such as a GPI anchor). In some embodiments, the cancer cell antigen is expressed at the cell surface (i.e. is expressed in or at the cell membrane) of a cancerous cell, but may be expressed inside the cell (i.e. is expressed inside comparable non-cancerous cells).

The cancer cell antigen may be a cancer-associated antigen. In some embodiments the cancer cell antigen is an antigen whose expression is associated with the development, progression and/or severity of symptoms of a cancer. The cancer-associated antigen may be associated with the cause or pathology of the cancer, or may be expressed abnormally as a consequence of the cancer. In some embodiments, the antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type).

In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

Cancer cell antigens are reviewed by Zarour H M, DeLeo A, Finn O J, et al. Categories of Tumor Antigens. In: Kufe D W, Pollock R E, Weichselbaum R R, et al., editors. Holland-Frei Cancer Medicine. 6th edition. Hamilton (ON): BC Decker; 2003. Cancer cell antigens include oncofetal antigens: CEA, Immature laminin receptor, TAG-72; oncoviral antigens such as HPV E6 and E7; overexpressed proteins: BING-4, calcium-activated chloride channel 2, cyclin-B1, 9D7, Ep-CAM, EphA3, HER2/neu, telomerase, mesothelin, SAP-1, surviving; cancer-testis antigens: BAGE, CAGE, GAGE, MAGE, SAGE, XAGE, CT9, CT10, NY-ESO-1, PRAME, SSX-2; lineage restricted antigens: MART1, Gp100, tyrosinase, TRP-1/2, MC1R, prostate specific antigen; mutated antigens: β-catenin, BRCA1/2, CDK4, CML66, Fibronectin, MART-2, p53, Ras, TGF-βRII; post-translationally altered antigens: MUC1, idiotypic antigens: Ig, TCR. Other cancer cell antigens include heat-shock protein 70 (HSP70), heat-shock protein 90 (HSP90), glucose-regulated protein 78 (GRP78), vimentin, nucleolin, feto-acinar pancreatic protein (FAPP), alkaline phosphatase placental-like 2 (ALPPL-2), siglec-5, stress-induced phosphoprotein 1 (STIP1), protein tyrosine kinase 7 (PTK7), and cyclophilin B.

In some embodiments, the cancer cell antigen is HER2. In some embodiments, the CAR of the present disclosure comprises an antigen binding domain capable of specific binding to HER2. In some embodiments, the CAR comprises an antigen binding domain comprising the CDRs of an antibody capable of specific binding to HER2. In some embodiments, the CAR comprises an antigen binding domain comprising the VL and VH regions of an antibody capable of specific binding to HER2.

In particular embodiments, the cell expressing the CAR comprises two, separate CARs each that target different cancer cell antigens, and in particular aspects at least one of the CARs targets HER2. In some cases, the CAR is bispecific for two different cancer cell antigens, one of which may be HER2.

In some embodiments the CAR comprises an antigen binding domain comprising a VL domain comprising:

LC-CRD1: SEQ ID NO:10, SEQ ID NO:18, SEQ ID NO:26 or SEQ ID NO: 57;

LC-CRD2: SEQ ID NO:11, SEQ ID NO:19, SEQ ID NO:27 or SEQ ID NO: 58;

LC-CRD3: SEQ ID NO:12, SEQ ID NO:20, SEQ ID NO:28 or SEQ ID NO: 59; and a VH domain comprising:

HC-CRD1: SEQ ID NO:13, SEQ ID NO:21, SEQ ID NO:29 or SEQ ID NO: 60;

HC-CRD2: SEQ ID NO:14, SEQ ID NO:22, SEQ ID NO:30 or SEQ ID NO: 61;

HC-CRD3: SEQ ID NO:15, SEQ ID NO:23, SEQ ID NO:31 or SEQ ID NO: 62.

In some embodiments the CAR comprises an antigen binding domain comprising a VL domain comprising:

LC-CRD1: SEQ ID NO:10;
LC-CRD2: SEQ ID NO:11;
LC-CRD3: SEQ ID NO:12;

and a VH domain comprising:

HC-CRD1: SEQ ID NO:13;
HC-CRD2: SEQ ID NO:14;
HC-CRD3: SEQ ID NO:15.

In some embodiments the CAR comprises an antigen binding domain comprising a VL domain comprising:

LC-CRD1: SEQ ID NO:18;
LC-CRD2: SEQ ID NO:19;
LC-CRD3: SEQ ID NO:20;

and a VH domain comprising:

HC-CRD1: SEQ ID NO:21;
HC-CRD2: SEQ ID NO:22;
HC-CRD3: SEQ ID NO:23.

In some embodiments the CAR comprises an antigen binding domain comprising a VL domain comprising:

LC-CRD1: SEQ ID NO:26;

LC-CRD2: SEQ ID NO:27;

LC-CRD3: SEQ ID NO:28;

and a VH domain comprising:

HC-CRD1: SEQ ID NO:29;

HC-CRD2: SEQ ID NO:30;

HC-CRD3: SEQ ID NO:31.

In some embodiments the CAR comprises an antigen binding domain comprising a VL domain comprising:

a VL domain comprising:

LC-CRD1: SEQ ID NO:57;

LC-CRD2: SEQ ID NO:58;

LC-CRD3: SEQ ID NO:59;

and a VH domain comprising:

HC-CRD1: SEQ ID NO:60;

HC-CRD2: SEQ ID NO:61;

HC-CRD3: SEQ ID NO:62.

In some embodiments the CAR comprises an antigen binding domain comprising a light chain variable region (VL) comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:16, 24, 32 or 63.

In some embodiments the CAR comprises an antigen binding domain comprising a heavy chain variable region (VH) comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:17, 25, 33 or 64.

In some embodiments the CAR comprises an antigen binding domain comprising a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:16 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:17. In some embodiments the CAR comprises an antigen binding domain comprising a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:24 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:25. In some embodiments the CAR comprises an antigen binding domain comprising a VL comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:32 and a VH comprising, or consisting of or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:33. In some embodiments the CAR comprises an antigen binding domain comprising a VL comprising, consisting of, or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:63 and a VH comprising, consisting of, or consisting essentially of, an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:64.

In some embodiments, the CAR of the present disclosure comprises an antigen binding region which comprises or consists of or consists essentially of an antibody/antigen binding fragment according to the present disclosure.

The cell membrane anchor region is provided between the antigen-binding region and the signalling region of the CAR. The cell membrane anchor region provides for anchoring the CAR to the cell membrane of a cell expressing a CAR, with the antigen-binding region in the extracellular space, and signalling region inside the cell. Suitable transmembrane domains include transmembrane region derived from CD28, CD3-ζ, CD4 or CD8.

In some embodiments the cell membrane anchor region comprises, or consists of or consists essentially of, an amino acid sequence having at least 80%, 85%, 90%, 91%, 92%, 93%, 94%, 95%, 96%, 97%, 98%, 99% or 100% sequence identity to SEQ ID NO:4.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins have also been employed in CARs, such as domains comprising the ITAM containing region of FcγRI (Haynes et al., 2001 J Immunol 166(1):182-187). CARs comprising a signalling region derived from the intracellular domain of CD3-ζ are often referred to as first generation CARs.

In some embodiments the cell membrane anchor region comprises, or consists of or consists essentially of, an amino acid sequence having at least 80%, 85%, 90%, 91%, 92%, 93%, 94%, 95%, 96%, 97%, 98%, 99% or 100% sequence identity to SEQ ID NO:6.

Signalling regions of CARs may also comprise co-stimulatory sequences derived from the signalling region of co-stimulatory molecules, to facilitate activation of CAR-expressing T cells upon binding to the target protein. Suitable co-stimulatory molecules include at least CD28, OX40, 4-1BB, ICOS and CD27. CARs having a signalling region including additional co-stimulatory sequences are often referred to as second generation CARs.

In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1 BB-mediated signalling is through TNF receptor associated factor (TRAF) adaptor proteins. Signalling regions of CARs therefore sometimes contain co-stimulatory sequences derived from signalling regions of more than one co-stimulatory molecule. CARs comprising a signalling region with multiple co-stimulatory sequences are often referred to as third generation CARs.

In some embodiments, the CAR of the present disclosure comprises one or more co-stimulatory sequences comprising or consisting of or consisting essentially of an amino acid sequence which comprises, consists of or consists essentially of, or is derived from, the amino acid sequence of the intracellular domain of one or more of CD28, OX40, 4-1BB, ICOS and CD27.

In some embodiments the cell membrane anchor region comprises, or consists of or consists essentially of, an amino acid sequence having at least 80%, 85%, 90%, 91%, 92%, 93%, 94%, 95%, 96%, 97%, 98%, 99% or 100% sequence identity to SEQ ID NO:5.

An optional hinge region may provide separation between the antigen-binding domain and the transmembrane domain, and may act as a flexible linker. Hinge regions may be flexible domains allowing the binding moiety to orient in different directions. Hinge regions may be derived from IgG1 or the $CH_2CH_3$ region of immunoglobulin. In some embodiments, the CAR of the present disclosure comprises a hinge region comprising or consisting of or consisting essentially of an amino acid sequence which comprises, consists of or consists essentially of, or is derived from, the amino acid sequence of the hinge region of IgG1 or the $CH_2CH_3$ region of immunoglobulin.

In some embodiments the cell membrane anchor region comprises, or consists of or consists essentially of, an amino acid sequence having at least 85%, 90%, 91%, 92%, 93%, 94%, 95%, 96%, 97%, 98%, 99% or 100% sequence identity to SEQ ID NO:9.

In some embodiments the CAR comprises, or consists of or consists essentially of, an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or having 100% sequence identity to SEQ ID NO:1, 2, 3 or 56.

The present disclosure also provides a cell comprising or expressing a CAR according to the present disclosure. Also provided is a cell comprising or expressing a nucleic acid encoding a CAR according to the disclosure. Engineering of CARs into T cells may be performed during culture, in vitro, for transduction and expansion, such as happens during expansion of T cells for adoptive T cell therapy. Methods for engineering immune cells to express CARs are known to the skilled person and are described e.g. in Wang and RiviMre Mol Ther Oncolytics. (2016) 3:16015, which is hereby incorporated by reference in its entirety. It will be appreciated that "at least one cell" encompasses plural cells, e.g. populations of such cells.

The cell comprising or expressing a CAR according to the present disclosure may be a eukaryotic cell, e.g. a mammalian cell. The mammal may be a human, or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments, the cell may be from, or may have been obtained from, a human subject. Where the CAR-expressing cell is to be used in the treatment of a subject, the cell may be from the subject to be treated with the CAR-expressing cell (i.e. the cell may be autologous), or the cell may be from a different subject (i.e. the cell may be allogeneic).

The cell may be an immune cell. The cell may be a cell of hematopoietic origin, e.g. a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. The cell may express e.g. CD3 polypeptides (e.g. CD3γ CD3ε CD3ζ or CD3δ), TCR polypeptides (TCRα or TCRβ), CD27, CD28, CD4 or CD8.

In some embodiments, the cell is a T cell. In some embodiments, the T cell is a CD3+ T cell. In some embodiments, the T cell is a CD3+, CD8+ T cell. In some embodiments, the T cell is a cytotoxic T cell (e.g. a cytotoxic T lymphocyte (CTL)).

The use of CAR T-cells is associated with advantages that they can be systemically administered, and will home to both primary and metastasized tumors (Manzo et al., Human Molecular Genetics (2015) R67-73).

In some embodiments, the cell is an antigen-specific T cell. In embodiments herein, an "antigen-specific" T cell is a cell which displays certain functional properties of a T cell in response to the antigen for which the T cell is specific, or a cell expressing said antigen. In some embodiments, the properties are functional properties associated with effector T cells, e.g. cytotoxic T cells.

In some embodiments, an antigen-specific T cell may display one or more of the following properties: cytotoxicity, e.g. to a cell comprising/expressing antigen for which the T cell is specific; proliferation, IFNγ expression, CD107a expression, IL-2 expression, TNFα expression, perforin expression, granzyme expression, granulysin expression, and/or FAS ligand (FASL) expression, e.g. in response to antigen for which the T cell is specific or a cell comprising/expressing antigen for which the T cell is specific. Antigen-specific T cells comprise a TCR capable of recognising a peptide of the antigen for which the T cell is specific when presented by the appropriate MHC molecule. Antigen-specific T cells may be CD4+ T cells and/or CD8+ T cells.

In some embodiments, the antigen for which the T cell is specific may be a peptide or polypeptide of a virus, e.g. Adenovirus, Cytomegalovius (CMV), Epstein-Barr virus (EBV), human papilloma virus (HPV), influenza virus, measles virus, hepatitis B virus (HBV), hepatitis C virus (HCV), human immunodeficiency virus (HIV), lymphocytic choriomeningitis virus (LCMV), or herpes simplex virus (HSV).

A T cell which is specific for an antigen of a virus may be referred to herein as a virus-specific T cell (VST). VSTs may be CD4+ T cells (e.g. TN cells) and/or CD8+ T cells (e.g. CTLs). A T cell which is specific for an antigen of a particular virus may be described as being being specific for the relevant virus; for example, a T cell which is specific for an antigen of an Adenovris may be referred to as an Adenovirus-specific T cell, or "AdVST". The use of virus-specific T cells for the generation of CAR-T cells is associated with the advantage that whilst naïve T cells may have limited long-term persistence after infusion, virus-specific T-cells (VSTs) derived from the memory compartment, and genetically-modified VSTs have been shown to persist for over 10 years after infusion in stem cell transplant recipients (Cruz et al., Cytotherapy (2010) 12:743-749). For example, VSTs expressing GD2.CARs have been shown to persist long-term after infusion and produce complete tumor responses in patients with low tumor burden (Sun et al., Journal for Immunotherapy of Cancer (2015) 3:5 and Pule et al. Nature Medicine (2008) 14: 1264-1270).

In some embodiments the cell comprising/expressing the CAR is a virus-specific T cell (VST, e.g. a virus-specific CD4+ T cell (e.g. TN cell) and/or a virus-specific CD8+ T cell (e.g. CTL). In some embodiments the CAR-expressing cell is an Adenovirus-specific T cell (AdVST), Cytomegalovius-specific T cell (CMVST), Epstein-Barr virus-specific T cell (EBVST), influenza virus-specific T cell, measles virus-specific T cell, hepatitis B virus-specific T cell (HBVST), hepatitis C virus-specific T cell (HCVST), human immunodeficiency virus-specific T cell (HIVST), lymphocytic choriomeningitis virus-specific T cell (LCMVST), Herpes simplex virus-specific T cell (HSVST) or human papilloma virus (HPVST).

In some embodiments the cell comprising/expressing the CAR is an oncolytic virus-specific immune cell (e.g. an oncolytic virus-specific T cell), e.g. as described herein.

Any cells of the disclosure may be included in an isolated population of cells that may or may not be homogeneous. In specific embodiments, the cell population has a majority of cells that are immune cells specific for an oncolytic virus and/or that express a CAR. The cells in the cell population may comprise an oncolytic adenovirus (OncAd), a helper-dependent adenovirus (HDAd), a chimeric antigen receptor (CAR) and/or nucleic acid or plurality of nucleic acids that encodes one or more of the OncAd, HDAd, and/or CAR. In particular embodiments, the cell population has at least 70, 75, 80, 85, 90, 91, 92, 93, 94, 95, 96, 97, 98, or 99% of cells that comprise an oncolytic adenovirus (OncAd), a helper-dependent adenovirus (HDAd), a chimeric antigen receptor (CAR) and/or nucleic acid or plurality of nucleic acids that encodes one or more of the OncAd, HDAd, and/or CAR.

Oncolytic Virus-Specific Immune Cells

Aspects of the present disclosure provide oncolytic virus-specific immune cells (also referred to herein as immune cells specific for an oncolytic virus). Oncolytic virus-specific immune cells express/comprise a receptor capable of recognising a peptide of an antigen of an oncolytic virus (e.g. when presented by an MHC molecule). The immune cell may express/comprise such a receptor as a result of expression of endogenous nucleic acid encoding such antigen receptor, or as a result of having been engineered to express such a receptor.

In some embodiments an oncolytic virus-specific immune cell may be a cell of hematopoietic origin, e.g. a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. The cell may express e.g. CD3 polypeptides (e.g. CD3γ CD3ε CD3ζ or CD3δ), TCR polypeptides (TCRα or TCRβ), CD27, CD28, CD4 or CD8. In some embodiments, the oncolytic virus-specific immune cell is a T cell, e.g. a CD3+ T cell. In some embodiments, the T cell is a CD3+, CD4+ T cell. In some embodiments, the T cell is a CD3+, CD8+ T cell. In some embodiments, the T cell is a T helper cell ($T_H$ cell)). In some embodiments, the T cell is a cytotoxic T cell (e.g. a cytotoxic T lymphocyte (CTL)).

The oncolytic virus-specific immune cell (e.g. oncolytic virus-specific T cell) may be specific for an oncolytic virus as described herein. That is to say, the oncolytic virus-specific immune cell may be specific for one or more antigens of an oncolytic virus described herein.

Methods for generating/expanding populations of immune cells specific for antigen(s) of interest and/or a virus of interest are well known in the art, and are described e.g. in Wang and Rivière Cancer Gene Ther. (2015) 22(2):85-94, which is hereby incorporated by reference in its entirety. Such methods may involve contacting heterogeneous populations of immune cells (e.g. peripheral blood mononuclear cells (PBMCs), peripheral blood lymphocytes (PBLs) tumor-infiltrating lymphocytes (TILs)) with one or more peptides of the antigen(s) of interest, or cells comprising/expressing the antigen(s)/peptides. Cells comprising/expressing the antigen(s)/peptides may do so as a consequence of infection with the virus comprising/encoding the antigen(s), uptake by the cell of the antigen(s)/peptides thereof or expression of the antigen(s)/peptides thereof. The presentation is typically in the context of an MHC molecule at the cell surface of the antigen-presenting cell.

Cells comprising/expressing the antigen(s)/peptides may have been contacted ("pulsed") with peptides of the antigen(s) according to methods well known to the skilled person. Antigenic peptides may be provided in a library of peptide mixtures (corresponding to one or more antigens), which may be referred to as pepmixes. Peptides of pepmixes may e.g. be overlapping peptides of 8-20 amino acids in length, and may cover all or part of the amino acid sequence of the relevant antigen.

Cells within the population of immune cells comprising receptors specific for the peptide(s) may be activated (and stimulated to proliferate), following recognition of peptide(s) of the antigen(s) presented by antigen-presenting cells (APCs) in the context of appropriate costimulatory signals. It will be appreciated that "an immune cell specific for an oncolytic virus" encompasses plural cells, e.g. populations of such cells. Such populations may be generated/expanded in vitro and/or ex vivo.

In some embodiments, an immune cell specific for an oncolytic virus is specific for an oncolytic adenovirus (OncAd), e.g. an OncAd as described herein. In some embodiments, an immune cell specific for an oncolytic virus is specific for an antigen of an OncAd. In some embodiments, the antigen is, or is derived from, an OncAd protein, e.g. a protein encoded by an early gene (e.g. E1 (e.g. E1A, E1B), E2 (e.g. E2A, E2B), E3 or E4), a protein encoded by a late gene (e.g. L1, L2, L3, L4 or L5), a protein encoded by IX, or a protein encoded by IVa2. In some embodiments, the antigen is, or is derived from, an OncAd hexon and/or penton.

In some embodiments in accordance with various aspects of the present disclosure an immune cell specific for a virus may be generated/expanded (or may have been generated/expanded) by a method comprising: stimulating a population of immune cells by culture in the presence of antigen presenting cells (APCs) presenting a peptide of the virus.

In some embodiments an immune cell specific for an oncolytic virus according to the present disclosure is prepared by a method employing a PepMix comprising a mixture of overlappying peptides corresponding to Human Adenovirus 3 hexon and/or a PepMix comprising a mixture of overlappying peptides corresponding to Human Adenovirus 5 penton.

In some embodiments the oncolytic virus-specific immune cell expresses/comprises a CAR, e.g. a CAR as described herein. The oncolytic virus-specific immune cell may be engineered to express a CAR e.g. by transfection/transduction of the oncolytic virus-specific immune cell with nucleic acid encoding a CAR.

Combinations of the Disclosure

Aspects of the present invention include compositions and methods comprising/employing (i) an oncolytic virus; (ii) a virus comprising nucleic acid encoding an immunomodulatory factor; and (iii) at least one cell comprising a chimeric antigen receptor (CAR) specific for a cancer cell antigen.

Also provided are compositions and methods comprising/employing (i) an oncolytic virus; and (ii) at least one cell comprising a chimeric antigen receptor (CAR) specific for a cancer cell antigen (i.e. without necessarily also employing a virus comprising nucleic acid encoding an immunomodulatory factor).

Also provided are compositions and methods comprising/employing (i) an oncolytic virus: and (ii) an immune cell specific for the oncolytic virus.

In some embodiments in accordance with various aspects described herein the cell comprising/expressing the CAR is specific for the oncolytic virus employed (e.g. comprises antigen receptor (e.g. TCR) specific for an antigen of the oncolytic virus). That is to say, in some embodiments the oncolytic virus and the specificity of the cell comprising/expressing the CAR are matched. By way of example, in some embodiments the oncolytic virus is an adenovirus, and the CAR-expressing cell comprising/expressing a CAR is an Adenovirus-specific T cell.

Similarly, in various aspects described herein an oncolytic virus is employed in combination with an immune cell specific for the oncolytic virus (i.e. the same oncolytic virus).

"Combinations" as referred to herein encompass products and compositions (e.g. pharmaceutical compositions) comprising the components of the combination. "Combinations" also encompass therapeutic regimens employing the the components of the combination.

In some embodiments the components of a combination are provided in separate compositions. In some embodiments more than one component of a combination is provided in a composition. In some embodiments the components of a combination are provided in one composition.

Similarly, in some embodiments the components of a combination are administered separately. In some embodiments a component of a combination is administered with another component of the combination. In some embodiments the components of a combination are administered together.

By way of illustration, in the example of a combination comprising an oncolytic virus, a virus comprising nucleic acid encoding an immunomodulatory factor and at least one cell comprising a CAR specific for a cancer cell antigen, the oncolytic virus and the virus comprising nucleic acid encoding an immunomodulatory factor may be administered together, and the at least one cell comprising a CAR specific for a cancer cell antigen may be administered separately (e.g. subsequently).

Where components of a combination are administered together administration may be simultaneous administration as described hereinbelow. Where components of a combination are administered separately, administration may be simultaneous administration or sequential administration, as described hereinbelow. In cases wherein components of a combination are administered separately, the administration of the separate components may or may not be administered via the same administration routes Functional Properties The agents of the present disclosure may be defined by reference to one of more functional properties. The agents may be evaluated for the functional properties, for example, by analysis as described in the experimental examples. Similarly, the combinations and methods of the present disclosure may be defined by reference to one or more functional properties and/or effects, and may be evaluated for such properties/effects e.g. by analysis as described in the experimental examples.

In some embodiments, an oncolytic virus according to the present disclosure may possess one or more of the following functional properties:

- ability to replicate in, and/or cause cell killing of, cancer cells;
- reduced ability to replicate in and/or cause cell killing of, non-cancerous cells as compared to the ability to replicate in, and/or cause cell killing of, cancer cells;
- comparable or improved ability to cause cell killing of cancer cells as compared to the ability of one or more oncolytic viruses known in the art;
- ability to help replication of helper-dependent adenovirus (HDAd);
- comparable or improved ability to replicate in cancer cells as compared to the ability of one or more oncolytic viruses known in the art.

In some embodiments, a cell comprising a chimeric antigen receptor (CAR) specific for a cancer cell antigen according to the present disclosure may possess one or more of the following functional properties:

- ability to bind to HER2;
- ability to bind to HER2-expressing cells;
- ability to cause cell killing of HER2-expressing cells;
- reduced ability to cause cell killing of cell not expressing HER2 as compared to the ability to cause cell killing of HER2-expressing cells.

In some embodiments the combination of an oncolytic virus, a virus comprising nucleic acid encoding an immunomodulatory and at least one cell comprising a CAR specific for a cancer cell antigen may possess one or more of the following functional properties:

- improved ability to cause cell killing of cancer cells as compared to the ability to cause cell killing of cancer cells by any one of the components use alone, or by any two of the components used in combination.
- ability to cause cell killing of cancer cells which is synergistic (i.e. super-additive) as compared to the ability to cause cell killing of cancer cells by the components used alone.

In some embodiments the combination of an oncolytic virus and at least one cell comprising a CAR specific for a cancer cell antigen may possess one or more of the following functional properties:

- improved ability to cause cell killing of cancer cells as compared to the ability to cause cell killing of cancer cells by either component used alone.
- ability to cause cell killing of cancer cells which is synergistic (i.e. super-additive) as compared to the ability to cause cell killing of cancer cells by the components used alone.

In some embodiments the combination of an oncolytic virus and an immune cell specific for the oncolytic virus may possess one or more of the following functional properties:

- improved ability to cause cell killing of cancer cells as compared to the ability to cause cell killing of cancer cells by either component used alone.
- ability to cause cell killing of cancer cells which is synergistic (i.e. super-additive) as compared to the ability to cause cell killing of cancer cells the components used alone.

Analysis of the ability to cause cell killing of cancer cells may be assessed e.g. in vitro, by analysis of number/viability of cancer cells. Analysis of the ability to cause cell killing of cancer cells may also be analysed in vivo in an appropriate model, e.g. by analysis of number of cancer cells, tumor size/volume and/or some other correlate of the number of cancer cells (e.g. disease progression, severity of symptoms of the cancer etc.).

Therapeutic Applications

Aspects of the present disclosure are concerned in particular with the use of an oncolytic virus, a virus comprising nucleic acid encoding an immunomodulatory factor and at least one T cell comprising a chimeric antigen receptor (CAR) specific for a cancer cell antigen, in the treatment of a cancer in a subject.

Accordingly, the present disclosure provides a method of treating a cancer, comprising administering to a subject: an oncolytic virus; a virus comprising nucleic acid encoding an immunomodulatory factor; and at least one T cell comprising a chimeric antigen receptor (CAR) specific for a cancer cell antigen.

The present disclosure also provides an oncolytic virus; a virus comprising nucleic acid encoding an immunomodulatory factor, and at least one T cell comprising a chimeric antigen receptor (CAR) specific for a cancer cell antigen; for use in a method of treating a cancer. Also provided is the use of an oncolytic virus; a virus comprising nucleic acid encoding an immunomodulatory factor; and at least one T cell comprising a chimeric antigen receptor (CAR) specific for a cancer cell antigen; in the manufacture of a medicament for treating a cancer.

The present disclosure also provides a method of treating a cancer, comprising administering to a subject: (i) an oncolytic virus; and (ii) at least one cell comprising a chimeric antigen receptor (CAR) specific for a cancer cell antigen. Also provided is (i) an oncolytic virus: and (ii) at least one cell comprising a chimeric antigen receptor (CAR) specific for a cancer cell antigen for use in a method of treating a cancer. Also provided is the use of (i) an oncolytic virus; and (ii) at least one cell comprising a chimeric antigen receptor (CAR) specific for a cancer cell antigen in the manufacture of a medicament for use in a method of treating a cancer.

The present disclosure also provides a method of treating a cancer, comprising administering to a subject: (i) an oncolytic virus; and (ii) an immune cell specific for the oncolytic virus. Also provided is (i) an oncolytic virus; and (ii) an immune cell specific for the oncolytic virus for use in a method of treating a cancer. Also provided is the use of (i) an oncolytic virus; and (ii) an immune cell specific for the oncolytic virus in the manufacture of a medicament for use in a method of treating a cancer.

Also provided are methods for treating cancer comprising administering the OncAds, HDAds, CARs, nucleic acids/plurality of nucleic acids, cells and pharmaceutical compositions of the present disclosure to a subject. Also provided are the OncAds, HDAds, CARs, nucleic acids/plurality of nucleic acids, cells and pharmaceutical compositions of the present disclosure for use in methods for treating cancer. Also provided are the use of the OncAds, HDAds, CARs, nucleic acids/plurality of nucleic acids, cells and pharmaceutical compositions of the present disclosure in the manufacture of a medicament for treating cancer.

'Treatment' may, for example, be reduction in the development or progression of a cancer, alleviation of the symptoms of a cancer or reduction in the pathology of a cancer. Treatment or alleviation of a cancer may be effective to prevent progression of the cancer, e.g. to prevent worsening of the condition or to slow the rate of development of a more severe disease state. In some embodiments treatment or alleviation may lead to an improvement in the cancer, e.g. a reduction in the symptoms of the cancer or reduction in some other correlate of the severity/activity of the cancer. Prevention of a cancer may refer to prevention of a worsening of the condition or prevention of the development of the cancer, e.g. preventing an early stage cancer developing to a later stage.

In some embodiments, the treatment may be aimed at reducing the number of cells of the cancer or the amount of tissue comprising cancerous cells in the subject. In some embodiments, the treatment may be aimed at reducing the size of and/or preventing the growth of at least one tumor in the subject.

In some embodiments, the treatment comprises administering an oncolytic virus according to the present disclosure to the subject. In some embodiments, the treatment may comprise administering to a subject a cell or population of cells comprising or encoding an oncolytic virus according to the present disclosure. In some embodiments, the treatment comprises administering an oncolytic virus and a virus encoding an immunomodulatory factor according to the present disclosure to the subject. In some embodiments, the treatment may comprise administering to a subject a cell or population of cells comprising or encoding an oncolytic virus and/or virus encoding an immunomodulatory factor according to the present disclosure.

In some embodiments, the treatment may comprise modifying a cell or population of cells to comprise/express a CAR according to the present disclosure. In some embodiments, the treatment may comprise administering to a subject a cell or population of cells modified to comprise/express a CAR of the present disclosure. In some embodiments, the treatment is aimed at providing the subject with an immune cell or population of immune cells which having specificity for a cancer cell antigen, e.g. by administering a CAR-expressing cell according to the present disclosure, or generating a CAR-expressing cell according to the present disclosure.

In some embodiments, the treatment may comprise administering to a subject an immune cell/population of immune cells specific for an oncolytic virus according to the present disclosure. In some embodiments, the treatment is aimed at providing the subject with an immune cell/population of immune cells having specificity for an oncolytic virus. In some embodiments, the treatment may comprise generating/expanding a population of immune cells specific for an oncolytic virus according to the present disclosure.

In some embodiments, the treatment may comprise administering to a subject an immune cell/population of immune cells specific for an oncolytic virus according to the present disclosure, modified to comprise/express a CAR according to the present disclosure. In some embodiments, the treatment is aimed at providing the subject with an immune cell/population of immune cells having specificity for an oncolytic virus also having specificity for a cancer cell antigen. In some embodiments, the treatment may comprise generating/expanding a population of immune cells specific for an oncolytic virus according to the present disclosure, and modifying a cell or cells of the population to comprise/express a CAR according to the present disclosure.

The subject to be treated may be any animal or human. The subject is preferably mammalian, more preferably human. The subject may be a non-human mammal, but is more preferably human. The subject may be male or female or of any gender. The subject may be a patient. A subject may have been diagnosed with a cancer requiring treatment, may be suspected of having such a cancer, or may be at risk of developing such a cancer.

In some embodiments, the cancer to be treated comprises cells expressing a cancer cell antigen, e.g. a cancer cell antigen as described herein (e.g. HER2). In some embodiments, the cells express the cancer cell antigen (e.g. HER2) at the cell surface.

In some embodiments, the cancer to be treated comprises cells expressing a cancer cell antigen for which the CAR is specific. In some embodiments, the CAR comprises a cancer cell antigen binding domain, and the cancer to be treated comprises cells expressing the cancer cell antigen, e.g. cells expressing the cancer cell antigen at the cell surface.

In some embodiments, the cancer over-expresses the cancer cell antigen. Overexpression of a cancer cell antigen can be determined by detection of a level of expression of the cancer cell antigen which is greater than the level of expression by equivalent non-cancerous cells/non-tumor tissue.

In some embodiments the cancer is a cancer expressing HER2, e.g. a cancer expressing HER2 at the cell surface. In some embodiments, the cancer over-expresses HER2. Overexpression of HER2 can be determined by detection of a level of expression of HER2 which is greater than the level of expression of HER2 by equivalent non-cancerous cells/non-tumor tissue.

In some embodiments, the subject to be treated according to the present disclosure is selected for treatment on the basis detection of expression/overexpression of the cancer cell antigen by a cancer cell or tumour obtained from the subject.

Expression of a given cancer cell antigen may be determined by any suitable means. Expression may be gene expression or protein expression. Gene expression can be determined e.g. by detection of mRNA encoding the cancer cell antigen, for example by quantitative real-time PCR (qRT-PCR). Protein expression can be determined e.g. by detection of the cancer cell antigen, for example by antibody-based methods, for example by western blot, immunohistochemistry, immunocytochemistry, flow cytometry, or ELISA.

The cancer to be treated/prevented in accordance with the present disclosure may be any unwanted cell proliferation (or any disease manifesting itself by unwanted cell proliferation), neoplasm or tumor. The cancer may be benign or malignant and may be primary or secondary (metastatic). The cancer may be resistant (initially or following treatment) and/or the cancer may be recurring. A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

The cancer to be treated/prevented may be any kind of cancer, including any one of an acute lymphoblastic leukemia (ALL), acute myeloid leukemia (AML), adrenocortical carcinoma, AIDS-related cancer (e.g. Kaposi sarcoma, AIDS-related lymphoma, primary CNS lymphoma), anal cancer, appendix cancer, astrocytoma, basal cell carcinoma of the skin, bile duct cancer (e.g. cholangiocarcinoma), bladder cancer, bone cancer (e.g. Ewing sarcoma, osteosarcoma, malignant fibrous histiocytoma), brain tumor, breast cancer, bronchial tumor, Burkitt lymphoma, carcinoid tumor, carcinoma of unknown primary, cardiac tumor, central nervous system cancer (e.g. atypical teratoid/rhabdoid tumor, embryonal tumor, germ cell tumor, primary CNS lymphoma), cervical cancer, chordoma, chronic lymphocytic leukemia (CLL), chronic myelogenous leukemia (CML), chronic myeloproliferative neoplasm, colorectal cancer, craniopharyngioma, cutaneous T-cell lymphoma (e.g. mycosis fungoides, Sézary syndrome), ductal carcinoma in situ (DCIS), endometrial cancer (uterine cancer), ependymoma, esophageal cancer, esthesioneuroblastoma, extracranial germ cell tumor, extragonadal germ cell tumor, eye cancer (e.g. intraocular melanoma, retinoblastoma) fallopian tube cancer, malignant fibrous histiocytoma of bone, gallbladder cancer, gastric (stomach) cancer, gastrointestinal carcinoid tumor, gastrointestinal stromal tumor (GIST), ovarian germ cell tumor, testicular cancer, gestational trophoblastic disease, hairy cell leukemia, head and neck cancer, heart tumor, hepatocellular (liver) cancer, histiocytosis, Langerhans cell, Hodgkin lymphoma, hypopharyngeal cancer, islet cell tumor (pancreatic neuroendocrine tumor), kidney (renal cell) cancer, laryngeal cancer, papillomatosis, leukemia, lip and oral cavity cancer, lung cancer (non-small cell lung cancer (NSCLC) and small cell lung cancer (SCLC)) lymphoma, male breast cancer, melanoma, Merkel cell carcinoma, mesothelioma, metastatic cancer, metastatic squamous neck cancer with occult primary, midline tract carcinoma involving NUT gene, mouth cancer, multiple endocrine neoplasia syndromes, multiple myeloma/plasma cell neoplasms, mycosis fungoides, myelodysplastic syndrome, myelodysplastic/myeloproliferative neoplasm, myelogenous leukemia, chronic myeloid leukemia, acute myeloid leukemia (AML), nasal cavity and paranasal sinus cancer, nasopharyngeal cancer, neuroblastoma, non-Hodgkin lymphoma, oral cancer, lip and oral cavity cancer, oropharyngeal cancer, osteosarcoma, ovarian cancer, pancreatic cancer, papillomatosis, paraganglioma, paranasal sinus cancer, nasal cavity cancer, parathyroid cancer, penile cancer, pharyngeal cancer, pheochromocytoma, pituitary tumor, plasma cell neoplasm/multiple myeloma, pleuropulmonary blastoma, pregnancy and breast cancer, primary peritoneal cancer, prostate cancer, rectal cancer, recurrent cancer, retinoblastoma, rhabdomyosarcoma, salivary gland cancer, vascular tumor, uterine sarcoma, skin cancer, small intestine cancer, squamous cell carcinoma of the skin, T-cell lymphoma, throat cancer, thymoma, thymic carcinoma, thyroid cancer, transitional cell cancer of the renal pelvis and ureter, urethral cancer, vaginal cancer, vulvar cancer or Wilms tumor.

In some embodiments, the cancer to be treated is one or more of nasopharyngeal carcinoma (NPC; e.g. Epstein-Barr Virus (EBV)-positive NPC), cervical carcinoma (CC; e.g. human papillomavirus (HPV)-positive CC), oropharyngeal carcinoma (OPC; e.g. HPV-positive OPC), gastric carcinoma (GC; e.g. EBV-positive GC), hepatocellular carcinoma (HCC; e.g. Hepatitis B Virus (HBV)-positive HCC), lung cancer (e.g. non-small cell lung cancer (NSCLC)) and head and neck cancer (e.g. cancer originating from tissues of the lip, mouth, nose, sinuses, pharynx or larynx, e.g. head and neck squamous cell carcinoma (HNSCC)).

In some embodiments the cancer is associated with, or caused by, a virus. In some embodiments the cancer is an EBV-positive cancer. In some embodiments the cancer is an HPV-positive cancer.

In some embodiments, the cancer is one of a head and neck cancer, nasopharyngeal carcinoma (NPC), oropharyngeal cancer (OPC), cervical cancer (CC), gastric/stomach cancer, gastric carcinoma or lung cancer.

Methods of medical treatment may also involve in vivo, ex vivo, and adoptive immunotherapies, including those using autologous and/or heterologous cells or immortalized cell lines.

Administration

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the condition to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Viruses, CARs, nucleic acids, and cells according to the present disclosure may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion. Suitable formulations may comprise the viruses, CARs, nucleic acids, or cells in sterile or isotonic medium. Medicaments and pharmaceutical compositions may be formulated in fluid, including gel, form. Fluid formulations may be formulated for administration by injection or infusion (e.g. via catheter) to a selected region of the human or animal body.

The oncolytic virus and/or the virus comprising nucleic acid encoding an immunomodulatory factor may be formulated for intratumoral administration. In some embodiments, the methods may comprise intratumoral administration of the oncolytic virus and/or the virus comprising nucleic acid encoding an immunomodulatory factor.

The cell comprising a CAR and/or the immune cell specific for an oncolytic virus may be formulated for intravenous administration. In some embodiments, the methods may comprise intravenous administration of the cell comprising a CAR and/or the immune cell specific for an oncolytic virus.

Administration of the components of combinations of the present disclosure (e.g. oncolytic virus, virus comprising nucleic acid encoding an immunomodulatory factor; at least one T cell comprising a CAR specific for a cancer cell antigen; immune cell specific for an oncolytic virus in accordance with the present disclosure) may be simultaneous or sequential. The present disclosure also contemplates simultaneous or sequential administration of the OncAds, HDAds, CARs, nucleic acids/plurality of nucleic acids, cells and pharmaceutical compositions of the present disclosure.

Simultaneous administration refers to administration of the agents together, for example as a pharmaceutical composition containing the agents (i.e. a combined preparation), or immediately after each other and optionally via the same route of administration, e.g. to the same artery, vein or other blood vessel. In particular embodiments, the oncolytic virus and virus comprising nucleic acid encoding an immunomodulatory factor may be administered simultaneously in a combined preparation. In certain embodiments upon simultaneous administration the two or more of the agents may be administered via different routes of administration. In some embodiments simultaneous administration refers to administration at the same time, or within e.g. 1 hr, 2 hrs, 3 hrs, 4 hrs, 5 hrs, 6 hrs, 8 hrs, 12 hrs, 24 hrs, 36 hrs or 48 hrs.

Sequential administration refers to administration of one or more of the agents followed after a given time interval by separate administration of another of the agents. It is not required that the two agents are administered by the same route, although this is the case in some embodiments.

The time interval may be any time interval, including hours, days, weeks, months, or years. In some embodiments sequential administration refers to administrations separated by a time interval of one of at least 10 min, 30 min, 1 hr, 6 hrs, 8 hrs, 12 hrs, 24 hrs, 36 hrs, 48 hrs, 3 days, 4 days, 5 days, 6 days, 1 week, 2 weeks, 3 weeks, 1 month, 6 weeks, 2 months, 3 months, 4 months, 5 months or 6 months.

In some embodiments, the treatment may further comprise other therapeutic or prophylactic intervention, e.g. chemotherapy, immunotherapy, radiotherapy, surgery, vaccination and/or hormone therapy. Such other therapeutic or prophylactic intervention may occur before, during and/or after the therapies encompassed by the disclosure, and the deliveries of the other therapeutic or prophylactic interventions may occur via different administration routes as the therapies of the disclosure. Chemotherapy and radiotherapy respectively refer to treatment of a cancer with a drug or with ionising radiation (e.g. radiotherapy using X-rays or γ-rays). The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA. RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracyline antibiotics) such as dactinomycin, doxorubicin (Adnamycin™), epirubicin, bleomycin, rapamycin; antibody based agents, such as anti-PD-1 antibodies, anti-PD-L1 antibodies, anti-TIM-3 antibodies, anti-CTLA-4, anti-4-1 BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; EGFR inihibitors such as erlotinib, cetuximab and gefitinib; anti-angiogenic agents such as bevacizumab (Avastin®); cancer vaccines such as Sipuleucel-T (Provenge®).

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aidesleukin, Alemtuzumab, ALIMTA, Alitretinoin, Alkaban-AQ®, Alkeran®, AII-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin), Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren, Cytarabine Cytosar-U®, Cytoxan®, Dacogen, Dactinomycin, Darbepoetin Alfa, Dasatinib, Daunomycn, Daunorubicin, Daunorubicin Hydrochloride, Daunorubicin Liposomal, DaunoXome®, Decadron, Decitabine, Delta-Cortemi, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatinm, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte—Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbinet, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinolt, Platinol-AQ®, Prednisolone, Prednisone, Prelone®, Procarbazine, PROCRIT®, Proleukin®, Prolifeprospan 20 with Carmnnustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

In embodiments of the present disclosure wherein a nucleic acid/virus encoding an enzyme capable of catalysing conversion of a non-toxic factor to a cytotoxic form is employed, the method may further comprise administration with a prodrug substrate for the enzyme. The prodrug may be administered simultaneously or sequentially to administration of the nucleic acid/virus encoding an enzyme capable of catalysing conversion of a non-toxic factor to a cytotoxic form.

In some embodiments the prodrug is selected from ganciclovir (GCV), aciclovir (ACV) and/or valaciclovir, e.g. where the nucleic acid/virus encodes a thymidine kinase. In some embodiments the prodrug is 5-fluorocytosine (5-FC), e.g. where the nucleic acid/virus encodes a cytosine deaminase. In some embodiments the prodrug is selected from CB1954, nitro-CBI-DEI and/or PR-104A, e.g. where the nucleic acid/virus encodes a nitroreductase. In some embodiments the prodrug is oxazaphosphorine (e.g. cyclophosphamide or ifosfamide), e.g. where the nucleic acid/virus encodes a cytochrome P450. In some embodiments the prodrug is a nitrogen mustard based drug (e.g. CMDA or ZD2767P), e.g. where the nucleic acid/virus encodes a carboxypeptidase G2. In some embodiments the prodrug is 6-methylpurine 2-deoxyriboside and/or fludarabine (e.g. 6-methylpurine-2'-deoxyriboside (MeP-dR), 2-F-2'-deoxyadenosine (F-dAdo) or arabinofuranosyl-2-F-adenine monophosphate (F-araAMP), e.g. where the nucleic acid/virus encodes a purine nucleoside phosphorylase. In some embodiments the prodrug is indole-3-acetic acid (IAA), e.g. where the nucleic acid/virus encodes a horseradish peroxidase. In some embodiments the prodrug is irinotecan, e.g. where the nucleic acid/virus encodes a carboxylesterase.

Multiple doses of the agents (e.g. viruses (OncAds, HdAds), CARs, nucleic acids/plurality of nucleic acids, vectors, cells, compositions, combinations, prodrugs) of the present disclosure may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, or more hours or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Adoptive Transfer

In embodiments of the present disclosure, the methods of treatment comprise adoptive transfer of immune cells. Adoptive cell transfer (ACT) generally refers to a process by which cells (e.g. immune cells) are obtained from a subject, typically by drawing a blood sample from which the cells are isolated. The cells are then typically treated or altered in some way, and then administered either to the same subject (adoptive transfer is of autologous cells) or to a different subject (adoptive transfer is of allogeneic cells). The treatment is typically aimed at providing population of cells with certain desired characteristics to a subject, or increasing the frequency of cells with such characteristics in that subject. In the present disclosure, adoptive transfer may be performed with the aim of introducing a cell or population of cells into a subject, and/or increasing the frequency of a cell or population of cells in a subject.

In some embodiments, the subject from which the cell is isolated is the subject administered with the modified cell (i.e., adoptive transfer is of autologous cells). In some embodiments, the subject from which the cell is isolated is a different subject to the subject to which the modified cell is administered (i.e., adoptive transfer is of allogeneic cells).

Adoptive transfer of T cells is described, for example, in Kalos and June 2013, Immunity 39(1): 49-60, which is hereby incorporated by reference in its entirety. Adoptive transfer of NK cells is described, for example, in Davis et al. 2015, Cancer J. 21(6): 486-491, which is hereby incorporated by reference in its entirety.

The cell may e.g. be a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. In some embodiments, the cell is a T cell. In some embodiments, the T cell is a CD3+ T cell. In some embodiments, the T cell is a CD3+, CD4+ T cell. In some embodiments, the T cell is a CD3+, CD8+ T cell. In some embodiments, the T cell is a T helper cell ($T_H$ cell)). In some embodiments, the T cell is a cytotoxic T cell (e.g. a cytotoxic T lymphocyte (CTL)). In some embodiments, the T cell is a virus-specific T cell. In some embodiments, the T cell is specific for EBV, HPV, HBV, HCV or sHIV.

In some embodiments the cell is an immune cell specific for an oncolytic virus, as described herein. Accordingly, in some embodiments the methods comprise administration of at least one immune cell specific for an oncolytic virus to a subject. In some embodiments, the methods of the disclosure comprise generating/expanding a population of immune cells specific for an oncolytic virus, and administering at least one immune cell specific for the oncolytic virus to a subject.

In some embodiments, the methods comprise:

(a) isolating immune cells from a subject:

(b) generating or expanding a population of immune cells specific for an oncolytic virus by a method comprising: stimulating the immune cells by culture in the presence of antigen presenting cells (APCs) presenting a peptide of the oncolytic virus, and;

(c) administering at least one immune cell specific for the oncolytic virus to a subject.

In some embodiments the method steps for production of an immune cell specific for an oncolytic virus may comprise one or more of: taking a blood sample from a subject; isolating PBMCs from the blood sample; generating/expanding a population of immune cells specific for an oncolytic virus (e.g. by culturing PBMCs in the presence of cells (e.g. APCs) comprising/expressing antigen(s)/peptide(s) of the oncolytic virus); culturing immune cells specific for an oncolytic virus in in vitro or ex vivo cell culture; collecting immune cells specific for an oncolytic virus; mixing immune cells specific for an oncolytic virus with an adjuvant, diluent, or carrier; administering the modified cell to a subject.

The present disclosure also provides methods of treating a cancer in a subject comprising administering at least one cell comprising a chimeric antigen receptor (CAR) specific for a cancer cell antigen. In connection with this feature of the disclosure, in some embodiments, the method additionally comprises steps for production of the at least one cell comprising a chimeric antigen receptor (CAR) specific for a cancer cell antigen. The CAR may be a first generation, second generation or third or subsequent generation CAR. The CAR may comprise one, two, three, or more costimulatory domains, for example.

In some embodiments, the methods comprise modifying at least one cell obtained from a subject to express or comprise a CAR according to the disclosure, optionally expanding the modified at least one cell, and administering the modified at least one cell to a subject.

In some embodiments, the methods comprise:

(a) isolating at least one cell from a subject;

(b) modifying the at least one cell to express or comprise a CAR according to the present disclosure, or a nucleic acid encoding a CAR according to the present disclosure, (c) optionally expanding the modified at least one cell, and;

(d) administering the modified at least one cell to a subject.

In some embodiments the cell comprising/expressing a CAR specific for a cancer cell antigen is an immune cell specific for an oncolytic virus, as described herein. In some embodiments, the methods comprise modifying an immune cell specific for an oncolytic virus to express or comprise a CAR according to the disclosure, optionally expanding the modified immune cell specific for an oncolytic virus, and administering the modified immune cell specific for an oncolytic virus to a subject.

In some embodiments, the methods comprise:

(a) isolating immune cells from a subject:

(b) generating or expanding a population of immune cells specific for an oncolytic virus by a method comprising: stimulating the immune cells by culture in the presence of antigen presenting cells (APCs) presenting a peptide of the oncolytic virus;

(c) modifying at least one immune cell specific for an oncolytic virus to express or comprise a CAR according to the present disclosure, or a nucleic acid encoding a CAR according to the present disclosure, (d) optionally expanding the modified at least one immune cell specific for an oncolytic virus, and;

(e) administering the modified at least one immune cell specific for an oncolytic virus to a subject.

The at least one cell modified according to the present disclosure can be modified to comprise/express a CAR according to methods well known to the skilled person. The modification may comprise nucleic acid transfer for permanent or transient expression of the transferred nucleic acid. Any suitable genetic engineering platform may be used to modify a cell according to the present disclosure. Suitable methods for modifying a cell include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, incorporated by reference hereinabove.

In some embodiments the method steps for production of the at least one cell comprising a chimeric antigen receptor (CAR) specific for a cancer cell antigen may comprise one or more of: taking a blood sample from a subject; isolating and/or expanding at least one cell from the blood sample; culturing the at least one cell in in vitro or ex vivo cell culture; introducing into the at least one cell a CAR as described herein, or a nucleic acid encoding a CAR as described herein, thereby modifying the at least one cell; expanding the at least one modified cell; collecting the at least one modified cell; mixing the modified cell with an adjuvant, diluent, or carrier; administering the modified cell to a subject.

In some embodiments, the methods may additionally comprise treating the cell to induce/enhance expression of the CAR or nucleic acid encoding the CAR. For example, the nucleic acid may comprise a control element for inducible upregulation of expression of the CAR from the nucleic acid in response to treatment with a particular agent. In some embodiments, treatment may be in vivo by administration of the agent to a subject having been administered with a modified cell according to the disclosure. In some embodiments, treatment may be ex vivo or in vitro by administration of the agent to cells in culture ex vivo or in vitro.

The skilled person is able to determine appropriate reagents and procedures for adoptive transfer of cells according to the present disclosure, for example by reference to Dai et al., 2016 J Nat Cancer Inst 108(7): djv439, which is incorporated by reference in its entirety.

In a related aspect, the present disclosure provides a method of preparing a modified cell, the method comprising introducing into a cell a CAR according to the present disclosure or a nucleic acid encoding a CAR according to the present disclosure, thereby modifying the at least one cell. The method is preferably performed in vitro or ex vivo.

Compositions/Products/Kits

The present disclosure also provides an oncolytic virus as described herein, optionally isolated. Also provided is a nucleic acid encoding the oncolytic virus, optionally isolated. Also provided is a cell comprising the oncolytic virus, or comprising nucleic acid encoding the oncolytic virus, optionally isolated.

The present disclosure also provides a virus comprising nucleic acid encoding an immunomodulatory factor as described herein, optionally isolated. Also provided is a nucleic acid encoding the virus, optionally isolated. Also provided is a cell comprising the virus, or comprising nucleic acid encoding the virus, optionally isolated.

The present disclosure also provides a chimeric antigen receptor (CAR) as described herein, optionally isolated. Also provided is a nucleic acid encoding the CAR, optionally isolated. Also provided is a cell comprising the CAR, or comprising nucleic acid encoding the CAR, optionally isolated.

The present disclosure also provides compositions comprising an oncolytic virus, a virus comprising nucleic acid encoding an immunomodulatory factor, a chimeric antigen receptor, a nucleic acid/plurality of nucleic acids, or a cell according to the disclosure.

The oncolytic virus, virus comprising nucleic acid encoding an immunomodulatory factor, chimeric antigen receptor, nucleic acid/plurality of nucleic acids or cell according to the present disclosure may be formulated as pharmaceutical compositions for clinical use and may comprise a pharmaceutically acceptable carrier, diluent, excipient or adjuvant. Combinations of the present disclosure may be provided in a single composition, or may be provided as plural compositions comprising the components of the combination.

In accordance with the present disclosure methods are also provided for the production of pharmaceutically useful compositions, such methods of production may comprise one or more steps selected from: isolating an oncolytic virus, a virus comprising nucleic acid encoding an immunomodulatory factor, a chimeric antigen receptor, a nucleic acid/plurality of nucleic acids, or a cell as described herein; and/or mixing an oncolytic virus, a virus comprising nucleic acid encoding an immunomodulatory factor, a chimeric antigen receptor, a nucleic acid/plurality of nucleic acids, or a cell as described herein with a pharmaceutically acceptable carrier, adjuvant, excipient or diluent.

For example, a further aspect of the present disclosure relates to a method of formulating or producing a medicament or pharmaceutical composition for use in the treatment of a cancer, the method comprising formulating a pharmaceutical composition or medicament by mixing an oncolytic virus, a virus comprising nucleic acid encoding an immunomodulatory factor, a chimeric antigen receptor, a nucleic acid/plurality of nucleic acids, or a cell as described herein with a pharmaceutically acceptable carrier, adjuvant, excipient or diluent.

The present disclosure also provides a kit of parts comprising one or more of an oncolytic virus, a virus comprising nucleic acid encoding an immunomodulatory factor, a chimeric antigen receptor, a nucleic acid, a cell or a composition according to the present disclosure.

In some embodiments the kit may have at least one container having a predetermined quantity of an oncolytic virus, a virus comprising nucleic acid encoding an immunomodulatory factor, a chimeric antigen receptor, a nucleic acid/plurality of nucleic acids, or a cell according to the disclosure or a composition according to the present disclosure. The kit may have containers containing individual components of the combinations of the present disclosure, or may have containers containing combinations of the components of the combinations of the present disclosure.

The kit may provide the oncolytic virus, virus comprising nucleic acid encoding immunomodulatory factor, CAR, nucleic acid, cell or composition with instructions for administration to a patient in order to treat a specified cancer. The oncolytic virus, virus comprising nucleic acid encoding immunomodulatory factor, CAR, nucleic acid/plurality of nucleic acids, cell or composition may be formulated so as to be suitable for injection or infusion to a tumor or to the blood.

In some embodiments the kit may comprise materials for producing a cell according to the present disclosure. For example, the kit may comprise materials for modifying a cell to express or comprise a virus or an antigen/peptide thereof, CAR or nucleic acid/plurality of nucleic acids according to the present disclosure, or materials for introducing into a cell the virus or an antigen/peptide thereof or nucleic acid/plurality of nucleic acids according to the present disclosure. The kit may comprise materials for producing an immune cell specific for an oncolytic virus; for example, the kit may comprise pepmixes of one or more antigens of the oncolytic virus.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the cancer. The therapeutic agent may also be formulated so as to be suitable for injection or infusion to a tumor or to the blood.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, Bioinformatics 21. 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | HER2(C5)-CD28TM, ICD-CD3Z CAR | MTRAMDWIWRILFLVGAATGAHSQVQLQESGPGLVKPSETLSLTCTV<br>SGGSISSSSYYWGWIRQPPGKGLEWIGSIYYSGSTYYNPSLKSRVTI<br>SVDTSKNQFSLKLSSVTAADTAVYYCARYAPDSSGYLVAFDIWGQGT<br>MVTVSSGGGGSGGGGSGGGGSQTVVTQEPSFSVSPGGTVTLTCGLSS<br>GSVSTGYYPSWYQQTPGQAPRTLIYSTNSRSSGVPDRFSGSILGNKA<br>ALTITGAQADDESDYYCVLYMGSGISVFGGGTKLTVLGSEPKSCDKT<br>HICPTRFWVLVVVGGVLACYSLLVTVAFIIFWVRSKRSRLLHSDYMN<br>MTPRRPGPTRKHYQPYAPPRDFAAYRSRVKFSRSADAPAYQQGQNQL<br>YNELNLGRREEYDVLDKRRGRDPEMGGKPQRRKNPQEGLYNELQKDK<br>MAEAYSEIGMKGERRRGKGHDGLYQGLSTATKDTYDALHMQALPPR |
| 2 | HER2(E4)-CD28TM, ICD-CD3Z CAR | MTRAMDWIWRILFLVGAATGAHSQVQLQQWGAGLLKPSETLSLTCAV<br>YGGSFSGYYWSWIRQPPGKGLEWIGEINHSGSTNYNPSLKSRVTISV<br>DTSKNQFSLKLSSVTTADTAVYYCARMGINSGGYLYGMDVWGQGTTV<br>TVSSGGGGSGGGGSGGGGSQTVVTQEPSFSVSPGGTVTLTCGLSSGS<br>VSTSYYPSWYQQIPGQAPRTLIYTTNIRSSGVPDRFGGSILGNKAAL<br>TITGAQAEDESDYYCMLYMGSGIWVFGGGTKLTVLGSEPKSCDKTHT<br>CPTRFWVLVVVGGVLACYSLLVTVAFIIFWVRSKRSRLLFISDYMNM<br>TPRRPGPTRKHYQPYAPPRDFAAYRSRVKFSRSADAPAYQQGQNQLY<br>NELNLGRREEYDVLDKRRGRDPEMGGKPQRRKNPQEGLYNELQKDKM<br>AEAYSEIGMKGERRRGKGHDGLYQGLSTATKDTYDALHMQALPPR |
| 3 | HER2(F1)-CD28TM, ICD-CD3Z CAR | MTRAMDWIWRILFLVGAATGAHSQVQLVESGPGLVKPSGTLSLTCAV<br>SGGSISSSNWWSWVRQPPGKGLEWIGEIYHSGSTNYNPSLKSRVTIS<br>VDTSKNQFSLKLSSVTAADTAVYYCARMGANSGGYLYGMDVWGQGTT<br>VTVSSGGGGSGGGGSGGGGSQTVVTQEPSFSVSPGGTVTLTCGLSSG<br>SVSTSYYPSWYQQTPGQAPRTLIYSTNTRSSGVPDRFSGSILGNKAA<br>LTITGAQADDESDYYCVLYMGSGIWVFGGGTKLTVLGSEPKSCDKTH<br>TCPTRFWVLVVVGGVLACYSLLVTVAFIIFWVRSKRSRLLHSDYMNM<br>TPRRPGPTRKHYQPYAPPRDFAAYRSRVKFSRSADAPAYQQGQNQLY<br>NELNLGRREEYDVLDKRRGRDPEMGGKPQRRKNPQEGLYNELQKDKM<br>AEAYSEIGMKGERRRGKGHDGLYQGLSTATKDTYDALHMQALPPR |
| 4 | CD28 TMD | FWVLVVVGGVLACYSLLVTVAFIIFWV |
| 5 | CD28 ICD | RSKRSRLLHSDYMNMTPRRPGPTRKHYQPYAPPRDFAAYRS |
| 6 | CD3Z ICD | RVKFSRSADAPAYQQGQNQLYNELNLGRREEYDVLDKRRGRDPEMGGKPQR<br>RKNPQEGLYNELQKDKMAEAYSEIGMKGERRRGKGHDGLYQGLSTATKDTYD<br>ALHMQALPPR |
| 7 | (G4S)3 linker | GGGGSGGGGSGGGGS |
| 8 | hulgG H leader | MDWIWRILFLVGAATGAHS |
| 9 | Hinge | EPKSCDKTHTCPTR |
| 10 | HER2(C5) LC-CDR1 | GLSSGSVSTGYYPS |

-continued

| SEQ ID NO: | DESCRIPTION | SEQUENCE |
|---|---|---|
| 11 | HER2(C5) LC-CDR2 | STNSRSS |
| 12 | HER2(C5) LC-CDR3 | VLYMGSGISV |
| 13 | HER2(C5) HC-CDR1 | SSSYYWG |
| 14 | HER2(C5) HC-CDR2 | SIYYSGSTYYNPSLKS |
| 15 | HER2(C5) HC-CDR3 | YAPDSSGYLVAFDI |
| 16 | HER2(C5) VL | QTVVTQEPSFSVSPGGTVTLTCGLSSGSVSTGYYPSWYQQTPGQAPRTLIYSTNSRSSGVPDRFSGSILGNKAALTITGAQADDESDYYCVLYMGSGISVFGGGTKLTVLGS |
| 17 | HER2(C5) VH | QVQLQESGPGLVKPSETLSLTCTVSGGSISSSSYYWGWIRQFPGKGLEWIGSIYYSGSTYYNPSLKSRVTISVDTSKNQFSLKLSSVTAADTAVYYCARYAPDSSGYLVAFDIWGQGTMVTVSS |
| 18 | HER2(E4) LC-CDR1 | GLSSGSVSTSYYPS |
| 19 | HER2(E4) LC-CDR2 | TTNIRSS |
| 20 | HER2(E4) LC-CDR3 | MLYMGSGIWV |
| 21 | HER2(E4) HC-CDR1 | SGYYWS |
| 22 | HER2(E4) HC-CDR2 | EINHSGSTNYNPSLKS |
| 23 | HER2(E4) HC-CDR3 | MGINSGGYLYGMDV |
| 24 | HER2(E4) VL | QTVVTQEPSFSVSPGGTVTLTCGLSSGSVSTSYYPSWYQQIPGQAPRTLIYTTNIRSSGVPDRFGGSILGNKAALTITGAQAEDESDYYCMLYMGSGIWVFGGGTKLTVLGS |
| 25 | HER2(E4) VH | QVQLQQWGAGLLKPSETLSLTCAVYGGSFSGYYWSWIRQPPGKGLEWIGEINHSGSTNYNPSLKSRVTISVDTSKNQFSLKLSSVTTADTAVYYCARMGINSGGYLYGMDVWGQGTTVTVSS |
| 26 | HER2(F1) LC-CDR1 | GLSSGSVSTSYYPS |
| 27 | HER2(F1) LC-CDR2 | STNTRSS |
| 28 | HER2(F1) LC-CDR3 | VLYMGSGIWV |
| 29 | HER2(F1) HC-CDR1 | SSNWWS |
| 30 | HER2(F1) HC-CDR2 | EIYHSGSTNYNPSLKS |
| 31 | HER2(F1) HC-CDR3 | MGANSGGYLYGMDV |
| 32 | HER2(F1) VL | QTVVTQEPSFSVSPGGTVTLTCGLSSGSVSTSYYPSWYQQTPGQAPRTLIYSTNTRSSGVPDRFSGSILGNKAALTITGAQADDESDYYCVLYMGSGIWVFGGGTKLTVLGS |
| 33 | HER2(F1) VH | QVQLVESGPGLVKPSGTLSLTCAVSGGSISSSNWWSWVRQPPGKGLEWIGEIYHSGSTNYNPSLKSRVTISVDTSKNQFSLKLSSVTAADTAVYYCARMGANSGGYLYGMDVWGQGTTVTVSS |

-continued

Sequences

| SEQ ID NO: | DESCRIPTION | SEQUENCE |
|---|---|---|
| 34 | Ad2 E1AΔ24 | MRHIICHGGVITEEMAASLLDQLIEEVLADNLPPPSHFEPPTLHELYDLDVTAPE<br>DPNEEAVSQIFPESVMLAVQEGIDLFTFPPAPGSPEPPHLSRQPEQPEQRALG<br>PVSMPNLVPEVIDPPSDDEDEEGEEFVLDYVEHPGHGCRSCHYHRRNTGDPD<br>IMCSLCYMRTCGMFVYSPVSEPEPEPEPEPEPARPTRRPKLVPAILRRPTSPV<br>SRECNSSTDSCDSGPSNTPPEIHPVVPLCPIKPVAVRVGGRRQAVECIEDLLNE<br>SGQPLDLSCKRPRP |
| 35 | hulL-12p70 | MGHQQLVISWFSLVFLASPLVAIWELKKDVYVVELDWYPDAPGEMVVLTCDTP<br>EEDGITWTLDQSSEVLGSGKTLTIQVKEFGDAGQYTCHKGGEVLSHSLLLLHK<br>KEDGIWSTDILKDQKEPKNKTFLRCEAKNYSGRFTCWWLTTISTDLTFSVKSSR<br>GSSDPQGVTCGAATLSAERVRGDNKEYEYSVECQEDSACPAAEESLPIEVMV<br>DAVHKLKYENYTSSFFIRDIIKPDPPKNLQLKPLKNSRQVEVSWEYPDTWSTPH<br>SYFSLTFCVQVQGKSKREKKDRVFTDKTSATVICRKNASISVRAQDRYYSSSW<br>SEWASVPCSVPGVGVPGVGARNLPVATPDPGMFPCLHHSQNLLRAVSNMLQ<br>KARQTLEFYPCTSEEIDHEDITKDKTSTVEACLPLELTKNESCLNSRETSFITNG<br>SCLASRKTSFMMALCLSSIYEDLKMYQVEFKTMNAKLLMDPKRQIFLDQNMLA<br>VIDELMQALNFNSETVPQKSSLEEPDFYKTKIKLCILLHAFRIRAVTIDRVMSYLN<br>AS |
| 36 | HSV1 TK | MASYPGHQHASAFDQAARSRGHSNRRTALRPRRQQEATEVRPEQKMPTLLR<br>VYIDGPHGMGKTTTTQLLVALGSRDDIVYVPEPMTYWRVLGASETIANIYTTQH<br>RLDQGEISAGDAAVVMTSAQITMGMPYAVTDAVLAPHIGGEAGSSHAPPPALT<br>LIFDRHPIAALLCYPAARYLMGSMTPQAVLAFVALIPPTLPGTNIVLGALPEDRHI<br>DRLAKRQRPGERLDLAMLAAIRRVYGLLANTVRYLQGGGSWREDWGQLSGT<br>AVPPQGAEPQSNAGPRPHIGDTLFTLFRAPELLAPNGDLYNVFAWALDVLAKR<br>LRPMHVFILDYDQSPAGCRDALLQLTSGMIQTHVTTPGSIPTICDLARTFAREM<br>GEAN |
| 37 | HA tag | YPYDVPDYA |
| 38 | PD-L1(H12_gl)<br>minibody | MDWIWRILFLVGAATGAHSEVQLVQSGAEVKKPGASVKVSCKASGGTFSSYAI<br>SWVRQAPGQGLEWMGRIIPILGIANYAQKFQGRVTITADKSTSTAYMELSSLRS<br>EDTAVYYCARSGHGYSYGAFDYWGQGTLVTVSSGGGGSGGGGSGGGGSQS<br>VLTQPPSVSGAPGQRVTISCTGSSSNIGAGYDVHWYQQLPGTAPKLLIYGNSN<br>RPSGVPDRFSGSKSGTSASLAITGLQAEDEADYYCQSYDSSLSGSYVVFGGG<br>TKLTVLEAKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGN<br>VFSCSVMHEALHNHYTQKSLSLSPGKGGGGSYPYDVPDYAGYPYDVPDYAG<br>YPYDVPDYA |
| 39 | PD-L1(H12_gl)<br>LC-CDR1 | TGSSSNIGAGYDVH |
| 40 | PD-L1(H12_gl)<br>LC-CDR2 | GNSNRPS |
| 41 | PD-L1(H12_gl)<br>LC-CDR3 | QSYDSSLSGSYVV |
| 42 | PD-L1(H12_gl)<br>HC-CDR1 | SYAIS |
| 43 | PD-L1(H12_gl)<br>HC-CDR2 | RIIPILGIANYAQKFQG |
| 44 | PD-L1(H12_gl)<br>HC-CDR3 | SGHGYSYGAFDY |
| 45 | PD-L1(H12_gl)<br>VL | QSVLTQPPSVSGARGQRVTISCTGSSSNIGAGYDVHWYQQLPGTAPKLLIYGN<br>SNRPSGVPDRFSGSKSGTSASLAITGLQAEDEADYYCQSYDSSLSGSYVVFG<br>GGTKLTVL |
| 46 | PD-L1(H12_gl)<br>VH | EVQLVQSGAEVKKPGASVKVSCKASGGTFSSYAISWVRQAPGQGLEWMGRII<br>PILGIANYAQKFQGRVTITADKSTSTAYMELSSLRSEDTAVYYCARSGHGYSYG<br>AFDYWGQGTLVTVSS |
| 47 | HER2(C5)-<br>CD28TM,<br>ICD-CD3Z<br>CAR | AAGTTCAGATCAAGGTCAGGAACAGATGGAACAGCTGAATATGGGCCAAAC<br>AGGATATCTGTGGTAAGCAGTTCCTGCCCCGGCTCAGGGCCAAGAACAGA<br>TGGAACAGCTGAATATGGGCCAAACAGGATATCTGTGGTAAGCAGTTCCTG<br>CCCCGGCTCAGGGCCAAGAACAGATGGTCCCCAGATGCGGTCCAGCCCTC<br>AGCAGTTTCTAGAGAACCATCAGATGTTTCCAGGGTGCCCCAAGGACCTGA |

-continued

Sequences

| SEQ ID NO: | DESCRIPTION | SEQUENCE |
|---|---|---|
| | | AATGACCCTGTGCCTTATTTGAACTAACCAATCAGTTCGCTTCTCGCTTCTG<br>TTCGCGCGCTTCTGCTCCCCGAGCTCAATAAAAGAGCCCACAACCCCTCAC<br>TCGGCGCGCCAGTCCTCCGATTGACTGAGTCGCCCGGGTACCCGTGTATC<br>CAATAAACCCTCTTGCAGTTGCATCCGACTTGTGGTCTCGCTGTTCCTTGG<br>GAGGGTCTCCTCTGAGTGATTGACTACCCGTCAGCGGGGGTCTTTCATTTG<br>GGGGCTCGTCCGGGATCGGGAGACCCCTGCCCAGGGACCACCGACCCAC<br>CACCGGGAGGTAAGCTGGCCAGCAACTTATCTGTGTCTGTCCGATTGTCTA<br>GTGTCTATGACTGATTTTATGCGCCTGCGTCGGTACTAGTTAGCTAACTAGC<br>TCTGTATCTGGCGGACCCGTGGTGGAACTGACGAGTTCGGAACACCCGGC<br>CGCAACCCTGGGAGACGTCCCAGGGACTTCGGGGGCCGTTTTTGTGGCCC<br>GACCTGAGTCCTAAAATCCCGATCGTTTAGGACTCTTTGGTGCACCCCCCT<br>TAGAGGAGGGATATGTGGTTCTGGTAGGAGACGAGAACCTAAAACAGTTCC<br>CGCCTCCGTCTGAATTTTTGCTTTCGGTTTGGGACCGAAGCCGCGCCGCG<br>CGTCTTGTCTGCTGCAGCATCGTTCTGTGTTGTCTCTGTCTGACTGTGTTTC<br>TGTATTTGTCTGAAAATATGGGCCCGGGCTAGCCTGTTACCACTCCCTTAA<br>GTTTGACCTTAGGTCACTGGAAAGATGTCGAGCGGATCGCTCACAACCAGT<br>CGGTAGATGTCAAGAAGAGACGTTGGGTTACCTTCTGCTCTGCAGAATGGC<br>CAACCTTTAACGTCGGATGGCCGCGAGACGGCACCTTTAACCGAGACCTC<br>ATCACCCAGGTTAAGATCAAGGTCTTTTCACCTGGCCCGCATGGACACCCA<br>GACCAGGTCCCCTACATCGTGACCTGGGAAGCCTTGGCTTTTGACCCCCCT<br>CCCTGGGTCAAGCCCTTTGTACACCCTAAGCCTCCGCCTCCTCTTCCTCCA<br>TCCGCCCCGTCTCTCCCCCTTGAACCTCCTCGTTCGACCCCGCCTCGATCC<br>TCCCTTTATCCAGCCCTCACTCCTTCTCTAGGCGCCCCCATATGGCCATAT<br>GAGATCTTATATGGGGCACCCCCGCCCCTTGTAAACTTCCCTGACCCTGAC<br>ATGACAAGAGTTACTAACAGCCCCTCTCTCCAAGCTCACTTACAGGCTCTCT<br>ACTTAGTCCAGCACGAAGTCTGGAGACCTCTGGCGGCAGCCTACCAAGAA<br>CAACTGGACCGACCGGTGGTACCTCACCCTTACCGAGTCGGCGACACAGT<br>GTGGGTCCGCCGACACCAGACTAAGAACCTAGAACCTCGCTGGAAAGGAC<br>CTTACACAGTCCTGCTGACCACCCCCACCGCCCTCAAAGTAGACGGCATC<br>GCAGCTTGGATACACGCCGCCCACGTGAAGGCTGCCGACCCCGGGGGTG<br>GACCATGACTCGAGCCATGGATTGGATCTGGCGCATCCTGTTTCTCGTGGG<br>AGCTGCCACAGGCGCCCATTCTCAGGTTCAGCTGCAAGAGTCTGGCCCTG<br>GCCTGGTCAAGCCTAGCGAAACACTGAGCCTGACCTGTACCGTGTCTGGC<br>GGCAGCATCAGCAGCAGCTCTTACTACTGGGGCTGGATCAGACAGCCTCC<br>TGGCAAAGGCCTGGAATGGATCGGCTCCATCTACTACAGCGGCAGCACCT<br>ACTACAACCCCAGCCTGAAGTCCAGAGTGACCATCAGCGTGGACACCAGC<br>AAGAACCAGTTCTCCCTGAAGCTGAGCAGCGTGACAGCCGCCGATACAGC<br>CGTGTACTACTGTGCCAGATACGCCCCTGATAGCAGCGGCTACCTGGTGG<br>CCTTTGATATCTGGGGCCAGGGCACAATGGTCACCGTTTCTAGCGGAGGC<br>GGAGGTTCTGGTGGCGGAGGAAGTGGCGGCGGAGGATCTCAGACAGTGG<br>TCACACAAGAGCCCAGCTTCTCCGTGTCTCCTGGCGGAACAGTGACCCTG<br>ACATGTGGCCTTAGCTCTGGCTCTGTGTCCACCGGCTACTACCCCAGCTGG<br>TATCAGCAGACACCTGGACAGGCCCCTCGGACACTGATCTACAGCACCAA<br>CAGCAGATCCAGCGGCGTGCCCGATAGATTCAGCGGCTCTATCCTGGGCA<br>ACAAGGCCGCACTGACAATCACAGGCGCTCAGGCCGATGACGAGAGCGAC<br>TACTACTGCGTGCTGTACATGGGCAGCGGCATCTCCGTTTTTGGCGGAGG<br>CACAAAGCTGACCGTGCTGGGATCCGAACCAAAGAGTTGCGACAAAACAC<br>ACACCTGCCCTACGCGTTTTTGGGTGCTCGTGGTGGTGGGTGGCGTGCTC<br>GCTTGCTACTCACTTCTGGTGACCGTAGCGTTTATCATTTTTTGGGTCAGGA<br>GCAAGCGATCCCGCCTATTGCACAGCGACTACATGAACATGACCCCCCGG<br>CGCCCCGGGCCAACCCGGAAGCACTACCAGCCATATGCGCCTCCCCGCG<br>ATTTCGCAGCGTATCGGTCCCGGGTCAAATTTTCACGGTCCGCTGACGCCC<br>CGGCCTATCAACAGGGCCAGAATCAGCTGTATAATGAATTAAACCTCGGTA<br>GACGCGAGGAGTACGACGTCCTCGACAAGAGAAGGGGGCGCGACCCAGA<br>GATGGGAGGCAAACCGCAGCGCAGGAAGAATCCACAGGAGGGCCTGTAC<br>AACGAATTACAGAAGGACAAGATGGCAGAGGCCTACAGCGAGATAGGAAT<br>GAAGGGTGAAAGGCGTCGTGGAAAGGGCCACGATGGGCTTTACCAGGGC<br>CTAAGTACTGCCACAAAAGATACGTATGACGCGCTGCATATGCAAGCCCTC<br>CCCCCCAGGTAAGCATGCAACCTCGATCCGGATTAGTCCAATTTGTTAAAG<br>ACAGGATATCAGTGGTCCAGGCTCTAGTTTTGACTCAACAATATCACCAGCT<br>GAAGCCTATAGAGTACGAGCCATAGATAAAATAAAAGATTTTATTTAGTCTC<br>CAGAAAAAGGGGGGAATGAAAGACCCCACCTGTAGGTTTGGCAAGCTAGC<br>TTAAGTAACGCCATTTTGCAAGGCATGGAAAAATACATAACTGAGAATAGAG<br>AAGTTCAGATCAAGGTCAGGAACAGATGGAACAGCTGAATATGGGCCAAAC<br>AGGATATCTGTGGTAAGCAGTTCCTGCCCCGGCTCAGGGCCAAGAACAGA<br>TGGAACAGCTGAATATGGGCCAAACAGGATATCTGTGGTAAGCAGTTCCTG<br>CCCCGGCTCAGGGCCAAGAACAGATGGTCCCCAGATGCGGTCCAGCCCTC<br>AGCAGTTTCTAGAGAACCATCAGATGTTTCCAGGGTGCCCCAAGGACCTGA<br>AATGACCCTGTGCCTTATTTGAACTAACCAATCAGTTCGCTTCTCGCTTCTG<br>TTCGCGCGCTTC |

-continued

Sequences

| SEQ ID NO: | DESCRIPTION | SEQUENCE |
|---|---|---|
| 48 | HER2(E4)-CD28TM, ICD-CD3Z CAR | AAGTTCAGATCAAGGTCAGGAACAGATGGAACAGCTGAATATGGGCCAAAC<br>AGGATATCTGTGGTAAGCAGTTCCTGCCCCGGCTCAGGGCCAAGAACAGA<br>TGGAACAGCTGAATATGGGCCAAACAGGATATCTGTGGTAAGCAGTTCCTG<br>CCCCGGCTCAGGGCCAAGAACAGATGGTCCCCAGATGCGGTCCAGCCCTC<br>AGCAGTTTCTAGAGAACCATCAGATGTTTCCAGGGTGCCCCAAGGACCTGA<br>AATGACCCTGTGCCTTATTTGAACTAACCAATCAGTTCGCTTCTCGCTTCTG<br>TTCGCGCGCTTCTGCTCCCCGAGCTCAATAAAAGAGCCCACAACCCCTCAC<br>TCGGCGCGCCAGTCCTCCGATTGACTGAGTCGCCCGGGTACCCGTGTATC<br>CAATAAACCCTCTTGCAGTTGCATCCGACTTGTGGTCTCGCTGTTCCTTGG<br>GAGGGTCTCCTCTGAGTGATTGACTACCCGTCAGCGGGGGTCTTTCATTTG<br>GGGGCTCGTCCGGGATCGGGAGACCCCTGCCCAGGGACCACCGACCCAC<br>CACCGGGAGGTAAGCTGGCCAGCAACTTATCTGTGTCTGTCCGATTGTCTA<br>GTGTCTATGACTGATTTTATGCGCCTGCGTCGGTACTAGTTAGCTAACTAGC<br>TCTGTATCTGGCGGACCCGTGGTGGAACTGACGAGTTCGGAACACCCGGC<br>CGCAACCCTGGGAGACGTCCCAGGGACTTCGGGGGCCGTTTTTGTGGCCC<br>GACCTGAGTCCTAAAATCCCGATCGTTTAGGACTCTTTGGTGCACCCCCCT<br>TAGAGGAGGGATATGTGGTTCTGGTAGGAGACGAGAACCTAAAACAGTTCC<br>CGCCTCCGTCTGAATTTTTGCTTTCGGTTTGGGACCGAAGCCGCGCCGCG<br>CGTCTTGTCTGCTGCAGCATCGTTCTGTGTTGTCTCTGTCTGACTGTGTTTC<br>TGTATTTGTCTGAAAATATGGGCCCGGGCTAGCCTGTTACCACTCCCTTAA<br>GTTTGACCTTAGGTCACTGGAAAGATGTCGAGCGGATCGCTCACAACCAGT<br>CGGTAGATGTCAAGAAGAGACGTTGGGTTACCTTCTGCTCTGCAGAATGGC<br>CAACCTTTAACGTCGGATGGCCGCGAGACGGCACCTTTAACCGAGACCTC<br>ATCACCCAGGTTAAGATCAAGGTCTTTTCACCTGGCCCGCATGGACACCCA<br>GACCAGGTCCCCTACATCGTGACCTGGGAAGCCTTGGCTTTTGACCCCCCT<br>CCCTGGGTCAAGCCCTTTGTACACCCTAAGCCTCCGCCTCCTCTTCCTCCA<br>TCCGCCCCGTCTCTCCCCCTTGAACCTCCTCGTTCGACCCCGCCTCGATCC<br>TCCCTTTATCCAGCCCTCACTCCTTCTCTAGGCGCCCCCATATGGCCATAT<br>GAGATCTTATATGGGGCACCCCCGCCCCTTGTAAACTTCCCTGACCCTGAC<br>ATGACAAGAGTTACTAACAGCCCCTCTCTCCAAGCTCACTTACAGGCTCTCT<br>ACTTAGTCCAGCACGAAGTCTGGAGACCTCTGGCGGCAGCCTACCAAGAA<br>CAACTGGACCGACCGGTGGTACCTCACCCTTACCGAGTCGGCGACACAGT<br>GTGGGTCCGCCGACACCAGACTAAGAACCTAGAACCTCGCTGGAAAGGAC<br>CTTACACAGTCCTGCTGACCACCCCCACCGCCCTCAAAGTAGACGGCATC<br>GCAGCTTGGATACACGCCGCCCACGTGAAGGCTGCCGACCCCGGGGGTG<br>GACCATGACTCGAGCCATGGATTGGATCTGGCGCATCCTGTTTCTCGTGGG<br>AGCTGCCACAGGCGCCCATTCTCAGGTTCAGCTGCAACAGTGGGGAGCCG<br>GACTGCTGAAGCCTAGCGAAACACTGAGCCTGACCTGTGCCGTGTACGGC<br>GGCAGCTTTAGCGGCTACTACTGGTCCTGGATCAGACAGCCTCCTGGCAA<br>AGGCCTGGAATGGATCGGCGAGATCAATCACAGCGGCAGCACCAACTACA<br>ACCCCAGCCTGAAGTCCAGAGTGACCATCAGCGTGGACACCAGCAAGAAC<br>CAGTTCTCCCTGAAGCTGAGCAGCGTGACCACAGCCGATACCGCCGTGTA<br>CTACTGTGCCCGGATGGGCATCAATAGCGGCGGCTACCTGTACGGCATGG<br>ATGTGTGGGGACAGGGCACCACCGTGACAGTTTCTAGCGGAGGCGGAGGT<br>TCTGGTGGCGGAGGAAGTGGCGGCGGAGGATCTCAGACAGTGGTCACAC<br>AAGAGCCCAGCTTCTCCGTGTCTCCTGGCGGAACAGTGACCCTGACATGT<br>GGCCTTAGCAGCGGCTCTGTGTCCACCAGCTACTACCCTAGCTGGTATCAG<br>CAGATCCCCGGACAGGCCCCTCGGACACTGATCTACACCACCAACATCAG<br>ATCCAGCGGCGTGCCCGATAGATTCGGCGGATCTATCCTGGGCAACAAGG<br>CCGCACTGACAATCACAGGTGCCCAGGCCGAGGACGAGTCCGACTACTAC<br>TGCATGCTGTACATGGGCAGCGGCATCTGGGTTTTCGGCGGAGGCACAAA<br>GCTGACCGTTCTGGGATCCGAACCAAAGAGTTGCGACAAAACACACACCTG<br>CCCTACGCGTTTTTGGGTGCTCGTGGTGGTGGGTGGCGTGCTCGCTTGCT<br>ACTCACTTCTGGTGACCGTAGCGTTTATCATTTTTTGGGTCAGGAGCAAGC<br>GATCCCGCCTATTGCACAGCGACTACATGAACATGACCCCCCGGCGCCCC<br>GGGCCAACCCGGAAGCACTACCAGCCATATGCGCCTCCCCGCGATTTCGC<br>AGCGTATCGGTCCCGGGTCAAATTTTCACGGTCCGCTGACGCCCCGGCCT<br>ATCAACAGGGCCAGAATCAGCTGTATAATGAATTAAACCTCGGTAGACGCG<br>AGGAGTACGACGTCCTCGACAAGAGAAGGGGGCGCGACCCAGAGATGGG<br>AGGCAAACCGCAGCGCAGGAAGAATCCACAGGAGGGCCTGTACAACGAAT<br>TACAGAAGGACAAGATGGCAGAGGCCTACAGCGAGATAGGAATGAAGGGT<br>GAAAGGCGTCGTGGAAAGGGCCACGATGGGCTTTACCAGGGCCTAAGTAC<br>TGCCACAAAAGATACGTATGACGCGCTGCATATGCAAGCCCTCCCCCCCAG<br>GTAAGCATGCAACCTCGATCCGGATTAGTCCAATTTGTTAAAGACAGGATAT<br>CAGTGGTCCAGGCTCTAGTTTTGACTCAACAATATCACCAGCTGAAGCCTA<br>TAGAGTACGAGCCATAGATAAAATAAAAGATTTTATTTAGTCTCCAGAAAAA<br>GGGGGGAATGAAAGACCCCACCTGTAGGTTTGGCAAGCTAGCTTAAGTAA<br>CGCCATTTTGCAAGGCATGGAAAAATACATAACTGAGAATAGAGAAGTTCA<br>GATCAAGGTCAGGAACAGATGGAACAGCTGAATATGGGCCAAACAGGATAT<br>CTGTGGTAAGCAGTTCCTGCCCCGGCTCAGGGCCAAGAACAGATGGAACA<br>GCTGAATATGGGCCAAACAGGATATCTGTGGTAAGCAGTTCCTGCCCCGG |

-continued

Sequences

| SEQ ID NO: | DESCRIPTION | SEQUENCE |
|---|---|---|
| | | CTCAGGGCCAAGAACAGATGGTCCCCAGATGCGGTCCAGCCCTCAGCAGT<br>TTCTAGAGAACCATCAGATGTTTCCAGGGTGCCCCAAGGACCTGAAATGAC<br>CCTGTGCCTTATTTGAACTAACCAATCAGTTCGCTTCTCGCTTCTGTTCGCG<br>CGCTTC |
| 49 | HER2(F1)-CD28TM, ICD-CD3Z CAR | AAGTTCAGATCAAGGTCAGGAACAGATGGAACAGCTGAATATGGGCCAAAC<br>AGGATATCTGTGGTAAGCAGTTCCTGCCCCGGCTCAGGGCCAAGAACAGA<br>TGGAACAGCTGAATATGGGCCAAACAGGATATCTGTGGTAAGCAGTTCCTG<br>CCCCGGCTCAGGGCCAAGAACAGATGGTCCCCAGATGCGGTCCAGCCCTC<br>AGCAGTTTCTAGAGAACCATCAGATGTTTCCAGGGTGCCCCAAGGACCTGA<br>AATGACCCTGTGCCTTATTTGAACTAACCAATCAGTTCGCTTCTCGCTTCTG<br>TTCGCGCGCTTCTGCTCCCCGAGCTCAATAAAAGAGCCCACAACCCCTCAC<br>TCGGCGCGCCAGTCCTCCGATTGACTGAGTCGCCCGGGTACCCGTGTATC<br>CAATAAACCCTCTTGCAGTTGCATCCGACTTGTGGTCTCGCTGTTCCTTGG<br>GAGGGTCTCCTCTGAGTGATTGACTACCCGTCAGCGGGGGTCTTTCATTTG<br>GGGGCTCGTCCGGGATCGGGAGACCCCTGCCCAGGGACCACCGACCCAC<br>CACCGGGAGGTAAGCTGGCCAGCAACTTATCTGTGTCTGTCCGATTGTCTA<br>GTGTCTATGACTGATTTTATGCGCCTGCGTCGGTACTAGTTAGCTAACTAGC<br>TCTGTATCTGGCGGACCCGTGGTGGAACTGACGAGTTCGGAACACCCGGC<br>CGCAACCCTGGGAGACGTCCCAGGGACTTCGGGGGCCGTTTTTGTGGCCC<br>GACCTGAGTCCTAAAATCCCGATCGTTTAGGACTCTTTGGTGCACCCCCCT<br>TAGAGGAGGGATATGTGGTTCTGGTAGGAGACGAGAACCTAAAACAGTTCC<br>CGCCTCCGTCTGAATTTTTGCTTTCGGTTTGGGACCGAAGCCGCGCCGCG<br>CGTCTTGTCTGCTGCAGCATCGTTCTGTGTTGTCTCTGTCTGACTGTGTTTC<br>TGTATTTGTCTGAAAATATGGGCCCGGGCTAGCCTGTTACCACTCCCTTAA<br>GTTTGACCTTAGGTCACTGGAAAGATGTCGAGCGGATCGCTCACAACCAGT<br>CGGTAGATGTCAAGAAGAGACGTTGGGTTACCTTCTGCTCTGCAGAATGGC<br>CAACCTTTAACGTCGGATGGCCGCGAGACGGCACCTTTAACCGAGACCTC<br>ATCACCCAGGTTAAGATCAAGGTCTTTTCACCTGGCCCGCATGGACACCCA<br>GACCAGGTCCCCTACATCGTGACCTGGGAAGCCTTGGCTTTTGACCCCCCT<br>CCCTGGGTCAAGCCCTTTGTACACCCTAAGCCTCCGCCTCCTCTTCCTCCA<br>TCCGCCCCGTCTCTCCCCCTTGAACCTCCTCGTTCGACCCCGCCTCGATCC<br>TCCCTTTATCCAGCCCTCACTCCTTCTCTAGGCGCCCCCATATGGCCATAT<br>GAGATCTTATATGGGGCACCCCCGCCCCTTGTAAACTTCCCTGACCCTGAC<br>ATGACAAGAGTTACTAACAGCCCCTCTCTCCAAGCTCACTTACAGGCTCTCT<br>ACTTAGTCCAGCACGAAGTCTGGAGACCTCTGGCGGCAGCCTACCAAGAA<br>CAACTGGACCGACCGGTGGTACCTCACCCTTACCGAGTCGGCGACACAGT<br>GTGGGTCCGCCGACACCAGACTAAGAACCTAGAACCTCGCTGGAAAGGAC<br>CTTACACAGTCCTGCTGACCACCCCCACCGCCCTCAAAGTAGACGGCATC<br>GCAGCTTGGATACACGCCGCCCACGTGAAGGCTGCCGACCCCGGGGGTG<br>GACCATGACTCGAGCCATGGATTGGATCTGGCGCATCCTGTTTCTCGTGGG<br>AGCTGCCACAGGCGCCCATTCTCAGGTTCAGCTGGTGGAATCTGGCCCTG<br>GCCTGGTTAAGCCTAGCGGCACACTGTCTCTGACCTGTGCTGTGTCTGGC<br>GGCAGCATCAGCAGCAGCAATTGGTGGTCTTGGGTCCGACAGCCTCCTGG<br>CAAAGGCCTGGAATGGATCGGCGAGATCTACCACAGCGGCAGCACCAACT<br>ACAACCCCAGCCTGAAGTCCAGAGTGACCATCAGCGTGGACACCAGCAAG<br>AACCAGTTCTCCCTGAAGCTGAGCAGCGTGACAGCCGCCGATACAGCCGT<br>GTACTACTGTGCCAGAATGGGAGCCAATAGCGGCGGCTACCTGTACGGCA<br>TGGATGTGTGGGGACAGGGCACCACCGTGACAGTTTCTAGCGGAGGCGGA<br>GGTTCTGGTGGCGGAGGAAGTGGCGGCGGAGGATCTCAGACAGTGGTCA<br>CACAAGAGCCCAGCTTCTCCGTGTCTCCTGGCGGAACAGTGACCCTGACA<br>TGTGGCCTTAGCAGCGGCTCTGTGTCTACCAGCTACTACCCCTCCTGGTAT<br>CAGCAGACCCCTGGACAGGCTCCCCGGACACTGATCTACTCCACCAACAC<br>CAGATCCAGCGGCGTGCCCGATAGATTCTCCGGCTCTATCCTGGGCAACA<br>AGGCCGCACTGACAATCACAGGCGCTCAGGCCGATGACGAGAGCGACTAC<br>TACTGCGTGCTGTACATGGGCAGCGGCATCTGGGTTTTCGGCGGAGGCAC<br>AAAGCTGACCGTTCTGGGATCCGAACCAAAGAGTTGCGACAAAACACACAC<br>CTGCCCTACGCGTTTTTGGGTGCTCGTGGTGGTGGGTGGCGTGCTCGCTT<br>GCTACTCACTTCTGGTGACCGTAGCGTTTATCATTTTTTGGGTCAGGAGCAA<br>GCGATCCCGCCTATTGCACAGCGACTACATGAACATGACCCCCCGGCGCC<br>CCGGGCCAACCCGGAAGCACTACCAGCCATATGCGCCTCCCCGCGATTTC<br>GCAGCGTATCGGTCCCGGGTCAAATTTTCACGGTCCGCTGACGCCCCGGC<br>CTATCAACAGGGCCAGAATCAGCTGTATAATGAATTAAACCTCGGTAGACG<br>CGAGGAGTACGACGTCCTCGACAAGAGAAGGGGGCGCGACCCAGAGATG<br>GGAGGCAAACCGCAGCGCAGGAAGAATCCACAGGAGGGCCTGTACAACG<br>AATTACAGAAGGACAAGATGGCAGAGGCCTACAGCGAGATAGGAATGAAG<br>GGTGAAAGGCGTCGTGGAAAGGGCCACGATGGGCTTTACCAGGGCCTAAG<br>TACTGCCACAAAAGATACGTATGACGCGCTGCATATGCAAGCCCTCCCCCC<br>CAGGTAAGCATGCAACCTCGATCCGGATTAGTCCAATTTGTTAAAGACAGG<br>ATATCAGTGGTCCAGGCTCTAGTTTTGACTCAACAATATCACCAGCTGAAGC<br>CTATAGAGTACGAGCCATAGATAAAATAAAAGATTTTATTTAGTCTCCAGAA<br>AAAGGGGGGAATGAAAGACCCCACCTGTAGGTTTGGCAAGCTAGCTTAAGT<br>AACGCCATTTTGCAAGGCATGGAAAAATACATAACTGAGAATAGAGAAGTTC<br>AGATCAAGGTCAGGAACAGATGGAACAGCTGAATATGGGCCAAACAGGATA |

-continued

Sequences

| SEQ ID NO: | DESCRIPTION | SEQUENCE |
|---|---|---|
| | | TCTGTGGTAAGCAGTTCCTGCCCCGGCTCAGGGCCAAGAACAGATGGAAC AGCTGAATATGGGCCAAACAGGATATCTGTGGTAAGCAGTTCCTGCCCCGG CTCAGGGCCAAGAACAGATGGTCCCCAGATGCGGTCCAGCCCTCAGCAGT TTCTAGAGAACCATCAGATGTTTCCAGGGTGCCCCAAGGACCTGAAATGAC CCTGTGCCTTATTTGAACTAACCAATCAGTTCGCTTCTCGCTTCTGTTCGCG CGCTTC |
| 50 | HDAdIL12p70_ TK_aPD-L1 | AAACATCATCAATAATATACCTTATTTTGGATTGAAGCCAATATGATAATGAG GGGGTGGAGTTTGTGACGTGGCGCGGGGCGTGGGAACGGGGCGGGTGA CGTAGTAGTGTGGCGGAAGTGTGATGTTGCAAGTGTGGCGGAACACATGT AAGCGACGGATGTGGCAAAAGTGACGTTTTTGGTGTGCGCCGGTGTACAC AGGAAGTGACAATTTTCGCGCGGTTTTAGGCGGATGTTGTAGTAAATTTGG GCGTAACCGAGTAAGATTTGGCCATTTTCGCGGGAAAACTGAATAAGAGGA AGTGAAATCTGAATAATTTTGTGTTACTCATAGCGCGTAATATTTGTCTAGG GCCGCGGGGACTTTGACCGTTTACGTGGAGACTCGCCCAGGTGTTTTTCTC AGGTGTTTTCCGCGTTCCGGGTCAAAGTTGGCGTTTTGATATCAAGCTTATC GATACCGTAAACAAGTCTTTAATTCAAGCAAGACTTTAACAAGTTAAAAGGA GCTTATGGGTAGGAAGTAGTGTTATGATGTATGGGCATAAAGGGTTTTAAT GGGATAGTGAAAATGTCTATAATAATACTTAAATGGCTGCCCAATCACCTAC AGGATTGATGTAAACATGGAAAAGGTCAAAAACTTGGGTCACTAAAATAGAT GATTAATGGAGAGGATGAGGTTGATAGTTAAATGTAGATAAGTGGTCTTATT CTCAATAAAAATGTGAACATAAGGCGAGTTTCTACAAAGATGGACAGGACT CATTCATGAAACAGCAAAAACTGGACATTTGTTCTAATCTTTGAAGAGTATG AAAAATTCCTATTTTAAAGGTAAAACAGTAACTCACAGGAAATACCAACCCA ACATAAAATCAGAAACAATAGTCTAAAGTAATAAAAATCAAACGTTTGCACG ATCAAATTATGAATGAAATTCACTACTAAAATTCACACTGATTTTGTTTCATC CACAGTGTCAATGTTGTGATGCATTTCAATTGTGTGACACAGGCAGACTGT GGATCAAAAGTGGTTTCTGGTGCGACTTACTCTCTTGAGTATACCTGCAGT CCCCTTTCTTAAGTGTGTTAAAAAAAAAGGGGGATTTCTTCAATTCGCCAAT ACTCTAGCTCTCCATGTGCTTTCTAGGAAACAAGTGTTAACCCACCTTATTT GTCAAACCTAGCTCCAAAGGACTTTTGACTCCCCACAAACCGATGTAGCTC AAGAGAGGGTATCTGTCACCAGTATGTATAGTGAAAAAAGTATCCCAAGTC CCAACAGCAATTCCTAAAAGGAGTTTATTTAAAAAACCACACACACCTGTAA AATAAGTATATATCCTCCAAGGTGACTAGTTTTAAAAAAACAGTATTGGCTTT GATGTAAAGTACTAGTGAATATGTTAGAAAAATCTCACTGTAACCAAGTGAA ATGAAAGCAAGTATGGTTTGCAGAGATTCAAAGAAAATATAAGAAAACCTAC TGTTGCCACTAAAAAGAATCATATATTAAATATACTCACACAATAGCTCTTCA GTCTGATAAAATCTACAGTCATAGGAATGGATCTATCACTATTTCTATTCAGT GCTTTGATGTAATCCAGCAGGTCAGCAAAGAATTTATAGCCCCCCTTGAGC ACACAGAGGGCTACAATGTGATGGCCTCCCATCTCCTTCATCACATCTCGA GCAAGACGTTCAGTCCTACAGAAATAAAATCAGGAATTTAATAGAAAGTTTC ATACATTAAACTTTATAACAAACACCTCTTAGTCATTAAACTTCCACACCAAC CTGGGCAATATAGTGAGACCCCATGCCTGCAAAAAAAAAAAAAATTAGCCAG GCATGGTAGCATGTACCTGTAGTCCCAGCTACTTGAGAGGTGAGGTGGGA AAATCACTTTAGTGCAGGATGTTGAGGCTGGAGTGAACTGTGATTGTGCCA CTGCACTCCAGCCTGGACAATAGAGCAAGACCTTGTCTCAAAAAAATGCAT TAAAAATTTTTTTAAATCTTCCACGTATCACATCCTTTGCCCTCATGTTTCAT AAGGTAAAAAATTTGATACCTTCAAAAAAACCAAGCATACCACTATCATAATT TTTTTTAAATGCAAATAAAAACAAGATACCATTTTCACCTATCAGACTGGCAG GTTCTGATTAAATGAAATTTTCTGGATAATATACAATATTAAGAGAGACTGTA GAAACTGGGCCAGTGGCTCATGCCTGTAATCCCAGCACTTTGGGAGGCTG GGTAACATGGCGAACCCTGTTTCTACAAAATAAAAATATTAGCTGGGAGTG GTGGCGCACACCTATAGTCCCAGCTACTCAGGAGGCTGAGGTGGAAGGAT CGCTTGAACCCAGGAGGTTGAGACTGCAGTGAACTGTGATCATTCTGCTGC ACTGCACCCCAGCCTGGGCAACAGAGACCTTGTCTCAAAAAAAAAAAAAA AGAGACAAATTGTGAAGAGAAAGGTACTCTCATATAACATCAGGAGTATAAA ATGATTCAACTTCTTAGAGGAAAATTTGGCAATACCAAAATATTCAATAAACT CTTTCCCCTTGACCCAGAAATTCCACTTGAATAAAGCTGAACAAGTACCAAA CATGTAAAAGAATGTTTCTTCTAGTACAGTCGGTAAGAACAAAATAGTGTCT ATCAATAGTGGACTGGTTAAATCAGTTATGGTATCTCCATAAGACAGAATGC TATGCAACCTTTAAAATATATTAGATAGCTCTAGACACACTAATATTAAAAGT GTCCAATAACATTTAAAACTATACTCATACGTTAAAATATAAATGTATATATG TACTTTTGCATATAGTATACATGCATAGGCCAGTGCTTGAGAAGAAATGTGT ACAGAAGGCTGAAAGGAGAGAACTTTAGTCTTCTTGTTTATGGCCTCCATA GTTAGAATATTTTATAACACAAATATTTTGATATTATAATTTTAAAATAAAAAC ACAGAATAGCCAGACATACAATGCAAGCATTCAATACCAGGTAAGGTTTTTC ACTGTAATTGACTTAACAGAAAATTTTCAAGCTAGATGTGCATAATAATAAAA ATCTGACCTTGCCTTCATGTGATTCAGCCCCAGTCCATTACCCTGTTTAGGA CTGAGAAATGCAAGACTCTGGCTAGAGTTCCTTCTTCCATCTCCCTTCAATG TTTACTTTGTTCTGGTCCCTACAGAGTCCCACTATACCACAACTGATACTAA GTAATTAGTAAGGCCCTCCTCTTTTATTTTTAATAAAGAAGATTTTAGAAAGC ATCAGTTATTTAATAAGTTGGCCTAGTTTATGTTCAAATAGCAAGTACTCAGA ACAGCTGCTGATGTTTGAAATTAACACAAGAAAAAGTAAAAAACCTCATTTT AAGATCTTACTTACCTGTCCATAATTAGTCCATGAGGAATAAACACCCTTTC |

-continued

Sequences

| SEQ ID NO: | DESCRIPTION | SEQUENCE |
|---|---|---|
| | | CAAATCCTCAGCATAATGATTAGGTATGCAAAATAAATCAAGGTCATAACCT<br>GGTTCATCATCACTAATCTGAAAAGAAATATAGCTGTTTCAATGAGAGCAT<br>TACAGGATACAAACATTTGATTGGATTAAGATGTTAAAAAATAACCTTAGTCT<br>ATCAGAGAAATTTAGGTGTAAGATGATATTAGTAACTGTTAACTTTGTAGGT<br>ATGATAATGAATTATGTAAGAAAACAACAGGCCGGGCGGGTTGGTTCACAC<br>GTGTAATCCCAGCACTTTGGGAGGCTGAGGCAGGCAGACTGCCTGAGCTC<br>AGGAGTTCGAGACCAGCCTGGGCAACACGGTGAAATCCCGTCTCTACTAAA<br>AATACAAAAAAATTAGCCGGGTGTGGTGACACATGCCTGTAGTCCCAGCTA<br>CTTGGGAGGCTGAGGCAGGAGAATCACTTGAACCTGGGAGGTGAAGGTTG<br>CAGTGAGCCAAGATGGCACCACTTCACTCCAGCCTGGGAAACAGAGCAAG<br>ACTCTGTCTCTGAGCTGAGATGGCACCACTTCACTCCAGCCTGGGAAACAG<br>AGCAAGACTCTGTCTCAAAAAAAACAAAACACACAAACAAAAAAAACAGGCTG<br>GGCGCGGTGGCTCACGCCTGTAATCCCAGCACTTTGGGAGGCCGAGGCG<br>GGTGGATCACCTGAGGTCAGGAGTTCCAGACCAGCCTTGTCAACATGGTG<br>AAACCTCCCCCCGCCGTCTCTACTAAAAATACAAAAATTAGCCAGGCGTGG<br>TGGCAGGAGCCTGTAATCCCAGCTACTTGGGAGGCTGAGGCAGGAGAATC<br>GCTTGTACCCAGAAGGCAGAGGTTGCACTGAGCTGAGATGGCACCATTGC<br>ACTCCAGCCTGGGGGACAAGAGCGAGATTTCGTCTTTAAAAAACAAAAACA<br>AAACAAAAAACCATGTAACTATATGTCTTAGTCATCTTAGTCAAGAATGTAGA<br>AGTAAAGTGATAAGATATGGAATTTCCTTTAGGTCACAAAGAGAAAAAGAAA<br>AATTTTAAAGAGCTAAGACAAACGCAGCAAAATCTTTATATTTAATAATATTC<br>TAAACATGGGTGATGAACATACGGGTATTCATTATACTATTCTCTCCACTTTT<br>GAGTATGTTTGAAAATTTAGTAAAACAAGTTTTAACACACTGTAGTCTAACAA<br>GATAAAATATCACACTGAACAGGAAAAACTGGCATGGTGTGGTGGCTCACA<br>CTTGTAATCCCAGTGCTTTGGGAGGCTGAGACAGGAGAGTTGCTTGAGGC<br>CAGGAGTTCAAGACCGACATGGGGAATGTAGCAAGACCCCGTCCCTACAA<br>AAAACTTTGTAAAAATTTGCCAGGTATGGTGGTGCATACCTGTAGTCCCAGC<br>TACTCGGGAGGCGGAGGCAGAAGGAATCACTTGAGCCCAGGAGTTTGAGG<br>CTGCAGTGAGCTACGATCATACCACAGCACTCCAGCGTGGACAACAGAGTA<br>AGACCCTATCTCAAAAACAAAACAAAACAAAACAAACAAAAAAAAACCACAAG<br>AAAAACTGCTGGCTGATGCAGCGGCTCATGCCTGTAATCCCAGTATTTTGG<br>GAGGCCCAGGTGGGCGTATCACCTGAGGTCAGGAGTTAGAGACCAGCCTG<br>GCCAACATGGTGAAACCCCATCTCTACTAAAAATACAAAATTAGCCAGGCAT<br>GTGGCACGCGCCTGTAGTCCCAGTTACTGGGAGGCTGAAGCAGGAGGATC<br>ACCTGAGCCCGGGAGGTGGAGGTTGCAGTGAGCCGAGATCACACCACTGC<br>ACTCCAGCCTGGGTGACACAGCAATACCCTACCTCAAAATAAAAAAGAAAA<br>AGAAAAGAAAAGTTGCTGTCCCCGCTACCCCAATCCCAAATCCAAACAGCC<br>TCTCTCATCTCACAGTAAGGGGGAAAAATCACCCAAAAAAGCTAAGTGATCT<br>TTTGAAAACCCAAACTCTTAGAAGTCTAAGATTATTATAGTCAACTCATGAAG<br>TGTCATCATAAAAGATACTCTAATATTATTTAAGTAGAACCACATATTGGTTG<br>TCTTGGTATGTCTAGCCCCTGGCATACAAAATATTTAATAACACTGATATGG<br>TACCTGTGATGTGAAAATGTACTATGAGTACAGCTTTATAAATACTATATATG<br>TACCTATATACAGAAAAAAATACAACAAAATCATAAAAGCACTTATCTTTGAA<br>AGAGGAGTTACAGCAATTTTATTTAGTTCTTTATTGCTTTGCTATATATTCTA<br>AATTTTTTTCAATGAATATATATCACTTTTAAAAAAATTCAATGGTCTTTCTTA<br>TAAATTATCTTTGGCAGCATGCGTTTTTATATATACATATAAAATGTATGGGA<br>AATTTTTAAAGGATACATTAAATTAAAGCAAAATATACAAACAAAAAATCAGA<br>ATACAAAAAGATAAAAAGATTGGGAAGGGAGGGAGGGAGTAAGGAGGAAG<br>GGTGGGTGGGTATAGAGAAATATACCAAATAATGGTAAGAAGTGGGGTCTT<br>GACACTTTCTACACTTTTTTTAAATAAAAAAAATTTTTTTCTCTCTCTTTTTTTT<br>TTTTAGAGACGAAGTCTCGCTATGTTGCCCAGGCTGGTCTTGAACTCCTGG<br>GATCAAGAGATCCTCCTGCCTCAGCCTCCCAAGGTGCTTGGATTACAGGTG<br>TGAGCCACCACGCCTGGTCACTTTCTACACTTTAATATATATATTTTTTCATT<br>TTCAATGTCATTTTTATTAGTTAATTTATAATACCCATTCACCATTATATTCAA<br>AGTCTATTTGAAGAAATAAACCAGAAAGAATGAAATACTCTAGCTCACATGC<br>TATTCAATACTAAATTACCTTTCAAATCACATTCAAGAAGCTGATGATTTAAG<br>CTTTGGCGGTTTCCAATAAATATTGGTCAAACCATAATTAAATCTCAATATAT<br>CAGTTAGTACCTATTGAGCATCTCCTTTTACAACCTAAGCATTGTATTAGGT<br>GCTTAAATACAAGCAGCTTGACTTTTAATACATTTAAAAATACATATTTAAGA<br>CTTAAAATCTTATTTATGGAATTCAGTTATATTTTGAGGTTTCCAGTGCTGAG<br>AAATTTGAGGTTTGTGCTGTCTTTCAGTCCCCAAAGCTCAGTTCTGAGTTCT<br>CAGACTTTGGTGGAACTTCATGTATTGTCAGGTTGGCCCGTAATACCTGTG<br>GGACAACTTCAGCCCCTGTGCACATGGCCAGGAGGCTGGTTGCAAACATTT<br>TCAGGTAGGTGGACCAGGACATGCCCCTGGTCATGGCCAGGTGGAGGCAT<br>AGTGCTATACAGCAGGCAGAAGTCAATATTGATTTGTTTTTAAAGAAACATG<br>TACTACTTTCATAAGCAGAAAAAATTTCTATTCTTGGGGGAAAAGATTATGC<br>CAGATCCTCTAGGATTAAATGCTGATGCATCTGCTAAACCTTCACATATCAG<br>AACATATTTACTATAGAAAGAATGAAAATGGGACATTTGTGTGTCACCTATG<br>TGAACATTCCAAAAATATTTTACAACAACTAAGTATTTTATAAATTTTATGAAC<br>TGAAATTTAGTTCAAGTTCTAGGAAAATACAAACCTTGCTAGATATTATAAAA<br>ATGATACAATATATATTCATTTCAGGCTCATCAGAATATATCTGTTATCACTT<br>GACAAGAATGAAAATGCACCATTTTGTAGTGCTTTAAAATCAGGAAGATCCA<br>GAGTACTAAAAATGACTTCTTCCTTGAAGCTTACTCACCAACTTCCTCCCAG<br>TTACTCACTGCTTCTGCCACAAGCATAAACTAGGACCCAGCCAGAACTCCC |

-continued

Sequences

| SEQ ID NO: | DESCRIPTION | SEQUENCE |
|---|---|---|
| | | TTGAAATATACACTTGCAACGATTACTGCATCTATCAAAATGGTTCAGTGCC<br>TGGCTACAGGTTCTGCAGATCGACTAAGAATTTGAAAAGTCTTGTTTATTTC<br>AAAGGAAGCCCATGTGAATTCTGCCCAGAGTTCATCCCAGATATGCAGTCT<br>AAGAATACAGACAGATCAGCAGAGATGTATTCTAAAACAGGAATTCTGGCA<br>ATATAACAAATTGATTTCCAATCAAAACAGATTTACATACCATACTTATGTCA<br>AGAAGTTGTTTTGTTTTATTGCATCCTAGATTTTATTTTTTTGATTTATGGTTT<br>ACTTTAAGCATAAAAAATTTGTCAATACAACTCTTCCCAAAAGGCATAAACAA<br>AAATTCATAAAACTTGCATCACTTGAGATACTTCAGGTATGAATTCACAACTT<br>TGTTACAACTTACTATATATATGCACACATATATATATATTTGGGTATATTGG<br>GGGGGTTCTAATTTAAGAAATGCATAATTGGCTATAGACAGACAGTTGTCTG<br>GAATGAAAATCAATACTTTTGCTATAATCGATTACTGAAATAATTTTACTTTC<br>CAGTAAAACTGGCATTATAATTTTTTTTAATTTTTAAAACTTCATAATTTTTTG<br>CCAGACTGACCCATGTAAACATACAAATTACTAATAATTATGCACGTCACAT<br>CTGTAATAATGGCCTTCATGTAAACATTTTTGTGGTTTACACATAAAATCTCT<br>AATTACAAAGCTATATTATCTAAAATTACAGTAAGCAAGAAAATTAATCCAAG<br>CTAAGACAATACTTGCAACATCAATTCATCATCTGTGACAAGGACTGCTTAA<br>GTCTCTTTGTGGTTAAAAAGGAAAAAAAAAAAAAAAGACATGTTGGCCAGATG<br>CGGTGGCTCACACCTGTAATCCCAGCACTTTGGGAGGCTGAGGTGGGCGG<br>ATCACCCCTGGCCTGCCCAACATGGTGAAACCCCGTCTCTACTAAAAACAC<br>AAAAATTAGCTGGGCGTGGTGGCGGGCGCCTGTAATTCCAGCTACTCGGG<br>AGGCTGAGGCAGGAGAATTGCTAGAACCCAGGAGGCAGAGATTGCAGTGA<br>GCTGAGATTGCACCATTGCACTACAGTCTGGGCAACAAAAGTGAAACTCCA<br>TCTTAAAAAAAAAAAGACAATGTTCGTGGGTCCAAACAAGACTTAATGGAAG<br>TGAGTCTAAAAATGAGCTATGTGGGCCAGGCGTAGTGGCTCCCACCTGTAA<br>TCCCAGCACTTTGGGAGGCCGAAGCAGGCAGATCATGAGGTCAGGAGATG<br>GAGACCATCCTGGCCAACACGGTGAAATCCTGTCTCTACAAAAATTAGCTG<br>GGCGTGGTGGTGCCTGCCTGTAATCCCAGCTACTCAGAAGGCTCAGGCAG<br>GAGAATCGCTTGAACCAGGGAGTCGGTGGCTAGAGTGAGCCGAGATTTGC<br>ATCACTGCACTCCTGCCTGGTGACAGAGCAAGACTCCATCTCAAAAAAAAC<br>AAACAAAAATAAAAGATAAAAATGAGCTATGTGAATTAAAAGAGGTATAACA<br>ATAGATAAACCATATTTTATTTAATTCCTAGTAATGAGTAATATTTCCAAACTT<br>CTGGAATGGGCAGAAATTGCTAGTTGGCATATTTTTACCTTTTATATTCAGA<br>TACATTAAAATTCTCAAAAAAAAACACCTCAAAGCAGATGATCCGCCATCTC<br>CTTGGATAATTTGTGTTAACTCAGGATAACAGAAAACCAAAATTATGAGTTA<br>CTGATGCAATATTCCTAAATGTAAAAATAATTAAAGCTAATAGTAGATTCATC<br>TTCCAATTTCATATCAGTCTTACAAATAAACTACATATATAACTTGCTTGCCT<br>TCCCTTCTGAGGGATAAAGCTGTTAGAAGAATTAAAATCAGCATTCTTGACT<br>ATTCAACCAAGGGAGGGATAAATTATTACTCATTCTAGGGACATGGGCTCAT<br>AACTACTACATGTGTAAGGACATGAATTTACCCAATATTACAATTTTTCCTTT<br>TATTAGTGTGTACAGTGGAAGAATAGACATGTTCACTCTGGACAAAAAAAAA<br>ATTATACTTATCAGTTATCAGAAGCACAATGCTGAAGACAGTAGTTCCATAA<br>CAATTTGAAGTATGTGATCGAACTAGTAGATTATCTTAGTAGTAGTGAATTAT<br>TGTAAATGTTAGTAATTTGGCAGCCACTGGGCAGAAAAATAAGAATTGAGG<br>CTCAATATTGATATTAATGGTGGTGATTGACACATAAATTTTATCAAGTCTAC<br>ACAATATAAAATTACAGAAAGGTAGAAGAGTATACCAGTACAACTTCAACAT<br>ATCTTCACTACAAGGGAGTAAAATGACATGGCCTAGTTACTATCTAATGAAC<br>TGCAGAAAACTAAAAGAAAACTCCAAGGCAACTCTTCTCTGCTGATCTGGTT<br>GGTCCTTTTCCTACCTTTTGCAATACCCAGATACAAACAATGGATAGAAAAC<br>AAAGTAGACTTGTAGTATGCAGGTCACAGTGCTAAATTCACAGAAAGAAAC<br>CCCTGAACTGAACTGCTCTATTTCCTGGTGGTCACAAAGAGTAATTCTGGTT<br>TACACCTACAGATTGATGTCAATCTACACCCTGTTGATAACAGTGTGGCCAA<br>GGACAAAAAAAAGGTGCTCCGTTTTACCAATTCTGTAAAAAATTATTGGCAG<br>GGTAAGCTCGGCTAGGGCAGGATTACATTTCTAGGACTACCATCCCCGAAA<br>TTTAGAAGATATTATATCCACATAAAGCATATCTTTCACATTAATTTGCAAAA<br>ATCTAAAAGCTTTTTCTTAGCTCAAGTGTGTCCAAGTTTACCCTGGCAGTTT<br>AAAACGATAGTTACAAGCAGCATGGGTTGTATCAGACACATTTGAGGGCCA<br>ATTTCATGTAAGTGATATTGGGCAAGTTACTTCAACTATCTGTGCCTCCAAG<br>GTCATACTAGTGTTTATTTACCTAAAGGGTACCTGTTATGTAACTTTAGGGT<br>GTTTACATTAGATAATGCCTGCAAAATATTTACTTCAACGCCTAAAACATAGT<br>TAAGTATTCAATAAATACCTACTATTGTCACTACTAACTTAAAAGTTTAGAGA<br>TTAAGAGCAGAATCTGGGGTGAGACAAACTTAGGTTCAAATCCTAGTATTGT<br>TGGGTAATCTTGGGCAAGTTACTTAACCTCTCTGATTTGTGTAATTTAAAAAA<br>TTAGTTAATATACATAACAGGGCTTAGAAGAGTATCTAGCACATAGCACCAT<br>TTAAGCATTTGTTATTGCTAACATGCAAACAATTTAAGGGAAAGAAATTTTTT<br>AAAAAGGAAGAGGGATTTGCAAACTAAAAACAATGAGTATCTTATGTTCAAA<br>GAAAACTAACAAACAGCCAGCTCTAGCAATAATTAAATTCACTATATACTGG<br>GGCAGGCATCACACCCCAAAGCTAAAAGCGTCTACCTAGGCCAGGCACGG<br>TGGCTCATGCCTGTAATCCCAGCACTTTGGGAAGCAGAGGCGGGCAGATC<br>GCTTGAGCTCAGGAGTTCAAGACCAGCCTGGACAACATGGCAAAACACCAT<br>CTCTACAAAAAATACAAATATTAGGCCGGGCGCAGTGGCTCACGCCTGTAA<br>TCCCAGCACTTTGGGAGGCCAAGGCGGGTGGATCACCTGAGATCAGGAGT<br>TCGAGAGTAGCCTGGCCAACATGGTGAAACCTCGTCTCTATTAAAAATACA<br>AAAAATTAGCCAGGCATGGTGGCAGGCGCCTGTAATCCCAGCTACTCAGG<br>GGGATGAGGTAGGAGAATCGCTTGAACCCGGGAGGCAGAGGTTGCACTGA |

-continued

Sequences

| SEQ ID NO: | DESCRIPTION | SEQUENCE |
|---|---|---|
| | | GCCGAGATCATGCCACTGTACTCCAGCCCGGGCAACAAGAGCGAAACTCC |
| | | ATCTCAAAAAATAAATAAATAAATAAATAAAATAAAGTACAAATATTAGCCAG |
| | | GGATGGTGGTGCGCACCTGTAGTCCCAGCTACTTGGGAGGCTGAAGTGGG |
| | | AGAATCCCCTGAGCCTGGGGAGAATCACCCGAGCCCGGGAAGTCGAGGCT |
| | | GCAGTGAGCAGTGATTGTGCCACTGCACTCCATCCTAGGTGACAGAGTGA |
| | | GACCCTGTCTCAAAAAAAAGAAATTGGCAGAATTAAGTAAGTTGATGTTTAG |
| | | AGATGAAAAATCAACATTTTTTCCTCAGCAACTGAATAAAAACAACAGCCAC |
| | | TACCATTTTTTTGAGTACCTATTTGTAGCCTATTTTTTAACTGGTATTACTCG |
| | | AGAGAGAGAGAGCTAGGTTCGAGACAGAGCTCCTTCTCTTAATAACTGTAT |
| | | GACCTAGGGTATGTCTGTTAGCCTCTCTGAGGCTTCAAAGGTTCCTCATCT |
| | | GTAAAATGGTAATAATCATACCATTGCTACAGGGCTGTTTTGAAGACTAATT |
| | | AGGACTATGTAAGTAAACATGATGATGGCTATTATTACTGTTCCCCGCCAGG |
| | | GGCCATGCAAGGGTTGCTGATTCACATAGACTGTCTTATAATCCTCTCAATA |
| | | ACTCCAAGAGGTAGCCAGCACCTCAGATATACATAAAATGACTTAAGCCCA |
| | | GAGAGGTGAAGTAAGTTGCCCACAGCCACACAACTAGTAAATAGCCCAAAC |
| | | AAGCTGGATTCCCAGTTAGACTCCGTTAATAGCACTGCTCTTTACCTTAAGT |
| | | CATTACAATGCCTAATATGAAATAGAATCGCTTCTTTCTTAGGGTTCAAGTG |
| | | GTTAATTATTTAATGTATTCATTCAACAAACCATCATCGAGGACCTCTTACAA |
| | | GCCAAGTACTGTGCTAAGTGCTAGAGTTACGGCGGTGATTCCTGCCCTTAA |
| | | AAAGTTTTAGTGGGAGAAACAACAGGTAACCAGGTCATTGCCAAAACAACA |
| | | AAAATAATCATAATAAAGCAGGCTAAAGCATATTTAACTGGCCGGGGTTTTG |
| | | ACTATTTTAGCAAGCATGATCAGAACGGTTGAGGAGGGAGGCCAGCAGCTT |
| | | GGCCGGTTCAACAAACAAGAAAAAACCAGTGAGGGTGGAGCTAAGATACC |
| | | AGAGGCTGATTACGGTTAAGAATGTTCTTGAAGGTAAGGACCAGATTCTCA |
| | | TTTTCTATATCCTGGGGCATCGGTCAGCATGGAATCTGGATTCTAGCACAT |
| | | GTGAATTTCGGCTTGAAATGACCTAATGCCTTTTCCCTAGTTCCTTCGTGTG |
| | | TCAAATACGCATGGTTACCGCTACCAGAGCTGTAGTGGGGCTTCAATGAGG |
| | | CCATGAGCATCTCCATAAAGATGAACTACAGTGTGTGCAAAACTAAAGGCA |
| | | AAACCTGGTCCCCACACGCCCTCCCAGGTGGTCGCTTTCCGTGCCGAGGC |
| | | CCCTCCAGAGGTGCCCCGAGAACCTCACCATCGCACCCCAAACTTCCAGG |
| | | GAAGGGCCTCTCCCGAGAAAGCCCCCACGCCCCCACCCCGCGCCATCATT |
| | | CCCGAATCTGCCCTCGGCCCCTCCCCGCAGCACGCTCGCAGGCGGCACAT |
| | | GTCAACCAAAACGCCATTTCCACCTTCTCTTCCCACACGCAGTCCTCTTTTC |
| | | CCAGGGCTCCCCCGAGGAGGGACCCACCCCAAACCCCGCCATTCCGTCCT |
| | | CCCTGCCGCCCTCGCGTGACGTAAAGCCGAACCCGGGAAACTGGCCGCC |
| | | CCCGCCTGCGGGGTTCCCTGGGCCCGGCCGCTCTAGAACTAGTGGATCCC |
| | | AATTGAAGGCCTGGTCTAAATGACTCCAAAATCACCACTTAATTCAAGAGAC |
| | | TGATTTCCCTGAGTCAGGCCCCTTAAAGCAGCTATTTCAATGGGACAGGGA |
| | | AACAACCCTAGGATCTGGATTAGAATCACTTGGGGGCTGCCACACCCCCAG |
| | | GGCTCTGATCCTGCCCTTCTCCCACACGCACATTCACATACTGCTGCAGTG |
| | | ACCTTCCATTTCTAATGGGTTCCTGGGCCATCTGTCAGGTATAGGGAATGG |
| | | AAAAGGGGTTGGGGAGGCTCTGCTTCAGAAAGTTTGTGTCAGGGGCTCCC |
| | | AGAGCCTCCACAGATAGATAGCAGGGGTCCCCACCCTACCATGGCAGCTA |
| | | TAAATGTGATCAACATTTATTGGCCTAGGATACAGCAGTTAGCAAAATGCCT |
| | | GATGTAGTTCCCACTCCGTGGAGGTTGCAGGCTAGCTCTTTCCTAATGAGC |
| | | TTTACAGCAGAAGCTGTTTTATCGTTAAGTGCCCCACAGAGACACTTTACCA |
| | | GGAGGCTGGGAGAGTTCTCCAGATTTGGGAGAGGCGCAGAGACAGTGTGT |
| | | GAGCCGAGCCCTGTCTCAGCAATCCACCTGGAGGAGCTAGAGTATCCTCC |
| | | TCCCTTTACCATTCAGACCGAGAGAAAAAGCCCAGCTTGTGTGCACCCTCG |
| | | TGGGGTTAAGGCGAGCTGTTCCTGGTTTAAAGCCTTTCAGTATTTGTTTTGA |
| | | TGTAAGGCTCTGTGGTTTGGGGGGGAACATCTGTAAACATTATTAGTTGATT |
| | | TGGGGTTTGTCTTTGATGGTTTCTATCTGCAATTATCGTCATGTATATTTAAG |
| | | TGTCTGTTATAGAAAACCCACACCCACTGTCCTGTAAACTTTTCTCAGTGTC |
| | | CAGACTTTCTGTAATCACATTTTAATTGCCACCTCGTATTTCACCTCTACATT |
| | | TGAAATCTGGCGTCTGTTTCAAGCCAGTGTGTTTTTTCTTCGTTCTGTAATAA |
| | | ACAGCCAGGAGAAAAGTGCCTCTATGTTTTTATTTTTCAAGGGAGTATTCAG |
| | | TACCTACAAACCCAAGTCAGGAAGCCTGCTAGTGGCTTTGGTTCTTTCAGA |
| | | GGCTGCTCGATGCCTTGTGTGTCAGAAAGAAAGATTCAGCAGTTTTGCATC |
| | | ATGGCAAAGAAGCCTGTTATTTTGGGGCTCAGCCCCTCATTTTATAGAGGA |
| | | TGAAACAGAGGGGGATGGGAGGTCACAAAGACAACTGCCCCGGGAGCAG |
| | | GTGTGGGGGAGACTTGCCCTGAGGGTCTAGACGCTCTGCACCACCGTCCT |
| | | GTCTCCCTTGCTGAAGACCACACATGCCCTTCTTTGACCAGACCCTGCCAC |
| | | CTGATAGGCCAGGACCTGGTAGGCGGGTACCCAGGTTTCATGGATGGAAC |
| | | CACATCTCCCCAAAAGTGGGGAGGTAGCTACTGGGATGCACGCCTCCCGC |
| | | CATGTGCTATAGGAGAGCAGCTGAAGCAACAGTTGGGATCAGATGTAGTCA |
| | | CAATTGAATGCATCATCACATTTATCCCTCTAAGTGGCTGGGAGAGTTGATA |
| | | TCCTCATCCCTAAGGTACAAAATGTTCCAATTTGATCAGTGGCTTTCAGGAG |
| | | CTGAGAAAGGCATGTGCTCTGAGGCAGAGCTGTTATGTCCCGCAGAGCCT |
| | | AAAAATGCTCTAAGAACATGCTCCCTGCCAAAATTCTCAATGGCTGTGACAA |
| | | GGGACAACGATCGACCAATGGGGGTGGAAGCAGACCTCCGCAGTCCAGG |
| | | GGCCAGAGCTAGGACAGAGGGGTCGGAGAAAGAGTCATTTTCCCAACACT |
| | | CCAGCTCTTGGCCAGTCCTCACACAGTCCCCTCCTGCTTCCTGCTGAGAGA |
| | | GATATCCTCATAGGTCTGGGTAAAGTCCTTCAGTCAGCTTTCATTCCCTGTC |
| | | ACCAACTTTGTCTCTGTTCTCCCTGCCCGTCTCAGGCAGCACTCCTCAGGA |

-continued

Sequences

| SEQ ID NO: | DESCRIPTION | SEQUENCE |
|---|---|---|
| | | AACCTCTCCAAGAGCCAGCCTCACTGCAGCGCCCACTATTGTCCCTCTGCC<br>TCAAGTGTCCCATCCATGCCAGGCCCCAGGCAGGCTGCAGCTTTCCCTCA<br>GGGCCACACCAAAGCACTTGGGCTCAGCTGTGCTGTCCCCCTCCATCACT<br>GAGCTCAGGGGCAGCAGGGGTGGGGTGCCAGGAGGCCCATTCACCCTTC<br>TCTGGCTCTGTGTTGGACCCACCTGCCCAGCCACTGCTGCTTAGAACCTAC<br>CCGCTGGGAAAATGAAGCCCTCCCGGAGGGGCCACCTCAACCTGAGAGCC<br>TCACGGATCACAGTTGTCCCCACTCAGCTCTGCCAGCCCTCAGAGACCCAT<br>AGATAAAAGCTGAGCTTGGCTCGCAGAGCTGGTTCCATCTTCCATTCCCAG<br>AGGGTTCAACTTCCTACCCCAACCACACAGGGAACCTCAAGGCTGAGCCA<br>GTGTGGGCTGCAGTGCAGACCAGCTTCCTGGACACGTCCTGCCACCTGAC<br>CCCAGGCTGGCCTCACTGCCCCTGGCACTCCTGACCCTATCCTCATTCCTC<br>CTGGCAGTGCGTGTTCTGCCATTCCGCTTTCCCTTAGCTGTCCTCTCACTG<br>TACTGTCAGCTTCTCCTTTTCCAGGTGCCCCCCAGGGGCTTTCCACATGAC<br>CCTGTCACCCCACAGCCCATCCAGCACCAATTCCAGCTCTCTGCCACCCTT<br>CAAAGGAGTGACAGTGCCCTGCTTCACCTCCCACTCACCCCTCAACCCAGA<br>GCAATCTGGCTCCAGTCTTGCCTCCTTCCCCCTAAGTACTCTAGTCACAGTT<br>CCAAATTCCTCCTGGTCATAAAGCCAAATGAAGCTTCCTGGTCCTCAGCGG<br>ACTTGCCACTTCAGCAGTACTGGACTCTCTCCTCCCAGAAACCTGTTTCCC<br>CTTGGCTCCTGGAGCCCACACTCTGCTGGAATCCTTCTGCCTCTCTGGCCT<br>GTAGCCTGGCCCTCTCTCCCAACCTGAGGTCCATTCTCTCCTGCTCCTCCA<br>CAAGATGTTGCTCCTTCCATTACTTCCTCCCTCTCAACCAAAGCTCCTTCAT<br>TAGCTCTTTATCTTCTGGTTTCTTCCCCTGGGCAGACGAATGGATTCAAGAG<br>CCTGTGGCCCAGCAGCCCAGCACTCCAGGATCTCAGCACTTCAGCATCCC<br>AGTACCCTAGCATCTCAATACCCCAGCACCCCAGCACCATAGTATTCCAGC<br>ACCCCATTGTCCAAGCATCTCAGCACTCCAGCATCCCAGCACCCCAACACT<br>CCAGCAGCCCAGAATCTCAGCACCCTAGCACTGCAGCATCTCAGGACCCC<br>AGCACTTCAGCATCCCAGCACACTAGTACTCCAGCATCTCGGCACCCCAGC<br>ACCTAGGCATCCCAACACCCAGCACCCCAGCACTTAAGCATCCCACCACTA<br>CAGTATCTCAACACTCCAGCACCCCAGCACCATAGTGTTCCAGCACCCCAG<br>CATCCCAACACCCCAGCACTTAAGCATCCCAACACCTCGGCATCCCAACAC<br>CCCAGCACTGCAGCATCTCAGCACCTTAGCATCCCAGTGCCCTAGCATCTC<br>AATGCTCCAGCACACCAGTACTACAGTATTCCAGCACCCCAGCACTCCAGC<br>ATCTCAGCACTGCAGCACTGCAGCACTCCAGCATCCCAAAATCCCAGCATC<br>CCAACACCCCAGCAGACCAGCAGACCAGCATCTCAGCACCGCAGCATCCA<br>AGGACTATCCCAGCATCCCAGCAACCCAGCACCTCAGCATCCCAACACCC<br>CAGCATTTCAGCATGGCAACACCCCAGTACCCCAGCACTTCAGCACCCCAG<br>TATCCCAGCATCTCAGCGACCCAGTATCACAAAACCTCAGCATCCTAGCAC<br>CCCAGCACCCCAGCACCTTAGCACCTTAGCATCCCAGCATCTCAGCGCCTC<br>AGCATCTTGATATTCTGGCTGAGGTCAGCGTGGTGTATCTAGTCAGGGTCC<br>TAACTTTCACTTCGCAGGGAAATGCTGCTGGACTGGGTCTCATGTTGGGCT<br>GAAGCTCTCTAGACCCCTTGAAGACAGCATAAAAGAGCTTGGAGACGCTGG<br>GTGTCCCCCATGGAAGAGTTCACTCTCATCCTGCTTTGACAACAGCCTTCT<br>CTGGGGTCCCTCACGGGCCCCTCTTTCTTACTGCAAGTTTGTCTCTGAGAA<br>GACTGTGATGCAGAAGTCACTCAGCTGCCTGTGGCTCCTGAAGAGCTGAA<br>GGTGGAGGCCTGTAGGCCTCCCTATGAGAGGCGCAGAAAAAACCATGATT<br>GCTAGTGGGGAGGTGCTCCCTCTACAACCCACTCCATAATCTGCCCCCGC<br>CCAGCTCTGAGGCCAGCCCCAGGGGAAAATGCCAGATCCCCAGGGAGGT<br>GTGTGAGACCTCAGGGGCTCCCTCCTCCCTTACAGCAGGCTCAGGCCCCT<br>GGGGGCCTCAGGGCCAAGGTCTGTGGGTAAGCTACTATCTCTCACTTGTC<br>CTCTAGCCACAAAAGCCAGGGAGATCTGGCAATGGACATGAGGTTCTGAA<br>GAAGCACATATGACTGGCTTCCTAATGCGTGGTTGTTCAGTGATTCAATAAA<br>CACGCATGGGCCAGGCATGGGGAAATAGACAAACATGATCCCCAACCTCT<br>CCCAGAGTGAACTGGGAGGGAGGAGTGTTCATCCCTCAGGATTACACCAG<br>AGAAACAAACCAGCAGGAGATATATATGGTTTTGGGGGGTCAAGAAAGAGG<br>AAAAACCTGGCAAGGCAAGTCCAAAATCATAGGACAGGCTGTCAGGAAGG<br>GCAGCCTGGAACCTCTCAAGCAGGAGCTGATGCTGCAGTCCACAGGCAGA<br>ATTTCTTCTTCCTCGGGGAAATCTCAGCTTTGTTCTTAAGGCCTTTCAACTG<br>ATTGGCTGAGGTCTGCCCCTTCCCCCACATTCTCCAGGATAATCTTCCTTAC<br>TTAAAGTCAACTATTAATCACAGCTACAAAATCCCTTCACAGCTACACATAG<br>ATCAGTGTTTGATTGACGAACAGCCCCTACAGCCTAGCCAAGTTGACACAT<br>AAAACTAACCATCACAGGGGGACAAATGATGTAAACACATCAACAAATAAAA<br>CAGTAACAAGTTAAGGTCTATGGAAAAAACACAGAAGGGGCAGAGAGAAAG<br>AAAGCAAGAAGGAGAGTCCCAGTTTGCTAGGGCTTGTGGGAAGTGGGGAG<br>CAGTTCTCTTTAGCTAGGATATTTGGGAAAGGCATATCTGAAGGAGTGATAT<br>TTGAGCTTAGATTAAAAGATGGGAAGGAGCAAGCCATGCAAAGAGCTAGGA<br>TGTTCCAAGCAGAGACGGAACAGCAAGTGCAAATGTCAGGAGGAATAGAA<br>GGAGGCTGGTGGGTGGGGTCCAGTGAGCAAGAGGAGGGCAGGCAGGAGA<br>GGGGATGGGGAGGTGGGCAGGCCCAGACCACCCAGGGCCCTGGAGACTA<br>TCCTGATCCAACAAGGGAAGCCTTGAGTCACTTCAGTGTCCATGTGGAGAA<br>TGGACCTCAGACTGAATGAGGGAGGCAGTAAGGAGGGCCTCTACCTCCAG<br>GGCTTCGCCCTGTGGACTGCGCATAGACATCTCCAACTCAGAAAGTCTGAA<br>CCAAACTTTCCATAGTTCCCCCAAGTCTGGGCATCCTCCTACTCAGTGAAA<br>GGCAGCCATCACACCTCCCTGCCCTGCTCCCGGATGCCCCAAATCCTCTT<br>GGTCTCCAAGTCCAGAACCTGAGACTTGTCCTTGATGTTTGTCTTTCCCTCA |

-continued

Sequences

| SEQ ID NO: | DESCRIPTION | SEQUENCE |
|---|---|---|
| | | CCCTTTCTGTATTCTGGGAAGATGGGTTTTTTTCCCCCAGATGAATCTGTAA |
| | | AACTTCTGTGATCACAATAAAAATTCTGGCAGTATTATTTTCTGGAACATGAC |
| | | AAAGTGATTCAAAATTATTTATCTGGAAGACTACAAAACAAGAATAGCCAGG |
| | | AAATTTCTAAAAAGAAAGAAGAAGGAGGAGGAGAAAGAAGGAGGAGGAAAA |
| | | GGAGGAGAAGAAGAAAAGAAAAAGAACCAAGAAAGGGTTCTAGCTCTACCA |
| | | AATATTAAAACATATCATGAAGCTATTTAAAACAATATGGTTGTGGATACTGA |
| | | AAAAGATGTGAATAAAGTGGAAGGAAAATAAATAGAAATGCACATGGGGAT |
| | | TGAGACTGTGAAAAAGGCAGCATCTCACATCAGTGAGGGATGTTCAACACC |
| | | TGGTGTTGGGAAAACTGGCTAGTCATTTAAACCAAACAACTGGGTCCTCTA |
| | | CCTCACTCCTGACATTAAGATACATTTAGATGATTCAAAGAGTAAGACAGAA |
| | | AAAATAACACGTGAAAACACTATCAGAAAACAACGTGGGCCAGGTGTGGTG |
| | | GGTCACGCCTGTAATCCCAGCACTTTGGGAGGCCGAGGCAGACAGATCAC |
| | | CTGAGGTGGGGAGTTCAAGACCAGCCTGACCAACATGGTGAAATCCTGTCT |
| | | CTACTAAAAATACAAAATTAGCTGAGCGTGGTGGCGCATGCCTGTAATCCC |
| | | AGCTACTCAGGAGGCCGAGGCAGGAGAATCACTTGAACCTGGGAGGCAGA |
| | | GGTTGTGGTGAGCCGAGATCACGCCATTGCACTCCAGCCTGGGCAACAAG |
| | | AGTGAAAATCCATCTAAAAAAAAAAAAAAAAAGCCAAGGTGGATATTTTTATA |
| | | GTATCAGGGTAGATCAAGCTTCTCCAATCATGACATGAAACCCAGAAACCA |
| | | TAAAAGAAAAGAATGATAAAATTGCCCACGTAAAGTAAAAAGCTTGCACACA |
| | | GAAAAACACCATACAGGTTACAAGATGAGCAGCAAAATCAGAGAAAAAACA |
| | | TTGCAATTCAGGACACACAGAGGCTATTGTTCCTAATATTTAAAAATAAAAG |
| | | TAGTGGATTGTCTACAAAAAGATGAAGACAAGAATTTCAGAAAACCAAATAC |
| | | TGCATGTTTTCACTTACAAGTGGAAGCTAAACACTGAGTACACGTGTACACA |
| | | AAGAATGGAACCATAGGCCAGGCACCGTGGCTCACGCCTGTAATCCCAGT |
| | | ACTTTGCGAGGCCGAAGCGGGCGGATCACCTGAGGTGAGGAGTTCGAGAC |
| | | CATCCTGGCCAACATGGTGAAACCCAGTCTCTACTAAAAATACAAAAATTAG |
| | | CCGGGCGTGGTGGTGGGTGCCTGTAATCCCAGCTACTCGGGAGGCTGCG |
| | | GCAGTAGAATCGCTTGAACCCTGGAGGTGGACCTTGCAGTGAGCCGAGAT |
| | | CGCACCACTGCACTCCAGCCTGGGCAACAGAGTGAGACTCCATCTCAAAAA |
| | | AAAAAAAAAGGAATAGAACAATAGACACTGGGGCCTACTTGAGGGAGGAG |
| | | GGTGAGGATCAAAAACCTGCCTATCAGGTACTATGCTTATTACCTGGGTGG |
| | | TGAAATAATCTGTACACCAAACCCCAGTGACATGCAATTTACCGATGTAACA |
| | | AACCTGCCCATGTACCCGCTGAACCTAAAATAAAAGTTGGAAAAAAATATAG |
| | | AAATTTTCTTTGTAATAGCCAAAAACTGCAAACAGCCCAGGTGTCTATTAGT |
| | | AGAATGCATAAACAAACTCGGGCATGTTCATACAATGTAAAACTACTCATCA |
| | | ATAAAAAGTGATACTTCTCAGCAATGAAAAGAAACTAGCTACTGATACCAGC |
| | | TACAACATGGATGGATTTCAAGTGCTTTATGATGAGAGCAAGAAGCCAGAC |
| | | ACAAAAGTGTCTATATATATATACAGTATATATACGTATATATACACATATATA |
| | | CAGTATATATATACATATACATGTATATATATACTGTATATATACTGTATATAT |
| | | ATACACAGTATATATATACATATATACAGTGTATATATACTGTGTATATATAC |
| | | ATGTATATATACTGTGTATATATACATGTATATATACTGTGTATATATACATGT |
| | | ATATATACTGTGTATATATACATGTATATATATGTATACTGTATATATACTGTA |
| | | TATATATATACACATATATACAGTATATATATACAGTATATACTGTATATATAC |
| | | AGTATATACGTGTATATATACATATATACAGTATATATGTAAATATACATATAT |
| | | ACAGTATATATGTAAATATACATATATACATGTATATATATACACTATATATAT |
| | | ACATATATAGTGTATATATACATATATACATGTATATATTTACTATATGATTCC |
| | | ATTTATATAAAGTGCCAAAACAGTCAAAAATAATCTATGTGGAAAAAATCAAC |
| | | AAAGGGATCCCCCGGGCTGCAGGAATTCGATGGCGCGCCGACGTCGCAT |
| | | GCAGTTAGGGATAACAGGGTAATACGACCATGGCATGTCCTCTAGACTCGA |
| | | GCGGCCGCAATAAAATATCTTTATTTTCATTACATCTGTGTGTTGGTTTTTTG |
| | | TGTGAATCGTAACTAACATACGCTCTCCATCAAAACAAAACGAAACAAAACA |
| | | AACTAGCAAAATAGGCTGTCCCCAGTGCAAGTGCAGGTGCCAGAACATTTC |
| | | TCTATCGAAGGATCTGCGATCGCTCCGGTGCCCGTCAGTGGGCAGAGCGC |
| | | ACATCGCCCACAGTCCCCGAGAAGTTGGGGGGAGGGGTCGGCAATTGAAC |
| | | CGGTGCCTAGAGAAGGTGGCGCGGGGTAAACTGGGAAAGTGATGTCGTGT |
| | | ACTGGCTCCGCCTTTTTCCCGAGGGTGGGGGAGAACCGTATATAAGTGCA |
| | | GTAGTCGCCGTGAACGTTCTTTTTCGCAACGGGTTTGCCGCCAGAACACAG |
| | | CTGAAGCTTCGAGGGGCTCGCATCTCTCCTTCACGCGCCCGCCGCCCTAC |
| | | CTGAGGCCGCCATCCACGCCGGTTGAGTCGCGTTCTGCCGCCTCCCGCCT |
| | | GTGGTGCCTCCTGAACTGCGTCCGCCGTCTAGGTAAGTTTAAAGCTCAGGT |
| | | CGAGACCGGGCCTTTGTCCGGCGCTCCCTTGGAGCCTACCTAGACTCAGC |
| | | CGGCTCTCCACGCTTTGCCTGACCCTGCTTGCTCAACTCTACGTCTTTGTTT |
| | | CGTTTTCTGTTCTGCGCCGTTACAGATCCAAGCTGTGACCGGCGCCTACGT |
| | | AAGTGATATCTACTAGATTTATCAAAAAGAGTGTTGACTTGTGAGCGCTCAC |
| | | AATTGATACTTAGATTCATCGAGAGGGACACGTCGACTACTAACCTTCTTCT |
| | | CTTTCCTACAGCTGAGATCACCGGCGAAGGAGGGCCACCATGGGTCACCA |
| | | GCAGTTGGTCATCTCTTGGTTTTCCCTGGTTTTTCTGGCATCTCCCCTCGTG |
| | | GCCATATGGGAACTGAAGAAAGATGTTTATGTCGTAGAATTGGATTGGTATC |
| | | CGGATGCCCCTGGAGAAATGGTGGTCCTCACCTGTGACACCCCTGAAGAA |
| | | GATGGTATCACCTGGACCTTGGACCAGAGCAGTGAGGTCTTAGGCTCTGG |
| | | CAAAACCCTGACCATCCAAGTCAAAGAGTTTGGAGATGCTGGCCAGTACAC |
| | | CTGTCACAAAGGAGGCGAGGTTCTAAGCCATTCGCTCCTGCTGCTTCACAA |
| | | AAAGGAAGATGGAATTTGGTCCACTGATATTTTAAAGGACCAGAAAGAACC |
| | | CAAAAATAAGACCTTTCTAAGATGCGAGGCCAAGAATTATTCTGGACGTTTC |

-continued

Sequences

| SEQ ID NO: | DESCRIPTION | SEQUENCE |
|---|---|---|
| | | ACCTGCTGGTGGCTGACGACAATCAGTACTGATTTGACATTCAGTGTCAAA<br>AGCAGCAGAGGCTCTTCTGACCCCCAAGGGGTGACGTGCGGAGCTGCTAC<br>ACTCTCTGCAGAGAGAGTCAGAGGGGACAACAAGGAGTATGAGTACTCAG<br>TGGAGTGCCAGGAGGACAGTGCCTGCCCAGCTGCTGAGGAGAGTCTGCC<br>CATTGAGGTCATGGTGGATGCCGTTCACAAGCTCAAGTATGAAAACTACAC<br>CAGCAGCTTCTTCATCAGGGACATCATCAAACCTGACCCACCCAAGAACTT<br>GCAGCTGAAGCCATTAAAGAATTCTCGGCAGGTGGAGGTCAGCTGGGAGT<br>ACCCTGACACCTGGAGTACTCCACATTCCTACTTCTCCCTGACATTCTGCGT<br>TCAGGTCCAGGGCAAGAGCAAGAGAGAAAAGAAAGATAGAGTCTTCACGG<br>ACAAGACCTCAGCCACGGTCATCTGCCGCAAAAATGCCAGCATTAGCGTGC<br>GGGCCCAGGACCGCTACTATAGCTCATCTTGGAGCGAATGGGCATCTGTG<br>CCCTGCAGTGTTCCTGGAGTAGGGGTACCTGGGGTGGGCGCCAGAAACCT<br>CCCCGTGGCCACTCCAGACCCAGGAATGTTCCCATGCCTTCACCACTCCCA<br>AAACCTGCTGAGGGCCGTCAGCAACATGCTCCAGAAGGCCAGACAAACTC<br>TAGAATTTTACCCTTGCACTTCTGAAGAGATTGATCATGAAGATATCACAAA<br>AGATAAAACCAGCACAGTGGAGGCCTGTTTACCATTGGAATTAACCAAGAA<br>TGAGAGTTGCCTAAATTCCAGAGAGACCTCTTTCATAACTAATGGGAGTTGC<br>CTGGCCTCCAGAAAGACCTCTTTTATGATGGCCCTGTGCCTTAGTAGTATTT<br>ATGAAGACTTGAAGATGTACCAGGTGGAGTTCAAGACCATGAATGCAAAGC<br>TGCTGATGGATCCTAAGAGGCAGATCTTTCTAGATCAAAACATGCTGGCAG<br>TTATTGATGAGCTGATGCAGGCCCTGAATTTCAACAGTGAGACTGTGCCAC<br>AAAAATCCTCCCTTGAAGAACCGGATTTTTATAAAACTAAAATCAAGCTCTG<br>CATACTTCTTCATGCTTTCAGAATTCGGGCAGTGACTATTGATAGAGTGATG<br>AGCTATCTGAATGCTTCCTAAAAAGCGAGGTCCCTCCAAACCGTTGTCATTT<br>TTATAAAACTTTGAAATGAGGAAACTTTGATAGGATGTGGATTAAGAACTAG<br>GGAGGGGCTAGCTCGACATGATAAGATACATTGATGAGTTTGGACAAACCA<br>CAACTAGAATGCAGTGAAAAAAATGCTTTATTTGTGAAATTTGTGATGCTATT<br>GCTTTATTTGTGAAATTTGTGATGCTATTGCTTTATTTGTAACCATTATAAGC<br>TGCAATAAACAAGTTAACAACAACAATTGCATTCATTTTATGTTTCAGGTTCA<br>GGGGGAGGTGTGGGAGGTTTTTTAAAGCAAGTAAAACCTCTACAAATGTGG<br>TAGATCCATTTATTAGCTAGGAGTTTCAGAAAAGGGGGCCTGAGTGGCCCC<br>TTTTTTCAACTTAATTAACCTGCAGGGCCTGAAATAACCTCTGAAAGAGGAA<br>CTTGGTTAGGTACCTTCTGAGGCTGAAAGAACCAGCTGTGGAATGTGTGTC<br>AGTTAGGGTGTGGAAAGTCCCCAGGCTCCCCAGCAGGCAGAAGTATGCAA<br>AGCATGCATCTCAATTAGTCAGCAACCAGGTGTGGAAAGTCCCCAGGCTCC<br>CCAGCAGGCAGAAGTATGCAAAGCATGCATCTCAATTAGTCAGCAACCATA<br>GTCCCACTAGTTTCATCACCACCGCCACCCCCCCGCCCCCCCGCCATCTG<br>AAAGGGTTCTAGGGGATTTGCAACCTCTCTCGTGTGTTTCTTCTTTCCGAGA<br>AGCGCCGCCACACGAGAAAGCTGGCCGCGAAAGTCGTGCTGGAATCACTT<br>CCAACGAAACCCCAGGCATAGATGGGAAAGGGTGAAGAACACGTTGTCAT<br>GGCTACCGTTTCCCCGGTCACGGAATAAACGCTCTCTAGGATCCGGAAGTA<br>GTTCCGCCGCGACCTCTCTAAAAGGATGGATGTGTTCTCTGCTTACATTCAT<br>TGGACGTTTTCCCTTAGAGGCCAAGGCCGCCCAGGCAAAGGGGCGGTCCC<br>ACGCGTGAGGGGCCCGCGGAGCCATTTGATTGGAGAAAAGCTGCAAACCC<br>TGACCAATCGGAAGGAGCCACGCTTCGGGCATCGGTCACCGCACCTGGAC<br>AGCTCCGATTGGTGGACTTCCGCCCCCCCTCACGAATCCTCATTGGGTGC<br>CGTGGGTGCGTGGTGCGGCGCGATTGGTGGGTTCATGTTTCCCGTCCCCC<br>GCCCGCGAGAAGTGGGGGTGAAAAGCGGCCCGACCTGCTTGGGGTGTAG<br>TGGGCGGACCGCGCGGCTGGAGGTGTGAGGATCCGAACCCAGGGGTGGG<br>GGGTGGAGGCGGCTCCTGCGATCGAAGGGGACTTGAGACTCACCGGTCG<br>CACGTCATGAATCTAGAACCATGGCTTCGTACCCCGGCCATCAGCACGCGT<br>CTGCGTTCGACCAGGCTGCGCGTTCTCGCGGCCATAGCAACCGACGTACG<br>GCGTTGCGCCCTCGCCGGCAGCAAGAAGCCACGGAAGTCCGCCCGGAGC<br>AGAAAATGCCCACGCTACTGCGGGTTTATATAGACGGTCCCCACGGGATG<br>GGGAAAACCACCACCACGCAACTGCTGGTGGCCCTGGGTTCGCGCGACGA<br>TATCGTCTACGTACCCGAGCCGATGACTTACTGGCGGGTGCTGGGGGCTT<br>CCGAGACAATCGCGAACATCTACACCACACAACACCGCCTTGACCAGGGT<br>GAGATATCGGCCGGGGACGCGGCGGTGGTAATGACAAGCGCCCAGATAA<br>CAATGGGCATGCCTTATGCCGTGACCGACGCCGTTCTGGCTCCTCATATCG<br>GGGGGGAGGCTGGGAGCTCACATGCCCCGCCCCCGGCCCTCACCCTCAT<br>CTTCGACCGCCATCCCATCGCCGCCCTCCTGTGCTACCCGGCCGCGCGAT<br>ACCTTATGGGCAGCATGACCCCCCAGGCCGTGCTGGCGTTCGTGGCCCTC<br>ATCCCGCCGACCTTGCCCGGCACAAACATCGTGTTGGGGGCCCTTCCGGA<br>GGACAGACACATCGACCGCCTGGCCAAACGCCAGCGCCCCGGCGAGCGG<br>CTTGACCTGGCTATGCTGGCCGCGATTCGCCGCGTTTACGGGCTGCTTGC<br>CAATACGGTGCGGTATCTGCAGGGCGGCGGGTCGTGGCGGGAGGATTGG<br>GGACAGCTTTCGGGGACGGCCGTGCCGCCCCAGGGTGCCGAGCCCCAGA<br>GCAACGCGGGCCCACGACCCCATATCGGGGACACGTTATTTACCCTGTTTC<br>GGGCCCCCGAGTTGCTGGCCCCCAACGGCGACCTGTACAACGTGTTTGCC<br>TGGGCCTTGGACGTCTTGGCCAAACGCCTCCGTCCCATGCACGTCTTTATC<br>CTGGATTACGACCAATCGCCCGCCGGCTGCCGGGACGCCCTGCTGCAACT<br>TACCTCCGGGATGATCCAGACCCACGTCACCACCCCAGGCTCCATACCGA<br>CGATCTGCGACCTGGCGCGCACGTTTGCCCGGGAGATGGGGGAGGCTAA<br>CTGAGTATACCCTAGGATTATCCCTAATACCTGCCACCCCACTCTTAATCAG |

-continued

Sequences

| SEQ ID NO: | DESCRIPTION | SEQUENCE |
|---|---|---|
| | | TGGTGGAAGAACGGTCTCAGAACTGTTTGTTTCAATTGGCCATTTAAGTTTA<br>GTAGTAAAAGACTGGTTAATGATAACAATGCATCGTAAAACCTTCAGAAGGA<br>AAGGAGAATGTTTTGTGGACCACTTTGGTTTTCTTTTTTGCGTGTGGCAGTT<br>TTAAGTTATTAGTTTTTAAAATCAGTACTTTTTAATGGAAACAACTTGACCAA<br>AAATTTGTCACAGAATTTTGAGACCCATTAAAAAAGTTAAATGAGAAACCTG<br>TGTGTTCCTTTGGTCAACACCGAGACATTTAGGTGAAAGACATCTAATTCTG<br>GTTTTACGAATCTGGAAACTTCTTGAAAATGTAATTCTTGAGTTAACACTTCT<br>GGGTGGAGAATAGGGTTGTTTTCCCCCCACATAATTGGAAGGGGAAGGAAT<br>ATCATTTAAAGCTATGGGAGGGTTTCTTTGATTACAACACTGGAGAGAAATG<br>CAGCATGTTGCTGATTGCCTGTCACTAAAACAGGCCAAAAACTGAGTCCTT<br>GGGTTGCATAGAAAGCTGCCTGCAGGCGTTACATAACTTACGGTAAATGGC<br>CCGCCTGGCTGACCGCCCAACGACCCCCGCCCATTGACGTCAATAATGAC<br>GTATGTTCCCATAGTAACGCCAATAGGGACTTTCCATTGACGTCAATGGGT<br>GGAGTATTTACGGTAAACTGCCCACTTGGCAGTACATCAAGTGTATCATATG<br>CCAAGTACGCCCCCTATTGACGTCAATGACGGTAAATGGCCCGCCTGGCAT<br>TATGCCCAGTACATGACCTTATGGGACTTTCCTACTTGGCAGTACATCTACG<br>TATTAGTCATCGCTATTACCATGATGATGCGGTTTTGGCAGTACATCAATGG<br>GCGTGGATAGCGGTTTGACTCACGGGGATTTCCAAGTCTCCACCCCATTGA<br>CGTCAATGGGAGTTTGTTTTGACTAGTTACCGGCGGAAACGGTCTCGGGTT<br>GAGAGGTCACCCGAGGGACAGGCAGCTGCTGAACCAATAGGACCGGCGC<br>ACAGGGCGGATGCTGCCCCTCATTGGCGGCCGTTGAGAGTGACCAAGAGC<br>CAATGAGTCAGCCCGGGGGGCGTAGCAGTGACGTAAGTTGCGGAGGAGG<br>CCGCTTCGAATCGGCAGCGGCCAGCTTGGTGGCATGGACCAATCAGCGTC<br>CTCCAACGAGGAGCGCCTTCGCCAATCGGAGGCCTCCACGACGGGGCTG<br>GGGGGAGGGTATATAAGCCGAGTCGGCGGCGGCGCGCTCCACACGGGCC<br>GAGACCACAGCGACGGGAGCGTCTGCCTCTGCGGGGCCGAGAGGTAAGC<br>GCCGCGGCCTGCCCTTTCCAGGCCAACTCGGAGCCCGTCTCGTGGCTCCG<br>CCTGATCGGGGGCTCCTGTCGCCCTCAGATCGGTCGGAACGCCGTCGCG<br>CTCCGGGACTACAAGCCTGTTGCTGGGCCCGGAGACTGCCGAAGGACCG<br>CTGAGCACTGTCCTCAGCGCCGGCACCATGGATTGGATCTGGCGGATCCT<br>GTTCCTTGTGGGAGCTGCCACAGGCGCCCATTCTGAAGTTCAGCTGGTTCA<br>GTCTGGCGCCGAAGTGAAGAAACCTGGCGCCTCTGTGAAGGTGTCCTGCA<br>AAGCTTCTGGCGGCACCTTCAGCAGCTACGCCATCTCTTGGGTTCGACAG<br>GCCCCTGGACAAGGCCTGGAATGGATGGGCAGAATCATCCCCATCCTGGG<br>AATCGCCAACTACGCCCAGAAATTCCAGGGCAGAGTGACCATCACCGCCG<br>ACAAGAGCACAAGCACCGCCTACATGGAACTGAGCAGCCTGAGAAGCGAG<br>GACACCGCCGTGTACTACTGTGCCAGAAGCGGCCACGGCTACAGCTACGG<br>CGCCTTTGATTATTGGGGCCAGGGCACCCTGGTCACCGTTTCTAGCGGAG<br>GCGGAGGTAGTGGTGGCGGAGGTTCAGGCGGCGGAGGATCTCAATCTGT<br>GCTGACACAGCCTCCAAGCGTGTCAGGTGCTCCTGGCCAGAGAGTGACAA<br>TCAGCTGTACAGGCAGCAGCAGCAACATCGGAGCCGGCTATGACGTGCAC<br>TGGTATCAGCAGCTGCCTGGCACAGCCCCTAAACTGCTGATCTACGGCAAC<br>AGCAACAGACCCAGCGGCGTGCCCGATAGATTTTCCGGCTCTAAGAGCGG<br>CACAAGCGCCAGCCTGGCTATTACTGGACTGCAGGCCGAGGACGAGGCC<br>GACTACTACTGTCAGAGCTACGACAGCAGCCTGTCCGGCAGCTACGTTGT<br>GTTTGGCGGCGGAACAAAGCTGACCGTGCTGGAAGCCAAGAGCTGCGACA<br>AGACCCACACCTGTCCTCCATGTCCTGCTCCAGAACTGCTCGGCGGACCTT<br>CCGTGTTCCTGTTTCCTCCAAAGCCTAAGGACACCCTGATGATCAGCAGAA<br>CCCCTGAAGTGACCTGCGTGGTGGTGGATGTGTCCCACGAGGACCCAGAA<br>GTGAAGTTCAATTGGTACGTGGACGGCGTGGAAGTGCACAACGCCAAGAC<br>CAAGCCTAGAGAGGAACAGTACAACAGCACCTACAGAGTGGTGTCCGTGC<br>TGACAGTGCTGCACCAGGATTGGCTGAACGGCAAAGAGTACAAGTGCAAG<br>GTGTCCAACAAGGCCCTGCCTGCTCCTATCGAGAAAACCATCAGCAAGGC<br>CAAGGGCCAGCCTAGGGAACCCCAGGTTTACACACTGCCACCTAGCAGGG<br>ACGAGCTGACCAAGAATCAGGTGTCCCTGACCTGCCTGGTCAAGGGCTTC<br>TACCCTTCCGATATCGCCGTGGAATGGGAGAGCAATGGCCAGCCAGAGAA<br>CAACTACAAGACAACCCCTCCTGTGCTGGACAGCGACGGCTCATTCTTCCT<br>GTACTCCAAGCTGACTGTGGACAAGAGCCGGTGGCAGCAGGGCAATGTGT<br>TCAGCTGTAGCGTGATGCACGAGGCCCTGCACAACCACTACACACAGAAG<br>TCCCTGTCTCTGAGCCCCGGAAAAGGTGGCGGTGGCTCTTACCCTTACGA<br>CGTGCCAGATTACGCCGGCTATCCCTACGATGTGCCTGACTATGCTGGCTA<br>CCCCTATGACGTCCCCGACTACGCTTAACTAGCTACGGAATTCCGGCTAGC<br>TGGCCAGACATGATAAGATACATTGATGAGTTTGGACAAACCACAACTAGA<br>ATGCAGTGAAAAAAATGCTTTATTTGTGAAATTTGTGATGCTATTGCTTTATT<br>TGTAACCATTATAAGCTGCAATAAACAAGTTAACAACAACAATTGCATTCATT<br>TTATGTTTCAGGTTCAGGGGGAGGTGTGGGAGGTTTTTTAAAGCAAGTAAA<br>ACCTCTACAAATGTGGTATGGAAATGTTAATTAACTAGCCATGACCAAAATC<br>CCTTAACGTGAGTTTTCGTTCCACTGAGCGTCAGACCCCGTAGAAAAGATC<br>AAAGGATCTTCTTGAGATCCTTTTTTTCTGCGCGTAATCTGCTGCTTGCAAA<br>CAAAAAAACCACCGCTACCAGCGGTGGTTTGTTTGCCGGATCAAGAGCTAC<br>CAACTCTTTTTCCGAAGGTAACTGGCTTCAGCAGAGCGCAGATACCAAATA<br>CTGTTCTTCTAGTGTAGCCGTAGTTAGGCCACCACTTCAAGAACTCTGTAG<br>CACCGCCTACATACCTCGCTCTGCTAATCCTGTTACCAGTGGCTGCTGCCA<br>GTGGCGATAAGTCGTGTCTTACCGGGTTGGACTCAAGACGATAGTTACCGG |

-continued

Sequences

| SEQ ID NO: | DESCRIPTION | SEQUENCE |
|---|---|---|
| | | ATAAGGCGCAGCGGTCGGGCTGAACGGGGGGTTCGTGCACACAGCCCAG<br>CTTGGAGCGAACGACCTACACCGAACTGAGATACCTACAGCGTGAGCTATG<br>AGAAAGCGCCACGCTTCCCGAAGGGAGAAAGGCGGACAGGTATCCGGTAA<br>GCGGCAGGGTCGGAACAGGAGAGCGCACGAGGGAGCTTCCAGGGGGAAA<br>CGCCTGGTATCTTTATAGTCCTGTCGGGTTTCGCCACCTCTGACTTGAGCG<br>TCGATTTTTGTGATGCTCGTCAGGGGGGCGGAGCCTATGGAAAAACGCCA<br>GCAACGCGGCCTTTTTACGGTTCCTGGCCTTTTGCTGGCCTTTTGCTCAGG<br>GTTCGAAATCGATAAGCTTGGATCCGGAGAGCTCCCAACGCGTCGGCTAG<br>CTAGTAGGGATAACAGGGTAATAAGCGTCGACGGCGCGCCCCTAGGGGCC<br>GGCCTTAATTAAATCAAGCTTATCGATACCGTCGAACCTCGAGGGGGGGCA<br>TCACTCCGCCCTAAAACCTACGTCACCCGCCCCGTTCCCACGCCCCGCGC<br>CACGTCACAAACTCCACCCCCTCATTATCATATTGGCTTCAATCCAAAATAA<br>GGTATATTATTGATGATGTTT |
| 51 | ICOSTAT | TAACATCATCAATTATACCTTCCATTTTGGATTGAAGCCAATATGATAATGAG<br>GGGGTGGAGTTTGTGACGTGGCGCGGGGCGTGGGAACGGGGCGGGTGA<br>CGTAGTAGTGTGGCGGAAGTGTGATGTTGCAAGTGTGGCGGAACACATGT<br>AAGCGACGGATGTGGCAAAAGTGACGTTTTTGGTGTGCGCCGGTGTACAC<br>AGGAAGTGACAATTTTCGCGCGGTTTTAGGCGGATGTTGTAGTAAATTTGG<br>GCGTAACCGAGTAAGATTTGGCCATTTTCGCGGGAAAACTGAATAAGAGGA<br>AGTGAAATCTGAATAATTTTGTGTTACTCATAGCGCGTAATATTTGTCTAGG<br>GCCGCGGGGACTTTGACCGTTTACGTGGAGACTCGCCCAGGTGTTTTTCTC<br>AGGTGTTTTCCGCGTACGTCGGCGGCTCGTGGCTCTTCCGGGAAAAGGAT<br>TCTCGGAAAGTGGTTCGAGTACGTCGGCGGCTCGTGGCTCTTCCGGGAAA<br>AGGATTCTCGGAAAGTGGTTCGAAGTACGTCGACCACAAACCCCGCCCAG<br>CGTCTTGTCATTGGCGTCGACGCTGTACGGGGTCAAAGTTGGCGTTTTATT<br>ATTATAGTCAGCTGACGTGTAGTGTATTTATACCCGGTGAGTTCCTCAAGAG<br>GCCACTCTTGAGTGCCAGCGAGTAGAGTTTTCTCCTCCGAGCCGCTCCGA<br>CACCGGGACTGAAAATGAGACATATTATCTGCCACGGAGGTGTTATTACCG<br>AAGAAATGGCCGCCAGTCTTTTGGACCAGCTGATCGAAGAGGTACTGGCT<br>GATAATCTTCCACCTCCTAGCCATTTTGAACCACCTACCCTTCACGAACTGT<br>ATGATTTAGACGTGACGGCCCCCGAAGATCCCAACGAGGAGGCGGTTTCG<br>CAGATTTTTCCCGACTCTGTAATGTTGGCGGTGCAGGAAGGGATTGACTTA<br>CTCACTTTTCCGCCGGCGCCCGGTTCTCCGGAGCCGCCTCACCTTTCCCG<br>GCAGCCCGAGCAGCCGGAGCAGAGAGCCTTGGGTCCGGTTTCTATGCCAA<br>ACCTTGTACCGGAGGTGATCGATCCACCCAGTGACGACGAGGATGAAGAG<br>GGTGAGGAGTTTGTGTTAGATTATGTGGAGCACCCCGGGCACGGTTGCAG<br>GTCTTGTCATTATCACCGGAGGAATACGGGGGACCCAGATATTATGTGTTC<br>GCTTTGCTATATGAGGACCTGTGGCATGTTTGTCTACAGTAAGTGAAAATTA<br>TGGGCAGTGGGTGATAGAGTGGTGGGTTTGGTGTGGTAATTTTTTTTTTAAT<br>TTTTACAGTTTTGTGGTTTAAAGAATTTTGTATTGTGATTTTTTTAAAAGGTCC<br>TGTGTCTGAACCTGAGCCTGAGCCCGAGCCAGAACCGGAGCCTGCAAGAC<br>CTACCCGCCGTCCTAAAATGGCGCCTGCTATCCTGAGACGCCCGACATCA<br>CCTGTGTCTAGAGAATGCAATAGTAGTACGGATAGCTGTGACTCCGGTCCT<br>TCTAACACACCTCCTGAGATACACCCGGTGGTCCCGCTGTGCCCCATTAAA<br>CCAGTTGCCGTGAGAGTTGGTGGGCGTCGCCAGGCTGTGGAATGTATCGA<br>GGACTTGCTTAACGAGCCTGGGCAACCTTTGGACTTGAGCTGTAAACGCCC<br>CAGGCCATAAGGTGTAAACCTGTGATTGCGTGTGTGGTTAACGCCTTTGTT<br>TGCTGAATGAGTTGATGTAAGTTTAATAAAGGGTGAGATAATGTTTAACTTG<br>CATGGCGTGTTAAATGGGGCGGGGCTTAAAGGGTATATAATGCGCCGTGG<br>GCTAATCTTGGTTACATCTGACCTCATGGAGGCTTGGGAGTGTTTGGAAGA<br>TTTTTCTGCTGTGCGTAACTTGCTGGAACAGAGCTCTAACAGTACCTCTTGG<br>TTTTGGAGGTTTCTGTGGGGCTCATCCCAGGCAAAGTTAGTCTGCAGAATT<br>AAGGAGGATTACAAGTGGGAATTTGAAGAGCTTTTGAAATCCTGTGGTGAG<br>CTGTTTGATTCTTTGAATCTGGGTCACCAGGCGCTTTTCCAAGAGAAGGTC<br>ATCAAGACTTTGGATTTTTCCACACCGGGGCGCGCTGCGGCTGCTGTTGCT<br>TTTTTGAGTTTTATAAAGGATAAATGGAGCGAAGAAACCCATCTGAGCGGG<br>GGGTACCTGCTGGATTTTCTGGCCATGCATCTGTGGAGAGCGGTTGTGAG<br>ACACAAGAATCGCCTGCTACTGTTGTCTTCCGTCCGCCCGGCGATAATACC<br>GACGGAGGAGCAGCAGCAGCAGCAGGAGGAAGCCAGGCGGCGGCGGCA<br>GGAGCAGAGCCCATGGAACCCGAGAGCCGGCCTGGACCCTCGGGAATGA<br>ATGTTGTACAGGTGGCTGAACTGTATCCAGAACTGAGACGCATTTTGACAA<br>TTACAGAGGATGGGCAGGGGCTAAAGGGGGTAAAGAGGGAGCGGGGGGC<br>TTGTGAGGCTACAGAGGAGGCTAGGAATCTAGCTTTTAGCTTAATGACCAG<br>ACACCGTCCTGAGTGTATTACTTTTCAACAGATCAAGGATAATTGCGCTAAT<br>GAGCTTGATCTGCTGGCGCAGAAGTATTCCATAGAGCAGCTGACCACTTAC<br>TGGCTGCAGCCAGGGGATGATTTTGAGGAGGCTATTAGGGTATATGCAAAG<br>GTGGCACTTAGGCCAGATTGCAAGTACAAGATCAGCAAACTTGTAAATATC<br>AGGAATTGTTGCTACATTTCTGGGAACGGGGCCGAGGTGGAGATAGATAC<br>GGAGGATAGGGTGGCCTTTAGATGTAGCATGATAAATATGTGGCCGGGGG<br>TGCTTGGCATGGACGGGGTGGTTATTATGAATGTAAGGTTTACTGGCCCCA<br>ATTTTAGCGGTACGGTTTTCCTGGCCAATACCAACCTTATCCTACACGGTGT<br>AAGCTTCTATGGGTTTAACAATACCTGTGTGGAAGCCTGGACCGATGTAAG<br>GGTTCGGGGCTGTGCCTTTTACTGCTGCTGGAAGGGGGTGGTGTGTCGCC |

-continued

| Sequences | | |
|---|---|---|
| SEQ ID NO: | DESCRIPTION | SEQUENCE |
| | | CCAAAAGCAGGGCTTCAATTAAGAAATGCCTCTTTGAAAGGTGTACCTTGG<br>GTATCCTGTCTGAGGGTAACTCCAGGGTGCGCCACAATGTGGCCTCCGAC<br>TGTGGTTGCTTCATGCTAGTGAAAAGCGTGGCTGTGATTAAGCATAACATG<br>GTATGTGGCAACTGCGAGGACAGGGCCTCTCAGATGCTGACCTGCTCGGA<br>CGGCAACTGTCACCTGCTGAAGACCATTCACGTAGCCAGCCACTCTCGCAA<br>GGCCTGGCCAGTGTTTGAGCATAACATACTGACCCGCTGTTCCTTGCATTT<br>GGGTAACAGGAGGGGGGTGTTCCTACCTTACCAATGCAATTTGAGTCACAC<br>TAAGATATTGCTTGAGCCCGAGAGCATGTCCAAGGTGAACCTGAACGGGGT<br>GTTTGACATGACCATGAAGATCTGGAAGGTGCTGAGGTACGATGAGACCC<br>GCACCAGGTGCAGACCCTGCGAGTGTGGCGGTAAACATATTAGGAACCAG<br>CCTGTGATGCTGGATGTGACCGAGGAGCTGAGGCCCGATCACTTGGTGCT<br>GGCCTGCACCCGCGCTGAGTTTGGCTCTAGCGATGAAGATACAGATTGAG<br>GTACTGAAATGTGTGGGCGTGGCTTAAGGGTGGGAAAGAATATATAAGGTG<br>GGGGTCTTATGTAGTTTTGTATCTGTTTTGCAGCAGCCGCCGCCGCCATGA<br>GCACCAACTCGTTTGATGGAAGCATTGTGAGCTCATATTTGACAACGCGCA<br>TGCCCCCATGGGCCGGGGTGCGTCAGAATGTGATGGGCTCCAGCATTGAT<br>GGTCGCCCCGTCCTGCCCGCAAACTCTACTACCTTGACCTACGAGACCGT<br>GTCTGGAACGCCGTTGGAGACTGCAGCCTCCGCCGCCGCTTCAGCCGCTG<br>CAGCCACCGCCCGCGGGATTGTGACTGACTTTGCTTTCCTGAGCCCGCTT<br>GCAAGCAGTGCAGCTTCCCGTTCATCCGCCCGCGATGACAAGTTGACGGC<br>TCTTTTGGCACAATTGGATTCTTTGACCCGGGAACTTAATGTCGTTTCTCAG<br>CAGCTGTTGGATCTGCGCCAGCAGGTTTCTGCCCTGAAGGCTTCCTCCCCT<br>CCCAATGCGGTTTAAAACATAAATAAAAAACCAGACTCTGTTTGGATTTGGA<br>TCAAGCAAGTGTCTTGCTGTCTTTATTTAGGGGTTTTGCGCGCGCGGTAGG<br>CCCGGGACCAGCGGTCTCGGTCGTTGAGGGTCCTGTGTATTTTTTCCAGG<br>ACGTGGTAAAGGTGACTCTGGATGTTCAGATACATGGGCATAAGCCCGTCT<br>CTGGGGTGGAGGTAGCACCACTGCAGAGCTTCATGCTGCGGGGTGGTGTT<br>GTAGATGATCCAGTCGTAGCAGGAGCGCTGGGCGTGGTGCCTAAAAATGT<br>CTTTCAGTAGCAAGCTGATTGCCAGGGGCAGGCCCTTGGTGTAAGTGTTTA<br>CAAAGCGGTTAAGCTGGGATGGGTGCATACGTGGGGATATGAGATGCATC<br>TTGGACTGTATTTTTAGGTTGGCTATGTTCCCAGCCATATCCCTCCGGGGAT<br>TCATGTTGTGCAGAACCACCAGCACAGTGTATCCGGTGCACTTGGGAAATT<br>TGTCATGTAGCTTAGAAGGAAATGCGTGGAAGAACTTGGAGACGCCCTTGT<br>GACCTCCAAGATTTTCCATGCATTCGTCCATAATGATGGCAATGGGCCCAC<br>GGGCGGCGGCCTGGGCGAAGATATTTCTGGGATCACTAACGTCATAGTTG<br>TGTTCCAGGATGAGATCGTCATAGGCCATTTTTACAAAGCGCGGGCGGAG<br>GGTGCCAGACTGCGGTATAATGGTTCCATCCGGCCCAGGGGCGTAGTTAC<br>CCTCACAGATTTGCATTTCCCACGCTTTGAGTTCAGATGGGGGGATCATGT<br>CTACCTGCGGGGCGATGAAGAAAACGGTTTCCGGGGTAGGGGAGATCAGC<br>TGGGAAGAAAGCAGGTTCCTGAGCAGCTGCGACTTACCGCAGCCGGTGGG<br>CCCGTAAATCACACCTATTACCGGGTGCAACTGGTAGTTAAGAGAGCTGCA<br>GCTGCCGTCATCCCTGAGCAGGGGGGCCACTTCGTTAAGCATGTCCCTGA<br>CTCGCATGTTTTCCCTGACCAAATCCGCCAGAAGGCGCTCGCCGCCCAGC<br>GATAGCAGTTCTTGCAAGGAAGCAAAGTTTTTCAACGGTTTGAGACCGTCC<br>GCCGTAGGCATGCTTTTGAGCGTTTGACCAAGCAGTTCCAGGCGGTCCCA<br>CAGCTCGGTCACCTGCTCTACGGCATCTCGATCCAGCATATCTCCTCGTTT<br>CGCGGGTTGGGGCGGCTTTCGCTGTACGGCAGTAGTCGGTGCTCGTCCAG<br>ACGGGCCAGGGTCATGTCTTTCCACGGGCGCAGGGTCCTCGTCAGCGTAG<br>TCTGGGTCACGGTGAAGGGGTGCGCTCCGGGCTGCGCGCTGGCCAGGGT<br>GCGCTTGAGGCTGGTCCTGCTGGTGCTGAAGCGCTGCCGGTCTTCGCCCT<br>GCGCGTCGGCCAGGTAGCATTTGACCATGGTGTCATAGTCCAGCCCCTCC<br>GCGGCGTGGCCCTTGGCGCGCAGCTTGCCCTTGGAGGAGGCGCCGCACG<br>AGGGGCAGTGCAGACTTTTGAGGGCGTAGAGCTTGGGCGCGAGAAATACC<br>GATTCCGGGGAGTAGGCATCCGCGCCGCAGGCCCCGCAGACGGTCTCGC<br>ATTCCACGAGCCAGGTGAGCTCTGGCCGTTCGGGGTCAAAAACCAGGTTT<br>CCCCCATGCTTTTTGATGCGTTTCTTACCTCTGGTTTCCATGAGCCGGTGTC<br>CACGCTCGGTGACGAAAAGGCTGTCCGTGTCCCCGTATACAGACTNNNGT<br>TTTGAGAGGCCTGTCCTCGAGCGGTGTTCCGCGGTCCTCCTCGTATAGAAA<br>CTCGGACCACTCTGAGACAAAGGCTCGCGTCCAGGCCAGCACGAAGGAGG<br>CTAAGTGGGAGGGGTAGCGGTCGTTGTCCACTAGGGGGTCCACTCGCTCC<br>AGGGTGTGAAGACACATGTCGCCCTCTTCGGCATCAAGGAAGGTGATTGG<br>TTTGTAGGTGTAGGCCACGTGACCGGGTGTTCCTGAAGGGGGGCTATAAA<br>AGGGGGTGGGGGCGCGTTCGTCCTCACTCTCTTCCGCATCGCTGTCTGCG<br>AGGGCCAGCTGTTGGGGTGAGTACTCCCTCTGAAAAGCGGGCATGACTTC<br>TGCGCTAAGATTGTCAGTTTCCAAAAACGAGGAGGATTTGATATTCACCTG<br>GCCCGCGGTGATGCCTTTGAGGGTGGCCGCATCCATCTGGTCAGAAAAGA<br>CAATCTTTTTGTTGTCAAGCTTGGTGGCAAACGACCCGTAGAGGGCGTTGG<br>ACAGCAACTTGGCGATGGAGCGCAGGGTTTGGTTTTTGTCGCGATCGGCG<br>CGCTCCTTGGCCGCGATGTTTAGCTGCACGTATTCGCGCGCAACGCACCG<br>CCATTCGGGAAAGACGGTGGTGCGCTCGTCGGGCACCAGGTGCACGCGC<br>CAACCGCGGTTGTGCAGGGTGACAAGGTCAACGCTGGTGGCTACCTCTCC<br>GCGTAGGCGCTCGTTGGTCCAGCAGAGGCGGCCGCCCTTGCGCGAGCAG<br>AATGGCGGTAGGGGGTCTAGCTGCGTCTCGTCCGGGGGGTCTGCGTCCA<br>CGGTAAAGACCCCGGGCAGCAGGCGCGCGTCGAAGTAGTCTATCTTGCAT |

-continued

| Sequences | | |
|---|---|---|
| SEQ ID NO: | DESCRIPTION | SEQUENCE |
| | | CCTTGCAAGTCTAGCGCCTGCTGCCATGCGCGGGCGGCAAGCGCGCGCT<br>CGTATGGGTTGAGTGGGGGACCCCATGGCATGGGGTGGGTGAGCGCGGA<br>GGCGTACATGCCGCAAATGTCGTAAACGTAGAGGGGCTCTCTGAGTATTCC<br>AAGATATGTAGGGTAGCATCTTCCACCGCGGATGCTGGCGCGCACGTAAT<br>CGTATAGTTCGTGCGAGGGAGCGAGGAGGTCGGGACCGAGGTTGCTACG<br>GGCGGGCTGCTCTGCTCGGAAGACTATCTGCCTGAAGATGGCATGTGAGT<br>TGGATGATATGGTTGGACGCTGGAAGACGTTGAAGCTGGCGTCTGTGAGA<br>CCTACCGCGTCACGCACGAAGGAGGCGTAGGAGTCGCGCAGCTTGTTGAC<br>CAGCTCGGCGGTGACCTGCACGTCTAGGGCGCAGTAGTCCAGGGTTTCCT<br>TGATGATGTCATACTTATCCTGTCCCTTTTTTTTCCACAGCTCGCGGTTGAG<br>GACAAACTCTTCGCGGTCTTTCCAGTACTCTTGGATCGGAAACCCGTCGGC<br>CTCCGAACGGTAAGAGCCTAGCATGTAGAACTGGTTGACGGCCTGGTAGG<br>CGCAGCATCCCTTTTCTACGGGTAGCGCGTATGCCTGCGCGGCCTTCCGG<br>AGCGAGGTGTGGGTGAGCGCAAAGGTGTCCCTGACCATGACTTTGAGGTA<br>CTGGTATTTGAAGTCAGTGTCGTCGCATCCGCCCTGCTCCCAGAGCAAAAA<br>GTCCGTGCGCTTTTTGGAACGCGGATTTGGCAGGGCGAAGGTGACATCGT<br>TGAAGAGTATCTTTCCCGCGCGAGGCATAAAGTTGCGTGTGATGCGGAAG<br>GGTCCCGGCACCTCGGAACGGTTGTTAATTACCTGGGCGGCGAGCACGAT<br>CTCGTCAAAGCCGTTGATGTTGTGGCCCACAATGTAAAGTTCCAAGAAGCG<br>CGGGATGCCCTTGATGGAAGGCAATTTTTTAAGTTCCTCGTAGGTGAGCTC<br>TTCAGGGGAGCTGAGCCCGTGCTCTGAAAGGGCCCAGTCTGCAAGATGAG<br>GGTTGGAAGCGACGAATGAGCTCCACAGGTCACGGGCCATTAGCATTTGC<br>AGGTGGTCGCGAAAGGTCCTAAACTGGCGACCTATGGCCATTTTTTCTGGG<br>GTGATGCAGTAGAAGGTAAGCGGGTCTTGTTCCCAGCGGTCCCATCCAAG<br>GTTCGCGGCTAGGTCTCGCGCGGCAGTCACTAGAGGCTCATCTCCGCCGA<br>ACTTCATGACCAGCATGAAGGGCACGAGCTGCTTCCCAAAGGCCCCCATC<br>CAAGTATAGGTCTCTACATCGTAGGTGACAAAGAGACGCTCGGTGCGAGG<br>ATGCGAGCCGATCGGGAAGAACTGGATCTCCCGCCACCAATTGGAGGAGT<br>GGCTATTGATGTGGTGAAAGTAGAAGTCCCTGCGACGGGCCGAACACTCG<br>TGCTGGCTTTTGTAAAAACGTGCGCAGTACTGGCAGCGGTGCACGGGCTG<br>TACATCCTGCACGAGGTTGACCTGACGACCGCGCACAAGGAAGCAGAGTG<br>GGAATTTGAGCCCCTCGCCTGGCGGGTTTGGCTGGTGGTCTTCTACTTCG<br>GCTGCTTGTCCTTGACCGTCTGGCTGCTCGAGGGGAGTTACGGTGGATCG<br>GACCACCACGCCGCGCGAGCCCAAAGTCCAGATGTCCGCGCGCGGCGGT<br>CGGAGCTTGATGACAACATCGCGCAGATGGGAGCTGTCCATGGTCTGGAG<br>CTCCCGCGGCGTCAGGTCAGGCGGGAGCTCCTGCAGGTTTACCTCGCATA<br>GACGGGTCAGGGCGCGGGCTAGATCCAGGTGATACCTAATTTCCAGGGGC<br>TGGTTGGTGGCGGCGTCGATGGCTTGCAAGAGGCCGCATCCCCGCGGCG<br>CGACTACGGTACCGCGCGGCGGGCGGTGGGCCGCGGGGGTGTCCTTGGA<br>TGATGCATCTAAAAGCGGTGACGCGGGCGAGCCCCCGGAGGTAGGGGGG<br>GCTCCGGACCCGCCGGGAGAGGGGGCAGGGGCACGTCGGCGCCGCGCG<br>CGGGCAGGAGCTGGTGCTGCGCGCGTAGGTTGCTGGCGAACGCGACGAC<br>GCGGCGGTTGATCTCCTGAATCTGGCGCCTCTGCGTGAAGACGACGGGCC<br>CGGTGAGCTTGAGCCTGAAAGAGAGTTCGACAGAATCAATTTCGGTGTCGT<br>TGACGGCGGCCTGGCGCAAAATCTCCTGCACGTCTCCTGAGTTGTCTTGAT<br>AGGCGATCTCGGCCATGAACTGCTCGATCTCTTCCTCCTGGAGATCTCCGC<br>GTCCGGCTCGCTCCACGGTGGCGGCGAGGTCGTTGGAAATGCGGGCCAT<br>GAGCTGCGAGAAGGCGTTGAGGCCTCCCTCGTTCCAGACGCGGCTGTAGA<br>CCACGCCCCCTTCGGCATCGCGGGCGCGCATGACCACCTGCGCGAGATT<br>GAGCTCCACGTGCCGGGCGAAGACGGCGTAGTTTCGCAGGCGCTGAAAG<br>AGGTAGTTGAGGGTGGTGGCGGTGTGTTCTGCCACGAAGAAGTACATAAC<br>CCAGCGTCGCAACGTGGATTCGTTGATATCCCCCAAGGCCTCAAGGCGCT<br>CCATGGCCTCGTAGAAGTCCACGGCGAAGTTGAAAAACTGGGAGTTGCGC<br>GCCGACACGGTTAACTCCTCCTCCAGAAGACGGATGAGCTCGGCGACAGT<br>GTCGCGCACCTCGCGCTCAAAGGCTACAGGGGCCTCTTCTTCTTCTTCAAT<br>CTCCTCTTCCATAAGGGCCTCCCCTTCTTCTTCTTCTGGCGGCGGTGGGG<br>AGGGGGGACACGGCGGCGACGACGGCGCACCGGGAGGCGGTCGACAAA<br>GCGCTCGATCATCTCCCCGCGGCGACGGCGCATGGTCTCGGTGACGGCG<br>CGGCCGTTCTCGCGGGGGCGCAGTTGGAAGACGCCGCCCGTCATGTCCC<br>GGTTATGGGTTGGCGGGGGGCTGCCATGCGGCAGGGATACGGCGCTAAC<br>GATGCATCTCAACAATTGTTGTGTAGGTACTCCGCCGCCGAGGGACCTGAG<br>CGAGTCCGCATCGACCGGATCGGAAAACCTCTCGAGAAAGGCGTCTAACC<br>AGTCACAGTCGCAAGGTAGGCTGAGCACCGTGGCGGGCGGCAGCGGGCG<br>GCGGTCGGGGTTGTTTCTGGCGGAGGTGCTGCTGATGATGTAATTAAAGTA<br>GGCGGTCTTGAGACGGCGGATGGTCGACAGAAGCACCATGTCCTTGGGTC<br>CGGCCTGCTGAATGCGCAGGCGGTCGGCCATGCCCCAGGCTTCGTTTTGA<br>CATCGGCGCAGGTCTTTGTAGTAGTCTTGCATGAGCCTTTCTACCGGCACT<br>TCTTCTTCTCCTTCCTCTTGTCCTGCATCTCTTGCATCTATCGCTGCGGCGG<br>CGGCGGAGTTTGGCCGTAGGTGGCGCCCTCTTCCTCCCATGCGTGTGACC<br>CCGAAGCCCCTCATCGGCTGAAGCAGGGCTAGGTCGGCGACAACGCGCT<br>CGGCTAATATGGCCTGCTGCACCTGCGTGAGGGTAGACTGGAAGTCATCC<br>ATGTCCACAAAGCGGTGGTATGCGCCCGTGTTGATGGTGTAAGTGCAGTTG<br>GCCATAACGGACCAGTTAACGGTCTGGTGACCCGGCTGCGAGAGCTCGGT<br>GTACCTGAGACGCGAGTAAGCCCTCGAGTCAAATACGTAGTCGTTGCAAGT |

-continued

Sequences

| SEQ ID NO: | DESCRIPTION | SEQUENCE |
|---|---|---|
| | | CCGCACCAGGTACTGGTATCCCACCAAAAAGTGCGGCGGCGGCTGGCGGT<br>AGAGGGGCCAGCGTAGGGTGGCCGGGGCTCCGGGGGCGAGATCTTCCAA<br>CATAAGGCGATGATATCCGTAGATGTACCTGGACATCCAGGTGATGCCGGC<br>GGCGGTGGTGGAGGCGCGCGGAAAGTCGCGGACGCGGTTCCAGATGTTG<br>CGCAGCGGCAAAAAGTGCTCCATGGTCGGGACGCTCTGGCCGGTCAGGC<br>GCGCGCAATCGTTGACGCTCTACCGTGCAAAAGGAGAGCCTGTAAGCGGG<br>CACTCTTCCGTGGTCTGGTGGATAAATTCGCAAGGGTATCATGGCGGACGA<br>CCGGGGTTCGAGCCCCGTATCCGGCCGTCCGCCGTGATCCATGCGGTTAC<br>CGCCCGCGTGTCGAACCCAGGTGTGCGACGTCAGACAACGGGGGAGTGC<br>TCCTTTTGGCTTCCTTCCAGGCGCGGCGGCTGCTGCGCTAGCTTTTTTGGC<br>CACTGGCCGCGCGCAGCGTAAGCGGTTAGGCTGGAAAGCGAAAGCATTAA<br>GTGGCTCGCTCCCTGTAGCCGGAGGGTTATTTTCCAAGGGTTGAGTCGCG<br>GGACCCCCGGTTCGAGTCTCGGACCGGCCGGACTGCGGCGAACGGGGGT<br>TTGCCTCCCCGTCATGCAAGACCCCGCTTGCAAATTCCTCCGGAAACAGGG<br>ACGAGCCCCTTTTTTGCTTTTCCCAGATGCATCCGGTGCTGCGGCAGATGC<br>GCCCCCCTCCTCAGCAGCGGCAAGAGCAAGAGCAGCGGCAGACATGCAG<br>GGCACCCTCCCCTCCTCCTACCGCGTCAGGAGGGGCGACATCCGCGGTTG<br>ACGCGGCAGCAGATGGTGATTACGAACCCCCGCGGCGCCGGGCCCGGCA<br>CTACCTGGACTTGGAGGAGGGCGAGGGCCTGGCGCGGCTAGGAGCGCCC<br>TCTCCTGAGCGGTACCCAAGGGTGCAGCTGAAGCGTGATACGCGTGAGGC<br>GTACGTGCCGCGGCAGAACCTGTTTCGCGACCGCGAGGGAGAGGAGCCC<br>GAGGAGATGCGGGATCGAAAGTTCCACGCAGGGCGCGAGCTGCGGCATG<br>GCCTGAATCGCGAGCGGTTGCTGCGCGAGGAGGACTTTGAGCCCGACGC<br>GCGAACCGGGATTAGTCCCGCGCGCGCACACGTGGCGGCCGCCGACCTG<br>GTAACCGCATACGAGCAGACGGTGAACCAGGAGATTAACTTTCAAAAAAGC<br>TTTAACAACCACGTGCGTACGCTTGTGGCGCGCGAGGAGGTGGCTATAGG<br>ACTGATGCATCTGTGGGACTTTGTAAGCGCGCTGGAGCAAAACCCAAATAG<br>CAAGCCGCTCATGGCGCAGCTGTTCCTTATAGTGCAGCACAGCAGGGACA<br>ACGAGGCATTCAGGGATGCGCTGCTAAACATAGTAGAGCCCGAGGGCCGC<br>TGGCTGCTCGATTTGATAAACATCCTGCAGAGCATAGTGGTGCAGGAGCGC<br>AGCTTGAGCCTGGCTGACAAGGTGGCCGCCATCAACTATTCCATGCTTAGC<br>CTGGGCAAGTTTTACGCCCGCAAGATATACCATACCCCTTACGTTCCCATA<br>GACAAGGAGGTAAAGATCGAGGGGTTCTACATGCGCATGGCGCTGAAGGT<br>GCTTACCTTGAGCGACGACCTGGGCGTTTATCGCAACGAGCGCATCCACA<br>AGGCCGTGAGCGTGAGCCGGCGGCGCGAGCTCAGCGACCGCGAGCTGAT<br>GCACAGCCTGCAAAGGGCCCTGGCTGGCACGGGCAGCGGCGATAGAGAG<br>GCCGAGTCCTACTTTGACGCGGGCGCTGACCTGCGCTGGGCCCCAAGCC<br>GACGCGCCCTGGAGGCAGCTGGGGCCGGACCTGGGCTGGCGGTGGCAC<br>CCGCGCGCGCTGGCAACGTCGGCGGCGTGGAGGAATATGACGAGGACGA<br>TGAGTACGAGCCAGAGGACGGCGAGTACTAAGCGGTGATGTTTCTGATCA<br>GATGATGCAAGACGCAACGGACCCGGCGGTGCGGGCGGCGCTGCAGAGC<br>CAGCCGTCCGGCCTTAACTCCACGGACGACTGGCGCCAGGTCATGGACCG<br>CATCATGTCGCTGACTGCGCGCAATCCTGACGCGTTCCGGCAGCAGCCGC<br>AGGCCAACCGGCTCTCCGCAATTCTGGAAGCGGTGGTCCCGGCGCGCGC<br>AAACCCCACGCACGAGAAGGTGCTGGCGATCGTAAACGCGCTGGCCGAAA<br>ACAGGGCCATCCGGCCCGACGAGGCCGGCCTGGTCTACGACGCGCTGCT<br>TCAGCGCGTGGCTCGTTACAACAGCGGCAACGTGCAGACCAACCTGGACC<br>GGCTGGTGGGGGATGTGCGCGAGGCCGTGGCGCAGCGTGAGCGCGCGC<br>AGCAGCAGGGCAACCTGGGCTCCATGGTTGCACTAAACGCCTTCCTGAGT<br>ACACAGCCCGCCAACGTGCCGCGGGGACAGGAGGACTACACCAACTTTGT<br>GAGCGCACTGCGGCTAATGGTGACTGAGACACCGCAAAGTGAGGTGTACC<br>AGTCTGGGCCAGACTATTTTTTCCAGACCAGTAGACAAGGCCTGCAGACCG<br>TAAACCTGAGCCAGGCTTTCAAAAACTTGCAGGGGCTGTGGGGGGTGCGG<br>GCTCCCACAGGCGACCGCGCGACCGTGTCTAGCTTGCTGACGCCCAACTC<br>GCGCCTGTTGCTGCTGCTAATAGCGCCCTTCACGGACAGTGGCAGCGTGT<br>CCCGGGACACATACCTAGGTCACTTGCTGACACTGTACCGCGAGGCCATA<br>GGTCAGGCGCATGTGGACGAGCATACTTTCCAGGAGATTACAAGTGTCAG<br>CCGCGCGCTGGGGCAGGAGGACACGGGCAGCCTGGAGGCAACCCTAAAC<br>TACCTGCTGACCAACCGGCGGCAGAAGATCCCCTCGTTGCACAGTTTAAAC<br>AGCGAGGAGGAGCGCATTTTGCGCTACGTGCAGCAGAGCGTGAGCCTTAA<br>CCTGATGCGCGACGGGGTAACGCCCAGCGTGGCGCTGGACATGACCGCG<br>CGCAACATGGAACCGGGCATGTATGCCTCAAACCGGCCGTTTATCAACCG<br>CCTAATGGACTACTTGCATCGCGCGGCCGCCGTGAACCCCGAGTATTTCAC<br>CAATGCCATCTTGAACCCGCACTGGCTACCGCCCCCTGGTTTCTACACCGG<br>GGGATTCGAGGTGCCCGAGGGTAACGATGGATTCCTCTGGGACGACATAG<br>ACGACAGCGTGTTTTCCCCGCAACCGCAGACCCTGCTAGAGTTGCAACAG<br>CGCGAGCAGGCAGAGGCGGCGCTGCGAAAGGAAAGCTTCCGCAGGCCAA<br>GCAGCTTGTCCGATCTAGGCGCTGCGGCCCCGCGGTCAGATGCTAGTAGC<br>CCATTTCCAAGCTTGATAGGGTCTCTTACCAGCACTCGCACCACCCGCCCG<br>CGCCTGCTGGGCGAGGAGGAGTACCTAAACAACTCGCTGCTGCAGCCGCA<br>GCGCGAAAAAAACCTGCCTCCGGCATTTCCCAACAACGGGATAGAGAGCC<br>TAGTGGACAAGATGAGTAGATGGAAGACGTACGCGCAGGAGCACAGGGAC<br>GTGCCAGGCCCGCGCCCGCCCACCCGTCGTCAAAGGCACGACCGTCAGC<br>GGGGTCTGGTGTGGGAGGACGATGACTCGGCAGACGACAGCAGCGTCCT |

-continued

Sequences

| SEQ ID NO: | DESCRIPTION | SEQUENCE |
|---|---|---|
| | | GGATTTGGGAGGGAGTGGCAACCCGTTTGCGCACCTTCGCCCCAGGCTGG |
| | | GGAGAATGTTTTAAAAAAAAAAAAAGCATGATGCAAAATAAAAAACTCACCAA |
| | | GGCCATGGCACCGAGCGTTGGTTTTCTTGTATTCCCCTTAGTATGCGGCGC |
| | | GCGGCGATGTATGAGGAAGGTCCTCCTCCCTCCTACGAGAGTGTGGTGAG |
| | | CGCGGCGCCAGTGGCGGCGGCGCTGGGTTCTCCCTTCGATGCTCCCCTG |
| | | GACCCGCCGTTTGTGCCTCCGCGGTACCTGCGGCCTACCGGGGGGAGAA |
| | | ACAGCATCCGTTACTCTGAGTTGGCACCCCTATTCGACACCACCCGTGTGT |
| | | ACCTGGTGGACAACAAGTCAACGGATGTGGCATCCCTGAACTACCAGAAC |
| | | GACCACAGCAACTTTCTGACCACGGTCATTCAAAACAATGACTACAGCCCG |
| | | GGGGAGGCAAGCACACAGACCATCAATCTTGACGACCGGTCGCACTGGGG |
| | | CGGCGACCTGAAAACCATCCTGCATACCAACATGCCAAATGTGAACGAGTT |
| | | CATGTTTACCAATAAGTTTAAGGCGCGGGTGATGGTGTCGCGCTTGCCTAC |
| | | TAAGGACAATCAGGTGGAGCTGAAATACGAGTGGGTGGAGTTCACGCTGC |
| | | CCGAGGGCAACTACTCCGAGACCATGACCATAGACCTTATGAACAACGCGA |
| | | TCGTGGAGCACTACTTGAAAGTGGGCAGACAGAACGGGGTTCTGGAAAGC |
| | | GACATCGGGGTAAAGTTTGACACCCGCAACTTCAGACTGGGGTTTGACCCC |
| | | GTCACTGGTCTTGTCATGCCTGGGGTATATACAAACGAAGCCTTCCATCCA |
| | | GACATCATTTTGCTGCCAGGATGCGGGGTGGACTTCACCCACAGCCGCCT |
| | | GAGCAACTTGTTGGGCATCCGCAAGCGGCAACCCTTCCAGGAGGGCTTTA |
| | | GGATCACCTACGATGATCTGGAGGGTGGTAACATTCCCGCACTGTTGGATG |
| | | TGGACGCCTACCAGGCGAGCTTGAAAGATGACACCGAACAGGGCGGGGG |
| | | TGGCGCAGGCGGCAGCAACAGCAGTGGCAGCGGCGCGGAAGAGAACTCC |
| | | AACGCGGCAGCCGCGGCAATGCAGCCGGTGGAGGACATGAACGATCATG |
| | | CCATTCGCGGCGACACCTTTGCCACACGGGCTGAGGAGAAGCGCGCTGAG |
| | | GCCGAAGCAGCGGCCGAAGCTGCCGCCCCCGCTGCGCAACCCGAGGTCG |
| | | AGAAGCCTCAGAAGAAACCGGTGATCAAACCCCTGACAGAGGACAGCAAG |
| | | AAACGCAGTTACAACCTAATAAGCAATGACAGCACCTTCACCCAGTACCGC |
| | | AGCTGGTACCTTGCATACAACTACGGCGACCCTCAGACCGGAATCCGCTCA |
| | | TGGACCCTGCTTTGCACTCCTGACGTAACCTGCGGCTCGGAGCAGGTCTA |
| | | CTGGTCGTTGCCAGACATGATGCAAGACCCCGTGACCTTCCGCTCCACGC |
| | | GCCAGATCAGCAACTTTCCGGTGGTGGGCGCCGAGCTGTTGCCCGTGCAC |
| | | TCCAAGAGCTTCTACAACGACCAGGCCGTCTACTCCCAACTCATCCGCCAG |
| | | TTTACCTCTCTGACCCACGTGTTCAATCGCTTTCCCGAGAACCAGATTTTGG |
| | | CGCGCCCGCCAGCCCCCACCATCACCACCGTCAGTGAAAACGTTCCTGCT |
| | | CTCACAGATCACGGGACGCTACCGCTGCGCAACAGCATCGGAGGAGTCCA |
| | | GCGAGTGACCATTACTGACGCCAGACGCCGCACCTGCCCCTACGTTTACA |
| | | AGGCCCTGGGCATAGTCTCGCCGCGCGTCCTATCGAGCCGCACTTTTTGA |
| | | GCAAGCATGTCCATCCTTATATCGCCCAGCAATAACACAGGCTGGGGCCTG |
| | | CGCTTCCCAAGCAAGATGTTTGGCGGGGCCAAGAAGCGCTCCGACCAACA |
| | | CCCAGTGCGCGTGCGCGGGCACTACCGCGCGCCCTGGGGCGCGCACAAA |
| | | CGCGGCCGCACTGGGCGCACCACCGTCGATGACGCCATCGACGCGGTGG |
| | | TGGAGGAGGCGCGCAACTACACGCCCACGCCGCCACCAGTGTCCACAGT |
| | | GGACGCGGCCATTCAGACCGTGGTGCGCGGAGCCCGGCGCTATGCTAAA |
| | | ATGAAGAGACGGCGGAGGCGCGTAGCACGTCGCCACCGCCGCCGACCCG |
| | | GCACTGCCGCCCAACGCGCGGCGGCGGCCCTGCTTAACCGCGCACGTCG |
| | | CACCGGCCGACGGGCGGCCATGCGGGCCGCTCGAAGGCTGGCCGCGGG |
| | | TATTGTCACTGTGCCCCCCAGGTCCAGGCGACGAGCGGCCGCCGCAGCA |
| | | GCCGCGGCCATTAGTGCTATGACTCAGGGTCGCAGGGGCAACGTGTATTG |
| | | GGTGCGCGACTCGGTTAGCGGCCTGCGCGTGCCCGTGCGCACCCGCCCC |
| | | CCGCGCAACTAGATTGCAAGAAAAAACTACTTAGACTCGTACTGTTGTATGT |
| | | ATCCAGCGGCGGCGGCGCGCAACGAAGCTATGTCCAAGCGCAAAATCAAA |
| | | GAAGAGATGCTCCAGGTCATCGCGCCGGAGATCTATGGCCCCCCGAAGAA |
| | | GGAAGAGCAGGATTACAAGCCCCGAAAGCTAAAGCGGGTCAAAAAGAAAA |
| | | AGAAAGATGATGATGATGAACTTGACGACGAGGTGGAACTGCTGCACGCTA |
| | | CCGCGCCCAGGCGACGGGTACAGTGGAAAGGTCGACGCGTAAAACGTGTT |
| | | TTGCGACCCGGCACCACCGTAGTCTTTACGCCCGGTGAGCGCTCCACCCG |
| | | CACCTACAAGCGCGTGTATGATGAGGTGTACGGCGACGAGGACCTGCTTG |
| | | AGCAGGCCAACGAGCGCCTCGGGGAGTTTGCCTACGGAAAGCGGCATAAG |
| | | GACATGCTGGCGTTGCCGCTGGACGAGGGCAACCCAACACCTAGCCTAAA |
| | | GCCCGTAACACTGCAGCAGGTGCTGCCCGCGCTTGCACCGTCCGAAGAAA |
| | | AGCGCGGCCTAAAGCGCGAGTCTGGTGACTTGGCACCCACCGTGCAGCTG |
| | | ATGGTACCCAAGCGCCAGCGACTGGAAGATGTCTTGGAAAAAATGACCGT |
| | | GGAACCTGGGCTGGAGCCCGAGGTCCGCGTGCGGCCAATCAAGCAGGTG |
| | | GCGCCGGGACTGGGCGTGCAGACCGTGGACGTTCAGATACCCACTACCAG |
| | | TAGCACCAGTATTGCCACCGCCACAGAGGGCATGGAGACACAAACGTCCC |
| | | CGGTTGCCTCAGCGGTGGCGGATGCCGCGGTGCAGGCGGTCGCTGCGGC |
| | | CGCGTCCAAGACCTCTACGGAGGTGCAAACGGACCCGTGGATGTTTCGCG |
| | | TTTCAGCCCCCCGGCGCCCGCGCGGTTCGAGGAAGTACGGCGCCGCCAG |
| | | CGCGCTACTGCCCGAATATGCCCTACATCCTTCCATTGCGCCTACCCCCGG |
| | | CTATCGTGGCTACACCTACCGCCCCAGAAGACGAGCAACTACCCGACGCC |
| | | GAACCACCACTGGAACCCGCCGCCGCCGTCGCCGTCGCCAGCCCGTGCT |
| | | GGCCCCGATTTCCGTGCGCAGGGTGGCTCGCGAAGGAGGCAGGACCCTG |
| | | GTGCTGCCAACAGCGCGCTACCACCCCAGCATCGTTTAAAAGCCGGTCTTT |
| | | GTGGTTCTTGCAGATATGGCCCTCACCTGCCGCCTCCGTTTCCCGGTGCC |

-continued

Sequences

| SEQ ID NO: | DESCRIPTION | SEQUENCE |
|---|---|---|
| | | GGGATTCCGAGGAAGAATGCACCGTAGGAGGGGCATGGCCGGCCACGGC |
| | | CTGACGGGCGGCATGCGTCGTGCGCACCACCGGCGGCGGCGCGCGTCG |
| | | CACCGTCGCATGCGCGGCGGTATCCTGCCCCTCCTTATTCCACTGATCGC |
| | | CGCGGCGATTGGCGCCGTGCCCGGAATTGCATCCGTGGCCTTGCAGGCG |
| | | CAGAGACACTGATTAAAAACAAGTTGCATGTGGAAAAATCAAAATAAAAAGT |
| | | CTGGACTCTCACGCTCGCTTGGTCCTGTAACTATTTTGTAGAATGGAAGAC |
| | | ATCAACTTTGCGTCTCTGGCCCCGCGACACGGCTCGCGCCCGTTCATGGG |
| | | AAACTGGCAAGATATCGGCACCAGCAATATGAGCGGTGGCGCCTTCAGCT |
| | | GGGGCTCGCTGTGGAGCGGCATTAAAAATTTCGGTTCCACCGTTAAGAACT |
| | | ATGGCAGCAAGGCCTGGAACAGCAGCACAGGCCAGATGCTGAGGGATAAG |
| | | TTGAAAGAGCAAAATTTCCAACAAAAGGTGGTAGATGGCCTGGCCTCTGGC |
| | | ATTAGCGGGGTGGTGGACCTGGCCAACCAGGCAGTGCAAAATAAGATTAA |
| | | CAGTAAGCTTGATCCCCGCCCTCCCGTAGAGGAGCCTCCACCGGCCGTGG |
| | | AGACAGTGTCTCCAGAGGGGCGTGGCGAAAAGCGTCCGCGCCCCGACAG |
| | | GGAAGAAACTCTGGTGACGCAAATAGACGAGCCTCCCTCGTACGAGGAGG |
| | | CACTAAAGCAAGGCCTGCCCACCACCCGTCCCATCGCGCCCATGGCTACC |
| | | GGAGTGCTGGGCCAGCACACACCCGTAACGCTGGACCTGCCTCCCCCCG |
| | | CCGACACCCAGCAGAAACCTGTGCTGCCAGGCCCGACCGCCGTTGTTGTA |
| | | ACCCGTCCTAGCCGCGCGTCCCTGCGCCGCGCCGCCAGCGGTCCGCGAT |
| | | CGTTGCGGCCCGTAGCCAGTGGCAACTGGCAAAGCACACTGAACAGCATC |
| | | GTGGGTCTGGGGGTGCAATCCCTGAAGCGCCGACGATGCTTCTGAATAGC |
| | | TAACGTGTCGTATGTGTGTCATGTATGCGTCCATGTCGCCGCCAGAGGAGC |
| | | TGCTGAGCCGCCGCGCGCCCGCTTTCCAGATGGCTACCCCTTCGATGAT |
| | | GCCGCAGTGGTCTTACATGCACATCTCGGGCCAGGACGCCTCGGAGTACC |
| | | TGAGCCCCGGGCTGGTGCAGTTTGCCCGCGCCACCGAGACGTACTTCAGC |
| | | CTGAATAACAAGTTTAGAAACCCCACGGTGGCGCCTACGCACGACGTGAC |
| | | CACAGACCGGTCCCAGCGTTTGACGCTGCGGTTCATCCCTGTGGACCGTG |
| | | AGGATACTGCGTACTCGTACAAGGCGCGGTTCACCCTAGCTGTGGGTGAT |
| | | AACCGTGTGCTGGACATGGCTTCCACGTACTTTGACATCCGCGGCGTGCT |
| | | GGACAGGGGCCCTACTTTTAAGCCCTACTCTGGCACTGCCTACAACGCCCT |
| | | GGCTCCCAAGGGTGCCCCAAATCCTTGCGAATGGGATGAAGCTGCTACTG |
| | | CTCTTGAAATAAACCTAGAAGAAGAGGACGATGACAACGAAGACGAAGTAG |
| | | ACGAGCAAGCTGAGCAGCAAAAAACTCACGTATTTGGGCAGGCGCCTTATT |
| | | CTGGTATAAATATTACAAAGGAGGGTATTCAAATAGGTGTCGAAGGTCAAAC |
| | | ACCTAAATATGCCGATAAAACATTTCAACCTGAACCTCAAATAGGAGAATCT |
| | | CAGTGGTACGAAACTGAAATTAATCATGCAGCTGGGAGAGTCCTTAAAAAG |
| | | ACTACCCCAATGAAACCATGTTACGGTTCATATGCAAAACCCACAAATGAAA |
| | | ATGGAGGGCAAGGCATTCTTGTAAAGCAACAAAATGGAAAGCTAGAAAGTC |
| | | AAGTGGAAATGCAATTTTTCTCAACTACTGAGGCGACCGCAGGCAATGGTG |
| | | ATAACTTGACTCCTAAAGTGGTATTGTACAGTGAAGATGTAGATATAGAAAC |
| | | CCCAGACACTCATATTTCTTACATGCCCACTATTAAGGAAGGTAACTCACGA |
| | | GAACTAATGGGCCAACAATCTATGCCCAACAGGCCTAATTACATTGCTTTTA |
| | | GGGACAATTTTATTGGTCTAATGTATTACAACAGCACGGGTAATATGGGTGT |
| | | TCTGGCGGGCCAAGCATCGCAGTTGAATGCTGTTGTAGATTTGCAAGACAG |
| | | AAACACAGAGCTTTCATACCAGCTTTTGCTTGATTCCATTGGTGATAGAACC |
| | | AGGTACTTTTCTATGTGGAATCAGGCTGTTGACAGCTATGATCCAGATGTTA |
| | | GAATTATTGAAAATCATGGAACTGAAGATGAACTTCCAAATTACTGCTTTCC |
| | | ACTGGGAGGTGTGATTAATACAGAGACTCTTACCAAGGTAAAACCTAAAAC |
| | | AGGTCAGGAAAATGGATGGGAAAAAGATGCTACAGAATTTTCAGATAAAAAT |
| | | GAAATAAGAGTTGGAAATAATTTTGCCATGGAAATCAATCTAAATGCCAACC |
| | | TGTGGAGAAATTTCCTGTACTCCAACATAGCGCTGTATTTGCCCGACAAGC |
| | | TAAAGTACAGTCCTTCCAACGTAAAAATTTCTGATAACCCAAACACCTACGA |
| | | CTACATGAACAAGCGAGTGGTGGCTCCCGGGTTAGTGGACTGCTACATTAA |
| | | CCTTGGAGCACGCTGGTCCCTTGACTATATGGACAACGTCAACCCATTTAA |
| | | CCACCACCGCAATGCTGGCCTGCGCTACCGCTCAATGTTGCTGGGCAATG |
| | | GTCGCTATGTGCCCTTCCACATCCAGGTGCCTCAGAAGTTCUTGCCATTA |
| | | AAAACCTCCTTCTCCTGCCGGGCTCATACACCTACGAGTGGAACTTCAGGA |
| | | AGGATGTTAACATGGTTCTGCAGAGCTCCCTAGGAAATGACCTAACGGTTG |
| | | ACGGAGCCAGCATTAAGTTTGATAGCATTTGCCTTTACGCCACCTTCTTCCC |
| | | CATGGCCCACAACACCGCCTCCACGCTTGAGGCCATGCTTAGAAACGACA |
| | | CCAACGACCAGTCCTTTAACGACTATCTCTCCGCCGCCAACATGCTCTACC |
| | | CTATACCCGCCAACGCTACCAACGTGCCCATATCCATCCCCTCCCGCAACT |
| | | GGGCGGCTTTCCGCGGCTGGGCCTTCACGCGCCTTAAGACTAAGGAAACC |
| | | CCATCACTGGGCTCGGGCTACGACCCTTATTACACCTACTCTGGCTCTATA |
| | | CCCTACCTAGATGGAACCTTTTACCTCAACCACACCTTTAAGAAGGTGGCC |
| | | ATTACCTTTGACTCTTCTGTCAGCTGGCCTGGCAATGACCGCCTGCTTACC |
| | | CCCAACGAGTTTGAAATTAAGCGCTCAGTTGACGGGGAGGGTTACAACGTT |
| | | GCCCAGTGTAACATGACCAAAGACTGGTTCCTGGTACAAATGCTAGCTAAC |
| | | TACAACATTGGCTACCAGGGCTTCTATATCCCAGAGAGCTACAAGGACCGC |
| | | ATGTACTCCTTCTTTAGAAACTTCCAGCCCATGAGCCGTCAGGTGGTGGAT |
| | | GATACTAAATACAAGGACTACCAACAGGTGGGCATCCTACACCAACACAAC |
| | | AACTCTGGATTTGTTGGCTACCTTGCCCCCACCATGCGCGAAGGACAGGC |
| | | CTACCCTGCTAACTTCCCCTATCCGCTTATAGGCAAGACCGCAGTTGACAG |
| | | CATTACCCAGAAAAAGTTTCTTTGCGATCGCACCCTTTGGCGCATCCCATTC |

-continued

Sequences

| SEQ ID NO: | DESCRIPTION | SEQUENCE |
|---|---|---|
| | | TCCAGTAACTTTATGTCCATGGGCGCACTCACAGACCTGGGCCAAAACCTT<br>CTCTACGCCAACTCCGCCCACGCGCTAGACATGACTTTTGAGGTGGATCCC<br>ATGGACGAGCCCACCCTTCTTTATGTTTTGTTTGAAGTCTTTGACGTGGTCC<br>GTGTGCACCGGCCGCACCGCGGCGTCATCGAAACCGTGTACCTGCGCAC<br>GCCCTTCTCGGCCGGCAACGCCACAACATAAAGAAGCAAGCAACATCAACA<br>ACAGCTGCCGCCATGGGCTCCAGTGAGCAGGAACTGAAAGCCATTGTCAA<br>AGATCTTGGTTGTGGGCCATATTTTTTGGGCACCTATGACAAGCGCTTTCCA<br>GGCTTTGTTTCTCCACACAAGCTCGCCTGCGCCATAGTCAATACGGCCGGT<br>CGCGAGACTGGGGGCGTACACTGGATGGCCTTTGCCTGGAACCCGCACTC<br>AAAAACATGCTACCTCTTTGAGCCCTTTGGCTTTTCTGACCAGCGACTCAAG<br>CAGGTTTACCAGTTTGAGTACGAGTCACTCCTGCGCCGTAGCGCCATTGCT<br>TCTTCCCCCGACCGCTGTATAACGCTGGAAAAGTCCACCCAAAGCGTACAG<br>GGGCCCAACTCGGCCGCCTGTGGACTATTCTGCTGCATGTTTCTCCACGC<br>CTTTGCCAACTGGCCCCAAACTCCCATGGATCACAACCCCACCATGAACCT<br>TATTACCGGGGTACCCAACTCCATGCTCAACAGTCCCCAGGTACAGCCCAC<br>CCTGCGTCGCAACCAGGAACAGCTCTACAGCTTCCTGGAGCGCCACTCGC<br>CCTACTTCCGCAGCCACAGTGCGCAGATTAGGAGCGCCACTTCTTTTTGTC<br>ACTTGAAAAACATGTAAAAATAATGTACTAGAGACACTTTCAATAAAGGCAA<br>ATGCTTTTATTTGTACACTCTCGGGTGATTATTTACCCCCACCCTTGCCGTC<br>TGCGCCGTTTAAAAATCAAAGGGGTTCTGCCGCGCATCGCTATGCGCCACT<br>GGCAGGGACACGTTGCGATACTGGTGTTTAGTGCTCCACTTAAACTCAGGC<br>ACAACCATCCGCGGCAGCTCGGTGAAGTTTTCACTCCACAGGCTGCGCAC<br>CATCACCAACGCGTTTAGCAGGTCGGGCGCCGATATCTTGAAGTCGCAGTT<br>GGGGCCTCCGCCCTGCGCGCGCGAGTTGCGATACACAGGGTTGCAGCAC<br>TGGAACACTATCAGCGCCGGGTGGTGCACGCTGGCCAGCACGCTCTTGTC<br>GGAGATCAGATCCGCGTCCAGGTCCTCCGCGTTGCTCAGGGCGAACGGAG<br>TCAACTTTGGTAGCTGCCTTCCCAAAAAGGGCGCGTGCCCAGGCTTTGAGT<br>TGCACTCGCACCGTAGTGGCATCAAAAGGTGACCGTGCCCGGTCTGGGCG<br>TTAGGATACAGCGCCTGCATAAAAGCCTTGATCTGCTTAAAAGCCACCTGA<br>GCCTTTGCGCCTTCAGAGAAGAACATGCCGCAAGACTTGCCGGAAAACTGA<br>TTGGCCGGACAGGCCGCGTCGTGCACGCAGCACCTTGCGTCGGTGTTGGA<br>GATCTGCACCACATTTCGGCCCCACCGGTTCTTCACGATCTTGGCCTTGCT<br>AGACTGCTCCTTCAGCGCGCGCTGCCCGTTTTCGCTCGTCACATCCATTTC<br>AATCACGTGCTCCTTATTTATCATAATGCTTCCGTGTAGACACTTAAGCTCG<br>CCTTCGATCTCAGCGCAGCGGTGCAGCCACAACGCGCAGCCCGTGGGCTC<br>GTGATGCTTGTAGGTCACCTCTGCAAACGACTGCAGGTACGCCTGCAGGA<br>ATCGCCCCATCATCGTCACAAAGGTCTTGTTGCTGGTGAAGGTCAGCTGCA<br>ACCCGCGGTGCTCCTCGTTCAGCCAGGTCTTGCATACGGCCGCCAGAGCT<br>TCCACTTGGTCAGGCAGTAGTTTGAAGTTCGCCTTTAGATCGTTATCCACGT<br>GGTACTTGTCCATCAGCGCGCGCGCAGCCTCCATGCCCTTCTCCCACGCA<br>GACACGATCGGCACACTCAGCGGGTTCATCACCGTAATTTCACTTTCCGCT<br>TCGCTGGGCTCTTCCTCTTCCTCTTGCGTCCGCATACCACGCGCCACTGGG<br>TCGTCTTCATTCAGCCGCCGCACTGTGCGCTTACCTCCTTTGCCATGCTTG<br>ATTAGCACCGGTGGGTTGCTGAAACCCACCATTTGTAGCGCCACATCTTCT<br>CTTTCTTCCTCGCTGTCCACGATTACCTCTGGTGATGGCGGGCGCTCGGGC<br>TTGGGAGAAGGGCGCTTCTTTTTCTTCTTGGGCGCAATGGCCAAATCCGCC<br>GCCGAGGTCGATGGCCGCGGGCTGGGTGTGCGCGGCACCAGCGCGTCTT<br>GTGATGAGTCTTCCTCGTCCTCGGACTCGATACGCCGCCTCATCCGCTTTT<br>TTGGGGGCGCCCGGGGAGGCGGCGGCGACGGGGACGGGGACGACACGT<br>CCTCCATGGTTGGGGGACGTCGCGCCGCACCGCGTCCGCGCTCGGGGGT<br>GGTTTCGCGCTGCTCCTCTTCCCGACTGGCCATTTCCTTCTCCTATAGGCA<br>GAAAAAGATCATGGAGTCAGTCGAGAAGAAGGACAGCCTAACCGCCCCCT<br>CTGAGTTCGCCACCACCGCCTCCACCGATGCCGCCAACGCGCCTACCACC<br>TTCCCCGTCGAGGCACCCCCGCTTGAGGAGGAGGAAGTGATTATCGAGCA<br>GGACCCAGGTTTTGTAAGCGAAGACGACGAGGACCGCTCAGTACCAACAG<br>AGGATAAAAAGCAAGACCAGGACAACGCAGAGGCAAACGAGGAACAAGTC<br>GGGCGGGGGGACGAAAGGCATGGCGACTACCTAGATGTGGGAGACGACG<br>TGCTGTTGAAGCATCTGCAGCGCCAGTGCGCCATTATCTGCGACGCGTTG<br>CAAGAGCGCAGCGATGTGCCCCTCGCCATAGCGGATGTCAGCCTTGCCTA<br>CGAACGCCACCTATTCTCACCGCGCGTACCCCCCAAACGCCAAGAAAACG<br>GCACATGCGAGCCCAACCCGCGCCTCAACTTCTACCCCGTATTTGCCGTG<br>CCAGAGGTGCTTGCCACCTATCACATCTTTTTCCAAAACTGCAAGATACCCC<br>TATCCTGCCGTGCCAACCGCAGCCGAGCGGACAAGCAGCTGGCCTTGCGG<br>CAGGGCGCTGTCATACCTGATATCGCCTCGCTCAACGAAGTGCCAAAAATC<br>TTTGAGGGTCTTGGACGCGACGAGAAGCGCGCGGCAAACGCTCTGCAACA<br>GGAAAACAGCGAAAATGAAAGTCACTCTGGAGTGTTGGTGGAACTCGAGG<br>GTGACAACGCGCGCCTAGCCGTACTAAAACGCAGCATCGAGGTCACCCAC<br>TTTGCCTACCCGGCACTTAACCTACCCCCCAAGGTCATGAGCACAGTCATG<br>AGTGAGCTGATCGTGCGCCGTGCGCAGCCCCTGGAGAGGGATGCAAATTT<br>GCAAGAACAAACAGAGGAGGGCCTACCCGCAGTTGGCGACGAGCAGCTAG<br>CGCGCTGGCTTCAAACGCGCGAGCCTGCCGACTTGGAGGAGCGACGCAA<br>ACTAATGATGGCCGCAGTGCTCGTTACCGTGGAGCTTGAGTGCATGCAGC<br>GGTTCTTTGCTGACCCGGAGATGCAGCGCAAGCTAGAGGAAACATTGCACT<br>ACACCTTTCGACAGGGCTACGTACGCCAGGCCTGCAAGATCTCCAACGTG |

-continued

Sequences

| SEQ ID NO: | DESCRIPTION | SEQUENCE |
|---|---|---|
| | | GAGCTCTGCAACCTGGTCTCCTACCTTGGAATTTTGCACGAAAACCGCCTT<br>GGGCAAAACGTGCTTCATTCCACGCTCAAGGGCGAGGCGCGCCGCGACTA<br>CGTCCGCGACTGCGTTTACTTATTTCTATGCTACACCTGGCAGACGGCCAT<br>GGGCGTTTGGCAGCAGTGCTTGGAGGAGTGCAACCTCAAGGAGCTGCAGA<br>AACTGCTAAAGCAAAACTTGAAGGACCTATGGACGGCCTTCAACGAGCGCT<br>CCGTGGCCGCGCACCTGGCGGACATCATTTTCCCCGAACGCCTGCTTAAA<br>ACCCTGCAACAGGGTCTGCCAGACTTCACCAGTCAAAGCATGTTGCAGAAC<br>TTTAGGAACTTTATCCTAGAGCGCTCAGGAATCTTGCCCGCCACCTGCTGT<br>GCACTTCCTAGCGACTTTGTGCCCATTAAGTACCGCGAATGCCCTCCGCCG<br>CTTTGGGGCCACTGCTACCTTCTGCAGCTAGCCAACTACCTTGCCTACCAC<br>TCTGACATAATGGAAGACGTGAGCGGTGACGGTCTACTGGAGTGTCACTGT<br>CGCTGCAACCTATGCACCCCGCACCGCTCCCTGGTTTGCAATTCGCAGCT<br>GCTTAACGAAAGTCAAATTATCGGTACCTTTGAGCTGCAGGGTCCCTCGCC<br>TGACGAAAAGTCCGCGGCTCCGGGGTTGAAACTCACTCCGGGGCTGTGGA<br>CGTCGGCTTACCTTCGCAAATTTGTACCTGAGGACTACCACGCCCACGAGA<br>TTAGGTTCTACGAAGACCAATCCCGCCCGCCAAATGCGGAGCTTACCGCCT<br>GCGTCATTACCCAGGGCCACATTCTTGGCCAATTGCAAGCCATCAACAAAG<br>CCCGCCAAGAGTTTCTGCTACGAAAGGGACGGGGGTTTACTTGGACCCC<br>CAGTCCGGCGAGGAGCTCAACCCAATCCCCCCGCCGCCGCAGCCCTATCA<br>GCAGCAGCCGCGGGCCCTTGCTTCCCAGGATGGCACCCAAAAAGAAGCTG<br>CAGCTGCCGCCGCCACCCACGGACGAGGAGGAATACTGGGACAGTCAGG<br>CAGAGGAGGTTTTGGACGAGGAGGAGGAGGACATGATGGAAGACTGGGA<br>GAGCCTAGACGAGGAAGCTTCCGAGGTCGAAGAGGTGTCAGACGAAACAC<br>CGTCACCCTCGGTCGCATTCCCCTCGCCGGCGCCCCAGAAATCGGCAACC<br>GGTTCCAGCATGGCTACAACCTCCGCTCCTCAGGCGCCGCCGGCACTGCC<br>CGTTCGCCGACCCAACCGTAGATGGGACACCACTGGAACCAGGGCCGGTA<br>AGTCCAAGCAGCCGCCGCCGTTAGCCCAAGAGCAACAACAGCGCCAAGGC<br>TACCGCTCATGGCGCGGGCACAAGAACGCCATAGTTGCTTGCTTGCAAGA<br>CTGTGGGGGCAACATCTCCTTCGCCCGCCGCTTTCTTCTCTACCATCACGG<br>CGTGGCCTTCCCCCGTAACATCCTGCATTACTACCGTCATCTCTACAGCCC<br>ATACTGCACCGGCGGCAGCGGCAGCGGCAGCAACAGCAGCGGCCACACA<br>GAAGCAAAGGCGACCGGATAGCAAGACTCTGACAAAGCCCAAGAAATCCA<br>CAGCGGCGGCAGCAGCAGGAGGAGGAGCGCTGCGTCTGGCGCCCAACGA<br>ACCCGTATCGACCCGCGAGCTTAGAAACAGGATTTTTCCCACTCTGTATGC<br>TATATTTCAACAGAGCAGGGGCCAAGAACAAGAGCTGAAAATAAAAAACAG<br>GTCTCTGCGATCCCTCACCCGCAGCTGCCTGTATCACAAAAGCGAAGATCA<br>GCTTCGGCGCACGCTGGAAGACGCGGAGGCTCTCTTCAGTAAATACTGCG<br>CGCTGACTCTTAAGGACTAGTTTCGCGCCCTTTCTCAAATTTAAGCGCGAAA<br>ACTACGTCATCTCCAGCGGCCACACCCGGCGCCAGCACCTGTCGTCAGCG<br>CCATTATGAGCAAGGAAATTCCCACGCCCTACATGTGGAGTTACCAGCCAC<br>AAATGGGACTTGCGGCTGGAGCTGCCCAAGACTACTCAACCCGAATAAACT<br>ACATGAGCGCGGGACCCCACATGATATCCCGGGTCAACGGAATCCGCGCC<br>CACCGAAACCGAATTCTCTTGGAACAGGCGGCTATTACCACCACACCTCGT<br>AATAACCTTAATCCCCGTAGTTGGCCCGCTGCCCTGGTGTACCAGGAAAGT<br>CCCGCTCCCACCACTGTGGTACTTCCCAGAGACGCCCAGGCCGAAGTTCA<br>GATGACTAACTCAGGGGCGCAGCTTGCGGGCGGCTTTCGTCACAGGGTGC<br>GGTCGCCCGGGCAGGGTATAACTCACCTGACAATCAGAGGGCGAGGTATT<br>CAGCTCAACGACGAGTCGGTGAGCTCCTCGCTTGGTCTCCGTCCGGACGG<br>GACATTTCAGATCGGCGGCGCCGGCCGCTCTTCATTCACGCCTCGTCAGG<br>CAATCCTAACTCTGCAGACCTCGTCCTCTGAGCCGCGCTCTGGAGGCATTG<br>GAACTCTGCAATTTATTGAGGAGTTTGTGCCATCGGTCTACTTTAACCCCTT<br>CTCGGGACCTCCCGGCCACTATCCGGATCAATTTATTCCTAACTTTGACGC<br>GGTAAAGGACTCGGCGGATGGCTACGACTGAATGTTAAGTGGAGAGGCAG<br>AGCAACTGCGCCTGAAACACCTGGTCCACTGTCGCCGCCACAAGTGCTTT<br>GCCCGCGACTCCGGTGAGTTTTGCTACTTTGAATTGCCCGAGGATCATATC<br>GAGGGCCCGGCGCACGGCGTCCGGCTTACCGCCCAGGGAGAGCTTGCCC<br>GTAGCCTGATTCGGGAGTTTACCCAGCGCCCCCTGCTAGTTGAGCGGGAC<br>AGGGGACCCTGTGTTCTCACTGTGATTTGCAACTGTCCTAACCCTGGATTA<br>CATCAAGATCTTTGTTGCCATCTCTGTGCTGAGTATAATAAATACAGAAATTA<br>AAATATACTGGGGCTCCTATCGCCATCCTGTAAACGCCACCGTCTTCACCC<br>GCCCAAGCAAACCAAGGCGAACCTTACCTGGTACTTTTAACATCTCTCCCT<br>CTGTGATTTACAACAGTTTCAACCCAGACGGAGTGAGTCTACGAGAGAACC<br>TCTCCGAGCTCAGCTACTCCATCAGAAAAAACACCACCCTCCTTACCTGCC<br>GGGAACGTACGACCTAGGGATAACAGGGTAATAAGCAATTGACTCTATGTG<br>GGATATGCTCCAGCGCTACAACCTTGAAGTCAGGCTTCCTGGATGTCAGCA<br>TCTGACTTTGGCCAGCACCTGTCCCGCGGATTTGTTCCAGTCCAACTACAG<br>CGACCCACCCTAACAGAGATGACCAACACAACCAACGCGGCCGCCGCTAC<br>CGGACTTACATCTACCACAAATACACCCCAAGTTTCTGCCTTTGTCAATAAC<br>TGGGATAACTTGGGCATGTGGTGGTTCTCCATAGCGCTTATGTTTGTATGC<br>CTTATTATTATGTGGCTCATCTGCTGCCTAAAGCGCAAACGCGCCCGACCA<br>CCCATCTATAGTCCCATCATTGTGCTACACCCAAACAATGATGGAATCCATA<br>GATTGGACGGACTGAAACACATGTTCTTTTCTCTTACAGTATGATTAAATGA<br>GACATGATTCCTCGAGTTTTTATATTACTGACCCTTGTTGCGCTTTTTTGTGC<br>GTGCTCCACATTGGCTGCGGTTTCTCACATCGAAGTAGACTGCATTCCAGC |

-continued

Sequences

| SEQ ID NO: | DESCRIPTION | SEQUENCE |
|---|---|---|

CTTCACAGTCTATTTGCTTTACGGATTTGTCACCCTCACGCTCATCTGCAGC
CTCATCACTGTGGTCATCGCCTTTATCCAGTGCATTGACTGGGTCTGTGTG
CGCTTTGCATATCTCAGACACCATCCCCAGTACAGGGACAGGACTATAGCT
GAGCTTCTTAGAATTCTTTAATTATGAAATTTACTGTGACTTTTCTGCTGATT
ATTTGCACCCTATCTGCGTTTTGTTCCCCGACCTCCAAGCCTCAAAGACATA
TATCATGCAGATTCACTCGTATATGGAATATTCCAAGTTGCTACAATGAAAA
AAGCGATCTTTCCGAAGCCTGGTTATATGCAATCATCTCTGTTATGGTGTTC
TGCAGTACCATCTTAGCCCTAGCTATATATCCCTACCTTGACATTGGCTGGA
AACGAATAGATGCCATGAACCACCCAACTTTCCCCGCGCCCGCTATGCTTC
CACTGCAACAAGTTGTTGCCGGCGGCTTTGTCCCAGCCAATCAGCCTCGC
CCCACTTCTCCCACCCCCACTGAAATCAGCTACTTTAATCTAACAGGAGGA
GATGACTGACACCCTAGATCTAGAAATGGACGGAATTATTACAGAGCAGCG
CCTGCTAGAAAGACGCAGGGCAGCGGCCGAGCAACAGCGCATGAATCAAG
AGCTCCAAGACATGGTTAACTTGCACCAGTGCAAAAGGGGTATCTTTTGTC
TGGTAAAGCAGGCCAAAGTCACCTACGACAGTAATACCACCGGACACCGC
CTTAGCTACAAGTTGCCAACCAAGCGTCAGAAATTGGTGGTCATGGTGGGA
GAAAAGCCCATTACCATAACTCAGCACTCGGTAGAAACCGAAGGCTGCATT
CACTCACCTTGTCAAGGACCTGAGGATCTCTGCACCCTTATTAAGACCCTG
TGCGGTCTCAAAGATCTTATTCCCTTTAACTAATAAAAAAAAATAATAAAGCA
TCACTTACTTAAAATCAGTTAGCAAATTTCTGTCCAGTTTATTCAGCAGCACC
TCCTTGCCCTCCTCCCAGCTCTGGTATTGCAGCTTCCTCCTGGCTGCAAAC
TTTCTCCACAATCTAAATGGAATGTCAGTTTCCTCCTGTTCCTGTCCATCCG
CACCCACTATCTTCATGTTGTTGCAGATGAAGCGCGCAAGACCGTCTGAAG
ATACCTTCAACCCCGTGTATCCATATGACACGGAAACCGGTCCTCCAACTG
TGCCTTTTCTTACTCCTCCCTTTGTATCCCCCAATGGGTTTCAAGAGAGTCC
CCCTGGGGTACTCTCTTTGCGCCTATCCGAACCTCTAGTTACCTCCAATGG
CATGCTTGCGCTCAAAATGGGCAACGGCCTCTCTCTGGACGAGGCCGGCA
ACCTTACCTCCCAAAATGTAACCACTGTGAGCCCACCTCTCAAAAAAACCAA
GTCAAACATAAACCTGGAAATATCTGCACCCCTCACAGTTACCTCAGAAGC
CCTAACTGTGGCTGCCGCCGCACCTCTAATGGTCGCGGGCAACACACTCA
CCATGCAATCACAGGCCCCGCTAACCGTGCACGACTCCAAACTTAGCATTG
CCACCCAAGGACCCCTCACAGTGTCAGAAGGAAAGCTAGCCCTGCAAACA
TCAGGCCCCCTCACCACCACCGATAGCAGTACCCTTACTATCACTGCCTCA
CCCCCTCTAACTACTGCCACTGGTAGCTTGGGCATTGACTTGAAAGAGCCC
ATTTATACACAAAATGGAAAACTAGGACTAAAGTACGGGGCTCCTTTGCATG
TAACAGACGACCTAAACACTTTGACCGTAGCAACTGGTCCAGGTGTGACTA
TTAATAATACTTCCTTGCAAACTAAAGTTACTGGAGCCTTGGGTTTTGATTCA
CAAGGCAATATGCAACTTAATGTAGCAGGAGGACTAAGGATTGATTCTCAA
AACAGACGCCTTATACTTGATGTTAGTTATCCGTTTGATGCTCAAAACCAAC
TAAATCTAAGACTAGGACAGGGCCCTCTTTTTATAAACTCAGCCCACAACTT
GGATATTAACTACAACAAAGGCCTTTACTTGTTTACAGCTTCAAACAATTCC
AAAAAGCTTGAGGTTAACCTAAGCACTGCCAAGGGGTTGATGTTTGACGCT
ACAGCCATAGCCATTAATGCAGGAGATGGGCTTGAATTTGGTTCACCTAAT
GCACCAAACACAAATCCCCTCAAAACAAAAATTGGCCATGGCCTAGAATTT
GATTCAAACAAGGCTATGGTTCCTAAACTAGGAACTGGCCTTAGTTTTGACA
GCACAGGTGCCATTACAGTAGGAAACAAAAATAATGATAAGCTAACCCTAT
GGACAGGTCCAAAACCAGAAGCCAACTGCATAATTGAATACGGGAAACAAA
ACCCAGATAGCAAACTAACTTTAATCCTTGTAAAAAATGGAGGAATTGTTAA
TGGATATGTAACGCTAATGGGAGCCTCAGACTACGTTAACACCTTATTTAAA
AACAAAAATGTCTCCATTAATGTAGAACTATACTTTGATGCCACTGGTCATAT
ATTACCAGACTCATCTTCTCTTAAAACAGATCTAGAACTAAAATACAAGCAAA
CCGCTGACTTTAGTGCAAGAGGTTTTATGCCAAGTACTACAGCGTATCCATT
TGTCCTTCCTAATGCGGGAACACATAATGAAAATTATATTTTTGGTCAATGC
TACTACAAAGCAAGCGATGGTGCCCTTTTTCCGTTGGAAGTTACTGTTATGC
TTAATAAACGCCTGCCAGATAGTCGCACATCCTATGTTATGACTTTTTTATG
GTCCTTGAATGCTGGTCTAGCTCCAGAAACTACTCAGGCAACCCTCATAAC
CTCCCCATTTACCTTTTCCTATATTAGAGAAGATGACTAATAAACTCTAAAGA
ATCGTTTGTGTTATGTTTCAACGTGTTTATTTTTCAATTGCAGAAAATTTCAA
GTCATTTTTCATTCAGTAGTATAGCCCCACCACCACATAGCTTATACAGATC
ACCGTACCTTAATCAAACTCACAGAACCCTAGTATTCAACCTGCCACCTCCC
TCCCAACACACAGAGTACACAGTCCTTTCTCCCCGGCTGGCCTTAAAAAGC
ATCATATCATGGGTAACAGACATATTCTTAGGTGTTATATTCCACACGGTTT
CCTGTCGAGCCAAACGCTCATCAAGTGATATTAATAAACTCCCCGGGCAGC
TCACTTAAGTTCATGTCGCTGTCCAGCTGCTGAGCCACAGGCTGCTGTCCA
ACTTGCGGTTGCTTAACGGGCGGCGAAGGAGAAGTCCACGCCTACATGGG
GGGAGAGTCATAATCGTGCATCAGGATAGGGCGGTGGTGCTGCAGCAGCG
CGCGAATAAACTGCTGCCGCCGCCGCTCCGTCCTGCAGGAATACAACATG
GCAGTGGTCTCCTCAGCGATGATTCGCACCGCCCGCAGCATAAGGCGCTT
GTCCTCCGGGCACAGCAGCGCACCCTGATCTCACTTAAATCAGCACAGTAA
CTGCAGCACAGCACCACAATATTGTTCAAAATCCCACAGTGCAAGGCGCTG
TATCCAAAGCTCATGGCGGGGACCACAGAACCCACGTGGCCATCATACCA
CAAGCGCAGGTAGATTAAGTGGCGACCCCTCATAAACACGCTGGACATAAA
CATTACCTCTTTTGGCATGTTGTAATTCACCACCTCCCGGTACCATATAAAC
CTCTGATTAAACATGGCGCCATCCACCACCATCCTAAACCAGCTGGCCAAA

-continued

Sequences

| SEQ ID NO: | DESCRIPTION | SEQUENCE |
|---|---|---|
| | | ACCTGCCCCGCCGGGNTATACACTGCAGGGAACCGGGACTTGGACAATGA CAAGTGGGAGAGCCCAGGACTCGTAACCATGGATCATCATGCTCGTCATGA TATCAATGTTGGCACAACACAGGCACACGTGCATACACTTCCTCAGGATTA CAAGCTCCTCCCGCGTTAGAACCATATCCCAGGGAACAACCCATTCCTGAA TCAGCGTAAATCCCACACTGCAGGGAAGACCTCGCACGTAACTCACGTTGT GCATTGTCAAAGTGTTACATTCGGGCAGCAGCGGATGATCCTCCAGTATGG TAGCGCGGGTTTCTGTCTCAAAAGGAGGTAGACGATCCCTACTGTACGGAG TGCGCCGAGACAACCGAGATCGTGTTGGTCGTAGTGTCATGCCAAATGGA ACGCCGGACGTAGTCATATTTCCTGAAGCAAAACCAGGTGCGGGCGTGAC AAACAGATCTGCGTCTCCGGTCTCGCCGCTTAGATCGCTCTGTGTAGTAGT TGTAGTATATCCACTCTCTCAAAGCATCCAGGCGCCCCCTGGCTTCGGGTT CTATGTAAACTCCTTCATGCGCCGCTGCCCTGATAACATCCACCACCGCAG AATAAGCCACACCCAGCCAACCTACACATTCGTTCTGCGAGTCACACACGG GAGGAGCGGGAAGAGCTGGAAGAACCATGTTTTTTTTTTTATTCCAAAAGAT TATCCAAAACCTCAAAATGAAGATCTATTAAGTGAACGCGCTCCCCTCCGGT GGCGTGGTCAAACTCTACAGCCAAAGAACAGATAATGGCATTTGTAAGATG TTGCACAATGGCTTCCAAAAGGCAAACGGCCCTCACGTCCAAGTGGACGTA AAGGCTAAACCCTTCAGGGTGAATCTCCTCTATAAACATTCCAGCACCTTCA ACCATGCCCAAATAATTCTCATCTCGCCACCTTCTCAATATATCTCTAAGCA AATCCCGAATATTTAAGTCCGGGCCATTGTAAAAAATTTGGCTCCAGAGCG CCCTCCACCTTCAGCCTCAAGCAGCGAATCATGATTGCAAAAATTCAGGTT CCTCACAGACCTGTATAAGATTCAAAAGCGGAACATTAACAAAAATACCGC GATCCCGTAGGTCCCTTCGCAGGGCCAGCTGAACATAATCGTGCAGGTCT GCACGGACCAGCGCGGCCACTTCCCCGCCAGGAACCATGACAAAAGAACC CACACTGATTATGACACGCATACTCGGAGCTATGCTAACCAGCGTAGCCCC GATGTAAGCTTGTTGCATGGGCGGCGATATAAAATGCAAGGTGCTGCTCAA AAAATCAGGCAAAGCCTCGCGCAAAAAAGAAAGCACATCGTAGTCATGCTC ATGCAGATAAAGGCAGGTAAGCTCCGGAACCACCACAGAAAAAGACACCAT TTTTCTCTCAAACATGTCTGCGGGTTTCTGCATAAACACAAAATAAAATAACA AAAAAACATTTAAACATTAGAAGCCTGTCTTACAACAGGAAAAACAACCCTT ATAAGCATAAGACGGACTACGGCCATGCCGGCGTGACCGTAAAAAAACTG GTCACCGTGATTAAAAAGCACCACCGACAGCTCCTCGGTCAGTCCGGAGT CATAATGTAAGACTCGGTAAACACATCAGGTTGATTCACATCGGTCAGTGTT AAAAAGCGACCGAAATAGCCNGGGGGAATACAATACCCGCAGGCGTAGAG ACAACATTACAGCCCCCATAGGAGGTATAACAAAATTAATAGGAGAGAAAAA CACATAAACACCTGAAAAACCCTCCTGCCTAGGCAAAATAGCACCCTCCCG CTCCAGAACAACATACAGCGCTTCCACAGCGGCAGCCATAACAGTCAGCCT TACCAGTAAAAAAGAAAACCTATTAAAAAAACACCACTCGACACGGCACCA GCTCAATCAGTCACAGTGTAAAAAAGGGCCAAGTGCAGAGCGAGTATATAT AGGACTAAAAAATGACGGTAACGGTTAAAGTCCACAAAAAACACCCAGAAA ACCGCACGCGAACCTACGCCCAGAAACGAAAGCCAAAAAACCCACAACTTC CTCAAATCGTCACTTCCGTTTTCCCACGTTACGTCACTTCCCATTTTAAGAA AACTACAATTCCCAACACATACAAGTTACTCCGCCCTAAAACCTACGTCACC CGCCCCGTTCCCACGCCCCGCGCCACGTCACAAACTCCACCCCCTCATTA TCATATTGGCTTCAATCCAAAATAAGGTATATTATTGATGATGTTAATTAACA TGCATGGATCCTCGTCTCGACGATGCCCTTGAGAGCCTTCAACCCAGTCAG CTCCTTCCGGTGGGCGCGGGGCATGACTATCGTCGCCGCACTTATGACTG TCTTCTTTATCATGCAACTCGTAGGACAGGTGCCGGCAGCGCTCTGGGTCA TTTTCGGCGAGGACCGCTTTCGCTGGAGCGCGACGATGATCGGCCTGTCG CTTGCGGTATTCGGAATCTTGCACGCCCTCGCTCAAGCCTTCGTCACTGGT CCCGCCACCAAACGTTTCGGCGAGAAGCAGGCCATTATCGCCGGCATGGC GGCCGACGCGCTGGGCTACGTCTTGCTGGCGTTCGCGACGCGAGGCTGG ATGGCCTTCCCCATTATGATTCTTCTCGCTTCCGGCGGCATCGGGATGCCC GCGTTGCAGGCCATGCTGTCCAGGCAGGTAGATGACGACCATCAGGGACA GCTTCAAGGATCGCTCGCGGCTCTTACCAGCCTAACTTCGATCACTGGACC GCTGATCGTCACGGCGATTTATGCCGCCTCGGCGAGCACATGGAACGGGT TGGCATGGATTGTAGGCGCCGCCCTATACCTTGTCTGCCTCCCCGCGTTG CGTCGCGGTGCATGGAGCCGGGCCACCTCGACCTGAATGGAAGCCGGCG GCACCTCGCTAACGGATTCACCACTCCAAGAATTGGAGCCAATCAATTCTT GCGGAGAACTGTGAATGCGCAAACCAACCCTTGGCAGAACATATCCATCGC GTCCGCCATCTCCAGCAGCCGCACGCGGCGCATCTCGGGCAGCGTTGGG TCCTGGCCACGGGTGCGCATGATCGTGCTCCTGTCGTTGAGGACCCGGCT AGGCTGGCGGGGTTGCCTTACTGGTTAGCAGAATGAATCACCGATACGCG AGCGAACGTGAAGCGACTGCTGCTGCAAAACGTCTGCGACCTGAGCAACA ACATGAATGGTCTTCGGTTTCCGTGTTTCGTAAAGTCTGGAAACGCGGAAG TCAGCGCCCTGCACCATTATGTTCCGGATCTGCATCGCAGGATGCTGCTGG CTACCCTGTGGAACACCTACATCTGTATTAACGAAGCGCTGGCATTGACCC TGAGTGATTTTTCTCTGGTCCCGCCGCATCCATACCGCCAGTTGTTTACCCT CACAACGTTCCAGTAACCGGGCATGTTCATCATCAGTAACCCGTATCGTGA GCATCCTCTCTCGTTTCATCGGTATCATTACCCCCATGAACAGAAATTCCCC CTTACACGGAGGCATCAAGTGACCAAACAGGAAAAAACCGCCCTTAACATG GCCCGCTTTATCAGAAGCCAGACATTAACGCTTCTGGAGAAACTCAACGAG CTGGACGCGGATGAACAGGCAGACATCTGTGAATCGCTTCACGACCACGC TGATGAGCTTTACCGCAGCTGCCTCGCGCGTTTCGGTGATGACGGTGAAAA |

-continued

Sequences

| SEQ ID NO: | DESCRIPTION | SEQUENCE |
|---|---|---|
| | | CCTCTGACACATGCAGCTCCCGGAGACGGTCACAGCTTGTCTGTAAGCGG<br>ATGCCGGGAGCAGACAAGCCCGTCAGGGCGCGTCAGCGGGTGTTGGCGG<br>GTGTCGGGGCGCAGCCATGACCCAGTCACGTAGCGATAGCGGAGTGTATA<br>CTGGCTTAACTATGCGGCATCAGAGCAGATTGTACTGAGAGTGCACCATAT<br>GCGGTGTGAAATACCGCACAGATGCGTAAGGAGAAAATACCGCATCAGGC<br>GCTCTTCCGCTTCCTCGCTCACTGACTCGCTGCGCTCGGTCGTTCGGCTGC<br>GGCGAGCGGTATCAGCTCACTCAAAGGCGGTAATACGGTTATCCACAGAAT<br>CAGGGGATAACGCAGGAAAGAACATGTGAGCAAAAGGCCAGCAAAAGGCC<br>AGGAACCGTAAAAAGGCCGCGTTGCTGGCGTTTTTCCATAGGCTCCGCCC<br>CCCTGACGAGCATCACAAAAATCGACGCTCAAGTCAGAGGTGGCGAAACC<br>CGACAGGACTATAAAGATACCAGGCGTTTCCCCCTGGAAGCTCCCTCGTGC<br>GCTCTCCTGTTCCGACCCTGCCGCTTACCGGATACCTGTCCGCCTTTCTCC<br>CTTCGGGAAGCGTGGCGCTTTCTCAATGCTCACGCTGTAGGTATCTCAGTT<br>CGGTGTAGGTCGTTCGCTCCAAGCTGGGCTGTGTGCACGAACCCCCCGTT<br>CAGCCCGACCGCTGCGCCTTATCCGGTAACTATCGTCTTGAGTCCAACCCG<br>GTAAGACACGACTTATCGCCACTGGCAGCAGCCACTGGTAACAGGATTAGC<br>AGAGCGAGGTATGTAGGCGGTGCTACAGAGTTCTTGAAGTGGTGGCCTAA<br>CTACGGCTACACTAGAAGGACAGTATTTGGTATCTGCGCTCTGCTGAAGCC<br>AGTTACCTTCGGAAAAAGAGTTGGTAGCTCTTGATCCGGCAAACAAACCAC<br>CGCTGGTAGCGGTGGTTTTTTTGTTTGCAAGCAGCAGATTACGCGCAGAAA<br>AAAAGGATCTCAAGAAGATCCTTTGATCTTTTCTACGGGGTCTGACGCTCA<br>GTGGAACGAAAACTCACGTTAAGGGATTTTGGTCATGAGATTATCAAAAAG<br>GATCTTCACCTAGATCCTTTTAAATTAAAAATGAAGTTTTAAATCAATCTAAA<br>GTATATATGAGTAAACTTGGTCTGACAGTTACCAATGCTTAATCAGTGAGGC<br>ACCTATCTCAGCGATCTGTCTATTTCGTTCATCCATAGTTGCCTGACTCCCC<br>GTCGTGTAGATAACTACGATACGGGAGGGCTTACCATCTGGCCCCAGTGCT<br>GCAATGATACCGCGAGACCCACGCTCACCGGCTCCAGATTTATCAGCAATA<br>AACCAGCCAGCCGGAAGGGCCGAGCGCAGAAGTGGTCCTGCAACTTTATC<br>CGCCTCCATCCAGTCTATTAATTGTTGCCGGGAAGCTAGAGTAAGTAGTTC<br>GCCAGTTAATAGTTTGCGCAACGTTGGTTGNNNNNNAAAAAGGATCTTCAC<br>CTAGATCCTTTTCACGTAGAAAGCCAGTCCGCAGAAACGGTGCTGACCCCG<br>GATGAATGTCAGCTACTGGGCTATCTGGACAAGGGAAAACGCAAGCGCAA<br>AGAGAAAGCAGGTAGCTTGCAGTGGGCTTACATGGCGATAGCTAGACTGG<br>GCGGTTTTATGGACAGCAAGCGAACCGGAATTGCCAGCTGGGGCGCCCTC<br>TGGTAAGGTTGGGAAGCCCTGCAAAGTAAACTGGATGGCTTTCTCGCCGC<br>CAAGGATCTGATGGCGCAGGGGATCAAGCTCTGATCAAGAGACAGGATGA<br>GGATCGTTTCGCATGATTGAACAAGATGGATTGCACGCAGGTTCTCCGGCC<br>GCTTGGGTGGAGAGGCTATTCGGCTATGACTGGGCACAACAGACAATCGG<br>CTGCTCTGATGCCGCCGTGTTCCGGCTGTCAGCGCAGGGGCGCCCGGTTC<br>TTTTTGTCAAGACCGACCTGTCCGGTGCCCTGAATGAACTGCAAGACGAGG<br>CAGCGCGGCTATCGTGGCTGGCCACGACGGGCGTTCCTTGCGCAGCTGT<br>GCTCGACGTTGTCACTGAAGCGGGAAGGGACTGGCTGCTATTGGGCGAAG<br>TGCCGGGGCAGGATCTCCTGTCATCTCACCTTGCTCCTGCCGAGAAAGTAT<br>CCATCATGGCTGATGCAATGCGGCGGCTGCATACGCTTGATCCGGCTACC<br>TGCCCATTCGACCACCAAGCGAAACATCGCATCGAGCGAGCACGTACTCG<br>GATGGAAGCCGGTCTTGTCGATCAGGATGATCTGGACGAAGAGCATCAGG<br>GGCTCGCGCCAGCCGAACTGTTCGCCAGGCTCAAGGCGAGCATGCCCGA<br>CGGCGAGGATCTCGTCGTGACCCATGGCGATGCCTGCTTGCCGAATATCA<br>TGGTGGAAAATGGCCGCTTTTCTGGATTCATCGACTGTGGCCGGCTGGGT<br>GTGGCGGACCGCTATCAGGACATAGCGTTGGCTACCCGTGATATTGCTGA<br>AGAGCTTGGCGGCGAATGGGCTGACCGCTTCCTCGTGCTTTACGGTATCG<br>CCGCTCCCGATTCGCAGCGCATCGCCTTCTATCGCCTTCTTGACGAGTTCT<br>TCTGAATTTTGTTAAAATTTTTGTTAAATCAGCTCATTTTTTAACCAATAGGC<br>CGAAATCGGCAACATCCCTTATAAATCAAAAGAATAGACCGCGATAGGGTT<br>GAGTGTTGTTCCAGTTTGGAACAAGAGTCCACTATTAAAGAACGTGGACTC<br>CAACGTCAAAGGGCGAAAAACCGTCTATCAGGGCGATGGCCCACTACGTG<br>AACCATCACCCAAATCAAGTTTTTTGCGGTCGAGGTGCCGTAAAGCTCTAA<br>ATCGGAACCCTAAAGGGAGCCCCCGATTTAGAGCTTGACGGGGAAAGCCG<br>GCGAACGTGGCGAGAAAGGAAGGGAAGAAAGCGAAAGGAGCGGGCGCTA<br>GGGCGCTGGCAAGTGTAGCGGTCACGCTGCGCGTAACCACCACACCCGC<br>GCGCTTAATGCGCCGCTACAGGGCGCGTCCATTCGCCATTCAGGATCGAA<br>TTAATTCTTAAT |
| 52 | Amino acids 121-128 of Ad E1A protein | LTCHEACF |
| 53 | STAT1 binding site (1) | TTCCGGGAA |
| 54 | STAT1 binding site (2) | TTCTCGGAA |

-continued

Sequences

| SEQ ID NO: | DESCRIPTION | SEQUENCE |
|---|---|---|
| 55 | Ad5/<br>3Ad2E1AΔ24 | TAACATCATCAATAATATACCTTATTTTGGATTGAAGCCAATATGATAATGAG<br>GGGGTGGAGTTTGTGACGTGGCGCGGGGCGTGGGAACGGGGCGGGTGA<br>CGTAGTAGTGTGGCGGAAGTGTGATGTTGCAAGTGTGGCGGAACACATGT<br>AAGCGACGGATGTGGCAAAAGTGACGTTTTTGGTGTGCGCCGGTGTACAC<br>AGGAAGTGACAATTTTCGCGCGGTTTTAGGCGGATGTTGTAGTAAATTTGG<br>GCGTAACCGAGTAAGATTTGGCCATTTTCGCGGGAAAACTGAATAAGAGGA<br>AGTGAAATCTGAATAATTTTGTGTTACTCATAGCGCGTAATATTTGTCTAGG<br>GCCGCGGGGACTTTGACCGTTTACGTGGAGACTCGCCCAGGTGTTTTTCTC<br>AGGTGTTTTCCGCGTTCCGGGTCAAAGTTGGCGTTTTATTATTATAGTCAGC<br>TGACGTGTAGTGTATTTATACCCGGTGAGTTCCTCAAGAGGCCACTCTTGA<br>GTGCCAGCGAGTAGAGTTTTCTCCTCCGAGCCGCTCCGACACCGGGACTG<br>AAAATGAGACATATTATCTGCCACGGAGGTGTTATTACCGAAGAAATGGCC<br>GCCAGTCTTTTGGACCAGCTGATCGAAGAGGTACTGGCTGATAATCTTCCA<br>CCTCCTAGCCATTTTGAACCACCTACCCTTCACGAACTGTATGATTTAGACG<br>TGACGGCCCCCGAAGATCCCAACGAGGAGGCGGTTTCGCAGATTTTTCCC<br>GAGTCTGTAATGTTGGCGGTGCAGGAAGGGATTGACTTATTCACTTTTCCG<br>CCGGCGCCCGGTTCTCCGGAGCCGCCTCACCTTTCCCGGCAGCCCGAGC<br>AGCCGGAGCAGAGAGCCTTGGGTCCGGTTTCTATGCCAAACCTTGTGCCG<br>GAGGTGATCGATCCACCCAGTGACGACGAGGATGAAGAGGGTGAGGAGTT<br>TGTGTTAGATTATGTGGAGCACCCCGGGCACGGTTGCAGGTCTTGTCATTA<br>TCACCGGAGGAATACGGGGGACCCAGATATTATGTGTTCGCTTTGCTATAT<br>GAGGACCTGTGGCATGTTTGTCTACAGTAAGTGAAAATTATGGGCAGTCGG<br>TGATAGAGTGGTGGGTTTGGTGTGGTAATTTTTTTTTAATTTTTACAGTTTTG<br>TGGTTTAAAGAATTTTGTATTGTGATTTTTTTAAAAGGTCCTGTGTCTGAACCT<br>GAGCCTGAGCCCGAGCCAGAACCGGAGCCTGCAAGACCTACCCGGCGTC<br>CTAAATTGGTGCCTGCTATCCTGAGACGCCCGACATCACCTGTGTCTAGAG<br>AATGCAATAGTAGTACGGATAGCTGTGACTCCGGTCCTTCTAACACACCTC<br>CTGAGATACACCCGGTGGTCCCGCTGTGCCCCATTAAACCAGTTGCCGTG<br>AGAGTTGGTGGGCGTCGCCAGGCTGTGGAATGTATCGAGGACTTGCTTAA<br>CGAGTCTGGGCAACCTTTGGACTTGAGCTGTAAACGCCCCAGGCCATAAG<br>GTGTAAACCTGTGATTGCGTGTGTGGTTAACGCCTTTGTTTGCTGAATGAGT<br>TGATGTAAGTTTAATAAAGGGTGAGATAATGTTTAACTTGCATGGCGTGTTA<br>AATGGGGCGGGGCTTAAAGGGTATATAATGCGCCGTGGGCTAATCTTGGTT<br>ACATCTGACCTCATGGAGGCTTGGGAGTGTTTGGAAGATTTTTCTGCTGTG<br>CGTAACTTGCTGGAACAGAGCTCTAACAGTACCTCTTGGTTTTGGAGGTTT<br>CTGTGGGGCTCATCCCAGGCAAAGTTAGTCTGCAGAATTAAGGAGGATTAC<br>AAGTGGGAATTTGAAGAGCTTTTGAAATCCTGTGGTGAGCTGTTTGATTCTT<br>TGAATCTGGGTCACCAGGCGCTTTTCCAAGAGAAGGTCATCAAGACTTTGG<br>ATTTTTCCACACCGGGGCGCGCTGCGGCTGCTGTTGCTTTTTTGAGTTTTAT<br>AAAGGATAAATGGAGCGAAGAAACCCATCTGAGCGGGGGGTACCTGCTGG<br>ATTTTCTGGCCATGCATCTGTGGAGAGCGGTTGTGAGACACAAGAATCGCC<br>TGCTACTGTTGTCTTCCGTCCGCCCGGCGATAATACCGACGGAGGAGCAG<br>CAGCAGCAGCAGGAGGAAGCCAGGCGGCGGCGGCAGGAGCAGAGCCCAT<br>GGAACCCGAGAGCCGGCCTGGACCCTCGGGAATGAATGTTGTTCAGGTGG<br>CTGAACTGTATCCAGAACTGAGACGCATTTTGACAATTACAGAGGATGGGC<br>AGGGGCTAAAGGGGGTAAAGAGGGAGCGGGGGGCTTGTGAGGCTACAGA<br>GGAGGCTAGGAATCTAGCTTTTAGCTTAATGACCAGACACCGTCCTGAGTG<br>TATTACTTTTCAACAGATCAAGGATAATTGCGCTAATGAGCTTGATCTGCTG<br>GCGCAGAAGTATTCCATAGAGCAGCTGACCACTTACTGGCTGCAGCCAGG<br>GGATGATTTTGAGGAGGCTATTAGGGTATATGCAAAGGTGGCACTTAGGCC<br>AGATTGCAAGTACAAGATCAGCAAACTTGTAAATATCAGGAATTGTTGCTAC<br>ATTTCTGGGAACGGGGCCGAGGTGGAGATAGATACGGAGGATAGGGTGGC<br>CTTTAGATGTAGCATGATAAATATGTGGCCGGGGGTGCTTGGCATGGACGG<br>GGTGGTTATTATGAATGTAAGGTTTACTGGCCCCAATTTTAGCGGTACGGTT<br>TTCCTGGCCAATACCAACCTTATCCTACACGGTGTAAGCTTCTATGGGTTTA<br>ACAATACCTGTGTGGAAGCCTGGACCGATGTAAGGGTTCGGGGCTGTGCC<br>TTTTACTGCTGCTGGAAGGGGGTGGTGTGTCGCCCCAAAAGCAGGGCTTC<br>AATTAAGAAATGCCTCTTTGAAAGGTGTACCTTGGGTATCCTGTCTGAGGGT<br>AACTCCAGGGTGCGCCACAATGTGGCCTCCGACTGTGGTTGCTTCATGCTA<br>GTGAAAAGCGTGGCTGTGATTAAGCATAACATGGTATGTGGCAACTGCGAG<br>GACAGGGCCTCTCAGATGCTGACCTGCTCGGACGGCAACTGTCACCTTCT<br>GAAGACCATTCACGTAGCCAGCCACTCTCGCAAGGCCTGGCCAGTGTTTG<br>AGCATAACATACTGACCCGCTGTTCCTTGCATTTGGGTAACAGGAGGGGGG<br>TGTTCCTACCTTACCAATGCAATTTGAGTCACACTAAGATATTGCTTGAGCC<br>CGAGAGCATGTCCAAGGTGAACCTGAACGGGGTGTTTGACATGACCATGA<br>AGATCTGGAAGGTGCTGAGGTACGATGAGACCCGCACCAGGTGCAGACCC<br>TGCGAGTGTGGCGGTAAACATATTAGGAACCAGCCTGTGATGCTGGATGTG<br>ACCGAGGAGCTGAGGCCCGATCACTTGGTGCTGGCCTGCACCCGCGCTGA<br>GTTTGGCTCTAGCGATGAAGATACAGATTGAGGTACTGAAATGTGTGGGCG<br>TGGCTTAAGGGTGGGAAAGAATATATAAGGTGGGGGTCTTATGTAGTTTTG<br>TATCTGTTTTGCAGCAGCCGCCGCCGCCATGAGCACCAACTCGTTTGATGG<br>AAGCATTGTGAGCTCATATTTGACAACGCGCATGCCCCCATGGGCCGGGG<br>TGCGTCAGAATGTGATGGGCTCCAGCATTGATGGTCGCCCCGTCCTGCCC<br>GCAAACTCTACTACCTTGACCTACGAGACCGTGTCTGGAACGCCGTTGGAG |

-continued

Sequences

| SEQ ID NO: | DESCRIPTION | SEQUENCE |
|---|---|---|
| | | ACTGCAGCCTCCGCCGCCGCTTCAGCCGCTGCAGCCACCGCCCGCGGGA |
| | | TTGTGACTGACTTTGCTTTCCTGAGCCCGCTTGCAAGCAGTGCAGCTTCCC |
| | | GTTCATCCGCCCGCGATGACAAGTTGACGGCTCTTTTGGCACAATTGGATT |
| | | CTTTGACCCGGGAACTTAATGTCGTTTCTCAGCAGCTGTTGGATCTGCGCC |
| | | AGCAGGTTTCTGCCCTGAAGGCTTCCTCCCCTCCCAATGCGGTTTAAAACA |
| | | TAAATAAAAAACCAGACTCTGTTTGGATTTGGATCAAGCAAGTGTCTTGCTG |
| | | TCTTTATTTAGGGGTTTTGCGCGCGCGGTAGGCCCGGGACCAGCGGTCTC |
| | | GGTCGTTGAGGGTCCTGTGTATTTTTTCCAGGACGTGGTAAAGGTGACTCT |
| | | GGATGTTCAGATACATGGGCATAAGCCCGTCTCTGGGGTGGAGGTAGCAC |
| | | CACTGCAGAGCTTCATGCTGCGGGGTGGTGTTGTAGATGATCCAGTCGTA |
| | | GCAGGAGCGCTGGGCGTGGTGCCTAAAAATGTCTTTCAGTAGCAAGCTGA |
| | | TTGCCAGGGGCAGGCCCTTGGTGTAAGTGTTTACAAAGCGGTTAAGCTGG |
| | | GATGGGTGCATACGTGGGGATATGAGATGCATCTTGGACTGTATTTTTAGG |
| | | TTGGCTATGTTCCCAGCCATATCCCTCCGGGGATTCATGTTGTGCAGAACC |
| | | ACCAGCACAGTGTATCCGGTGCACTTGGGAAATTTGTCATGTAGCTTAGAA |
| | | GGAAATGCGTGGAAGAACTTGGAGACGCCCTTGTGACCTCCAAGATTTTCC |
| | | ATGCATTCGTCCATAATGATGGCAATGGGCCCACGGGCGGCGGCCTGGGC |
| | | GAAGATATTTCTGGGATCACTAACGTCATAGTTGTGTTCCAGGATGAGATC |
| | | GTCATAGGCCATTTTTACAAAGCGCGGGCGGAGGGTGCCAGACTGCGGTA |
| | | TAATGGTTCCATCCGGCCCAGGGGCGTAGTTACCCTCACAGATTTGCATTT |
| | | CCCACGCTTTGAGTTCAGATGGGGGGATCATGTCTACCTGCGGGGCGATG |
| | | AAGAAAACGGTTTCCGGGGTAGGGGAGATCAGCTGGGAAGAAAGCAGGTT |
| | | CCTGAGCAGCTGCGACTTACCGCAGCCGGTGGGCCCGTAAATCACACCTA |
| | | TTACCGGGTGCAACTGGTAGTTAAGAGAGCTGCAGCTGCCGTCATCCCTGA |
| | | GCAGGGGGGCCACTTCGTTAAGCATGTCCCTGACTCGCATGTTTTCCCTGA |
| | | CCAAATCCGCCAGAAGGCGCTCGCCGCCCAGCGATAGCAGTTCTTGCAAG |
| | | GAAGCAAAGTTTTTCAACGGTTTGAGACCGTCCGCCGTAGGCATGCTTTTG |
| | | AGCGTTTGACCAAGCAGTTCCAGGCGGTCCCACAGCTCGGTTACCTGCTCT |
| | | ACGGCATCTCGATCCAGCATATCTCCTCGTTTCGCGGGTTGGGGCGGCTTT |
| | | CGCTGTACGGCAGTAGTCGGTGCTCGTCCAGACGGGCCAGGGTCATGTCT |
| | | TTCCACGGGCGCAGGGTCCTCGTCAGCGTAGTCTGGGTCACGGTGAAGGG |
| | | GTGCGCTCCGGGCTGCGCGCTGGCCAGGGTGCGCTTGAGGCTGGTCCTG |
| | | CTGGTGCTGAAGCGCTGCCGGTCTTCGCCCTGCGCGTCGGCCAGGTAGCA |
| | | TTTGACCATGGTGTCATAGTCCAGCCCCTCCGCGGCGTGGCCCTTGGCGC |
| | | GCAGCTTGCCCTTGGAGGAGGCGCCGCACGAGGGGCAGTGCAGACTTTT |
| | | GAGGGCGTAGAGCTTGGGCGCGAGAAATACCGATTCCGGGGAGTAGGCAT |
| | | CCGCGCCGCAGGCCCCGCAGACGGTCTCGCATTCCACGAGCCAGGTGAG |
| | | CTCTGGCCGTTCGGGGTCAAAAACCAGGTTTCCCCCATGCTTTTTGATGCG |
| | | TTTCTTACCTCTGGTTTCCATGAGCCGGTGTCCACGCTCGGTGACGAAAAG |
| | | GCTGTCCGTGTCCCCGTATACAGACTTGAGAGGCCTGTCCTCGAGCGGTG |
| | | TTCCGCGGTCCTCCTCGTATAGAAACTCGGACCACTCTGAGACAAAGGCTC |
| | | GCGTCCAGGCCAGCACGAAGGAGGCTAAGTGGGAGGGGTAGCGGTCGTT |
| | | GTCCACTAGGGGGTCCACTCGCTCCAGGGTGTGAAGACACATGTCGCCCT |
| | | CTTCGGCATCAAGGAAGGTGATTGGTTTGTAGGTGTAGGCCACGTGACCG |
| | | GGTGTTCCTGAAGGGGGGCTATAAAAGGGGGTGGGGGCGCGTTCGTCCT |
| | | CACTCTCTTCCGCATCGCTGTCTGCGAGGGCCAGCTGTTGGGGTGAGTAC |
| | | TCCCTCTGAAAAGCGGGCATGACTTCTGCGCTAAGATTGTCAGTTTCCAAA |
| | | AACGAGGAGGATTTGATATTCACCTGGCCCGCGGTGATGCCTTTGAGGGT |
| | | GGCCGCATCCATCTGGTCAGAAAAGACAATCTTTTTGTTGTCAAGCTTGGT |
| | | GGCAAACGACCCGTAGAGGGCGTTGGACAGCAACTTGGCGATGGAGCGC |
| | | AGGGTTTGGTTTTTGTCGCGATCGGCGCGCTCCTTGGCCGCGATGTTTAGC |
| | | TGCACGTATTCGCGCGCAACGCACCGCCATTCGGGAAAGACGGTGGTGCG |
| | | CTCGTCGGGCACCAGGTGCACGCGCCAACCGCGGTTGTGCAGGGTGACA |
| | | AGGTCAACGCTGGTGGCTACCTCTCCGCGTAGGCGCTCGTTGGTCCAGCA |
| | | GAGGCGGCCGCCCTTGCGCGAGCAGAATGGCGGTAGGGGGTCTAGCTGC |
| | | GTCTCGTCCGGGGGGTCTGCGTCCACGGTAAAGACCCCGGGCAGCAGGC |
| | | GCGCGTCGAAGTAGTCTATCTTGCATCCTTGCAAGTCTAGCGCCTGCTGCC |
| | | ATGCGCGGGCGGCAAGCGCGCGCTCGTATGGGTTGAGTGGGGGACCCCA |
| | | TGGCATGGGGTGGGTGAGCGCGGAGGCGTACATGCCGCAAATGTCGTAAA |
| | | CGTAGAGGGGCTCTCTGAGTATTCCAAGATATGTAGGGTAGCATCTTCCAC |
| | | CGCGGATGCTGGCGCGCACGTAATCGTATAGTTCGTGCGAGGGAGCGAG |
| | | GAGGTCGGGACCGAGGTTGCTACGGGCGGGCTGCTCTGCTCGGAAGACT |
| | | ATCTGCCTGAAGATGGCATGTGAGTTGGATGATATGGTTGGACGCTGGAAG |
| | | ACGTTGAAGCTGGCGTCTGTGAGACCTACCGCGTCACGCACGAAGGAGGC |
| | | GTAGGAGTCGCGCAGCTTGTTGACCAGCTCGGCGGTGACCTGCACGTCTA |
| | | GGGCGCAGTAGTCCAGGGTTTCCTTGATGATGTCATACTTATCCTGTCCCT |
| | | TTTTTTTCCACAGCTCGCGGTTGAGGACAAACTCTTCGCGGTCTTTCCAGTA |
| | | CTCTTGGATCGGAAACCCGTCGGCCTCCGAACGGTAAGAGCCTAGCATGT |
| | | AGAACTGGTTGACGGCCTGGTAGGCGCAGCATCCCTTTTCTACGGGTAGC |
| | | GCGTATGCCTGCGCGGCCTTCCGGAGCGAGGTGTGGGTGAGCGCAAAGG |
| | | TGTCCCTGACCATGACTTTGAGGTACTGGTATTTGAAGTCAGTGTCGTCGC |
| | | ATCCGCCCTGCTCCCAGAGCAAAAAGTCCGTGCGCTTTTTGGAACGCGGAT |
| | | TTGGCAGGGCGAAGGTGACATCGTTGAAGAGTATCTTTCCCGCGCGAGGC |
| | | ATAAAGTTGCGTGTGATGCGGAAGGGTCCCGGCACCTCGGAACGGTTGT |

-continued

Sequences

| SEQ ID NO: | DESCRIPTION | SEQUENCE |
|---|---|---|
| | | AATTACCTGGGCGGCGAGCACGATCTCGTCAAAGCCGTTGATGTTGTGGC<br>CCACAATGTAAAGTTCCAAGAAGCGCGGGATGCCCTTGATGGAAGGCAATT<br>TTTTAAGTTCCTCGTAGGTGAGCTCTTCAGGGGAGCTGAGCCCGTGCTCTG<br>AAAGGGCCCAGTCTGCAAGATGAGGGTTGGAAGCGACGAATGAGCTCCAC<br>AGGTCACGGGCCATTAGCATTTGCAGGTGGTCGCGAAAGGTCCTAAACTG<br>GCGACCTATGGCCATTTTTTCTGGGGTGATGCAGTAGAAGGTAAGCGGGTC<br>TTGTTCCCAGCGGTCCCATCCAAGGTTCGCGGCTAGGTCTCGCGCGGCAG<br>TCACTAGAGGCTCATCTCCGCCGAACTTCATGACCAGCATGAAGGGCACGA<br>GCTGCTTCCCAAAGGCCCCCATCCAAGTATAGGTCTCTACATCGTAGGTGA<br>CAAAGAGACGCTCGGTGCGAGGATGCGAGCCGATCGGGAAGAACTGGATC<br>TCCCGCCACCAATTGGAGGAGTGGCTATTGATGTGGTGAAAGTAGAAGTCC<br>CTGCGACGGGCCGAACACTCGTGCTGGCTTTTGTAAAAACGTGCGCAGTA<br>CTGGCAGCGGTGCACGGGCTGTACATCCTGCACGAGGTTGACCTGACGAC<br>CGCGCACAAGGAAGCAGAGTGGGAATTTGAGCCCCTCGCCTGGCGGGTTT<br>GGCTGGTGGTCTTCTACTTCGGCTGCTTGTCCTTGACCGTCTGGCTGCTCG<br>AGGGGAGTTACGGTGGATCGGACCACCACGCCGCGCGAGCCCAAAGTCC<br>AGATGTCCGCGCGCGGCGGTCGGAGCTTGATGACAACATCGCGCAGATGG<br>GAGCTGTCCATGGTCTGGAGCTCCCGCGGCGTCAGGTCAGGCGGGAGCT<br>CCTGCAGGTTTACCTCGCATAGACGGGTCAGGGCGCGGGCTAGATCCAGG<br>TGATACCTAATTTCCAGGGGCTGGTTGGTGGCGGCGTCGATGGCTTGCAA<br>GAGGCCGCATCCCCGCGGCGCGACTACGGTACCGCGCGGCGGGCGGTG<br>GGCCGCGGGGGTGTCCTTGGATGATGCATCTAAAAGCGGTGACGCGGGC<br>GAGCCCCCGGAGGTAGGGGGGGCTCCGGACCCGCCGGGAGAGGGGGCA<br>GGGGCACGTCGGCGCCGCGCGCGGGCAGGAGCTGGTGCTGCGCGCGTA<br>GGTTGCTGGCGAACGCGACGACGCGGCGGTTGATCTCCTGAATCTGGCGC<br>CTCTGCGTGAAGACGACGGGCCCGGTGAGCTTGAGCCTGAAAGAGAGTTC<br>GACAGAATCAATTTCGGTGTCGTTGACGGCGGCCTGGCGCAAAATCTCCTG<br>CACGTCTCCTGAGTTGTCTTGATAGGCGATCTCGGCCATGAACTGCTCGAT<br>CTCTTCCTCCTGGAGATCTCCGCGTCCGGCTCGCTCCACGGTGGCGGCGA<br>GGTCGTTGGAAATGCGGGCCATGAGCTGCGAGAAGGCGTTGAGGCCTCCC<br>TCGTTCCAGACGCGGCTGTAGACCACGCCCCCTTCGGCATCGCGGGCGC<br>GCATGACCACCTGCGCGAGATTGAGCTCCACGTGCCGGGCGAAGACGGC<br>GTAGTTTCGCAGGCGCTGAAAGAGGTAGTTGAGGGTGGTGGCGGTGTGTT<br>CTGCCACGAAGAAGTACATAACCCAGCGTCGCAACGTGGATTCGTTGATAT<br>CCCCCAAGGCCTCAAGGCGCTCCATGGCCTCGTAGAAGTCCACGGCGAAG<br>TTGAAAAACTGGGAGTTGCGCGCCGACACGGTTAACTCCTCCTCCAGAAGA<br>CGGATGAGCTCGGCGACAGTGTCGCGCACCTCGCGCTCAAAGGCTACAGG<br>GGCCTCTTCTTCTTCTTCAATCTCCTCTTCCATAAGGGCCTCCCCTTCTTCT<br>TCTTCTGGCGGCGGTGGGGGAGGGGGGACACGGCGGCGACGACGGCGC<br>ACCGGGAGGCGGTCGACAAAGCGCTCGATCATCTCCCCGCGGCGACGGC<br>GCATGGTCTCGGTGACGGCGCGGCCGTTCTCGCGGGGGCGCAGTTGGAA<br>GACGCCGCCCGTCATGTCCCGGTTATGGGTTGGCGGGGGGCTGCCATGC<br>GGCAGGGATACGGCGCTAACGATGCATCTCAACAATTGTTGTGTAGGTACT<br>CCGCCGCCGAGGGACCTGAGCGAGTCCGCATCGACCGGATCGGAAAACC<br>TCTCGAGAAAGGCGTCTAACCAGTCACAGTCGCAAGGTAGGCTGAGCACC<br>GTGGCGGGCGGCAGCGGGCGGCGGTCGGGGTTGTTTCTGGCGGAGGTG<br>CTGCTGATGATGTAATTAAAGTAGGCGGTCTTGAGACGGCGGATGGTCGAC<br>AGAAGCACCATGTCCTTGGGTCCGGCCTGCTGAATGCGCAGGCGGTCGGC<br>CATGCCCCAGGCTTCGTTTTGACATCGGCGCAGGTCTTTGTAGTAGTCTTG<br>CATGAGCCTTTCTACCGGCACTTCTTCTTCTCCTTCCTCTTGTCCTGCATCT<br>CTTGCATCTATCGCTGCGGCGGCGGCGGAGTTTGGCCGTAGGTGGCGCC<br>CTCTTCCTCCCATGCGTGTGACCCCGAAGCCCCTCATCGGCTGAAGCAGG<br>GCTAGGTCGGCGACAACGCGCTCGGCTAATATGGCCTGCTGCACCTGCGT<br>GAGGGTAGACTGGAAGTCATCCATGTCCACAAAGCGGTGGTATGCGCCCG<br>TGTTGATGGTGTAAGTGCAGTTGGCCATAACGGACCAGTTAACGGTCTGGT<br>GACCCGGCTGCGAGAGCTCGGTGTACCTGAGACGCGAGTAAGCCCTCGA<br>GTCAAATACGTAGTCGTTGCAAGTCCGCACCAGGTACTGGTATCCCACCAA<br>AAAGTGCGGCGGCGGCTGGCGGTAGAGGGGCCAGCGTAGGGTGGCCGG<br>GGCTCCGGGGGCGAGATCTTCCAACATAAGGCGATGATATCCGTAGATGT<br>ACCTGGACATCCAGGTGATGCCGGCGGCGGTGGTGGAGGCGCGCGGAAA<br>GTCGCGGACGCGGTTCCAGATGTTGCGCAGCGGCAAAAAGTGCTCCATGG<br>TCGGGACGCTCTGGCCGGTCAGGCGCGCGCAATCGTTGACGCTCTAGACC<br>GTGCAAAAGGAGAGCCTGTAAGCGGGCACTCTTCCGTGGTCTGGTGGATA<br>AATTCGCAAGGGTATCATGGCGGACGACCGGGGTTCGAGCCCCGTATCCG<br>GCCGTCCGCCGTGATCCATGCGGTTACCGCCCGCGTGTCGAACCCAGGTG<br>TGCGACGTCAGACAACGGGGGAGTGCTCCTTTTGGCTTCCTTCCAGGCGC<br>GGCGGCTGCTGCGCTAGCTTTTTTGGCCACTGGCCGCGCGCAGCGTAAGC<br>GGTTAGGCTGGAAAGCGAAAGCATTAAGTGGCTCGCTCCCTGTAGCCGGA<br>GGGTTATTTTCCAAGGGTTGAGTCGCGGGACCCCCGGTTCGAGTCTCGGA<br>CCGGCCGGACTGCGGCGAACGGGGGTTTGCCTCCCCGTCATGCAAGACC<br>CCGCTTGCAAATTCCTCCGGAAACAGGGACGAGCCCCTTTTTTGCTTTTCC<br>CAGATGCATCCGGTGCTGCGGCAGATGCGCCCCCCTCCTCAGCAGCGGCA<br>AGAGCAAGAGCAGCGGCAGACATGCAGGGCACCCTCCCCTCCTCCTACCG<br>CGTCAGGAGGGGCGACATCCGCGGTTGACGCGGCAGCAGATGGTGATTA |

-continued

| SEQ ID NO: | DESCRIPTION | SEQUENCE |
|---|---|---|
| | | CGAACCCCCGCGGCGCCGGGCCCGGCACTACCTGGACTTGGAGGAGGGC<br>GAGGGCCTGGCGCGGCTAGGAGCGCCCTCTCCTGAGCGGTACCCAAGGG<br>TGCAGCTGAAGCGTGATACGCGTGAGGCGTACGTGCCGCGGCAGAACCTG<br>TTTCGCGACCGCGAGGGAGAGGAGCCCGAGGAGATGCGGGATCGAAAGT<br>TCCACGCAGGGCGCGAGCTGCGGCATGGCCTGAATCGCGAGCGGTTGCT<br>GCGCGAGGAGGACTTTGAGCCCGACGCGCGAACCGGGATTAGTCCCGCG<br>CGCGCACACGTGGCGGCCGCCGACCTGGTAACCGCATACGAGCAGACGG<br>TGAACCAGGAGATTAACTTTCAAAAAAGCTTTAACAACCACGTGCGTACGCT<br>TGTGGCGCGCGAGGAGGTGGCTATAGGACTGATGCATCTGTGGGACTTTG<br>TAAGCGCGCTGGAGCAAAACCCAAATAGCAAGCCGCTCATGGCGCAGCTG<br>TTCCTTATAGTGCAGCACAGCAGGGACAACGAGGCATTCAGGGATGCGCT<br>GCTAAACATAGTAGAGCCCGAGGGCCGCTGGCTGCTCGATTTGATAAACAT<br>CCTGCAGAGCATAGTGGTGCAGGAGCGCAGCTTGAGCCTGGCTGACAAGG<br>TGGCCGCCATCAACTATTCCATGCTTAGCCTGGGCAAGTTTTACGCCCGCA<br>AGATATACCATACCCCTTACGTTCCCATAGACAAGGAGGTAAAGATCGAGG<br>GGTTCTACATGCGCATGGCGCTGAAGGTGCTTACCTTGAGCGACGACCTG<br>GGCGTTTATCGCAACGAGCGCATCCACAAGGCCGTGAGCGTGAGCCGGC<br>GGCGCGAGCTCAGCGACCGCGAGCTGATGCACAGCCTGCAAAGGGCCCT<br>GGCTGGCACGGGCAGCGGCGATAGAGAGGCCGAGTCCTACTTTGACGCG<br>GGCGCTGACCTGCGCTGGGCCCCAAGCCGACGCGCCCTGGAGGCAGCTG<br>GGGCCGGACCTGGGCTGGCGGTGGCACCCGCGCGCGCTGGCAACGTCG<br>GCGGCGTGGAGGAATATGACGAGGACGATGAGTACGAGCCAGAGGACGG<br>CGAGTACTAAGCGGTGATGTTTCTGATCAGATGATGCAAGACGCAACGGAC<br>CCGGCGGTGCGGGCGGCGCTGCAGAGCCAGCCGTCCGGCCTTAACTCCA<br>CGGACGACTGGCGCCAGGTCATGGACCGCATCATGTCGCTGACTGCGCGC<br>AATCCTGACGCGTTCCGGCAGCAGCCGCAGGCCAACCGGCTCTCCGCAAT<br>TCTGGAAGCGGTGGTCCCGGCGCGCGCAAACCCCACGCACGAGAAGGTG<br>CTGGCGATCGTAAACGCGCTGGCCGAAAACAGGGCCATCCGGCCCGACG<br>AGGCCGGCCTGGTCTACGACGCGCTGCTTCAGCGCGTGGCTCGTTACAAC<br>AGCGGCAACGTGCAGACCAACCTGGACCGGCTGGTGGGGGATGTGCGCG<br>AGGCCGTGGCGCAGCGTGAGCGCGCGCAGCAGCAGGGCAACCTGGGCTC<br>CATGGTTGCACTAAACGCCTTCCTGAGTACACAGCCCGCCAACGTGCCGC<br>GGGGACAGGAGGACTACACCAACTTTGTGAGCGCACTGCGGCTAATGGTG<br>ACTGAGACACCGCAAAGTGAGGTGTACCAGTCTGGGCCAGACTATTTTTTC<br>CAGACCAGTAGACAAGGCCTGCAGACCGTAAACCTGAGCCAGGCTTTCAA<br>AAACTTGCAGGGGCTGTGGGGGGTGCGGGCTCCCACAGGCGACCGCGCG<br>ACCGTGTCTAGCTTGCTGACGCCCAACTCGCGCCTGTTGCTGCTGCTAATA<br>GCGCCCTTCACGGACAGTGGCAGCGTGTCCCGGGACACATACCTAGGTCA<br>CTTGCTGACACTGTACCGCGAGGCCATAGGTCAGGCGCATGTGGACGAGC<br>ATACTTTCCAGGAGATTACAAGTGTCAGCCGCGCGCTGGGGCAGGAGGAC<br>ACGGGCAGCCTGGAGGCAACCCTAAACTACCTGCTGACCAACCGGCGGCA<br>GAAGATCCCCTCGTTGCACAGTTTAAACAGCGAGGAGGAGCGCATTTTGCG<br>CTACGTGCAGCAGAGCGTGAGCCTTAACCTGATGCGCGACGGGGTAACGC<br>CCAGCGTGGCGCTGGACATGACCGCGCGCAACATGGAACCGGGCATGTAT<br>GCCTCAAACCGGCCGTTTATCAACCGCCTAATGGACTACTTGCATCGCGCG<br>GCCGCCGTGAACCCCGAGTATTTCACCAATGCCATCTTGAACCCGCACTGG<br>CTACCGCCCCCTGGTTTCTACACCGGGGGATTCGAGGTGCCCGAGGGTAA<br>CGATGGATTCCTCTGGGACGACATAGACGACAGCGTGTTTTCCCCGCAACC<br>GCAGACCCTGCTAGAGTTGCAACAGCGCGAGCAGGCAGAGGCGGCGCTG<br>CGAAAGGAAAGCTTCCGCAGGCCAAGCAGCTTGTCCGATCTAGGCGCTGC<br>GGCCCCGCGGTCAGATGCTAGTAGCCCATTTCCAAGCTTGATAGGGTCTCT<br>TACCAGCACTCGCACCACCCGCCCGCGCCTGCTGGGCGAGGAGGAGTAC<br>CTAAACAACTCGCTGCTGCAGCCGCAGCGCGAAAAAAACCTGCCTCCGGC<br>ATTTCCCAACAACGGGATAGAGAGCCTAGTGGACAAGATGAGTAGATGGAA<br>GACGTACGCGCAGGAGCACAGGGACGTGCCAGGCCCGCGCCCGCCCACC<br>CGTCGTCAAAGGCACGACCGTCAGCGGGGTCTGGTGTGGGAGGACGATG<br>ACTCGGCAGACGACAGCAGCGTCCTGGATTTGGGAGGGAGTGGCAACCC<br>GTTTGCGCACCTTCGCCCCAGGCTGGGGAGAATGTTTTAAAAAAAAAAAAG<br>CATGATGCAAAATAAAAAACTCACCAAGGCCATGGCACCGAGCGTTGGTTT<br>TCTTGTATTCCCCTTAGTATGCGGCGCGCGGCGATGTATGAGGAAGGTCCT<br>CCTCCCTCCTACGAGAGTGTGGTGAGCGCGGCGCCAGTGGCGGCGGCGC<br>TGGGTTCTCCCTTCGATGCTCCCCTGGACCCGCCGTTTGTGCCTCCGCGG<br>TACCTGCGGCCTACCGGGGGGAGAAACAGCATCCGTTACTCTGAGTTGGC<br>ACCCCTATTCGACACCACCCGTGTGTACCTGGTGGACAACAAGTCAACGGA<br>TGTGGCATCCCTGAACTACCAGAACGACCACAGCAACTTTCTGACCACGGT<br>CATTCAAAACAATGACTACAGCCCGGGGGAGGCAAGCACACAGACCATCA<br>ATCTTGACGACCGGTCGCACTGGGGCGGCGACCTGAAAACCATCCTGCAT<br>ACCAACATGCCAAATGTGAACGAGTTCATGTTTACCAATAAGTTTAAGGCGC<br>GGGTGATGGTGTCGCGCTTGCCTACTAAGGACAATCAGGTGGAGCTGAAA<br>TACGAGTGGGTGGAGTTCACGCTGCCCGAGGGCAACTACTCCGAGACCAT<br>GACCATAGACCTTATGAACAACGCGATCGTGGAGCACTACTTGAAAGTGGG<br>CAGACAGAACGGGGTTCTGGAAAGCGACATCGGGGTAAAGTTTGACACCC<br>GCAACTTCAGACTGGGGTTTGACCCCGTCACTGGTCTTGTCATGCCTGGG<br>GTATATACAAACGAAGCCTTCCATCCAGACATCATTTTGCTGCCAGGATGC |

-continued

Sequences

| SEQ ID NO: | DESCRIPTION | SEQUENCE |
|---|---|---|
| | | GGGGTGGACTTCACCCACAGCCGCCTGAGCAACTTGTTGGGCATCCGCAA<br>GCGGCAACCCTTCCAGGAGGGCTTTAGGATCACCTACGATGATCTGGAGG<br>GTGGTAACATTCCCGCACTGTTGGATGTGGACGCCTACCAGGCGAGCTTG<br>AAAGATGACACCGAACAGGGCGGGGGTGGCGCAGGCGGCAGCAACAGCA<br>GTGGCAGCGGCGCGGAAGAGAACTCCAACGCGGCAGCCGCGGCAATGCA<br>GCCGGTGGAGGACATGAACGATCATGCCATTCGCGGCGACACCTTTGCCA<br>CACGGGCTGAGGAGAAGCGCGCTGAGGCCGAAGCAGCGGCCGAAGCTGC<br>CGCCCCCGCTGCGCAACCCGAGGTCGAGAAGCCTCAGAAGAAACCGGTG<br>ATCAAACCCCTGACAGAGGACAGCAAGAAACGCAGTTACAACCTAATAAGC<br>AATGACAGCACCTTCACCCAGTACCGCAGCTGGTACCTTGCATACAACTAC<br>GGCGACCCTCAGACCGGAATCCGCTCATGGACCCTGCTTTGCACTCCTGA<br>CGTAACCTGCGGCTCGGAGCAGGTCTACTGGTCGTTGCCAGACATGATGC<br>AAGACCCCGTGACCTTCCGCTCCACGCGCCAGATCAGCAACTTTCCGGTG<br>GTGGGCGCCGAGCTGTTGCCCGTGCACTCCAAGAGCTTCTACAACGACCA<br>GGCCGTCTACTCCCAACTCATCCGCCAGTTTACCTCTCTGACCCACGTGTT<br>CAATCGCTTTCCCGAGAACCAGATTTTGGCGCGCCCGCCAGCCCCCACCA<br>TCACCACCGTCAGTGAAAACGTTCCTGCTCTCACAGATCACGGGACGCTAC<br>CGCTGCGCAACAGCATCGGAGGAGTCCAGCGAGTGACCATTACTGACGCC<br>AGACGCCGCACCTGCCCCTACGTTTACAAGGCCCTGGGCATAGTCTCGCC<br>GCGCGTCCTATCGAGCCGCACTTTTTGAGCAAGCATGTCCATCCTTATATC<br>GCCCAGCAATAACACAGGCTGGGGCCTGCGCTTCCCAAGCAAGATGTTTG<br>GCGGGGCCAAGAAGCGCTCCGACCAACACCCAGTGCGCGTGCGCGGGCA<br>CTACCGCGCGCCCTGGGGCGCGCACAAACGCGGCCGCACTGGGCGCACC<br>ACCGTCGATGACGCCATCGACGCGGTGGTGGAGGAGGCGCGCAACTACA<br>CGCCCACGCCGCCACCAGTGTCCACAGTGGACGCGGCCATTCAGACCGTG<br>GTGCGCGGAGCCCGGCGCTATGCTAAAATGAAGAGACGGCGGAGGCGCG<br>TAGCACGTCGCCACCGCCGCCGACCCGGCACTGCCGCCCAACGCGCGGC<br>GGCGGCCCTGCTTAACCGCGCACGTCGCACCGGCCGACGGGCGGCCATG<br>CGGGCCGCTCGAAGGCTGGCCGCGGGTATTGTCACTGTGCCCCCCAGGT<br>CCAGGCGACGAGCGGCCGCCGCAGCAGCCGCGGCCATTAGTGCTATGAC<br>TCAGGGTCGCAGGGGCAACGTGTATTGGGTGCGCGACTCGGTTAGCGGC<br>CTGCGCGTGCCCGTGCGCACCCGCCCCCCGCGCAACTAGATTGCAAGAAA<br>AAACTACTTAGACTCGTACTGTTGTATGTATCCAGCGGCGGCGGCGCGCAA<br>CGAAGCTATGTCCAAGCGCAAAATCAAAGAAGAGATGCTCCAGGTCATCGC<br>GCCGGAGATCTATGGCCCCCCGAAGAAGGAAGAGCAGGATTACAAGCCCC<br>GAAAGCTAAAGCGGGTCAAAAAGAAAAAGAAAGATGATGATGATGAACTTG<br>ACGACGAGGTGGAACTGCTGCACGCTACCGCGCCCAGGCGACGGGTACA<br>GTGGAAAGGTCGACGCGTAAAACGTGTTTTGCGACCCGGCACCACCGTAG<br>TCTTTACGCCCGGTGAGCGCTCCACCCGCACCTACAAGCGCGTGTATGAT<br>GAGGTGTACGGCGACGAGGACCTGCTTGAGCAGGCCAACGAGCGCCTCG<br>GGGAGTTTGCCTACGGAAAGCGGCATAAGGACATGCTGGCGTTGCCGCTG<br>GACGAGGGCAACCCAACACCTAGCCTAAAGCCCGTAACACTGCAGCAGGT<br>GCTGCCCGCGCTTGCACCGTCCGAAGAAAAGCGCGGCCTAAAGCGCGAGT<br>CTGGTGACTTGGCACCCACCGTGCAGCTGATGGTACCCAAGCGCCAGCGA<br>CTGGAAGATGTCTTGGAAAAAATGACCGTGGAACCTGGGCTGGAGCCCGA<br>GGTCCGCGTGCGGCCAATCAAGCAGGTGGCGCCGGGACTGGGCGTGCAG<br>ACCGTGGACGTTCAGATACCCACTACCAGTAGCACCAGTATTGCCACCGCC<br>ACAGAGGGCATGGAGACACAAACGTCCCCGGTTGCCTCAGCGGTGGCGG<br>ATGCCGCGGTGCAGGCGGTCGCTGCGGCCGCGTCCAAGACCTCTACGGA<br>GGTGCAAACGGACCCGTGGATGTTTCGCGTTTCAGCCCCCCGGCGCCCGC<br>GCGGTTCGAGGAAGTACGGCGCCGCCAGCGCGCTACTGCCCGAATATGC<br>CCTACATCCTTCCATTGCGCCTACCCCCGGCTATCGTGGCTACACCTACCG<br>CCCCAGAAGACGAGCAACTACCCGACGCCGAACCACCACTGGAACCCGCC<br>GCCGCCGTCGCCGTCGCCAGCCCGTGCTGGCCCCGATTTCCGTGCGCAG<br>GGTGGCTCGCGAAGGAGGCAGGACCCTGGTGCTGCCAACAGCGCGCTAC<br>CACCCCAGCATCGTTTAAAAGCCGGTCTTTGTGGTTCTTGCAGATATGGCC<br>CTCACCTGCCGCCTCCGTTTCCCGGTGCCGGGATTCCGAGGAAGAATGCA<br>CCGTAGGAGGGGCATGGCCGGCCACGGCCTGACGGGCGGCATGCGTCGT<br>GCGCACCACCGGCGGCGGCGCGCGTCGCACCGTCGCATGCGCGGCGGT<br>ATCCTGCCCCTCCTTATTCCACTGATCGCCGCGGCGATTGGCGCCGTGCC<br>CGGAATTGCATCCGTGGCCTTGCAGGCGCAGAGACACTGATTAAAAACAAG<br>TTGCATGTGGAAAAATCAAAATAAAAAGTCTGGACTCTCACGCTCGCTTGGT<br>CCTGTAACTATTTTGTAGAATGGAAGACATCAACTTTGCGTCTCTGGCCCCG<br>CGACACGGCTCGCGCCCGTTCATGGGAAACTGGCAAGATATCGGCACCAG<br>CAATATGAGCGGTGGCGCCTTCAGCTGGGGCTCGCTGTGGAGCGGCATTA<br>AAAATTTCGGTTCCACCGTTAAGAACTATGGCAGCAAGGCCTGGAACAGCA<br>GCACAGGCCAGATGCTGAGGGATAAGTTGAAAGAGCAAAATTTCCAACAAA<br>AGGTGGTAGATGGCCTGGCCTCTGGCATTAGCGGGGTGGTGGACCTGGC<br>CAACCAGGCAGTGCAAAATAAGATTAACAGTAAGCTTGATCCCCGCCCTCC<br>CGTAGAGGAGCCTCCACCGGCCGTGGAGACAGTGTCTCCAGAGGGGCGT<br>GGCGAAAAGCGTCCGCGCCCCGACAGGGAAGAAACTCTGGTGACGCAAAT<br>AGACGAGCCTCCCTCGTACGAGGAGGCACTAAAGCAAGGCCTGCCCACCA<br>CCCGTCCCATCGCGCCCATGGCTACCGGAGTGCTGGGCCAGCACACACCC<br>GTAACGCTGGACCTGCCTCCCCCCGCCGACACCCAGCAGAAACCTGTGCT |

-continued

Sequences

| SEQ ID NO: | DESCRIPTION | SEQUENCE |
|---|---|---|
| | | GCCAGGCCCGACCGCCGTTGTTGTAACCCGTCCTAGCCGCGCGTCCCTGC<br>GCCGCGCCGCCAGCGGTCCGCGATCGTTGCGGCCCGTAGCCAGTGGCAA<br>CTGGCAAAGCACACTGAACAGCATCGTGGGTCTGGGGGTGCAATCCCTGA<br>AGCGCCGACGATGCTTCTGAATAGCTAACGTGTCGTATGTGTGTCATGTAT<br>GCGTCCATGTCGCCGCCAGAGGAGCTGCTGAGCCGCCGCGCGCCCGCTT<br>TCCAAGATGGCTACCCCTTCGATGATGCCGCAGTGGTCTTACATGCACATC<br>TCGGGCCAGGACGCCTCGGAGTACCTGAGCCCCGGGCTGGTGCAGTTTG<br>CCCGCGCCACCGAGACGTACTTCAGCCTGAATAACAAGTTTAGAAACCCCA<br>CGGTGGCGCCTACGCACGACGTGACCACAGACCGGTCCCAGCGTTTGACG<br>CTGCGGTTCATCCCTGTGGACCGTGAGGATACTGCGTACTCGTACAAGGC<br>GCGGTTCACCCTAGCTGTGGGTGATAACCGTGTGCTGGACATGGCTTCCA<br>CGTACTTTGACATCCGCGGCGTGCTGGACAGGGGCCCTACTTTTAAGCCCT<br>ACTCTGGCACTGCCTACAACGCCCTGGCTCCCAAGGGTGCCCCAAATCCTT<br>GCGAATGGGATGAAGCTGCTACTGCTCTTGAAATAAACCTAGAAGAAGAGG<br>ACGATGACAACGAAGACGAAGTAGACGAGCAAGCTGAGCAGCAAAAAACT<br>CACGTATTTGGGCAGGCGCCTTATTCTGGTATAAATATTACAAAGGAGGGT<br>ATTCAAATAGGTGTCGAAGGTCAAACACCTAAATATGCCGATAAAACATTTC<br>AACCTGAACCTCAAATAGGAGAATCTCAGTGGTACGAAACTGAAATTAATCA<br>TGCAGCTGGGAGAGTCCTTAAAAAGACTACCCCAATGAAACCATGTTACGG<br>TTCATATGCAAAACCCACAAATGAAAATGGAGGGCAAGGCATTCTTGTAAA<br>GCAACAAAATGGAAAGCTAGAAAGTCAAGTGGAAATGCAATTTTTCTCAACT<br>ACTGAGGCGACCGCAGGCAATGGTGATAACTTGACTCCTAAAGTGGTATTG<br>TACAGTGAAGATGTAGATATAGAAACCCCAGACACTCATATTTCTTACATGC<br>CCACTATTAAGGAAGGTAACTCACGAGAACTAATGGGCCAACAATCTATGC<br>CCAACAGGCCTAATTACATTGCTTTTAGGGACAATTTTATTGGTCTAATGTAT<br>TACAACAGCACGGGTAATATGGGTGTTCTGGCGGGCCAAGCATCGCAGTT<br>GAATGCTGTTGTAGATTTGCAAGACAGAAACACAGAGCTTTCATACCAGCTT<br>TTGCTTGATTCCATTGGTGATAGAACCAGGTACTTTTCTATGTGGAATCAGG<br>CTGTTGACAGCTATGATCCAGATGTTAGAATTATTGAAAATCATGGAACTGA<br>AGATGAACTTCCAAATTACTGCTTTCCACTGGGAGGTGTGATTAATACAGAG<br>ACTCTTACCAAGGTAAAACCTAAAACAGGTCAGGAAAATGGATGGGAAAAA<br>GATGCTACAGAATTTTCAGATAAAAATGAAATAAGAGTTGGAAATAATTTTG<br>CCATGGAAATCAATCTAAATGCCAACCTGTGGAGAAATTTCCTGTACTCCAA<br>CATAGCGCTGTATTTGCCCGACAAGCTAAAGTACAGTCCTTCCAACGTAAA<br>AATTTCTGATAACCCAAACACCTACGACTACATGAACAAGCGAGTGGTGGC<br>TCCCGGGTTAGTGGACTGCTACATTAACCTTGGAGCACGCTGGTCCCTTGA<br>CTATATGGACAACGTCAACCCATTTAACCACCACCGCAATGCTGGCCTGCG<br>CTACCGCTCAATGTTGCTGGGCAATGGTCGCTATGTGCCCTTCCACATCCA<br>GGTGCCTCAGAAGTTCTTTGCCATTAAAAACCTCCTTCTCCTGCCGGGCTC<br>ATACACCTACGAGTGGAACTTCAGGAAGGATGTTAACATGGTTCTGCAGAG<br>CTCCCTAGGAAATGACCTAAGGGTTGACGGAGCCAGCATTAAGTTTGATAG<br>CATTTGCCTTTACGCCACCTTCTTCCCCATGGCCCACAACACCGCCTCCAC<br>GCTTGAGGCCATGCTTAGAAACGACACCAACGACCAGTCCTTTAACGACTA<br>TCTCTCCGCCGCCAACATGCTCTACCCTATACCCGCCAACGCTACCAACGT<br>GCCCATATCCATCCCCTCCCGCAACTGGGCGGCTTTCCGCGGCTGGGCCT<br>TCACGCGCCTTAAGACTAAGGAAACCCCATCACTGGGCTCGGGCTACGAC<br>CCTTATTACACCTACTCTGGCTCTATACCCTACCTAGATGGAACCTTTTACC<br>TCAACCACACCTTTAAGAAGGTGGCCATTACCTTTGACTCTTCTGTCAGCTG<br>GCCTGGCAATGACCGCCTGCTTACCCCCAACGAGTTTGAAATTAAGCGCTC<br>AGTTGACGGGGAGGGTTACAACGTTGCCCAGTGTAACATGACCAAAGACT<br>GGTTCCTGGTACAAATGCTAGCTAACTACAACATTGGCTACCAGGGCTTCT<br>ATATCCCAGAGAGCTACAAGGACCGCATGTACTCCTTCTTTAGAAACTTCCA<br>GCCCATGAGCCGTCAGGTGGTGGATGATACTAAATACAAGGACTACCAACA<br>GGTGGGCATCCTACACCAACACAACAACTCTGGATTTGTTGGCTACCTTGC<br>CCCCACCATGCGCGAAGGACAGGCCTACCCTGCTAACTTCCCCTATCCGC<br>TTATAGGCAAGACCGCAGTTGACAGCATTACCCAGAAAAAGTTTCTTTGCG<br>ATCGCACCCTTTGGCGCATCCCATTCTCCAGTAACTTTATGTCCATGGGCG<br>CACTCACAGACCTGGGCCAAAACCTTCTCTACGCCAACTCCGCCCACGCG<br>CTAGACATGACTTTTGAGGTGGATCCCATGGACGAGCCCACCCTTCTTTAT<br>GTTTTGTTTGAAGTCTTTGACGTGGTCCGTGTGCACCGGCCGCACCGCGG<br>CGTCATCGAAACCGTGTACCTGCGCACGCCCTTCTCGGCCGGCAACGCCA<br>CAACATAAAGAAGCAAGCAACATCAACAACAGCTGCCGCCATGGGCTCCAG<br>TGAGCAGGAACTGAAAGCCATTGTCAAAGATCTTGGTTGTGGGCCATATTT<br>TTTGGGCACCTATGACAAGCGCTTTCCAGGCTTTGTTTCTCCACACAAGCT<br>CGCCTGCGCCATAGTCAATACGGCCGGTCGCGAGACTGGGGGCGTACACT<br>GGATGGCCTTTGCCTGGAACCCGCACTCAAAAACATGCTACCTCTTTGAGC<br>CCTTTGGCTTTTCTGACCAGCGACTCAAGCAGGTTTACCAGTTTGAGTACG<br>AGTCACTCCTGCGCCGTAGCGCCATTGCTTCTTCCCCCGACCGCTGTATAA<br>CGCTGGAAAAGTCCACCCAAAGCGTACAGGGGCCCAACTCGGCCGCCTGT<br>GGACTATTCTGCTGCATGTTTCTCCACGCCTTTGCCAACTGGCCCCAAACT<br>CCCATGGATCACAACCCCACCATGAACCTTATTACCGGGGTACCCAACTCC<br>ATGCTCAACAGTCCCCAGGTACAGCCCACCCTGCGTCGCAACCAGGAACA<br>GCTCTACAGCTTCCTGGAGCGCCACTCGCCCTACTTCCGCAGCCACAGTG<br>CGCAGATTAGGAGCGCCACTTCTTTTTGTCACTTGAAAAACATGTAAAAATA |

-continued

| Sequences | | |
|---|---|---|
| SEQ ID NO: | DESCRIPTION | SEQUENCE |
| | | ATGTACTAGAGACACTTTCAATAAAGGCAAATGCTTTTATTTGTACACTCTC GGGTGATTATTTACCCCCACCCTTGCCGTCTGCGCCGTTTAAAAATCAAAG GGGTTCTGCCGCGCATCGCTATGCGCCACTGGCAGGGACACGTTGCGATA CTGGTGTTTAGTGCTCCACTTAAACTCAGGCACAACCATCCGCGGCAGCTC GGTGAAGTTTTCACTCCACAGGCTGCGCACCATCACCAACGCGTTTAGCAG GTCGGGCGCCGATATCTTGAAGTCGCAGTTGGGGCCTCCGCCCTGCGCGC GCGAGTTGCGATACACAGGGTTGCAGCACTGGAACACTATCAGCGCCGGG TGGTGCACGCTGGCCAGCACGCTCTTGTCGGAGATCAGATCCGCGTCCAG GTCCTCCGCGTTGCTCAGGGCGAACGGAGTCAACTTTGGTAGCTGCCTTC CCAAAAAGGGCGCGTGCCCAGGCTTTGAGTTGCACTCGCACCGTAGTGGC ATCAAAAGGTGACCGTGCCCGGTCTGGGCGTTAGGATACAGCGCCTGCAT AAAAGCCTTGATCTGCTTAAAAGCCACCTGAGCCTTTGCGCCTTCAGAGAA GAACATGCCGCAAGACTTGCCGGAAAACTGATTGGCCGGACAGGCCGCGT CGTGCACGCAGCACCTTGCGTCGGTGTTGGAGATCTGCACCACATTTCGG CCCCACCGGTTCTTCACGATCTTGGCCTTGCTAGACTGCTCCTTCAGCGCG CGCTGCCCGTTTTCGCTCGTCACATCCATTTCAATCACGTGCTCCTTATTTA TCATAATGCTTCCGTGTAGACACTTAAGCTCGCCTTCGATCTCAGCGCAGC GGTGCAGCCACAACGCGCAGCCCGTGGGCTCGTGATGCTTGTAGGTCACC TCTGCAAACGACTGCAGGTACGCCTGCAGGAATCGCCCCATCATCGTCACA AAGGTCTTGTTGCTGGTGAAGGTCAGCTGCAACCCGCGGTGCTCCTCGTT CAGCCAGGTCTTGCATACGGCCGCCAGAGCTTCCACTTGGTCAGGCAGTA GTTTGAAGTTCGCCTTTAGATCGTTATCCACGTGGTACTTGTCCATCAGCGC GCGCGCAGCCTCCATGCCCTTCTCCCACGCAGACACGATCGGCACACTCA GCGGGTTCATCACCGTAATTTCACTTTCCGCTTCGCTGGGCTCTTCCTCTTC CTCTTGCGTCCGCATACCACGCGCCACTGGGTCGTCTTCATTCAGCCGCC GCACTGTGCGCTTACCTCCTTTGCCATGCTTGATTAGCACCGGTGGGTTGC TGAAACCCACCATTTGTAGCGCCACATCTTCTCTTTCTTCCTCGCTGTCCAC GATTACCTCTGGTGATGGCGGGCGCTCGGGCTTGGGAGAAGGGCGCTTCT TTTTCTTCTTGGGCGCAATGGCCAAATCCGCCGCCGAGGTCGATGGCCGC GGGCTGGGTGTGCGCGGCACCAGCGCGTCTTGTGATGAGTCTTCCTCGTC CTCGGACTCGATACGCCGCCTCATCCGCTTTTTTGGGGGCGCCCGGGGAG GCGGCGGCGACGGGGACGGGGACGACACGTCCTCCATGGTTGGGGGAC GTCGCGCCGCACCGCGTCCGCGCTCGGGGGTGGTTTCGCGCTGCTCCTC TTCCCGACTGGCCATTTCCTTCTCCTATAGGCAGAAAAAGATCATGGAGTC AGTCGAGAAGAAGGACAGCCTAACCGCCCCCTCTGAGTTCGCCACCACCG CCTCCACCGATGCCGCCAACGCGCCTACCACCTTCCCCGTCGAGGCACCC CCGCTTGAGGAGGAGGAAGTGATTATCGAGCAGGACCCAGGTTTTGTAAG CGAAGACGACGAGGACCGCTCAGTACCAACAGAGGATAAAAAGCAAGACC AGGACAACGCAGAGGCAAACGAGGAACAAGTCGGGCGGGGGGACGAAAG GCATGGCGACTACCTAGATGTGGGAGACGACGTGCTGTTGAAGCATCTGC AGCGCCAGTGCGCCATTATCTGCGACGCGTTGCAAGAGCGCAGCGATGTG CCCCTCGCCATAGCGGATGTCAGCCTTGCCTACGAACGCCACCTATTCTCA CCGCGCGTACCCCCCAAACGCCAAGAAAACGGCACATGCGAGCCCAACCC GCGCCTCAACTTCTACCCCGTATTTGCCGTGCCAGAGGTGCTTGCCACCTA TCACATCTTTTTCCAAAACTGCAAGATACCCCTATCCTGCCGTGCCAACCGC AGCCGAGCGGACAAGCAGCTGGCCTTGCGGCAGGGCGCTGTCATACCTG ATATCGCCTCGCTCAACGAAGTGCCAAAAATCTTTGAGGGTCTTGGACGCG ACGAGAAGCGCGCGGCAAACGCTCTGCAACAGGAAAACAGCGAAAATGAA AGTCACTCTGGAGTGTTGGTGGAACTCGAGGGTGACAACGCGCGCCTAGC CGTACTAAAACGCAGCATCGAGGTCACCCACTTTGCCTACCCGGCACTTAA CCTACCCCCCAAGGTCATGAGCACAGTCATGAGTGAGCTGATCGTGCGCC GTGCGCAGCCCCTGGAGAGGGATGCAAATTTGCAAGAACAAACAGAGGAG GGCCTACCCGCAGTTGGCGACGAGCAGCTAGCGCGCTGGCTTCAAACGC GCGAGCCTGCCGACTTGGAGGAGCGACGCAAACTAATGATGGCCGCAGTG CTCGTTACCGTGGAGCTTGAGTGCATGCAGCGGTTCTTTGCTGACCCGGA GATGCAGCGCAAGCTAGAGGAAACATTGCACTACACCTTTCGACAGGGCTA CGTACGCCAGGCCTGCAAGATCTCCAACGTGGAGCTCTGCAACCTGGTCT CCTACCTTGGAATTTTGCACGAAAACCGCCTTGGGCAAAACGTGCTTCATT CCACGCTCAAGGGCGAGGCGCGCCGCGACTACGTCCGCGACTGCGTTTA CTTATTTCTATGCTACACCTGGCAGACGGCCATGGGCGTTTGGCAGCAGTG CTTGGAGGAGTGCAACCTCAAGGAGCTGCAGAAACTGCTAAAGCAAAACTT GAAGGACCTATGGACGGCCTTCAACGAGCGCTCCGTGGCCGCGCACCTG GCGGACATCATTTTCCCCGAACGCCTGCTTAAAACCCTGCAACAGGGTCTG CCAGACTTCACCAGTCAAAGCATGTTGCAGAACTTTAGGAACTTTATCCTAG AGCGCTCAGGAATCTTGCCCGCCACCTGCTGTGCACTTCCTAGCGACTTTG TGCCCATTAAGTACCGCGAATGCCCTCCGCCGCTTTGGGGCCACTGCTAC CTTCTGCAGCTAGCCAACTACCTTGCCTACCACTCTGACATAATGGAAGAC GTGAGCGGTGACGGTCTACTGGAGTGTCACTGTCGCTGCAACCTATGCAC CCCGCACCGCTCCCTGGTTTGCAATTCGCAGCTGCTTAACGAAAGTCAAAT TATCGGTACCTTTGAGCTGCAGGGTCCCTCGCCTGACGAAAAGTCCGCGG CTCCGGGGTTGAAACTCACTCCGGGGCTGTGGACGTCGGCTTACCTTCGC AAATTTGTACCTGAGGACTACCACGCCCACGAGATTAGGTTCTACGAAGAC CAATCCCGCCCGCCAAATGCGGAGCTTACCGCCTGCGTCATTACCCAGGG CCACATTCTTGGCCAATTGCAAGCCATCAACAAAGCCCGCCAAGAGTTTCT |

-continued

Sequences

| SEQ ID NO: | DESCRIPTION | SEQUENCE |
|---|---|---|
| | | GCTACGAAAGGGACGGGGGGTTTACTTGGACCCCCAGTCCGGCGAGGAG<br>CTCAACCCAATCCCCCCGCCGCCGCAGCCCTATCAGCAGCAGCCGCGGG<br>CCCTTGCTTCCCAGGATGGCACCCAAAAAGAAGCTGCAGCTGCCGCCGCC<br>ACCCACGGACGAGGAGGAATACTGGGACAGTCAGGCAGAGGAGGTTTTGG<br>ACGAGGAGGAGGAGGACATGATGGAAGACTGGGAGAGCCTAGACGAGGA<br>AGCTTCCGAGGTCGAAGAGGTGTCAGACGAAACACCGTCACCCTCGGTCG<br>CATTCCCCTCGCCGGCGCCCCAGAAATCGGCAACCGGTTCCAGCATGGCT<br>ACAACCTCCGCTCCTCAGGCGCCGCCGGCACTGCCCGTTCGCCGACCCAA<br>CCGTAGATGGGACACCACTGGAACCAGGGCCGGTAAGTCCAAGCAGCCGC<br>CGCCGTTAGCCCAAGAGCAACAACAGCGCCAAGGCTACCGCTCATGGCGC<br>GGGCACAAGAACGCCATAGTTGCTTGCTTGCAAGACTGTGGGGGCAACAT<br>CTCCTTCGCCCGCCGCTTTCTTCTCTACCATCACGGCGTGGCCTTCCCCCG<br>TAACATCCTGCATTACTACCGTCATCTCTACAGCCCATACTGCACCGGCGG<br>CAGCGGCAGCGGCAGCAACAGCAGCGGCCACACAGAAGCAAAGGCGACC<br>GGATAGCAAGACTCTGACAAAGCCCAAGAAATCCACAGCGGCGGCAGCAG<br>CAGGAGGAGGAGCGCTGCGTCTGGCGCCCAACGAACCCGTATCGACCCG<br>CGAGCTTAGAAACAGGATTTTTCCCACTCTGTATGCTATATTTCAACAGAGC<br>AGGGGCCAAGAACAAGAGCTGAAAATAAAAAACAGGTCTCTGCGATCCCTC<br>ACCCGCAGCTGCCTGTATCACAAAAGCGAAGATCAGCTTCGGCGCACGCT<br>GGAAGACGCGGAGGCTCTCTTCAGTAAATACTGCGCGCTGACTCTTAAGGA<br>CTAGTTTCGCGCCCTTTCTCAAATTTAAGCGCGAAAACTACGTCATCTCCAG<br>CGGCCACACCCGGCGCCAGCACCTGTCGTCAGCGCCATTATGAGCAAGGA<br>AATTCCCACGCCCTACATGTGGAGTTACCAGCCACAAATGGGACTTGCGGC<br>TGGAGCTGCCCAAGACTACTCAACCCGAATAAACTACATGAGCGCGGGAC<br>CCCACATGATATCCCGGGTCAACGGAATCCGCGCCCACCGAAACCGAATT<br>CTCTTGGAACAGGCGGCTATTACCACCACACCTCGTAATAACCTTAATCCC<br>CGTAGTTGGCCCGCTGCCCTGGTGTACCAGGAAAGTCCCGCTCCCACCAC<br>TGTGGTACTTCCCAGAGACGCCCAGGCCGAAGTTCAGATGACTAACTCAG<br>GGGCGCAGCTTGCGGGCGGCTTTCGTCACAGGGTGCGGTCGCCCGGGCA<br>GGGTATAACTCACCTGACAATCAGAGGGCGAGGTATTCAGCTCAACGACGA<br>GTCGGTGAGCTCCTCGCTTGGTCTCCGTCCGGACGGGACATTTCAGATCG<br>GCGGCGCCGGCCGCTCTTCATTCACGCCTCGTCAGGCAATCCTAACTCTG<br>CAGACCTCGTCCTCTGAGCCGCGCTCTGGAGGCATTGGAACTCTGCAATTT<br>ATTGAGGAGTTTGTGCCATCGGTCTACTTTAACCCCTTCTCGGGACCTCCC<br>GGCCACTATCCGGATCAATTTATTCCTAACTTTGACGCGGTAAAGGACTCG<br>GCGGATGGCTACGACTGAATGTTAAGTGGAGAGGCAGAGCAACTGCGCCT<br>GAAACACCTGGTCCACTGTCGCCGCCACAAGTGCTTTGCCCGCGACTCCG<br>GTGAGTTTTGCTACTTTGAATTGCCCGAGGATCATATCGAGGGCCCGGCGC<br>ACGGCGTCCGGCTTACCGCCCAGGGAGAGCTTGCCCGTAGCCTGATTCGG<br>GAGTTTACCCAGCGCCCCCTGCTAGTTGAGCGGGACAGGGGACCCTGTGT<br>TCTCACTGTGATTTGCAACTGTCCTAACCCTGGATTACATCAAGATCTTTGT<br>TGCCATCTCTGTGCTGAGTATAATAAATACAGAAATTAAAATATACTGGGGC<br>TCCTATCGCCATCCTGTAAACGCCACCGTCTTCACCCGCCCAAGCAAACCA<br>AGGCGAACCTTACCTGGTACTTTTAACATCTCTCCCTCTGTGATTTACAACA<br>GTTTCAACCCAGACGGAGTGAGTCTACGAGAGAACCTCTCCGAGCTCAGCT<br>ACTCCATCAGAAAAAACACCACCCTCCTTACCTGCCGGGAACGTACGACCT<br>AGGGATAACAGGGTAATAAGCAATTGACTCTATGTGGGATATGCTCCAGCG<br>CTACAACCTTGAAGTCAGGCTTCCTGGATGTCAGCATCTGACTTTGGCCAG<br>CACCTGTCCCGCGGATTTGTTCCAGTCCAACTACAGCGACCCACCCTAACA<br>GAGATGACCAACACAACCAACGCGGCCGCCGCTACCGGACTTACATCTAC<br>CACAAATACACCCCAAGTTTCTGCCTTTGTCAATAACTGGGATAACTTGGGC<br>ATGTGGTGGTTCTCCATAGCGCTTATGTTTGTATGCCTTATTATTATGTGGC<br>TCATCTGCTGCCTAAAGCGCAAACGCGCCCGACCACCCATCTATAGTCCCA<br>TCATTGTGCTACACCCAAACAATGATGGAATCCATAGATTGGACGGACTGA<br>AACACATGTTCTTTTCTCTTACAGTATGATTAAATGAGACATGATTCCTCGAG<br>TTTTTATATTACTGACCCTTGTTGCGCTTTTTTGTGCGTGCTCCACATTGGCT<br>GCGGTTTCTCACATCGAAGTAGACTGCATTCCAGCCTTCACAGTCTATTTGC<br>TTTACGGATTTGTCACCCTCACGCTCATCTGCAGCCTCATCACTGTGGTCAT<br>CGCCTTTATCCAGTGCATTGACTGGGTCTGTGTGCGCTTTGCATATCTCAG<br>ACACCATCCCCAGTACAGGGACAGGACTATAGCTGAGCTTCTTAGAATTCT<br>TTAATTATGAAATTTACTGTGACTTTTCTGCTGATTATTTGCACCCTATCTGC<br>GTTTTGTTCCCCGACCTCCAAGCCTCAAAGACATATATCATGCAGATTCACT<br>CGTATATGGAATATTCCAAGTTGCTACAATGAAAAAAGCGATCTTTCCGAAG<br>CCTGGTTATATGCAATCATCTCTGTTATGGTGTTCTGCAGTACCATCTTAGC<br>CCTAGCTATATATCCCTACCTTGACATTGGCTGGAAACGAATAGATGCCATG<br>AACCACCCAACTTTCCCCGCGCCCGCTATGCTTCCACTGCAACAAGTTGTT<br>GCCGGCGGCTTTGTCCCAGCCAATCAGCCTCGCCCCACTTCTCCCACCCC<br>CACTGAAATCAGCTACTTTAATCTAACAGGAGGAGATGACTGACACCCTAG<br>ATCTAGAAATGGACGGAATTATTACAGAGCAGCGCCTGCTAGAAAGACGCA<br>GGGCAGCGGCCGAGCAACAGCGCATGAATCAAGAGCTCCAAGACATGGTT<br>AACTTGCACCAGTGCAAAAGGGGTATCTTTTGTCTGGTAAAGCAGGCCAAA<br>GTCACCTACGACAGTAATACCACCGGACACCGCCTTAGCTACAAGTTGCCA<br>ACCAAGCGTCAGAAATTGGTGGTCATGGTGGGAGAAAAGCCCATTACCATA<br>ACTCAGCACTCGGTAGAAACCGAAGGCTGCATTCACTCACCTTGTCAAGGA |

-continued

Sequences

| SEQ ID NO: | DESCRIPTION | SEQUENCE |
|---|---|---|
| | | CCTGAGGATCTCTGCACCCTTATTAAGACCCTGTGCGGTCTCAAAGATCTT<br>ATTCCCTTTAACTAATAAAAAAAAATAATAAAGCATCACTTACTTAAAATCAG<br>TTAGCAAATTTCTGTCCAGTTTATTCAGCAGCACCTCCTTGCCCTCCTCCCA<br>GCTCTGGTATTGCAGCTTCCTCCTGGCTGCAAACTTTCTCCACAATCTAAAT<br>GGAATGTCAGTTTCCTCCTGTTCCTGTCCATCCGCACCCACTATCTTCATGT<br>TGTTGCAGATGAAGCGCGCAAGACCGTCTGAAGATACCTTCAACCCCGTGT<br>ATCCATATGACACGGAAACCGGTCCTCCAACTGTGCCTTTTCTTACTCCTCC<br>CTTTGTATCCCCCAATGGGTTTCAAGAGAGTCCCCCTGGGGTACTCTCTTT<br>GCGCCTATCCGAACCTCTAGTTACCTCCAATGGCATGCTTGCGCTCAAAAT<br>GGGCAACGGCCTCTCTCTGGACGAGGCCGGCAACCTTACCTCCCAAAATG<br>TAACCACTGTGAGCCCACCTCTCAAAAAAACCAAGTCAAACATAAACCTGG<br>AAATATCTGCACCCCTCACAGTTACCTCAGAAGCCCTAACTGTGGCTGCCG<br>CCGCACCTCTAATGGTCGCGGGCAACACACTCACCATGCAATCACAGGCC<br>CCGCTAACCGTGCACGACTCCAAACTTAGCATTGCCACCCAAGGACCCCTC<br>ACAGTGTCAGAAGGAAAGCTAGCCCTGCAAACATCAGGCCCCCTCACCAC<br>CACCGATAGCAGTACCCTTACTATCACTGCCTCACCCCCTCTAACTACTGC<br>CACTGGTAGCTTGGGCATTGACTTGAAAGAGCCCATTTATACACAAAATGG<br>AAAACTAGGACTAAAGTACGGGGCTCCTTTGCATGTAACAGACGACCTAAA<br>CACTTTGACCGTAGCAACTGGTCCAGGTGTGACTATTAATAATACTTCCTTG<br>CAAACTAAAGTTACTGGAGCCTTGGGTTTTGATTCACAAGGCAATATGCAAC<br>TTAATGTAGCAGGAGGACTAAGGATTGATTCTCAAAACAGACGCCTTATACT<br>TGATGTTAGTTATCCGTTTGATGCTCAAAACCAACTAAATCTAAGACTAGGA<br>CAGGGCCCTCTTTTTATAAACTCAGCCCACAACTTGGATATTAACTACAACA<br>AAGGCCTTTACTTGTTTACAGCTTCAAACAATTCCAAAAAGCTTGAGGTTAA<br>CCTAAGCACTGCCAAGGGGTTGATGTTTGACGCTACAGCCATAGCCATTAA<br>TGCAGGAGATGGGCTTGAATTTGGTTCACCTAATGCACCAAACACAAATCC<br>CCTCAAAACAAAAATTGGCCATGGCCTAGAATTTGATTCAAACAAGGCTATG<br>GTTCCTAAACTAGGAACTGGCCTTAGTTTTGACAGCACAGGTGCCATTACA<br>GTAGGAAACAAAAATAATGATAAGCTAACCCTATGGACAGGTCCAAAACCA<br>GAAGCCAACTGCATAATTGAATACGGGAAACAAAACCCAGATAGCAAACTA<br>ACTTTAATCCTTGTAAAAAATGGAGGAATTGTTAATGGATATGTAACGCTAAT<br>GGGAGCCTCAGACTACGTTAACACCTTATTTAAAAACAAAAATGTCTCCATT<br>AATGTAGAACTATACTTTGATGCCACTGGTCATATATTACCAGACTCATCTT<br>CTCTTAAAACAGATCTAGAACTAAAATACAAGCAAACCGCTGACTTTAGTGC<br>AAGAGGTTTTATGCCAAGTACTACAGCGTATCCATTTGTCCTTCCTAATGCG<br>GGAACACATAATGAAAATTATATTTTTGGTCAATGCTACTACAAAGCAAGCG<br>ATGGTGCCCTTTTTCCGTTGGAAGTTACTGTTATGCTTAATAAACGCCTGCC<br>AGATAGTCGCACATCCTATGTTATGACTTTTTTATGGTCCTTGAATGCTGGT<br>CTAGCTCCAGAAACTACTCAGGCAACCCTCATAACCTCCCCATTTACCTTTT<br>CCTATATTAGAGAAGATGACTAATAAACTCTAAAGAATCGTTTGTGTTATGTT<br>TCAACGTGTTTATTTTTCAATTGCAGAAAATTTCAAGTCATTTTTCATTCAGT<br>AGTATAGCCCCACCACCACATAGCTTATACAGATCACCGTACCTTAATCAAA<br>CTCACAGAACCCTAGTATTCAACCTGCCACCTCCCTCCCAACACACAGAGT<br>ACACAGTCCTTTCTCCCCGGCTGGCCTTAAAAAGCATCATATCATGGGTAA<br>CAGACATATTCTTAGGTGTTATATTCCACACGGTTTCCTGTCGAGCCAAACG<br>CTCATCAGTGATATTAATAAACTCCCCGGGCAGCTCACTTAAGTTCATGTCG<br>CTGTCCAGCTGCTGAGCCACAGGCTGCTGTCCAACTTGCGGTTGCTTAACG<br>GGCGGCGAAGGAGAAGTCCACGCCTACATGGGGGTAGAGTCATAATCGTG<br>CATCAGGATAGGGCGGTGGTGCTGCAGCAGCGCGCGAATAAACTGCTGCC<br>GCCGCCGCTCCGTCCTGCAGGAATACAACATGGCAGTGGTCTCCTCAGCG<br>ATGATTCGCACCGCCCGCAGCATAAGGCGCCTTGTCCTCCGGGCACAGCA<br>GCGCACCCTGATCTCACTTAAATCAGCACAGTAACTGCAGCACAGCACCAC<br>AATATTGTTCAAAATCCCACAGTGCAAGGCGCTGTATCCAAAGCTCATGGC<br>GGGGACCACAGAACCCACGTGGCCATCATACCACAAGCGCAGGTAGATTA<br>AGTGGCGACCCCTCATAAACACGCTGGACATAAACATTACCTCTTTTGGCA<br>TGTTGTAATTCACCACCTCCCGGTACCATATAAACCTCTGATTAAACATGGC<br>GCCATCCACCACCATCCTAAACCAGCTGGCCAAAACCTGCCCGCCGGCTA<br>TACACTGCAGGGAACCGGGACTGGAACAATGACAGTGGAGAGCCCAGGAC<br>TCGTAACCATGGATCATCATGCTCGTCATGATATCAATGTTGGCACAACACA<br>GGCACACGTGCATACACTTCCTCAGGATTACAAGCTCCTCCCGCGTTAGAA<br>CCATATCCCAGGGAACAACCCATTCCTGAATCAGCGTAAATCCCACACTGC<br>AGGGAAGACCTCGCACGTAACTCACGTTGTGCATTGTCAAAGTGTTACATT<br>CGGGCAGCAGCGGATGATCCTCCAGTATGGTAGCGCGGGTTTCTGTCTCA<br>AAAGGAGGTAGACGATCCCTACTGTACGGAGTGCGCCGAGACAACCGAGA<br>TCGTGTTGGTCGTAGTGTCATGCCAAATGGAACGCCGGACGTAGTCATATT<br>TCCTGAAGCAAAACCAGGTGCGGGCGTGACAAACAGATCTGCGTCTCCGG<br>TCTCGCCGCTTAGATCGCTCTGTGTAGTAGTTGTAGTATATCCACTCTCTCA<br>AAGCATCCAGGCGCCCCCTGGCTTCGGGTTCTATGTAAACTCCTTCATGCG<br>CCGCTGCCCTGATAACATCCACCACCGCAGAATAAGCCACACCCAGCCAA<br>CCTACACATTCGTTCTGCGAGTCACACACGGGAGGAGCGGGAAGAGCTGG<br>AAGAACCATGTTTTTTTTTTTATTCCAAAAGATTATCCAAAACCTCAAAATGA<br>AGATCTATTAAGTGAACGCGCTCCCCTCCGGTGGCGTGGTCAAACTCTACA<br>GCCAAAGAACAGATAATGGCATTTGTAAGATGTTGCACAATGGCTTCCAAAA<br>GGCAAACGGCCCTCACGTCCAAGTGGACGTAAAGGCTAAACCCTTCAGGG |

-continued

| Sequences | | |
|---|---|---|
| SEQ ID NO: | DESCRIPTION | SEQUENCE |
| | | TGAATCTCCTCTATAAACATTCCAGCACCTTCAACCATGCCCAAATAATTCT<br>CATCTCGCCACCTTCTCAATATATCTCTAAGCAAATCCCGAATATTAAGTCC<br>GGCCATTGTAAAAATCTGCTCCAGAGCGCCCTCCACCTTCAGCCTCAAGCA<br>GCGAATCATGATTGCAAAAATTCAGGTTCCTCACAGACCTGTATAAGATTCA<br>AAAGCGGAACATTAACAAAAATACCGCGATCCCGTAGGTCCCTTCGCAGGG<br>CCAGCTGAACATAATCGTGCAGGTCTGCACGGACCAGCGCGGCCACTTCC<br>CCGCCAGGAACCTTGACAAAAGAACCCACACTGATTATGACACGCATACTC<br>GGAGCTATGCTAACCAGCGTAGCCCCGATGTAAGCTTTGTTGCATGGGCG<br>GCGATATAAAATGCAAGGTGCTGCTCAAAAAATCAGGCAAAGCCTCGCGCA<br>AAAAAGAAAGCACATCGTAGTCATGCTCATGCAGATAAAGGCAGGTAAGCT<br>CCGGAACCACCACAGAAAAAGACACCATTTTTCTCTCAAACATGTCTGCGG<br>GTTTCTGCATAAACACAAAATAAAATAACAAAAAAACATTTAAACATTAGAAG<br>CCTGTCTTACAACAGGAAAAACAACCCTTATAAGCATAAGACGGACTACGG<br>CCATGCCGGCGTGACCGTAAAAAAACTGGTCACCGTGATTAAAAAGCACCA<br>CCGACAGCTCCTCGGTCATGTCCGGAGTCATAATGTAAGACTCGGTAAACA<br>CATCAGGTTGATTCATCGGTCAGTGCTAAAAAGCGACCGAAATAGCCCGGG<br>GGAATACATACCCGCAGGCGTAGAGACAACATTACAGCCCCCATAGGAGG<br>TATAACAAAATTAATAGGAGAGAAAAACACATAAACACCTGAAAAACCCTCC<br>TGCCTAGGCAAAATAGCACCCTCCCGCTCCAGAACAACATACAGCGCTTCA<br>CAGCGGCAGCCTAACAGTCAGCCTTACCAGTAAAAAAGAAAACCTATTAAA<br>AAAACACCACTCGACACGGCACCAGCTCAATCAGTCACAGTGTAAAAAAGG<br>GCCAAGTGCAGAGCGAGTATATATAGGACTAAAAAATGACGTAACGGTTAA<br>AGTCCACAAAAAACACCCAGAAAACCGCACGCGAACCTACGCCCAGAAAC<br>GAAAGCCAAAAAACCCACAACTTCCTCAAATCGTCACTTCCGTTTTCCCACG<br>TTACGTAACTTCCCATTTTAAGAAAACTACAATTCCCAACACATACAAGTTAC<br>TCCGCCCTAAAACCTACGTCACCCGCCCCGTTCCCACGCCCCGCGCCACG<br>TCACAAACTCCACCCCCTCATTATCATATTGGCTTCAATCCAAAATAAGGTA<br>TATTATTGATGATGTTAAT |
| 56 | HER2(A3)-CD28TM, ICD-CD3Z CAR | MTRAMDWIWRILFLVGAATGAHSEVQLVQSGTEVKKPGASVRVSCKSSGYTF<br>TSYYIHWVRQAPGQGLEWMAIINPGNGDTNYAQRFQGRVTMTRDTSTSTVYM<br>ELRSLRSDDTAVYFCAREIASYSGSYYDYWGQGTLVTVSSGGGGSGGGGSG<br>GGGSQAVVLQEPSLSVSPGGTVTLTCGLSSGSVSTGHYASWYQQTPGQAPR<br>TLFYNTNTRSSGVPDRFSGSIVGNKAALTITGAQADDESDYYCVLYVGDGIWVF<br>GGGTKLTVLEPKSCDKTHTCPTRFWVLVVVGGVLACYSLLVTVARIFWVRSKR<br>SRLLHSDYMNMTPRRPGPTRKHYQPYAPPRDFAAYRSRVKFSRSADAPAYQ<br>QGQNQLYNELNLGRREEYDVLDKRRGRDPEMGGKPQRRKNPQEGLYNELQK<br>DKMAEAYSEIGMKGERRRGKGHDGLYQGLSTATKDTYDALHMQALPPR |
| 57 | HER2(A3) LC-CDR1 | GLSSGSVSTGHYAS |
| 58 | HER2(A3) LC-CDR2 | NTNTRSS |
| 59 | HER2(A3) LC-CDR3 | VLYVGDGIWV |
| 60 | HER2(A3) HC-CDR1 | SYYIHWVRQA |
| 61 | HER2(A3) HC-CDR2 | IINPGNGDTNYAQRFQG |
| 62 | HER2(A3) HC-CDR3 | EIASYSGSYYDY |
| 63 | HER2(A3) VL | QAVVLQEPSLSVSPGGTVTLTCGLSSGSVSTGHYASWYQQTPGQAPRTLFYN<br>TNTRSSGVPDRFSGSIVGNKAALTITGAQADDESDYYCVLYVGDGIWVFGGGT<br>KLTVL |
| 64 | HER2(A3) VH | EVQLVQSGTEVKKPGASVRVSCKSSGYTFTSYYIHWVRQAPGQGLEWMAIINP<br>GNGDTNYAQRFQGRVTMTRDTSTSTVYMELRSLRSDDTAVYFCAREIASYSG<br>YYDYWGQGTLVTVSS |

The disclosure includes the combination of the aspects and preferred features described except where such a combination is clearly impermissible or expressly avoided.

The section headings used herein are for organizational purposes only and are not to be construed as limiting the subject matter described.

Aspects and embodiments of the present disclosure will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence in disclosed the reverse complement thereof is also expressly contemplated.

BRIEF DESCRIPTION OF THE FIGURES

Embodiments and studies illustrating the principles of the disclosure will now be discussed with reference to the accompanying figures.

FIG. 1A shows schematic representations of examples of HER2-specific CAR constructs. FIG. 1B shows a schematic of an example of a protocol for transducing T cells to produce HER2-specific CAR-T.

FIG. 4A is a bar chart showing in vitro cell killing of MDA cells (which do not express HER2 at the cell surface; negative control), MDA-HER2 cells (which express HER2 at the cell surface; positive control), FaDu and SCC47 cells by anti-HER2 clone C5, E4 and F1 CAR-T cells (or non-transduced (NT) cells), as determined by $^{51}$Cr release assay. FIG. 4B shows graphs indicating expression of HER2 on MDA-HER2 cells, FaDu and SCC47 cells but not on MDA cells, as determined by flow cytometry.

FIG. 6 shows a schematic representation of the sequences of an example of an ICOSTAT oncolytic adenovirus construct.

FIG. 10A is a schematic representation of the HDAdIL-12_TK_PDL1 construct. FIG. 10B is a bar chart showing production of IL-12p70 by cells transfected with the indicated helper-dependent adenovirus (HDAd) constructs. FIG. 10C is a photograph of a western blot showing production of anti-PD-L1 minibody by cells transfected with the HDAd constructs. FIG. 10D is a photograph of a wells demonstrating HSV thymidine kinase production by cells transfected with the HDAd constructs.

FIGS. 15A and 15B show the number and location of luciferase-expressing non-transduced T cells (NT), and cells expressing luciferase-expressing T cells expressing C5, F1 or A3 HER2-specific CARs within mice at the indicated number of days after infusion of the cells. FIG. 15C shows the percentage of surviving subjects in the different treatment groups at the indicated number of days after infusion of the cells. A negative control condition wherein mice were not administered with T cells is also shown (−).

FIG. 16A shows the number and location of luciferase-expressing non-transduced T cells (NT), and cells expressing luciferase-expressing T cells expressing C5, F1 or A3 HER2-specific CARs within mice at the indicated number of days after infusion of the cells. FIG. 16B shows measurements for total flux (in photons per second; p/s) of ventral surface for mice of the different groups at the indicated number of days after infusion of the cells. FIG. 16C shows the weights of mice in the different treatment groups at the indicated number of days after infusion of the cells, expressed as a percentage of body weight at day 0.

FIG. 17A shows the percentages of CD4+ T cells and CD8+ T cells within the F1.CAR-T population. FIG. 17B shows the percentage cells expressing HER2 CAR at the cell surface. FIG. 17C shows the percentages of cells within the F1.CAR-T population expressing CCR7 and/or CD45RO.

FIG. 18A shows the number and location of luciferase-expressing non-transduced T cells (NT), and cells expressing luciferase-expressing T cells expressing F1 HER2-specific CAR within mice at the indicated number of days after infusion of the cells Top right figure (Y-axis is labelled as Total Flux) is "Days post-injection of CAR T-cells". Bottom 2 figures are "Days post-injection of CAdtrio. FIG. 18B shows measurements for total flux (in photons per second; p/s) of ventral surface for mice of the different groups at the indicated number of days after administration of CAdtrio. FIG. 18C shows the weights of mice in the different treatment groups at the indicated number of days after administration of CAdtrio, expressed as a percentage of body weight at day 0. FIG. 18D shows the percentage of surviving subjects in the different treatment groups at the inciated number of days after administration of CAdtrio. A negative control condition wherein mice were not administered with CAdtrio or T cells is also shown (−).

FIG. 19A shows the number and location of luciferase-expressing FaDu cells within mice at the indicated number of days after administration of CAdtrio. FIG. 19B shows measurements for total flux (in photons per second; p/s) of ventral surface for mice of the different groups at the indicated number of days after administration of CAdtrio. FIG. 19C shows the weights of mice in the different treatment groups at the indicated number of days after administration of CAdtrio, expressed as a percentage of body weight at day 0.

FIGS. 20A and 20B show the GAPDH-normalised copy number of (FIG. 20A) Onc5/3Ad2E1Δ24 and (FIG. 20B) HDAdIL-12_TK_PD-L1 in tumors of mice administered with the combination of Onc5/3Ad2E1Δ24 and HDAdIL-12 TK_PD-L1 (CAdtrio) at 22 days post infection, with or without GCV treatment. FIG. 20C shows tumor volume in $mm^3$ of mice administered with the combination of Onc5/3Ad2E1Δ24 and HDAdIL-12_TK_PD-L1 (CAdtrio) at the indicated number of days post-injection of CAdtrio, with or without GCV treatment. FIG. 20D shows IL-12 levels detected by ELISA analysis of blood samples obtained at the indicated number of days post-injection of CAdtrio, with or without GCV treatment.

FIG. 21A shows the level of IL-12 in cell culture supernatant as determined by ELISA. FIG. 21B shows anti-PD-L1 minibody detected in cell culture supernatant by western blot. FIG. 21C shows viable cells detected by Cystal Violet staining at the end of the experiment.

FIG. 22A shows the percentages of CD4+ T cells and CD8+ T cells within the AdVST population. FIG. 22B shows the percentages of cells within the AdVST population expressing CCR7 and/or CD45RO.

FIG. 23A shows the percentages of CD4+ T cells and CD8+ T cells within the transduced population. FIG. 23B shows the percentage cells expressing HER2 CAR at the cell surface. FIG. 23C shows the percentages of cells within the F1.CAR-AdVST population expressing CCR7 and/or CD45RO.

FIG. 24A shows the number and location of luciferase-expressing FaDu cells within mice at the indicated number of days after administration of CAdtrio. FIG. 24B shows measurements for total flux (in photons per second; p/s) of ventral surface for mice of the different groups at the indicated number of days after administration of CAdtrio. FIG. 24C shows the weights of mice in the different treatment groups at the indicated number of days after administration of CAdtrio, expressed as a percentage of body weight at day 0. FIG. 24D shows the percentage of surviving subjects in the different treatment groups at the indicated number of days after administration of CAdtrio. $*P<0.04$, $*P<0.07$, $P<0.02$ for FIG. 24**B. $*P<0.01$, $P<0.04$, $P<0.02$ for 24C. $*P=0.03$, $*P=0.02$ for FIG. 24D.

NUMBERED STATEMENTS OF DISCLOSURE

Figure 1A:
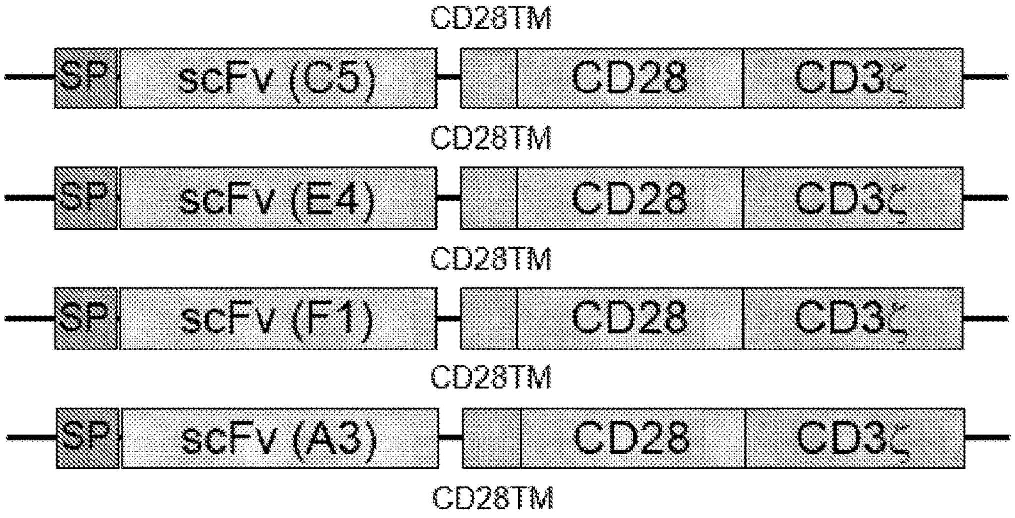
FIGS. 1A and 1B.

Following numbered paragraphs (paras) describe particular aspects and embodiments of the present disclosure:

1. A method of treating a cancer, comprising administering to a subject:
   (i) an oncolytic virus;
   (ii) a virus comprising nucleic acid encoding an immunomodulatory factor: and (iii) at least one cell comprising a chimeric antigen receptor (CAR) specific for a cancer cell antigen.

2. The method of para 1, wherein the oncolytic virus is an oncolytic adenovirus (OncAd).

3. The method of para 1 or para 2, wherein the oncolytic virus is derived from adenovirus 5 (Ad5).

4. The method of any one of paras 1 to 3, wherein the oncolytic virus encodes an E1A protein which displays reduced binding to Rb protein as compared to E1A protein encoded by Ad5.

5. The method of any one of paras 1 to 4, wherein the oncolytic virus encodes an E1A protein lacking the amino acid sequence LTCHEACF (SEQ ID NO:52).

6. The method of any one of paras 1 to 5, wherein the oncolytic virus encodes an E1A protein comprising, or consisting of, the amino acid sequence SEQ ID NO:34.

7. The method of any one of paras 1 to 6, wherein the oncolytic virus comprises nucleic acid having one or more binding sites for one or more transcription factors.

8. The method of any one of paras 1 to 7, wherein the oncolytic virus comprises nucleic acid having one or more binding sites for STAT1.

9. The method of any one of paras 1 to 8, wherein the virus comprising nucleic acid encoding an immunomodulatory factor is a helper-dependent adenovirus (HDAd).

10. The method of any one of paras 1 to 9, wherein the immunomodulatory factor is selected from: an agonist of an effector immune response or antagonist of an immunoregulatory response.

11. The method of any one of paras 1 to 10, wherein the virus comprising nucleic acid encoding an immunomodulatory factor comprises nucleic acid encoding IL-12 and/or antagonist anti-PD-L1 antibody.

12. The method of any one of paras 1 to 11, wherein the virus comprising nucleic acid encoding an immunomodulatory factor comprises nucleic acid encoding a thymidine kinase.

13. The method of any one of paras 1 to 12, wherein the at least one cell comprising a CAR specific for a cancer cell antigen is a T cell.

14. The method of any one of paras 1 to 13, wherein the CAR comprises an antigen binding domain capable of specific binding to HER2.

15. The method of any one of paras 1 to 14, wherein the CAR comprises an antigen binding domain comprising:

a VL domain comprising:
LC-CRD1: SEQ ID NO:10;
LC-CRD2: SEQ ID NO:11;
LC-CRD3: SEQ ID NO:12;
and a VH domain comprising:
HC-CRD1: SEQ ID NO:13;
HC-CRD2: SEQ ID NO:14;
HC-CRD3: SEQ ID NO:15;

or a VL domain comprising:
LC-CRD1: SEQ ID NO:18;
LC-CRD2: SEQ ID NO:19;
LC-CRD3: SEQ ID NO:20;
and a VH domain comprising:
HC-CRD1: SEQ ID NO:21;
HC-CRD2: SEQ ID NO:22;
HC-CRD3: SEQ ID NO:23;

or a VL domain comprising:
LC-CRD1: SEQ ID NO:26;
LC-CRD2: SEQ ID NO:27;
LC-CRD3: SEQ ID NO:28;
and a VH domain comprising:
HC-CRD1: SEQ ID NO:29;
HC-CRD2: SEQ ID NO:30;
HC-CRD3: SEQ ID NO:31.

16. The method of any one of paras 1 to 15, wherein the CAR comprises an antigen binding domain comprising:

a VL comprising, or consisting of or consisting essentially of, an amino acid sequence having at least 75% sequence identity to SEQ ID NO:16 and a VH comprising, or consisting of or consisting essentially of, an amino acid sequence having at least 75% sequence identity to SEQ ID NO:17;

or a VL comprising, or consisting of or consisting essentially of, an amino acid sequence having at least 75% sequence identity to SEQ ID NO:24 and a VH comprising, or consisting of or consisting essentially of, an amino acid sequence having at least 75% sequence identity to SEQ ID NO:25;

or a VL comprising, or consisting of or consisting essentially of, an amino acid sequence having at least 75% sequence identity to SEQ ID NO:32 and a VH comprising, or consisting of or consisting essentially of, an amino acid sequence having at least 75% sequence identity to SEQ ID NO:33.

17. The method of any one of paras 1 to 16, wherein the method additionally comprises:

(a) isolating at least one cell from a subject;
(b) modifying the at least one cell to express or comprise a CAR specific for a cancer cell antigen, or a nucleic acid encoding a CAR specific for a cancer cell antigen,
(c) optionally expanding the modified at least one cell, and;
(d) administering the modified at least one cell to a subject.

18. The method of any one of paras 1 to 17, wherein the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

19. An oncolytic adenovirus (OncAd) encoding an E1A protein comprising, or consisting of, the amino acid sequence SEQ ID NO:34.

20. An oncolytic adenovirus (OncAd) comprising nucleic acid having one or more binding sites for STAT1.

21. The OncAd according to para 20, wherein the OncAd comprises a nucleic acid sequence having at least 60% sequence identity to SEQ ID NO:51 or an equivalent sequence as a result of codon degeneracy.

22. A helper-dependent adenovirus (HDAd) comprising nucleic acid encoding IL-12 and/or antagonist anti-PD-L1 antibody.

23. The HDAd according to para 22, wherein the HDAd additionally comprises nucleic acid encoding a thymidine kinase.

24. A chimeric antigen receptor (CAR) comprising an antigen binding domain comprising:

a VL domain comprising:
LC-CRD1: SEQ ID NO:10;
LC-CRD2: SEQ ID NO:11;
LC-CRD3: SEQ ID NO:12;
and a VH domain comprising:
HC-CRD1: SEQ ID NO:13;
HC-CRD2: SEQ ID NO:14;
HC-CRD3: SEQ ID NO:15;

or a VL domain comprising:
LC-CRD1: SEQ ID NO:18;
LC-CRD2: SEQ ID NO:19;
LC-CRD3: SEQ ID NO:20;
and a VH domain comprising:
HC-CRD1: SEQ ID NO:21;
HC-CRD2: SEQ ID NO:22;
HC-CRD3: SEQ ID NO:23;

or a VL domain comprising:
LC-CRD1: SEQ ID NO:26;
LC-CRD2: SEQ ID NO:27;
LC-CRD3: SEQ ID NO:28;
and a VH domain comprising:
HC-CRD1: SEQ ID NO:29;
HC-CRD2: SEQ ID NO:30;
HC-CRD3: SEQ ID NO:31.

25. The CAR according to para 24, wherein the CAR comprises an antigen binding domain comprising:

a VL comprising, or consisting of, an amino acid sequence having at least 75% sequence identity to SEQ ID NO:16 and a VH comprising, or consisting of or consisting essentially of, an amino acid sequence having at least 75% sequence identity to SEQ ID NO:17;

or a VL comprising, or consisting of or consisting essentially of, an amino acid sequence having at least 75% sequence identity to SEQ ID NO:24 and a VH comprising, or consisting of or consisting essentially of, an amino acid sequence having at least 75% sequence identity to SEQ ID NO:25:

or a VL comprising, or consisting of, an amino acid sequence having at least 75% sequence identity to SEQ ID NO:32 and a VH comprising, or consisting of or consisting essentially of, an amino acid sequence having at least 75% sequence identity to SEQ ID NO:33.

26. A nucleic acid, optionally isolated or man-made, encoding the oncolytic adenovirus (OncAd) according to any one of paras 19 to 21, the helper-dependent adenovirus (HDAd) according to para 22 or para 23, or the chimeric antigen receptor (CAR) according to para 24 or para 25.

27. A cell comprising the oncolytic adenovirus (OncAd) according to any one of paras 19 to 21, the helper-dependent adenovirus (HDAd) according to para 22 or para 23, the chimeric antigen receptor (CAR) according to para 24 or para 25, or the nucleic acid according to para 26, optionally wherein the cell is man-made and not found in nature.

28. A pharmaceutical composition comprising the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26 or the cell according to para 27 and a pharmaceutically acceptable carrier, diluent, excipient or adjuvant.

29. A method of treating cancer comprising administering to a subject the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28.

30. The oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28 for use in a method of treating a cancer.

31. Use of the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28 in the manufacture of a medicament for treating a cancer.

32. The method, the use or the use according to any one of paras 29 to 31, wherein the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

33. A kit of parts comprising a predetermined quantity of the oncolytic adenovirus (OncAd) according to any one of paras 19 to 21, the helper-dependent adenovirus (HDAd) according to para 22 or para 23, the chimeric antigen receptor (CAR) according to para 24 or para 25, the nucleic acid according to para 26, the cell according to para 27 or the pharmaceutical composition according to para 28.

EXAMPLES

In the following Examples, the inventors describe the generation functional characterisation of novel HER-2 specific CARs and CAR-T cells, oncolytic adenoviruses and helper-dependent adenovirus.

Example 1: HER2-Specific CAR-T Cells 1.1 Generation of HER2-Specific CAR Constructs and CAR-T Cells HER2-binding CAR constructs were prepared. Briefly, DNA encoding scFv (i.e. VL domain and VH domain joined by a linker sequence) for the anti-HER2 antibody clone C5. E4, F1 or A3 was cloned into a CAR construct backbone comprising a 5' signal peptide (SP), and CD28 transmembrane (TM) and intracellular domain sequence, with a 3' CD34 intracellular domain sequence. The three HER2-binding CAR constructs are represented schematically in FIG. 1A.

Figure 1B:
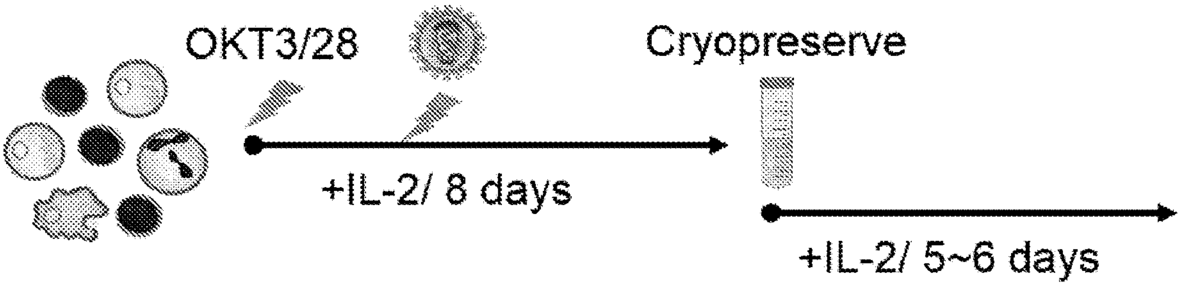
Figure 14:
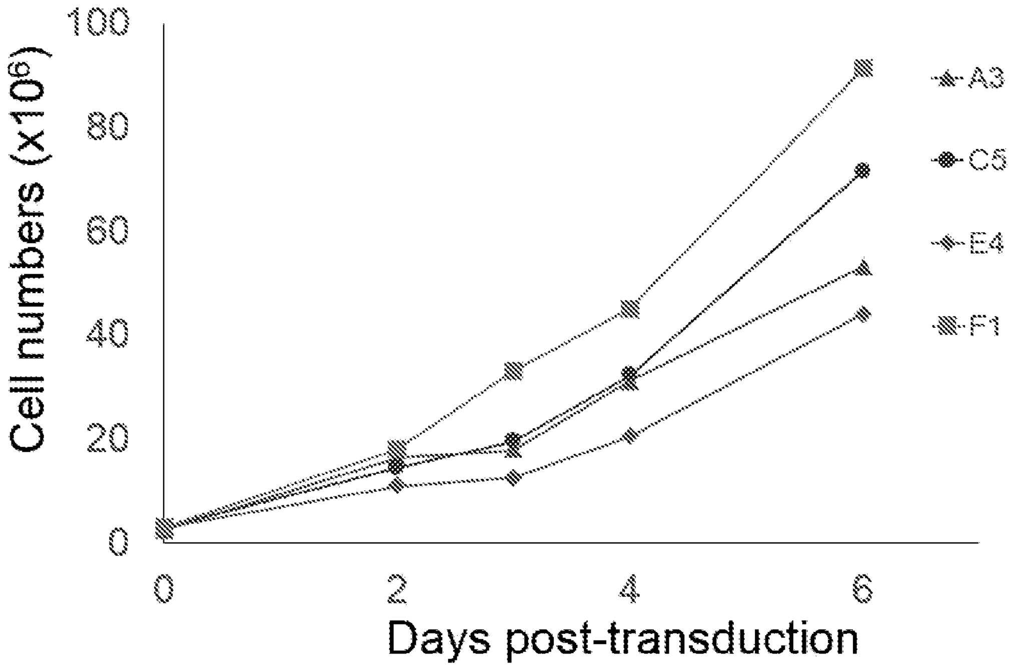
FIG. 14. Graph showing numbers of HER2-specific CAR T cells following the indicated number of days of in vitro cell culture after transuction with the indicated CAR constructs.

HER2 specific CAR-T cells were generated as represented graphically in FIG. 1B. Briefly, human PBMCs were isolated from blood samples by with Ficoll density gradient centrifugation. Cells were treated by stimulation with anti-CD3(OKT3)/anti-CD28 in the presence of IL-2 to promote T cell activation and proliferation, and the cells were transduced with retrovirus encoding the HER2 CAR constructs. T-cells were expanded by culture in the presence of 100 IU/mL recombinant human IL-2, and were frozen at 6 days post-transduction. The HER2-specific CAR construct-transduced T cells were readily expanded by culture in vitro (see e.g. FIG. 14).

T-cells were thawed and expanded in the presence of 100 IU/mL of recombinant human IL-2 for 5 days and used for in vitro/in vive experiments and phenotypic analysis.

1.2 Characterisation of the HER2-Specific CAR-T Cells 1.2.1 Expression of Surface Markers and HER2 CARs T cells transduced with HER2 CAR construct encoding scFv for anti-HER2 antibody clone E4 were characterised by flow cytometry for expression of different cell surface molecules. Expanded HER2 specific CAR T-cells were stained with fluorescently-labelled monoclonal antibodies for 30 minutes at 4° C. Discrimination of live/dead cells was achieved by including 7AAD in stainings (BD Pharmingen). Stained cells were analyzed using a Gallios flow cytometer and Kaluza software (BD Bioscience), according to manufacturer's instructions.

Figure 2:
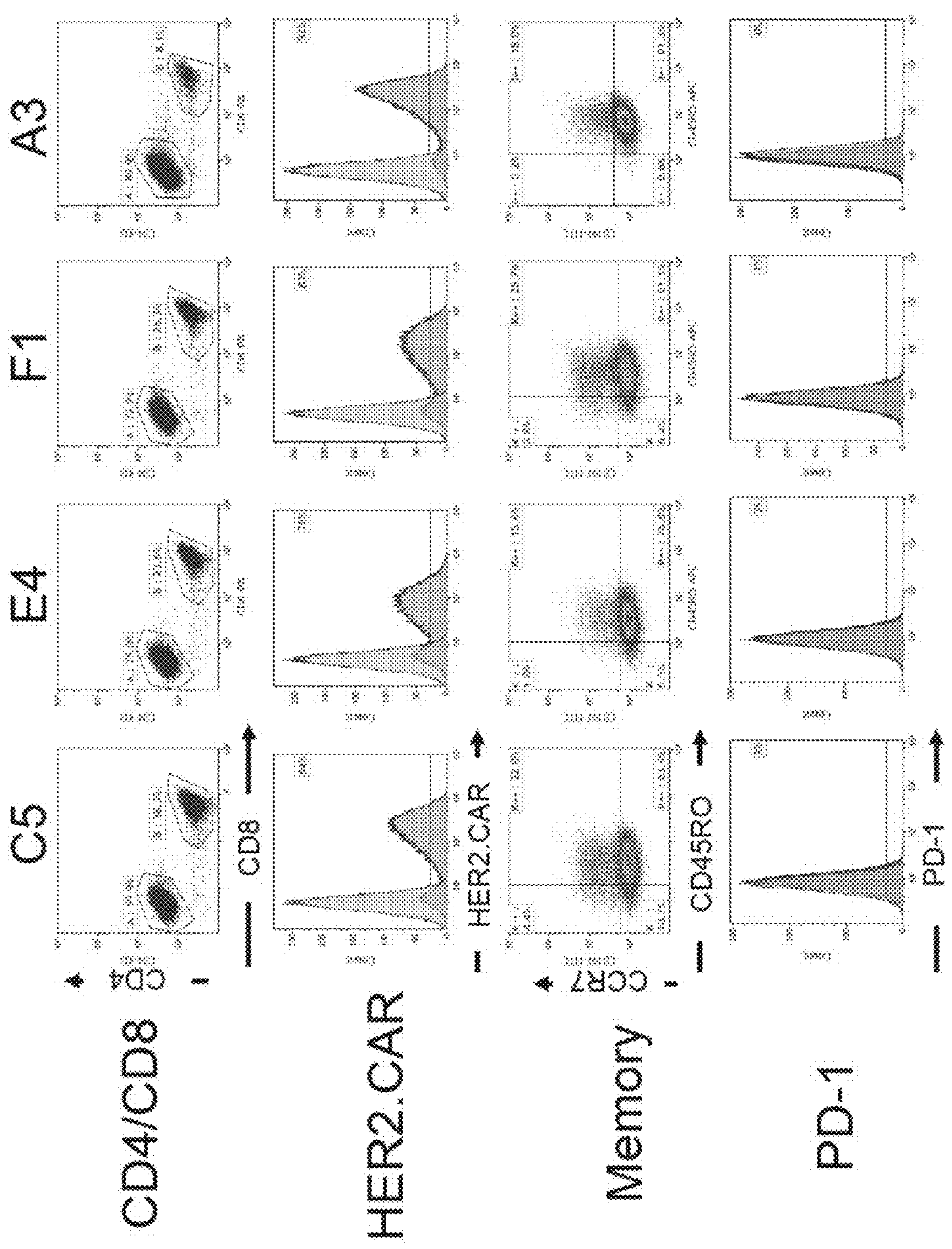
FIG. 2. Graphs showing expression of the HER2-CARs, CCR7, CD45RO and PD-1 on T cells transduced with the indicated HER2-CAR constructs, as determined by flow cytometry.
Figure 3:
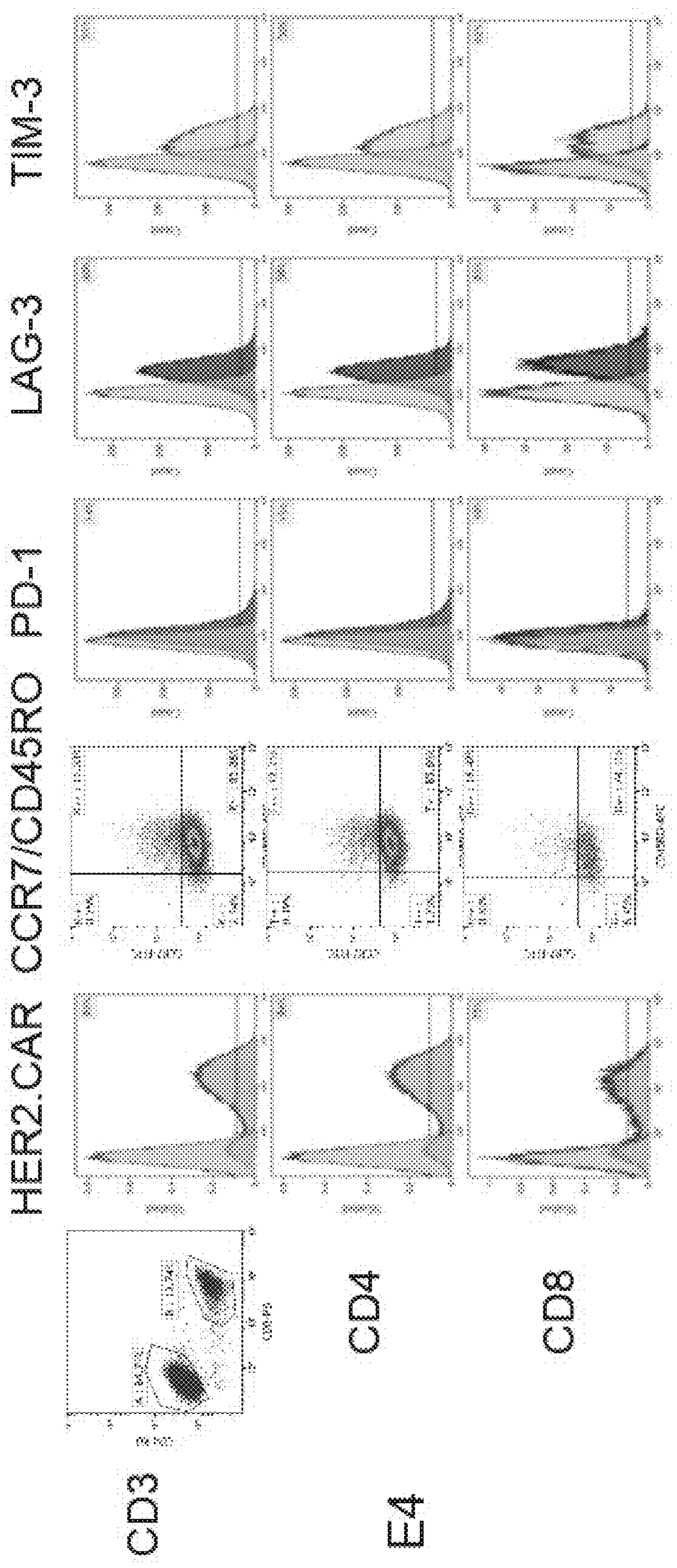
FIG. 3. Graphs showing expression of HER2-CAR, CCR7, CD45RO, PD-1, LAG-3 and TIM-3 on CD4 and CD8 T cells following transduction with anti-HER2 clone E4 CAR construct, as determined by flow cytometry.

The results are shown in FIGS. 2 and 3. Strong surface expression of the HER2-CARs was detected on the transduced cells (FIG. 2).

FIG. 3 shows the results of characterisation of T cells transduced with HER2(E4)-CAR. CD3+ cells, CD4+ cells and CD8+ cells expressing HER2(E4)-CAR were shown to have increased expression of PD-1, LAG-3 and TIM-3, and to have reduced level of expression of CCR7 as compared to non-transduced cells (FIG. 3).

1.2.2 Cell Killing Activity

The HER2-CAR-T cells were analysed for their ability to kill HER2 expressing cancer cells in vitro in cell killing assays.

Figure 4A:
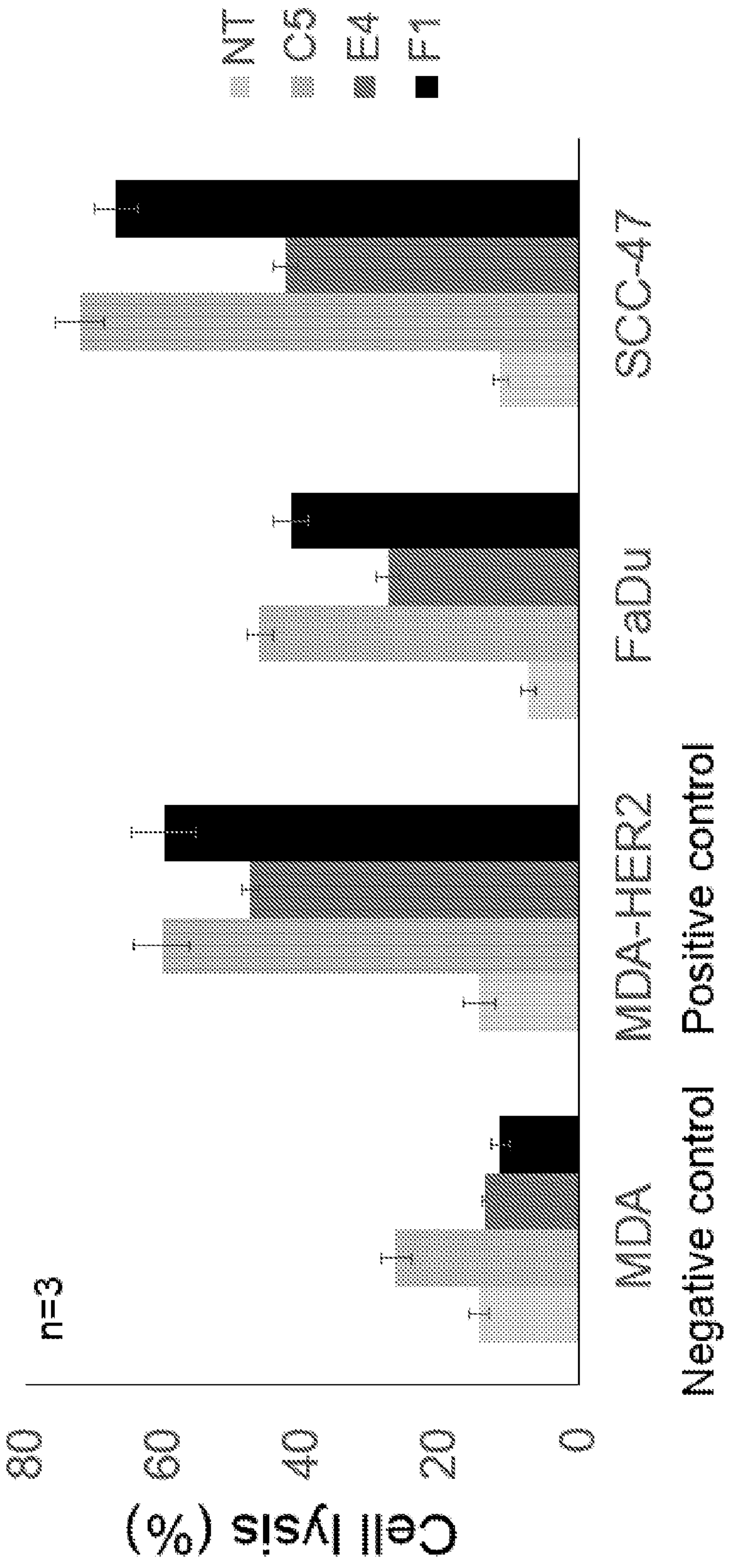
FIGS. 4A and 4B.

In a first experiment, cells of the HER2 negative MDA cell line (negative control), MDA cells stably expressing HER2 (MDA-HER2; positive control), pharynx squamous cell carcinoma cell line FaDu or the head and neck squamous carcinoma cell line SCC47 cells were labelled with Chromium-51 ($^{51}$Cr) and co-cultured with non-transduced T-cells (NT) or the HER2-CAR-T cells expressing the indicated CARs at an effector:target cell ratio of 20:1 for 4 hours. After centrifugation, $^{51}$Cr levels in the cell culture media were counted using a liquid scintillation counter. The results are shown in FIG. 4A; the HER2-CAR-T cells were shown to kill HER2-expressing cancer cells. Similar results were obtained when the experiments were performed using an effector:target cell ratio of 10:1.

Figure 4B:
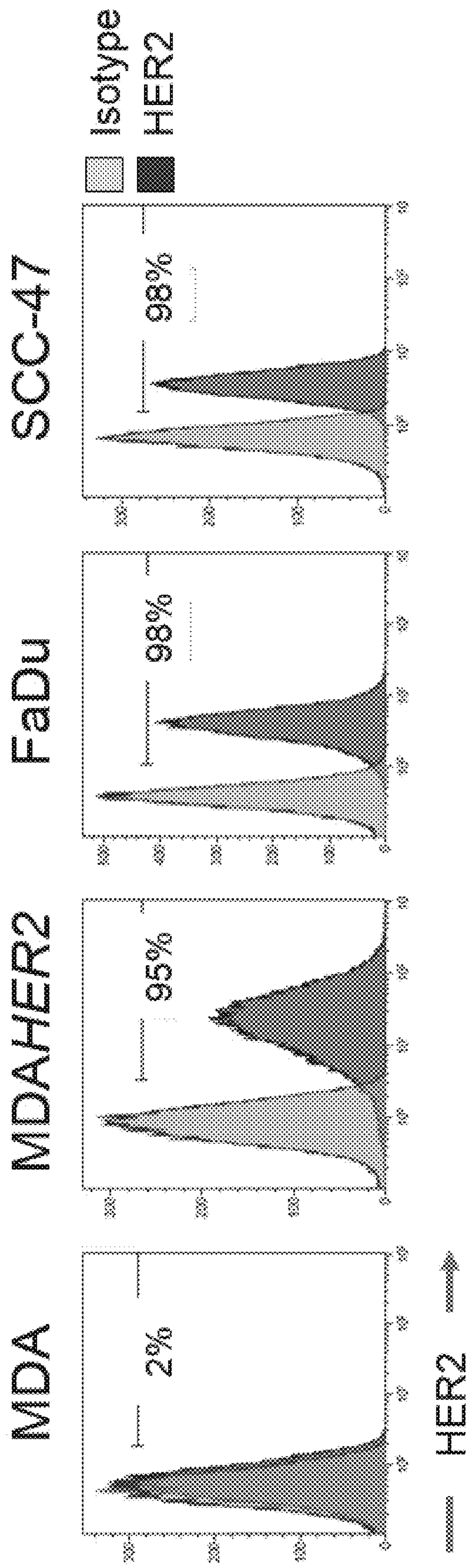

Expression of HER2 on MDA-HER2, FaDu and SCC47 was confirmed by flow cytometry. Briefly, the cells were were stained with fluorescently-labelled monoclonal anti-HER2 antibody or isotype control antibody for 30 minutes at 4° C. Discrimination of live/dead cells was achieved by including 7AAD in stainings (BD Pharmingen). Stained cells were analyzed using a Gallios flow cytometer and Kaluza software (BD Bioscience), according to manufacturer's instructions. The results are shown in FIG. 4B; MDA cells were confirmed not to express HER2, whilst MDA-HER2, FaDu and SCC47 express HER2.

Figure 5:
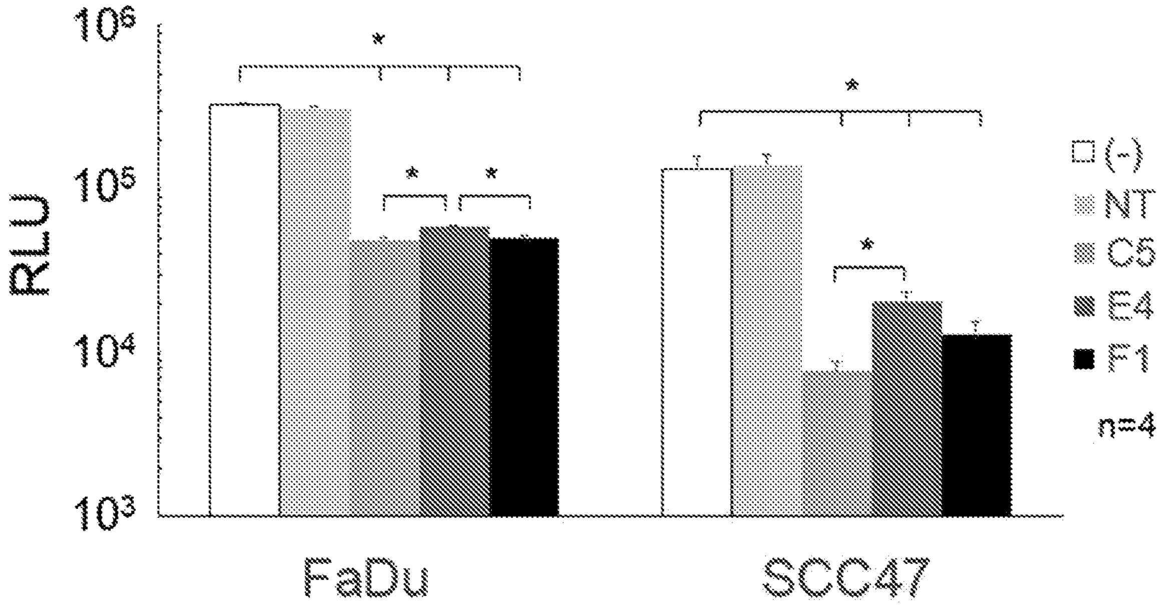
FIG. 5. Bar chart showing in vitro cell killing of FaDu and SCC47 cells genetically modified to express firefly luciferase (ffLuc) by anti-HER2 clone C5, E4 and F1 CAR-T cells (or non-transduced (NT) cells), as determined by ffLuc activity assay. Data are presented as mean±SD (n=4). *P<0.001.

In a separate experiment, FaDu and SCC47 cells genetically modified to express firefly luciferase (ffluc) were seeded in wells of 24-well plates, and co-cultured with HER2(C5)-CAR-T cells, HER2(E4)-CAR-T cells, or HER2 (F1)-CAR-T cells at an effector:target cell ratio of 1:5 for 3 days, and ffLuc activity was measured using a plate reader (Life Technologies). The results are shown in FIG. 5; the HER2-CAR-T cells were shown to kill HER2-expressing cancer cells, as evidenced by a reduction in ffLuc activity (relative light units, RLU). Similar results were obtained when the experiment was performed using an effector:target cell ratio of 1:20.

Example 2: OncAd Constructs 2.1 Generation of OncAd Constructs

Novel constructs encoding oncolytic adenovirus are prepared using recombinant DNA techniques.

In particular embodiments, an OncAd is produced upon modification of a known virus. For example, a region encoding E1A protein from adenovirus 5, such as one lacking the sequence LTCHEACF (SEQ ID NO:52) involved in binding the Rb protein, is replaced with sequence encoding E1A protein from adenovirus 2, similarly lacking the sequence LTCHEACF (SEQ ID NO:52).

Figure 6:
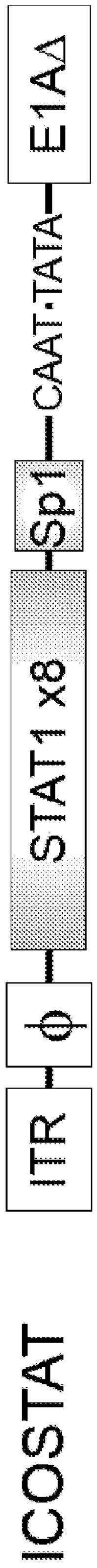
FIG. 6.

ICOSTAT shown in FIG. 6 was produced from ICOVIR15 disclosed e.g. in Rojas et al. 2010 Mol Ther 18 1960-1971. Briefly, the region of ICOVIR15 encoding eight copies of a binding site for the transcription factor E2F was replaced with a region encoding eight tandem copies of a binding site for the transcription factor STAT1. The sequence of ICOSTAT is shown in SEQ ID NO:51.

Figure 12A:
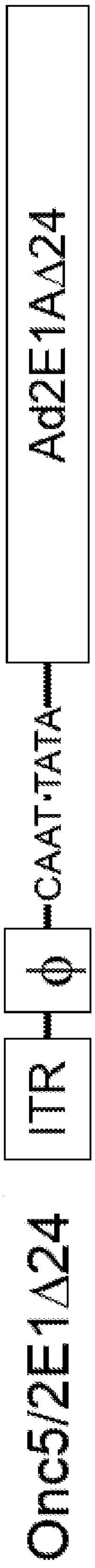
FIGS. 12A and 12B. Schematic representations of the sequences of (FIG. 12A) an example of an Onc5/2E1Δ24 oncolytic adenovirus construct, and (FIG. 12B) a plasmid encoding an Onc5/2E1Δ24 oncolytic adenovirus construct.
Figure 12B:
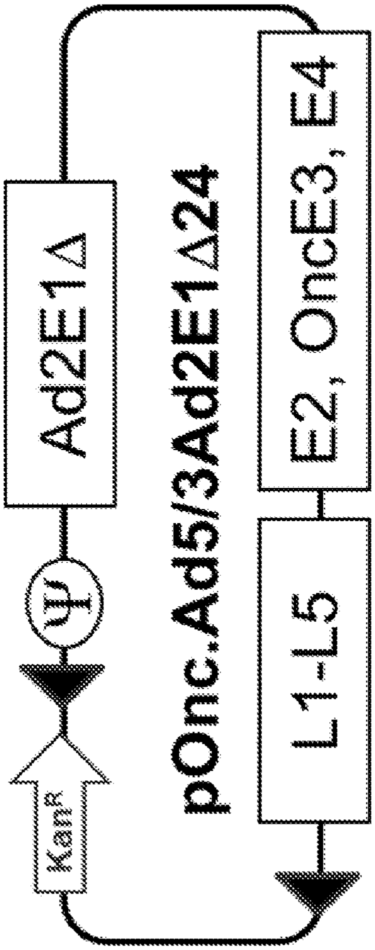

Onc5/3Ad2E1Δ24 (also referred to herein as "Onc5/2E1Δ24" shown in SEQ ID NO:55 and represented schematically in FIG. 12 was also prepared by using recombinant DNA techniques. Onc5/3Ad2E1Δ24 has a similar structure as Onc5Δ24 disclosed e.g. in Fueyo et al. 2000 Oncogene 19:2-12 (hereby incorporated by reference in its entirety; Onc5Δ24 is also referred to in Fueyo et al. as "Δ24"), but differs in that Onc5/3Ad2E1Δ24 encodes E1A protein from adenovirus type 2 (Ad2) lacking the sequence LTCHEACF (SEQ ID NO:52), rather than E1A protein from adenovirus type 5 (Ad5) lacking the sequence LTCHEACF (SEQ ID NO:52).

2.2 Cell Killing Activity

The ability of an oncolytic adenovirus of choice or ICOSTAT as generated in Example 2.1 to kill cancer cells may be analysed for example by MTS assay. Briefly, cells of the human alveolar basal epithelial adenocarcinoma cell line A549 cells, FaDu cells, SCC47 cells, or non-cancerous WI-38 human lung fibroblasts or ARPE-19 human retinal pigmented epithelial cells were seeded in wells of 96-well plates and infected with different amounts of a helper-dependent, non-replicating adenovirus (HDAd; as a negative control), an oncolytic adenovirus of choice (e.g. Onc5/3Ad2E1Δ24 described in Example 2.1), or ICOSTAT described in Example 2.1 above.

Cells may be cultured for 4 days, for example, and then MTS reagents (Promega) may be added to each well, with cells being incubated at 37° C. for 2 hours. Live cells may be analyzed by measuring the absorbance at 490 nm with a plate reader. Readings may be normalized using the readings for untreated cells of each type (i.e. untreated cells=100% cell viability), and wells lacking cells would be considered 0%.

In particular embodiments, the oncolytic virus of choice is able to kill cancer cells in a dose-dependent manner. The oncolytic virus of choice also exhibits a lower level of cell killing of non-cancerous cells, such as WI-38 and ARPE-19 cells as compared to the level of killing by the virus of cancerous cells, in specific embodiments.

Figure 7A:
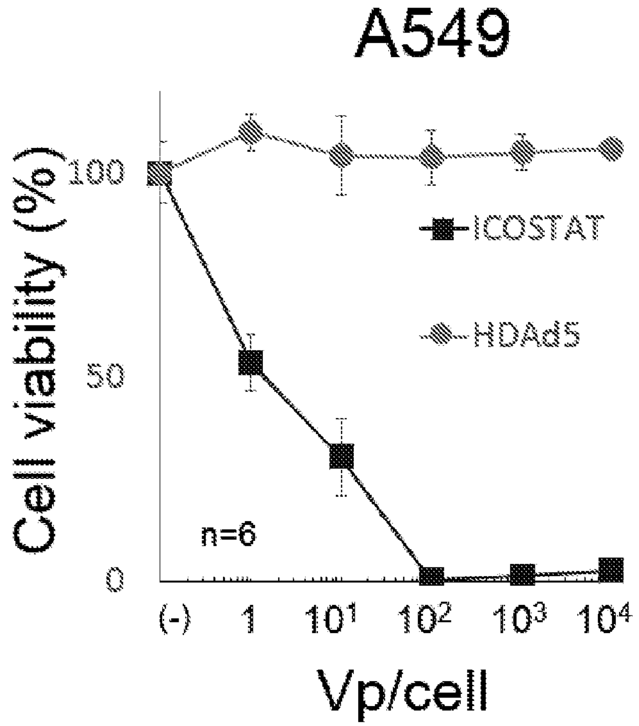
FIGS. 7A to 7F. Graphs showing the ability of ICOSTAT oncolytic adenovirus to kill A549 cells (FIGS. 7A and 7F), FaDu cells (FIG. 7B), SCC47 cells (FIG. 7C), WI-38 cells (FIG. 7D) and ARPE-19 cells (FIG. 7E) following infection with the indicated concentration of viral particles (Vp), as determined by MTS viability assay. Helper-dependent adenovirus (HDAd) is included as a control condition.
Figure 7B:
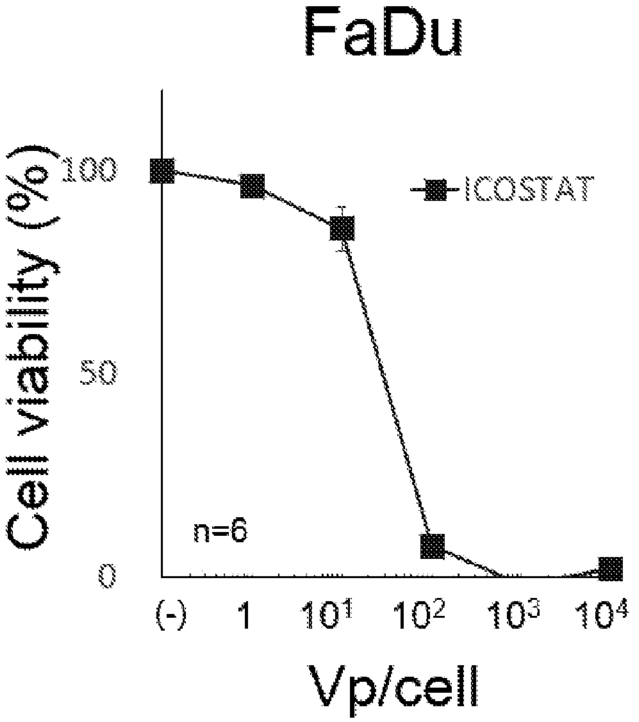
Figure 7C:
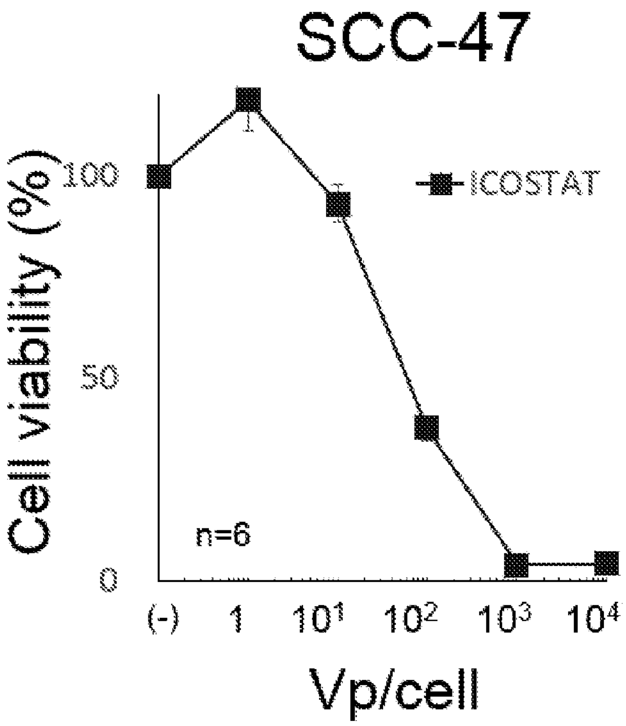
Figure 7D:
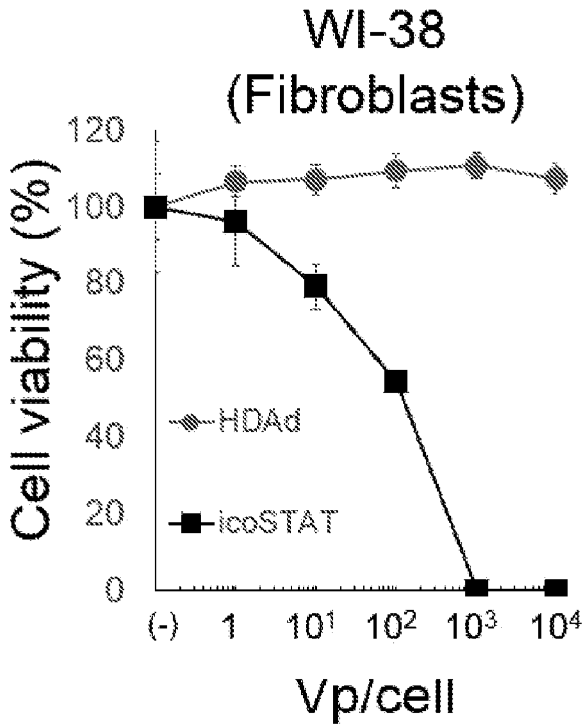
Figure 7E:
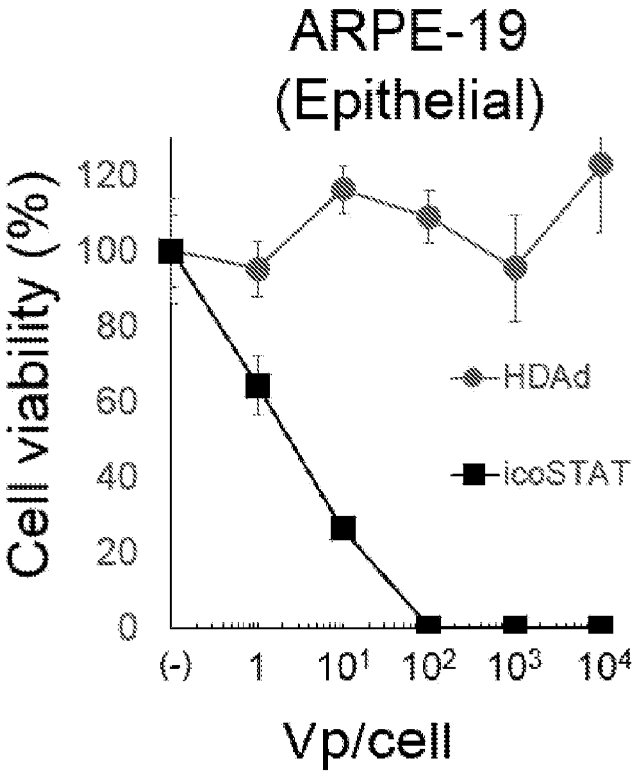
Figure 7F:
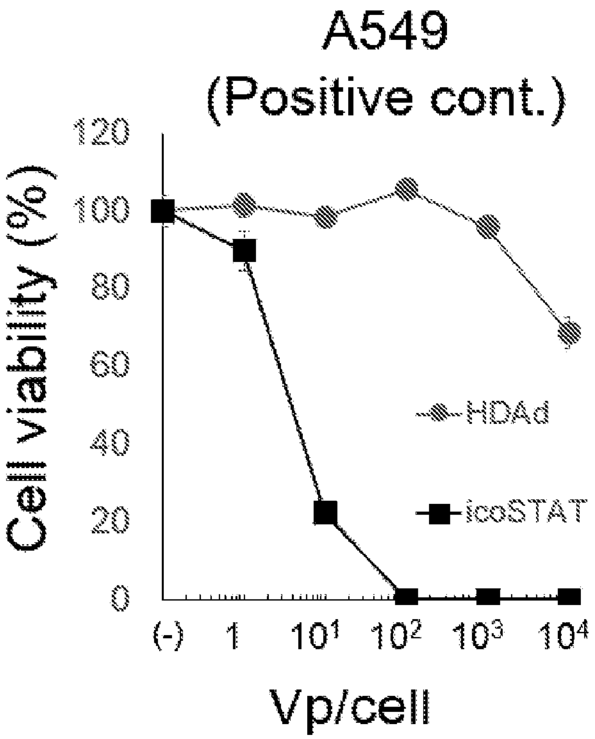

FIGS. 7A to 7F show that ICOSTAT is able to kill cancer cells (i.e. A549, FaDu and SCC47 cells) in a dose-dependent manner (FIGS. 7A to 7C and 7F), and exhibits a lower level of cell killing of non-cancerous cells WI-38 and ARPE-19 cells as compared to the level of killing of the cancerous cells (FIGS. 7D and 7E).

Figure 13A:
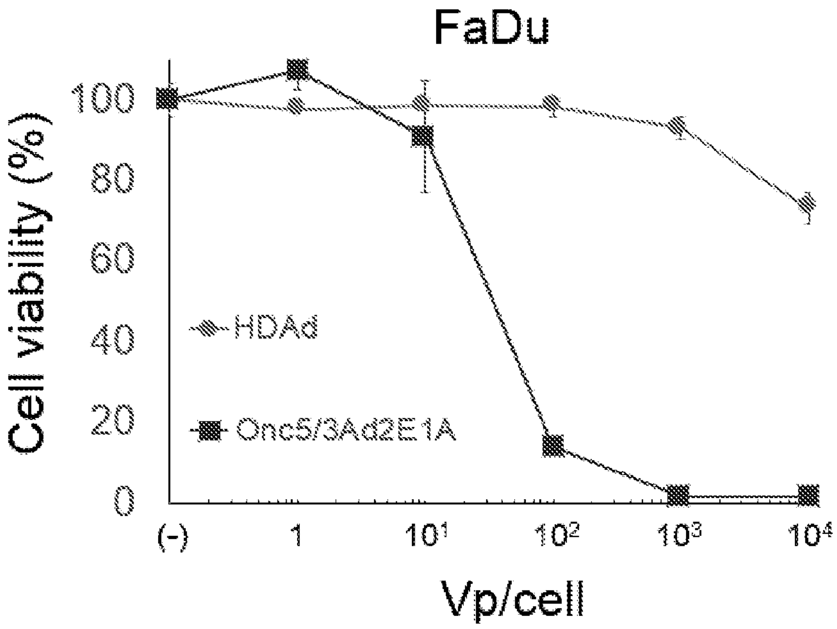
FIGS. 13A to 13D. Graphs showing the ability of Onc5/3Ad2E1A oncolytic adenovirus to kill FaDu cells (FIG. 13A), SCC47 cells (FIG. 13B), WI-38 cells (FIG. 13C) and ARPE-19 cells (FIG. 13D) following infection with the indicated concentration of viral particles (Vp), as determined by MTS viability assay. Helper-dependent adenovirus (HDAd) is included as a control condition.
Figure 13B:
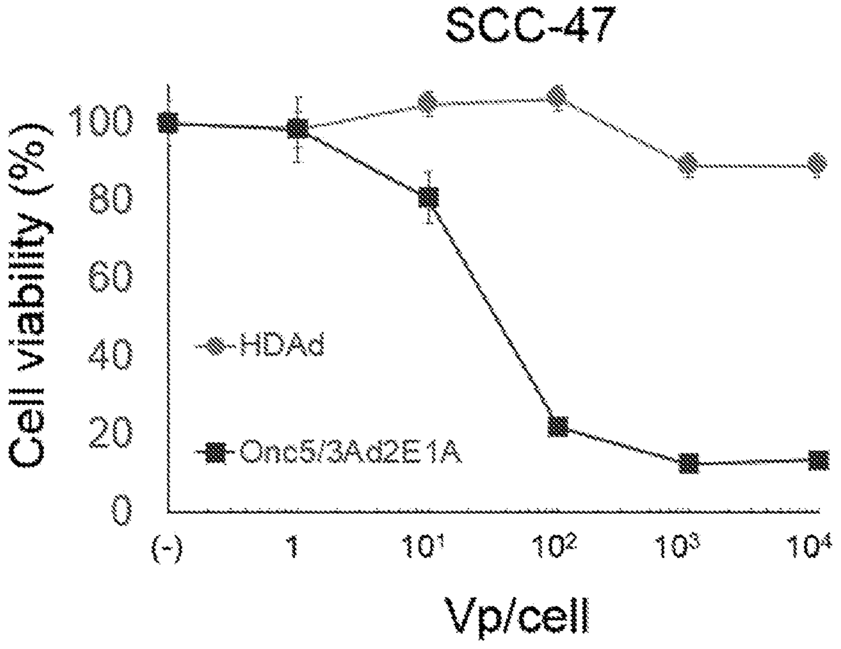
Figure 13C:
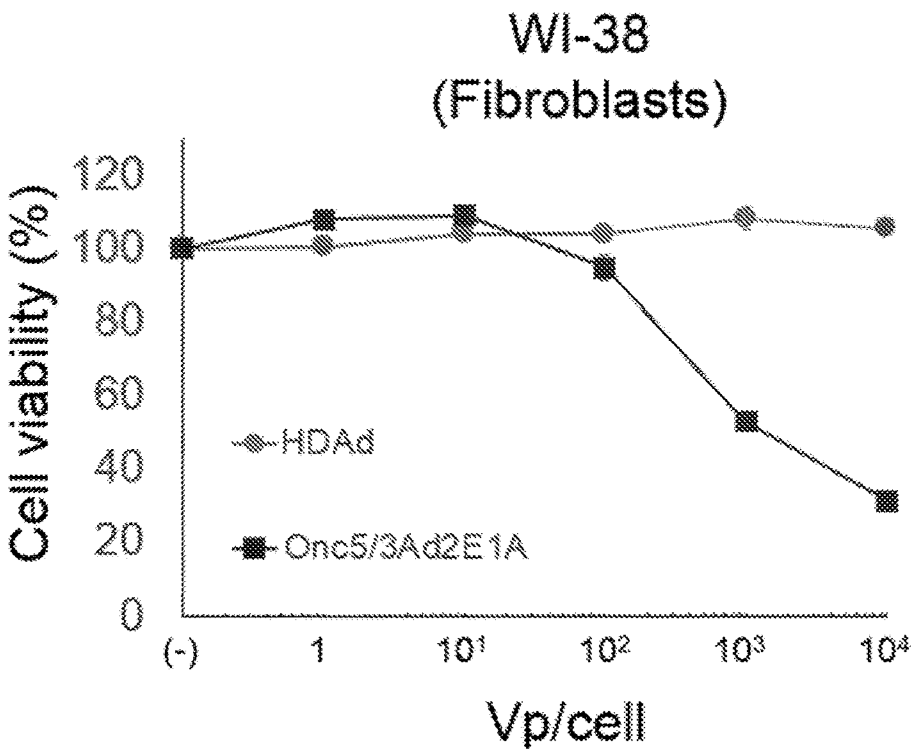
Figure 13D:
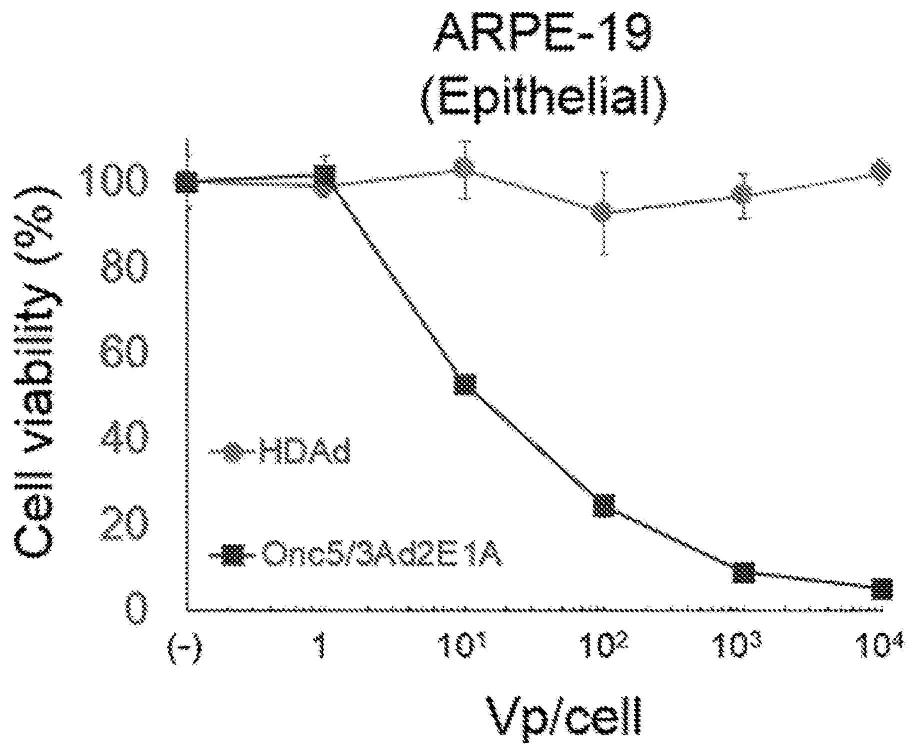

FIGS. 13A to 13D show that Onc5/3Ad2E1Δ24 is able to kill cancer cells (i.e. FaDu and SCC47 cells) in a dose-dependent manner (FIGS. 13A and 13B), and exhibits a lower level of cell killing of non-cancerous WI-38 and ARPE-19 cells as compared to the level of killing of the cancerous cells (FIGS. 13C and 13D).

2.3 Ability to Help Helper-Dependent Adenovirus (HDAd)

The ability of an oncolytic adenovirus of choice or ICOSTAT as generated in Example 2.1 to assist replication of a helper-dependent adenovirus (HDAd) may be analysed by co-infecting cancer cells with the OncoAd and HDAd, and determining virus copy number. Briefly, FaDu or SCC47 cells are plated in 24-well plates and infected with 10 viral particles per cell of HDAd alone, or OncAd+HDAd (at an OncAd:HDAd ratio of 1:10). Cells are harvested at 48 hours post-infection, DNA is extracted and both HDAd and Onc.Ad vector copies are analyzed by quantitative real-time PCR (10 min at 95° C. and then 45 cycles of 10 s at 95° C., 15 s at 60° C., and 30 s at 72° C.) using a Bio-Rad iQ5 real-time PCR detection system (Bio-Rad), and Applied Biosystems SYBR green PCR master mix (Life Technologies). Copy number is normalized using copy number detected for GAPDH.

In particular embodiments, the oncolytic virus of choice is able to replicate itself and the HDAd sufficiently.

Figure 8A:
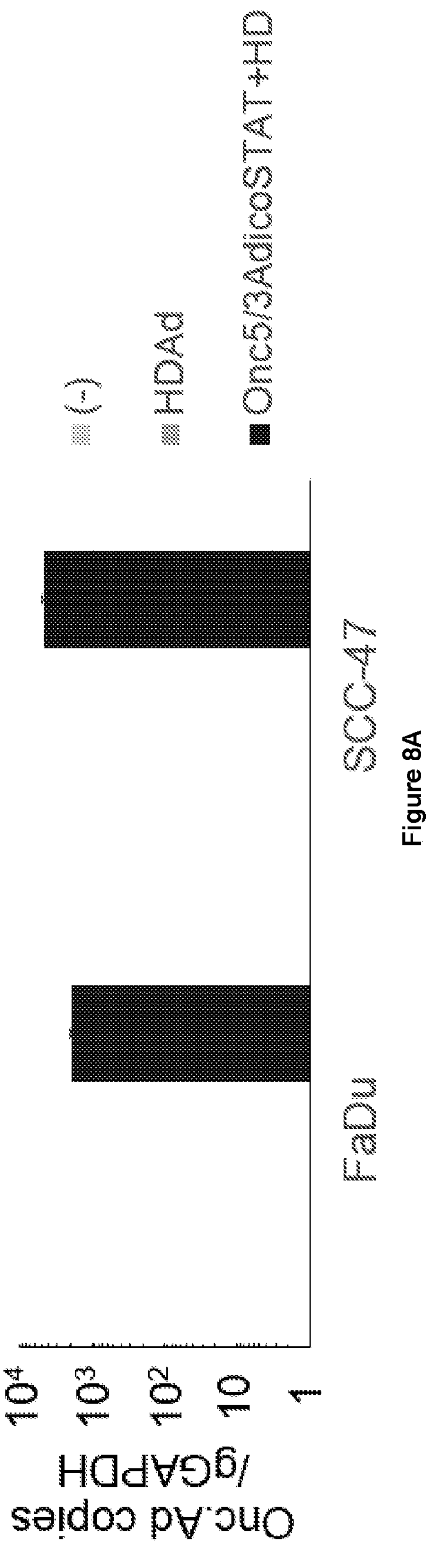
FIGS. 8A and 8B. Bar charts showing ability of ICOSTAT oncolytic adenovirus to replicate and act as helper for replication of helper-dependent adenovirus (HDAd), as determined by copy number analysis by quantitative real-time PCR. The virus designated "Onc5/3AdicoSTAT" is ICOSTAT. "+HD" indicates co-infection of ICOSTAT with HDAd.
Figure 8B:
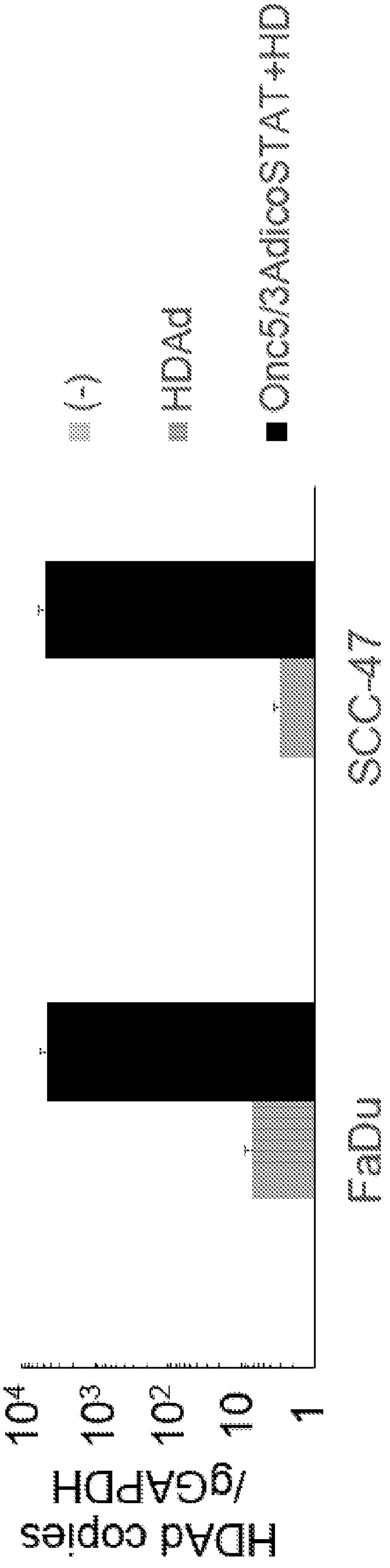

FIGS. 8A and 8B show that ICOSTAT (designated "Onc5/3AdicoSTAT" in the figures) was found to be able to replicate itself (FIG. 8A) and the HDAd (FIG. 8B).

2.4 Effect of IFNγ on Replication of ICOSTAT in Cancer Cells

The effect of IFNγ treatment on replication of ICOSTAT OncAd was analysed. Briefly, FaDu and SCC47 cells are plated in 24-well plates, and the cells are infected with 10 vp/cell of the oncolytic virus of choice or icoSTAT 3 hours post-infection cell culture medium is replaced with medium containing, or not containing, 10 ng/mL recombinant IFNγ at 3 hours post-infection, and cell culture media are replaced with fresh media with/without 10 ng/mL recombinant IFNγ again at 24 and 48 hours post-infection. Cells are harvested at 3, 24, 48 and 72 hours post-infection, DNA is extracted from the cells, viral copy numbers are analysed by quantitative real-time PCR and normalized using copy number detected for GAPDH.

Figure 9A:
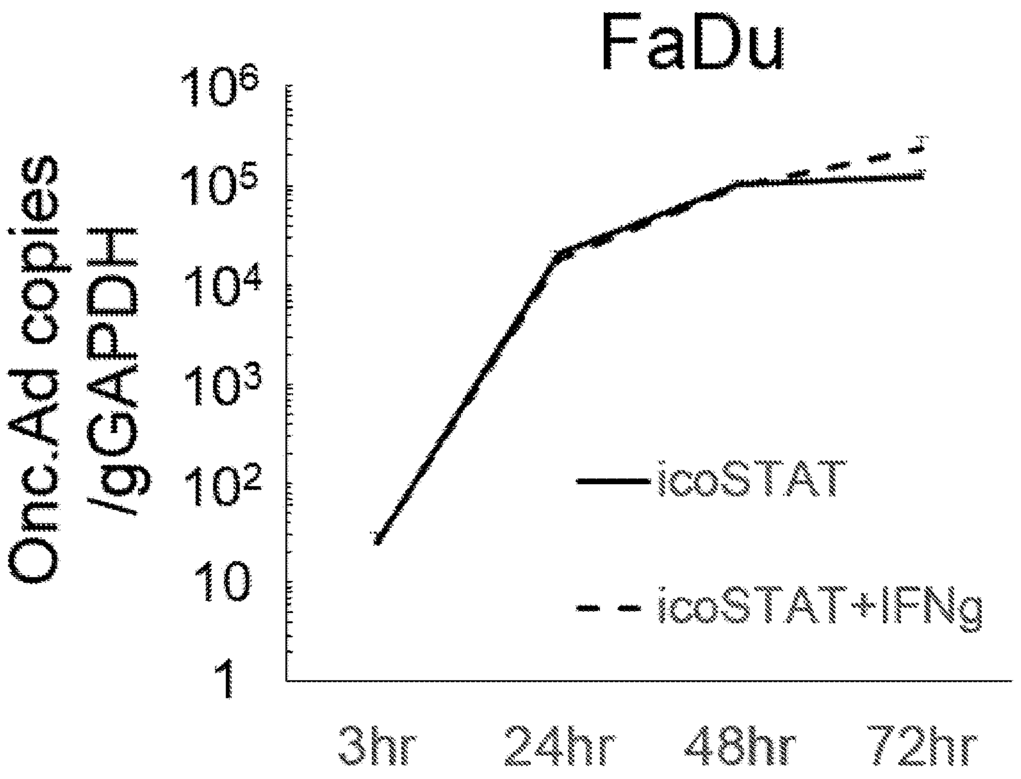
FIGS. 9A and 9B. Graphs showing the replication of ICOSTAT oncolytic adenovirus in FaDu cells (FIG. 9A) and SCC47 cells (FIG. 9B), in the presence or absence of 10 ng/ml IFNγ in the cell culture media.
Figure 9B:
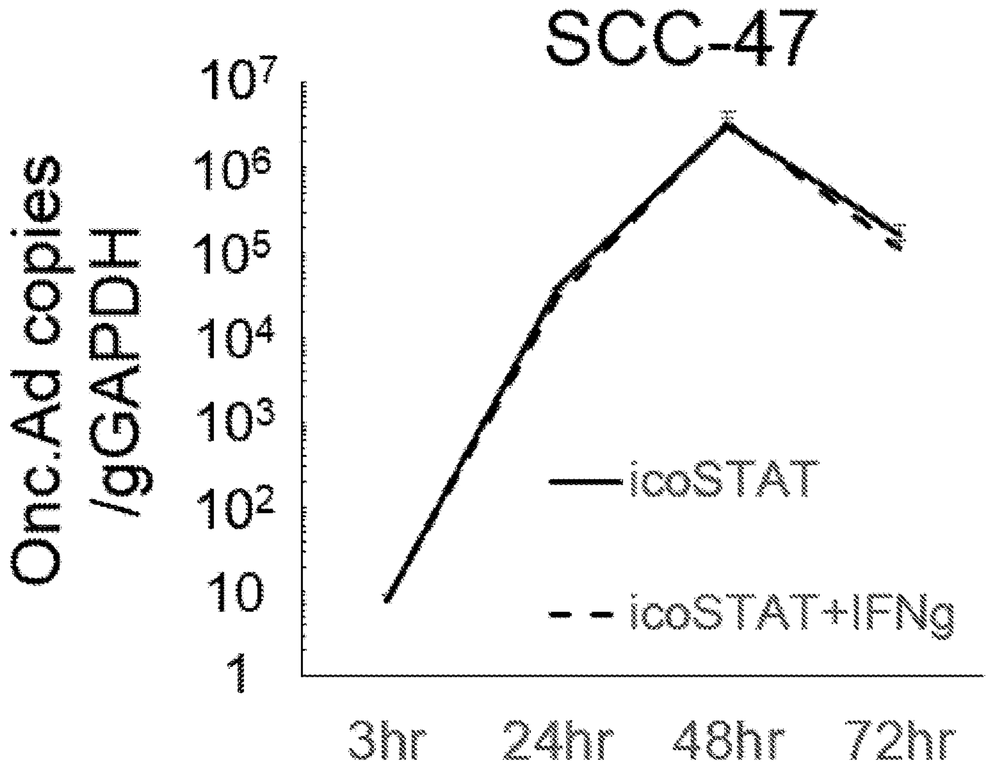

FIGS. 9A and 9B show that ICOSTAT was able to replicate in FaDu cells and SCC47 cells, in the presence or absence of IFNγ.

Figure 10A:
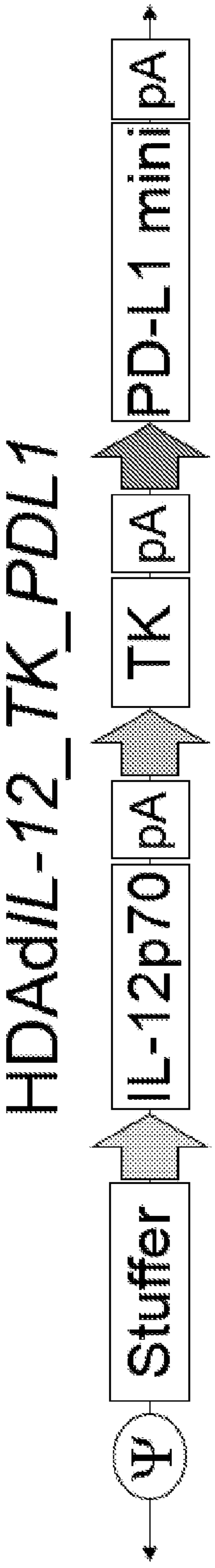
FIGS. 10A to 10D.

Example 3: Helper-Dependent Ad (HDAd) Constructs 3.1 HDAd Constructs and Production A novel construct encoding a helper-dependent adenovirus was prepared using recombinant DNA techniques. The coding sequence of the resulting construct designated HDAdIL-12_TK_PD-L1 is represented schematically in FIG. 10A. HDAdIL-12_TK_PD-L1 contains sequence encoding expression cassettes for (i) human IL-12p70 (sequence encoding alpha and beta chains), (ii) HSV-1 thymidine kinase, and (iii) an anti-PD-L1 minibody (comprising the CDRs of anti-PD-L1 clone H12_gl described e.g. in WO 2016111645 A1) including a HA tag. The three coding sequences each have their own polyA signal sequences.

The HDAd HDΔ28E4EGFP construct containing an EGFP transgene driven by the CMV promoter (HDAdeGFP) was produced as described in Farzad et al. Oncolytics 2014 1: 14008.

The HDAd "HDIL12_PDL1" contains sequence encoding human IL-12p70 protein and anti-PD-L1 minibody derived from YW243.55.S70 (atezolizumab). The anti-PD-L1 minibody of this construct consists of scFv for YW243.55.S70 fused with a hinge, CH2 and CH3 regions of human IgG1 and a C-terminal HA tag (as described e.g. in Tanoue et al. Cancer Res. (2017) 77(8):2040-2051).

3.2 Expression of Encoded Proteins

Cancer cells were transfected with plasmid HDAd vectors, and medium samples were collected to analyze IL-12p70 and anti-PD-L1 minibody levels in the cell culture media of the transfected cells at 48 hours post-transfection.

Figure 10B:
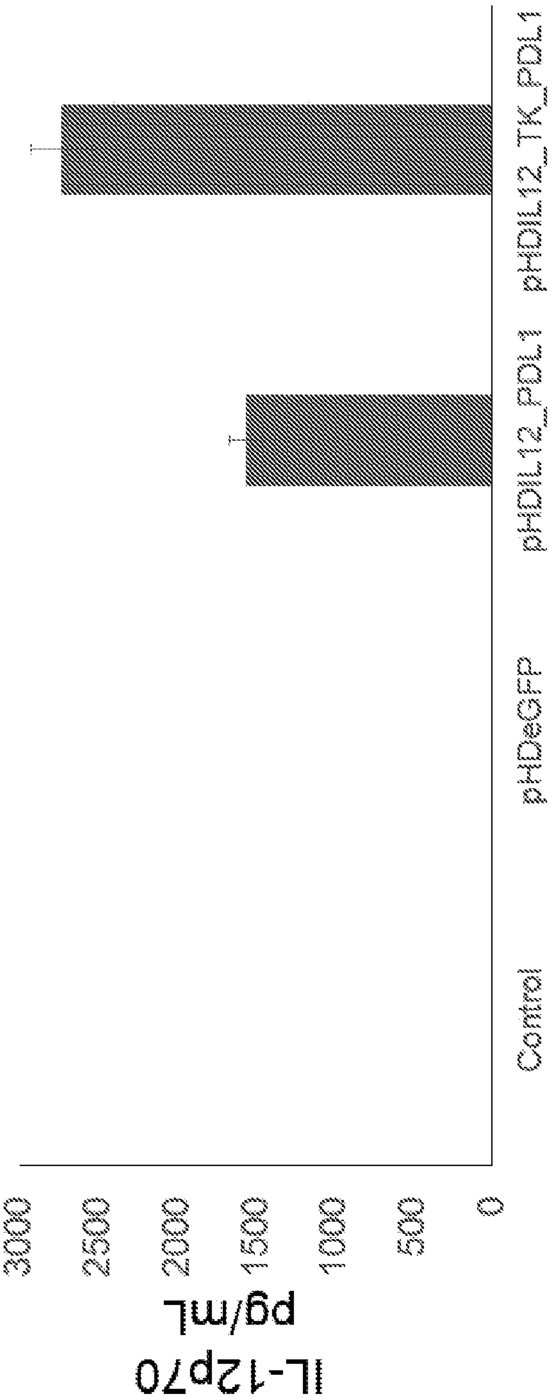

IL-12p70 levels in media were measured using the BD cytokine multiplex bead array system (BD Biosciences), according to manufacturer's instructions. The results are shown in FIG. 10B. Cells transfected with the HDAdIL-12_TK_PD-L1 construct were found to produce higher levels of IL-12p70 than cells transfected with the HDIL-12_PD-L1 construct.

Figure 10C:
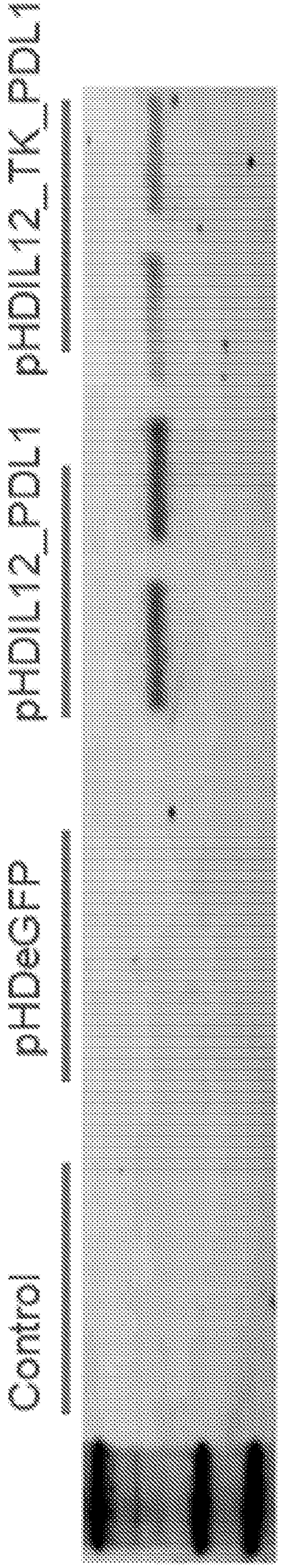

Secretion of anti-PD-L1 minibodies into the cell culture medium was detected by western blot analysis, using an anti-HA antibody (to detect the HA-tagged minibodies). FIG. 10C shows that cells transfected with the HDAdIL-12_TK_PD-L1 construct secreted the anti-PD-L1 minibody into the cell culture medium.

In another experiment, cells were transfected with the different constructs and at 8 hours post-transfection the cell culture media was replaced with medium containing 10 ng/ml Ganciclovir (GCV). Cell culture medium was then replaced with medium containing 10 ng/ml every 24 hours, and after 7 days, the wells were stained with Crystal Violet solution to reveal viable cells.

Figure 10D:
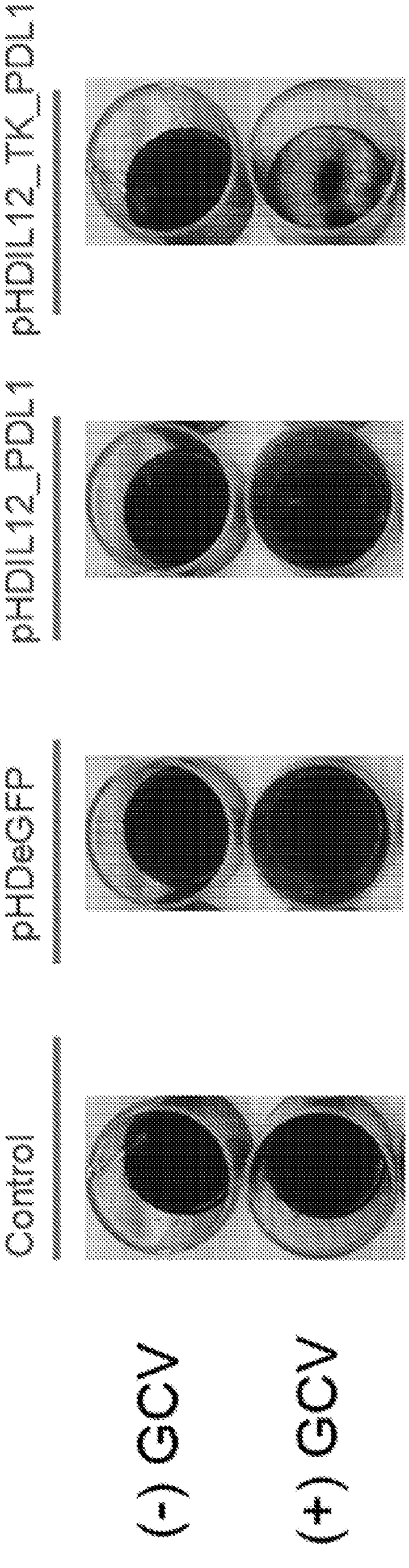

The results are shown in FIG. 10D, and confirm that cells transfected with the HDAdIL-12_TK_PD-L1 construct express thymidine kinase.

In further experiments A549, FaDu or SCC47 cells (n=4 wells per condition) were infected in vitro with HDAdIL-12_TK_PD-L1, HDAd_PD-L1 (see e.g. Tanoue et al., supra), or a control HDAd encoding eGFP (see Farzad et al., supra). The cells were either cultured for 48 hours in the absence of ganciclovir, or medium was changed at 8 hours post-infection and every 24 hours thereafter with medium containing 10 ng/ml ganciclovir.

Secretion of IL-12 into the cell culture supernatant was analysed by ELISA, and secretion of anti-PD-L1 minibody was analysed by western blot using an anti-HA antibody (the anti-PD-L1 minibody comprises a C-terminal HA-tag). At the end of the experiment wells were stained with Crystal Violet solution to reveal viable cells.

Figure 21A:
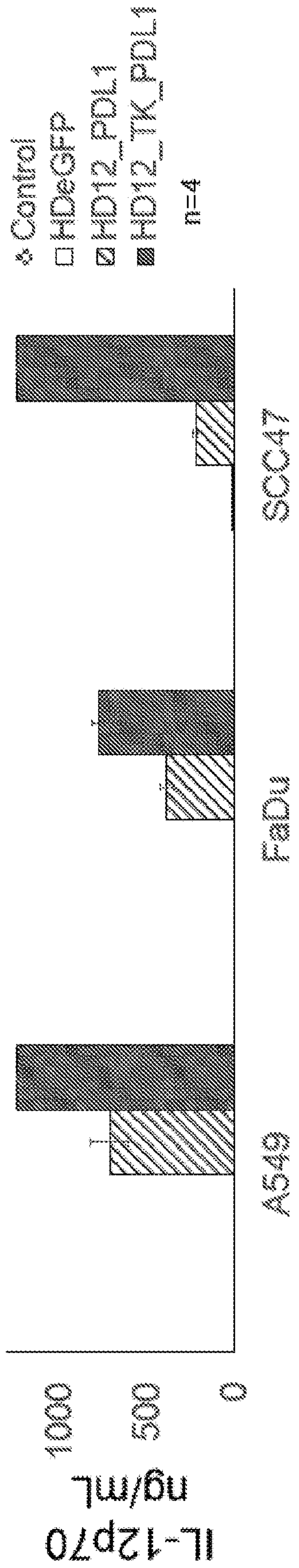
FIGS. 21A to 21C. Bar chart and images showing the results of analysis of transgene expression in cancer cell lines infected with different HDAd viruses, cultured in the presence or absence of ganciclovir (GCV).
Figure 21B:
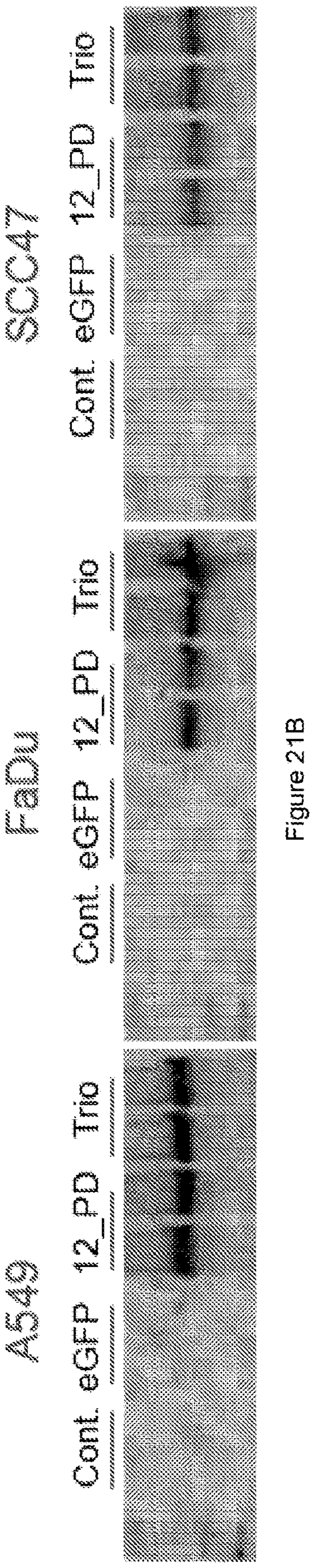
Figure 21C:
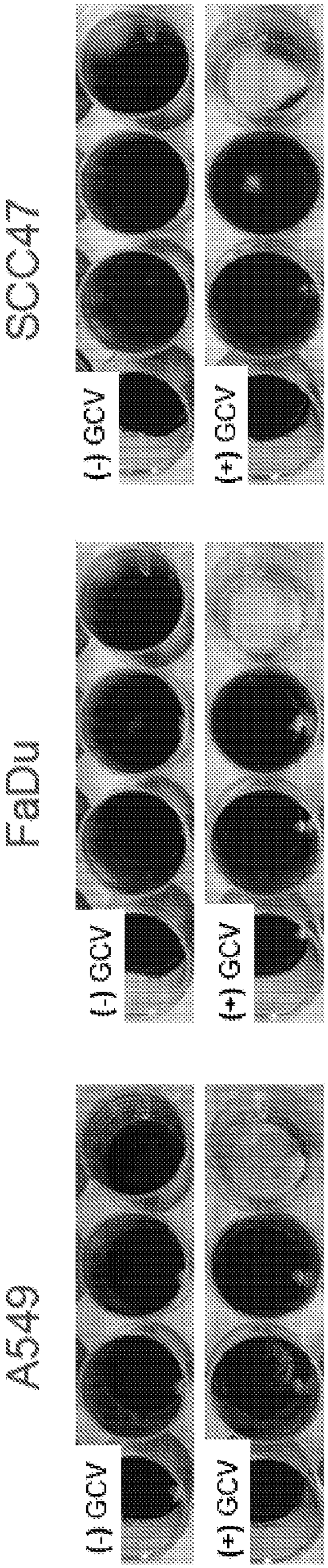
Figure 22A:
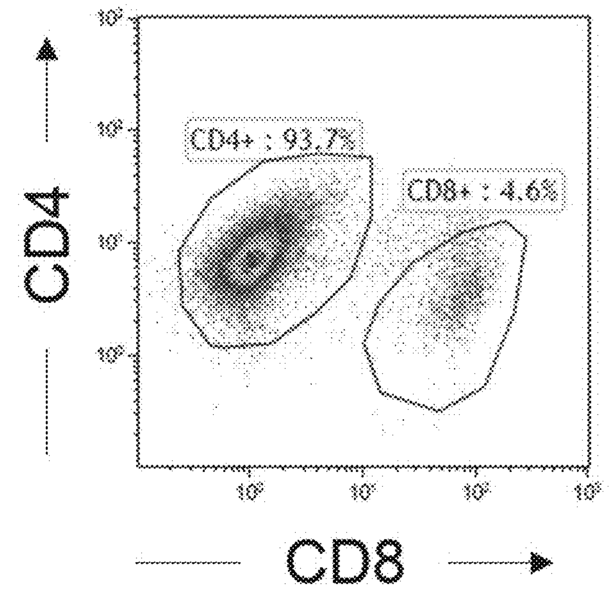
FIGS. 22A and 22B. Scatterplots showing the results of characterisation by flow cytometry of Adenovirus-specific T cells (AdVSTs) used in experiments of Example 9.
Figure 22B:
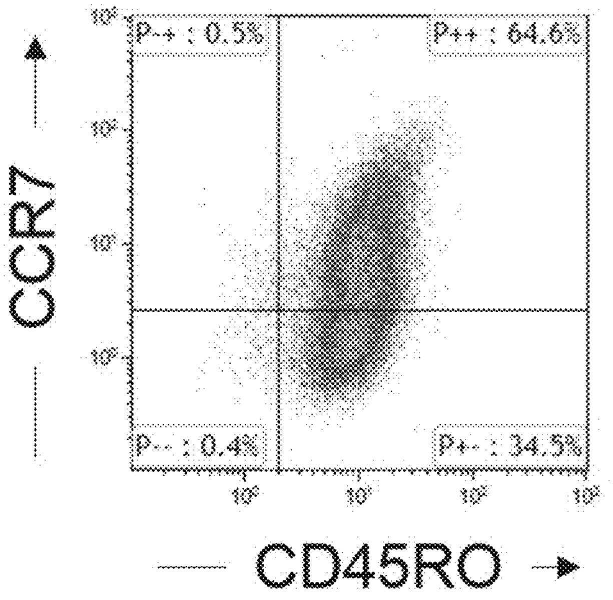
Figure 23A:
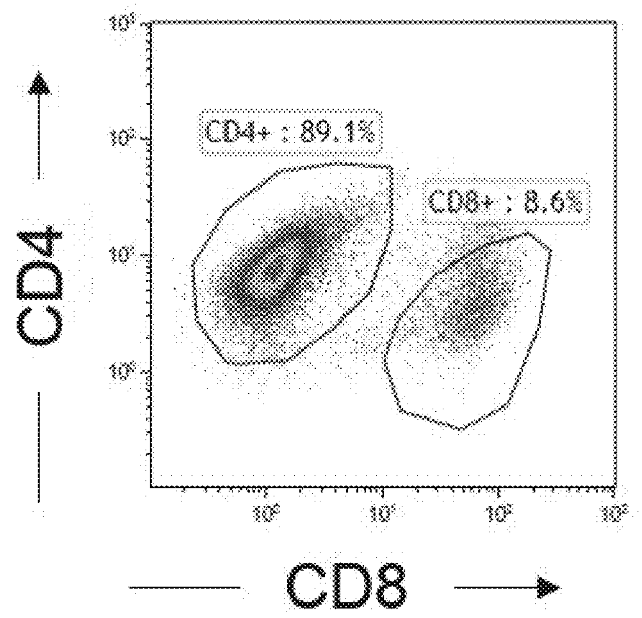
FIGS. 23A to 23C. Scatterplots and histograms showing the results of characterisation by flow cytometry F1.CAR-transduced AdVSTs used in experiments of Example 9.
Figure 23B:
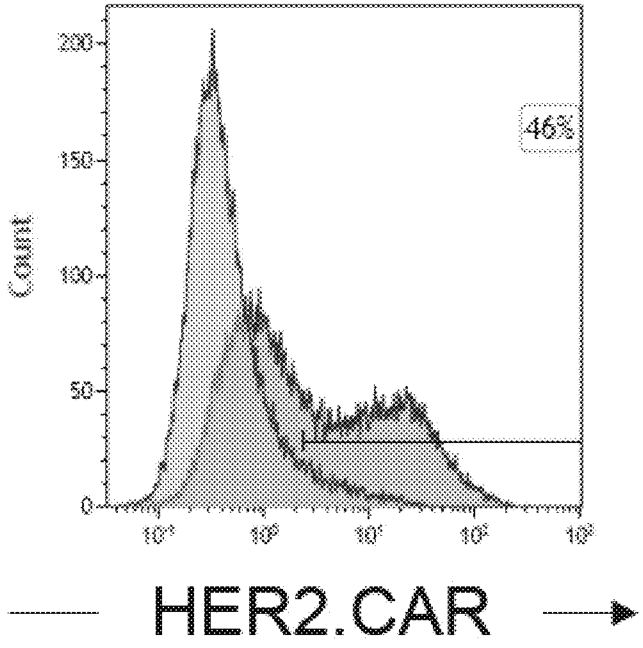
Figure 23C:
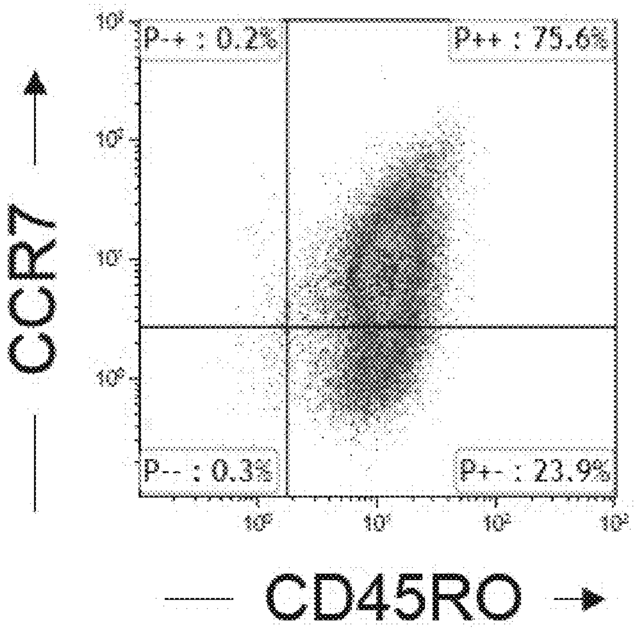
Figure 24A:
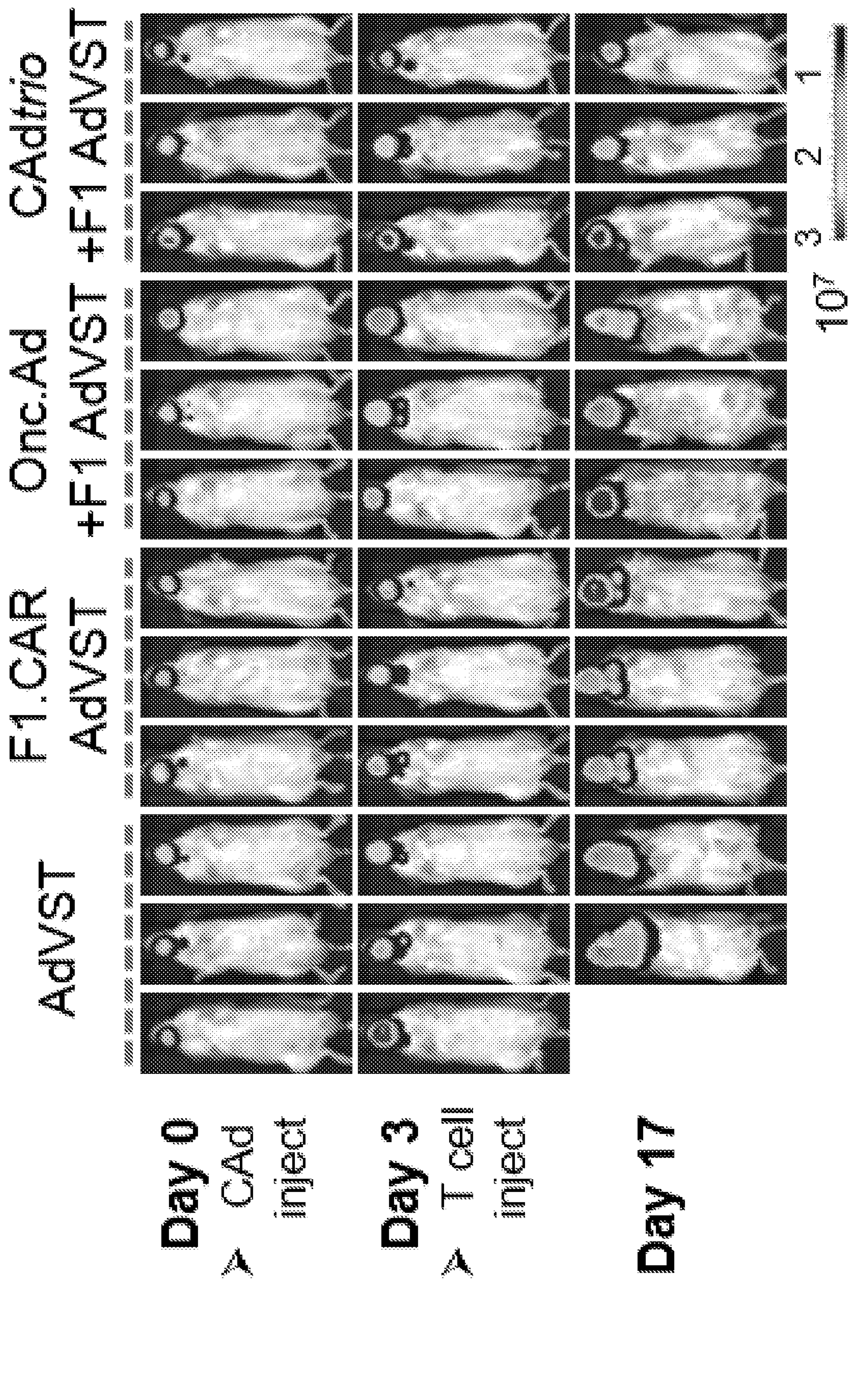
FIGS. 24A to 24D. Images and graphs showing the results of in vivo analysis of the anti-cancer activity of Adenovirus-specific T cells (AdVSTs), F1.CAR-transduced AdVSTs, the combination of F1.CAR-transduced AdVSTs with Onc5/3Ad2E1Δ24, and the combination of F1.CAR-transduced AdVSTs with Onc5/3Ad2E1Δ24+HDAdIL-12_TK_PD-L1 ("CAdtrio").
Figure 24B:
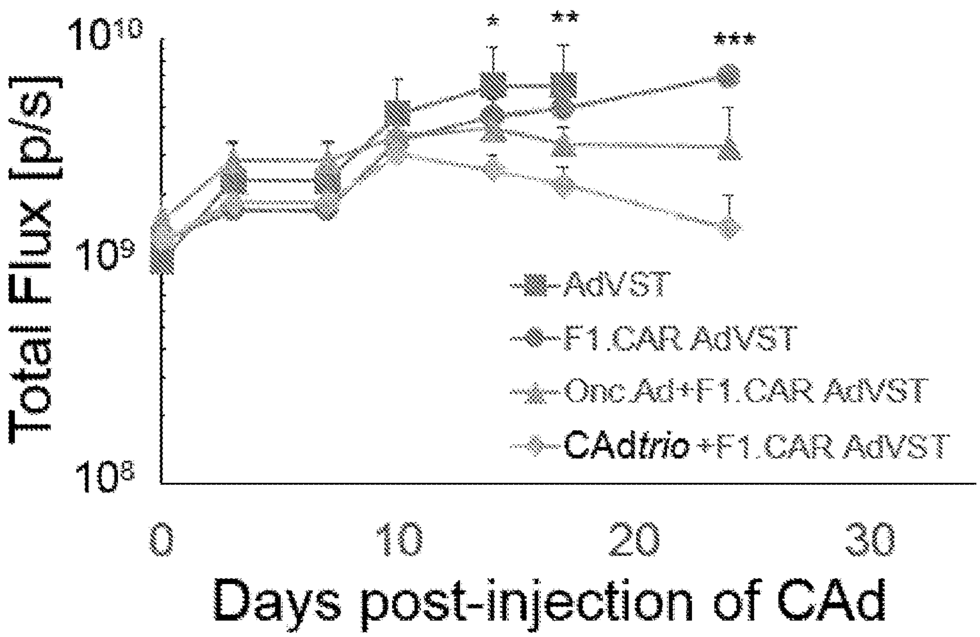
Figure 24C:
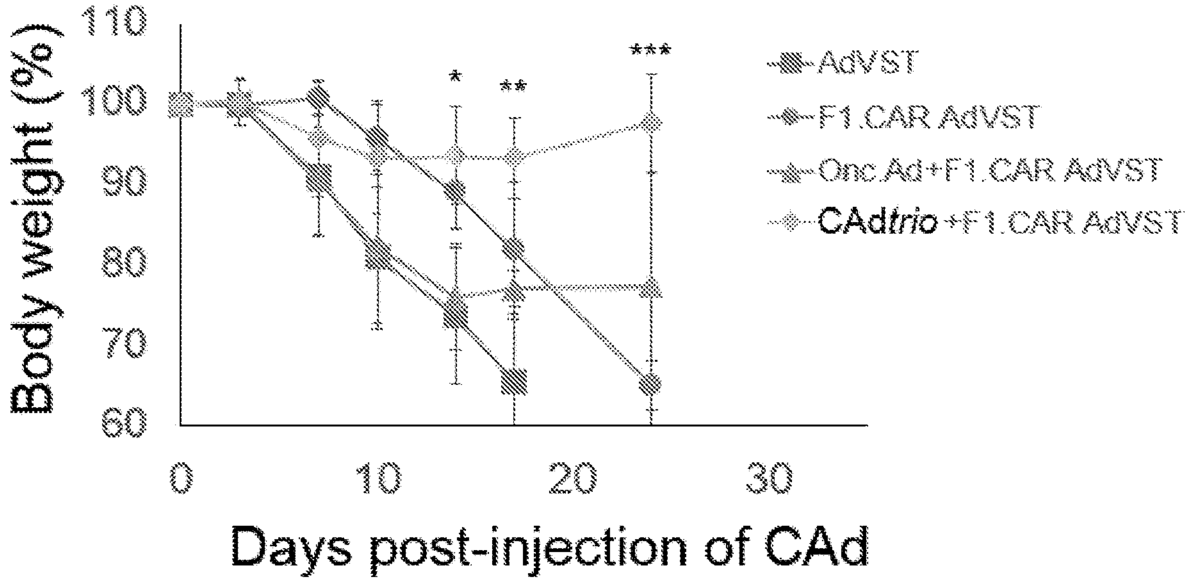
Figure 24D:
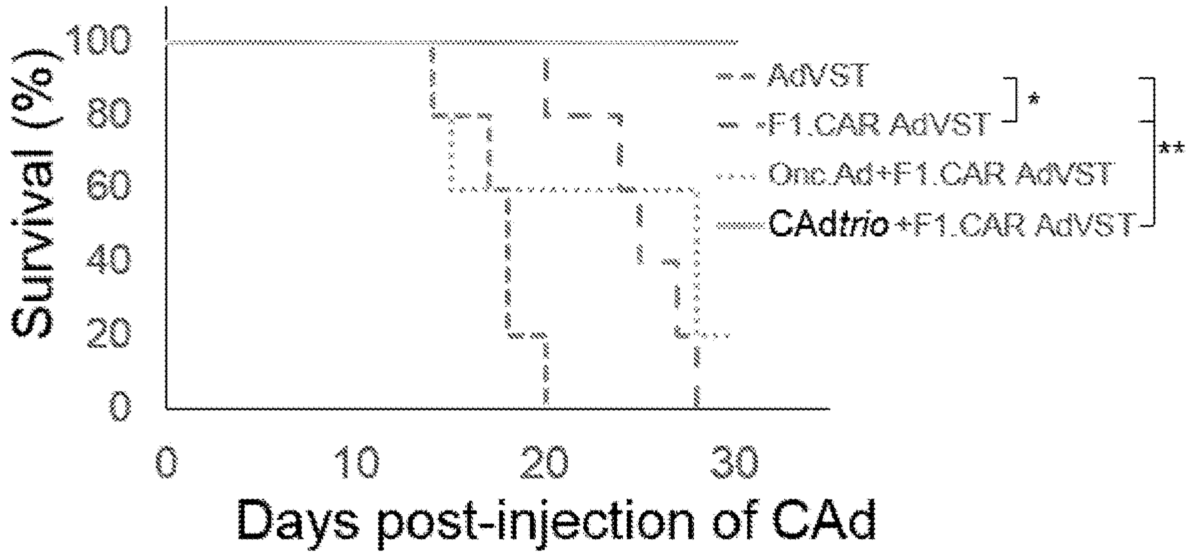

The results are shown in FIGS. 21A to 21C, and confirmed expression of the transgenes encoded by the HDAds in the different cancer cell lines analysed.

3.3 Confirmation of Anti-PD-L1 Minibody Binding to PD-L1

The ability of the anti-PD-L1 minibody encoded by HDAdIL-12_TK_PD-L1 to bind to PD-L1 was analysed by ELISA.

Briefly, Immulon 2 high binding 96-well plates (VWR) were coated with 500 ng/well of recombinant human PD-L1 (BioVision). After blocking plate with PBS-T containing 3% BSA, serially diluted cell culture media of A549 cells which had been transfected with plasmid encoding GFP (pGFP; negative control), plasmid encoding the anti-PD-L1 minibody described in Tanoue et al. supra. (pPDL1 mini Tanoue) or plasmid encoding the anti-PD-L1 minibody encoded by HDAdIL-12_TK_PD-L1 (pPDL1 mini) were added and incubated at 4° C. for 24 hours. Serially diluted anti-human PD-L1 antibody starting from 10 μg/well (BioLegend) was used as a positive control (PDL1 IgG). After washing plate with PBS-T, HRP-labeled anti-human IgG (for PD-L1 mini and PDL1 mini Tanoue) or HRP-labeled anti-mouse IgG (BioRad; for PD-L1 IgG and Iso IgG) were added for detection, and incubated at room temperature for 1 hour. The plate was then developed, and absorbance at 450 nm was measured using Tecan reader (TECAN).

Figure 11:
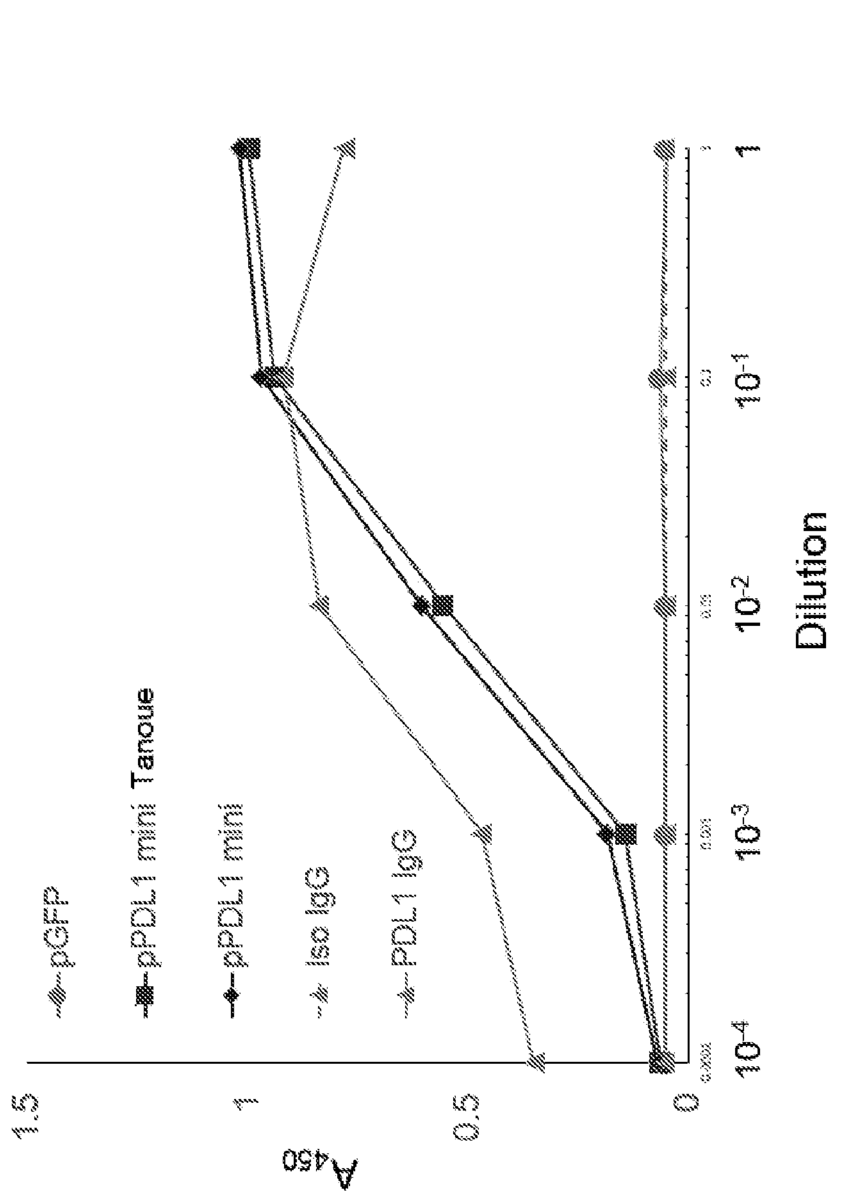
FIG. 11. Graph showing ELISA analysis of PD-L1 minibody avidity to recombinant human PD-L1, using serially diluted cell culture media of A549 cells which had been transfected with plasmid encoding GFP (pGFP; negative control), plasmid encoding the anti-PD-L1 minibody described in Tanoue et al. supra, (pPDL1 mini Tanoue) or plasmid encoding the anti-PD-L1 minibody encoded by HDAdIL-12_TK_PD-L1 (pPDL1 mini). Serially diluted anti-human PD-L1 antibody was used as a positive control (PDL1 IgG).

The results are shown in FIG. 11. The anti-PD-L1 minibody comprising the CDRs of anti-PD-L1 antibody clone H12 was found to bind to human PD-L1 in a dose-dependent fashion, with comparable (or greater) avidity as compared to the avidity of binding by anti-PD-L1 minibody described in Tanoue et al. supra.

Example 4: Analysis of Treatment of Cancer In Vivo

The anticancer effect of treatment with the combination of (1) an oncolytic virus of choice+HDAdIL-12_TK_PD-L1+HER2-CAR-T and (2) ICOSTAT+HDAdIL-12_TK_PD-L1+HER2-CAR-T is demonstrated in vivo in mouse xenograt tumour models.

In a first experiment, $1\times10^6$ FaDu cells are injected subcutaneously in PBS into NSG male mice. After 12 days, $1\times10^6$ viral particles (1) oncolytic virus and HDAdIL-12_TK_PD-L1 or (2) ICOSTAT+HDAdIL-12_TK_PD-L1 are injected intratumorally at an OncAd:HDAd ratio of 1:20.

In a second experiment. $0.5\times10^6$ FaDu cells are injected orthotopically into NSG male mice. After 6 days, $1\times10^6$ viral particles (1) oncolytic virus and HDAdIL-12_TK_PD-L1 or (2) ICOSTAT+HDAdIL-12_TK_PD-L1 are injected intratumorally at an OncAd:HDAd ratio of 1:20.

In both experiments, 3 days after administration of the viral particles, $1\times10^6$ HER2-CAR T cells are administered intravenously.

In both experiments, control conditions are included as follows:

| Condition | OncAd | HDAd | CAR T |
|---|---|---|---|
| 1 (test condition) | Of choice | HDAdIL-12_TK_PD-L1 | HER2 CAR-T |
| 2 (test condition) | ICOSTAT | HDAdIL-12_TK_PD-L1 | HER2 CAR-T |
| 3 | — | HDAdIL-12_TK_PD-L1 | HER2 CAR-T |
| 4 | Of choice | — | HER2 CAR-T |
| 5 | ICOSTAT | — | HER2 CAR-T |
| 6 | Of choice | HDAdIL-12_TK_PD-L1 | — |
| 7 | ICOSTAT | HDAdIL-12_TK_PD-L1 | — |
| 8 | Of choice | — | — |
| 9 | ICOSTAT | — | — |
| 10 | — | HDAdIL-12_TK_PD-L1 | — |
| 11 | — | — | HER2 CAR-T |

Tumor size is monitored and tumour volumes are calculated using the formula: $\text{Width}^2\times\text{Length}\times0.5$.

The use of the combination of oncolytic virus, HDAdIL-12_TK_PD-L1 and HER2 CAR-T (test condition 1) is found to have an improved antitumour effect as compared to the use of any of the agents alone (conditions 8, 10 or 11), or compared to the use of two of the three agents (conditions 3, 4 and 6).

Similarly, the use of the combination of ICOSTAT, HDAdIL-12_TK_PD-L1 and HER2 CAR-T (test condition 2) is found to have an improved antitumour effect as compared to the use of any of the agents alone (conditions 9, 10 or 11), or compared to the use of two of the three agents (conditions 3, 5 and 7).

Similar results are observed when xenograft tumours are established using SCC47 cells and A549 cells.

Example 5: Analysis of the Anti-Cancer Activity of the HER2-Specific CAR-T Cells In Vivo The anti-cancer activity of the HER2-specific CAR-T cells (see Example 1 above) was investigated in vivo in a FaDu cell-derived xenograft model of squamous cell head and neck cancer.

Briefly, $0.5\times10^6$ FaDu cells were injected orthotopically into NSG male mice. After 9 days, mice were injected via the tail vein with $1\times10^6$ T cells genetically modified to express firefly luciferase, which had not been transduced with a HER2-CAR construct, or with $1\times10^6$ firefly luciferase-expressing T cells which had been transduced with the C5, F1 or A3 CAR constructs. A control condition was included in the experiment in which mice were not injected with T cells at day 9.

Luciferase activity (and thus number and distribution of the administered T cells), body weight, survival of the mice was monitored over time. Luciferase activity was monitored by intraperitoneal injection of D-Luciferin (1.5 mg per mouse), and imaging of the mice 10 min later using an IVIS imager (Xenogen).

Figure 15A:
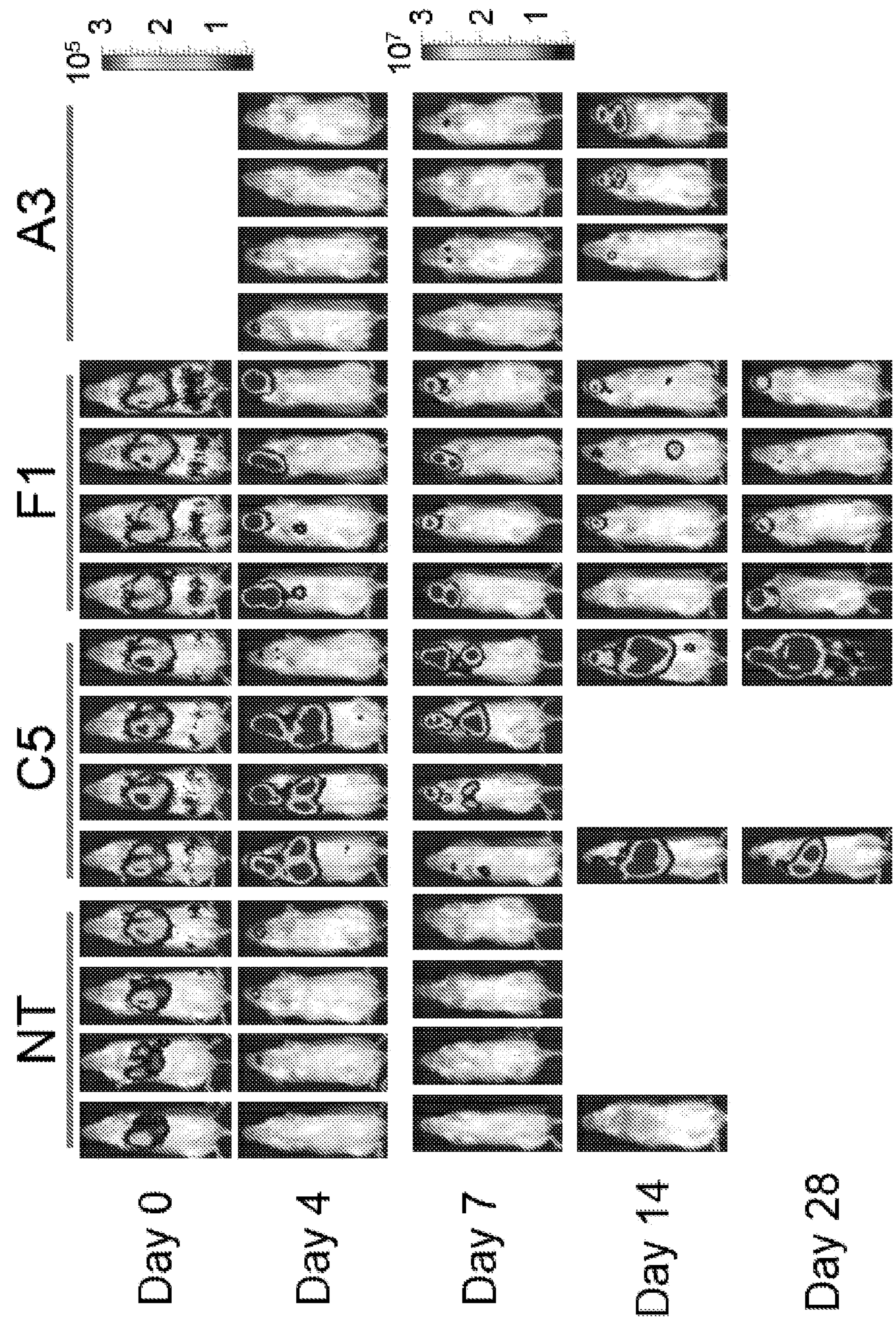
FIGS. 15A to 15C. Images and graph showing the results of in vivo analysis of the anticancer activity of adoptively-transferred luciferase-expressing T cells in an orthotopic FaDu cell-derived model of squamous cell head and neck carcinoma.
Figure 15B:
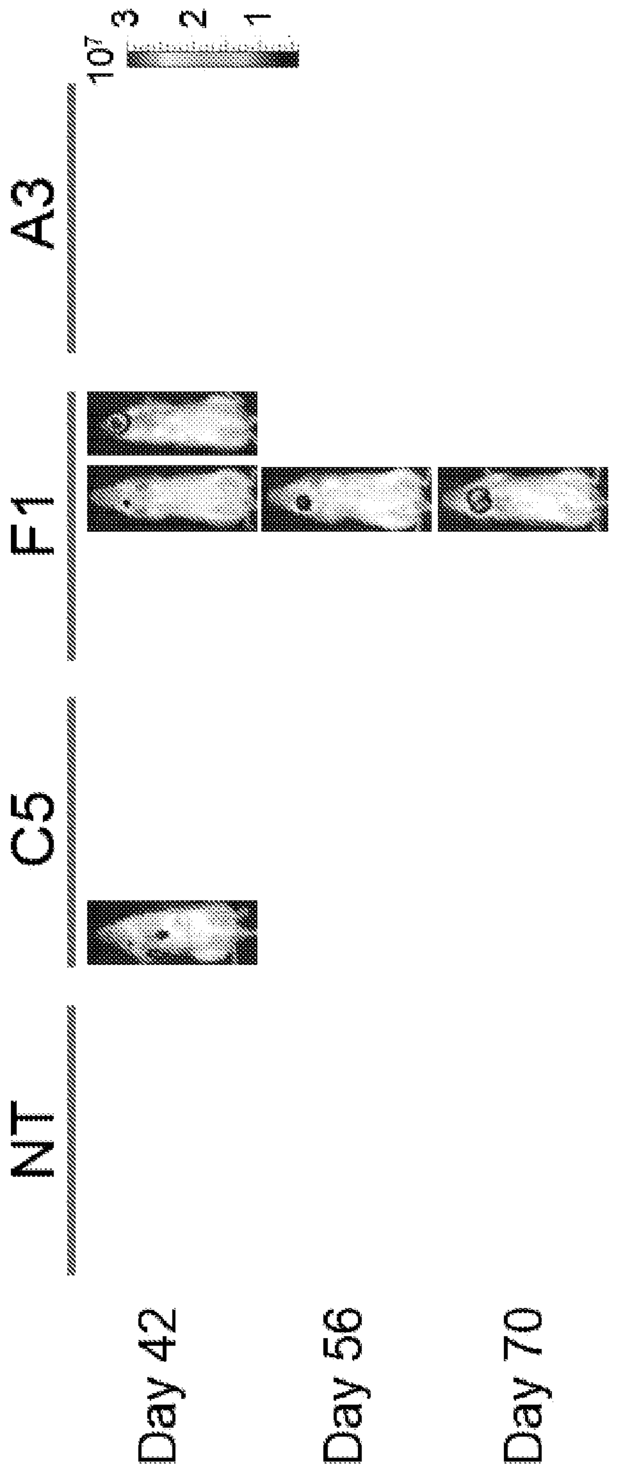

FIGS. 15A and 15B show the images acquired on days 0, 4, 7, 14, 28, 42, 56 and 70 following injection of the luciferase-expressing T cells (i.e. the non-transduced T cells or HER2-specific CAR-T cells) (days refer to days after ffLuc T cell injection). The systemically infused T cells were shown to migrate to the site of the orthotopic tumors. The T cells which had not been modified to express HER2-specific CARs were undetectable after 7 days. By contrast, the HER2-specific CAR-T cells persisted and remained detectable throughout the experiment.

Figure 15C:
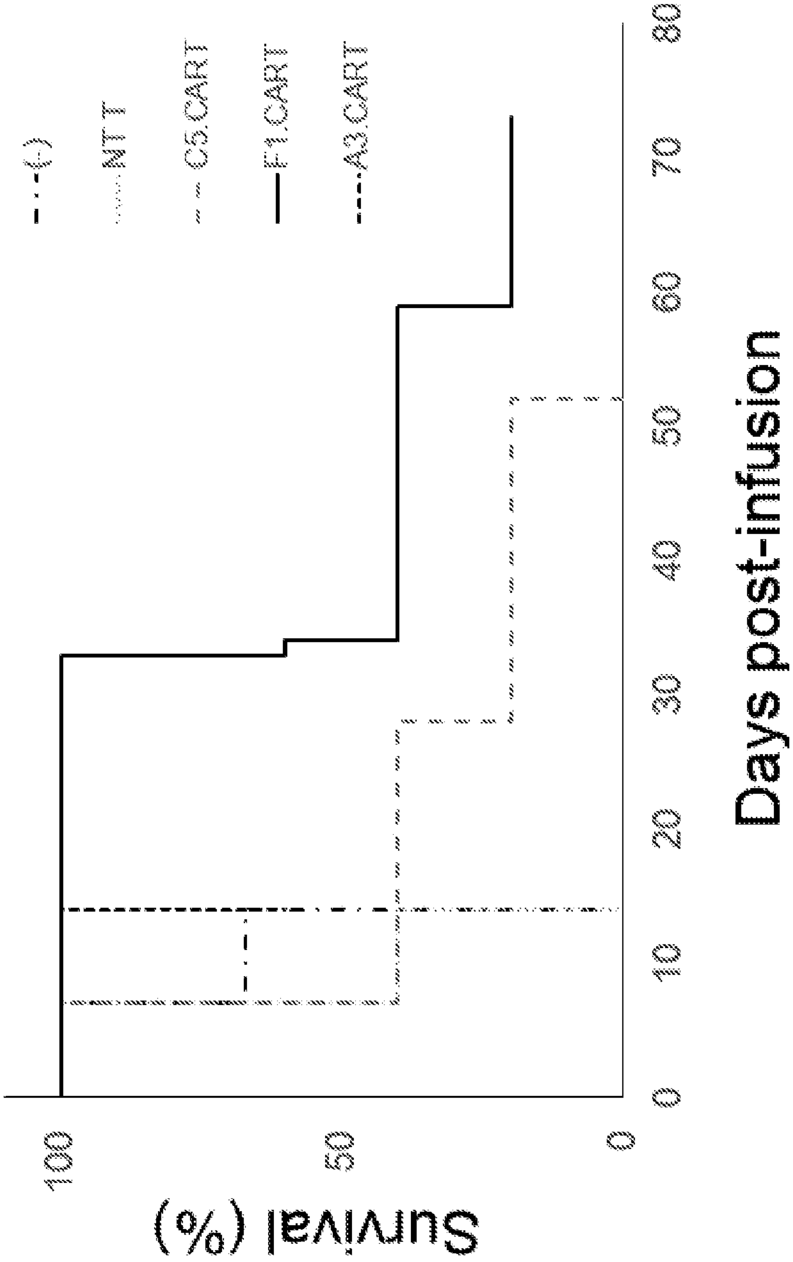

FIG. 15C shows percentage survival of mice subjected to the different treatments over the course of the experiment. Administration of HER2-specific CAR-T cells was found to increase survival.

In a separate experiment NOD scid gamma (NSG) mice were injected via the tail vein with $1\times10^6$ firefly luciferase-expressing T cells which had not been transduced with a HER2-CAR construct, or with $1\times10^6$ firefly luciferase-expressing T cells which had been transduced with the C5, F1 or A3 CAR construct. Luciferase activity was monitored as described above, and body weight of the mice was also monitored overtime.

Figure 16A:
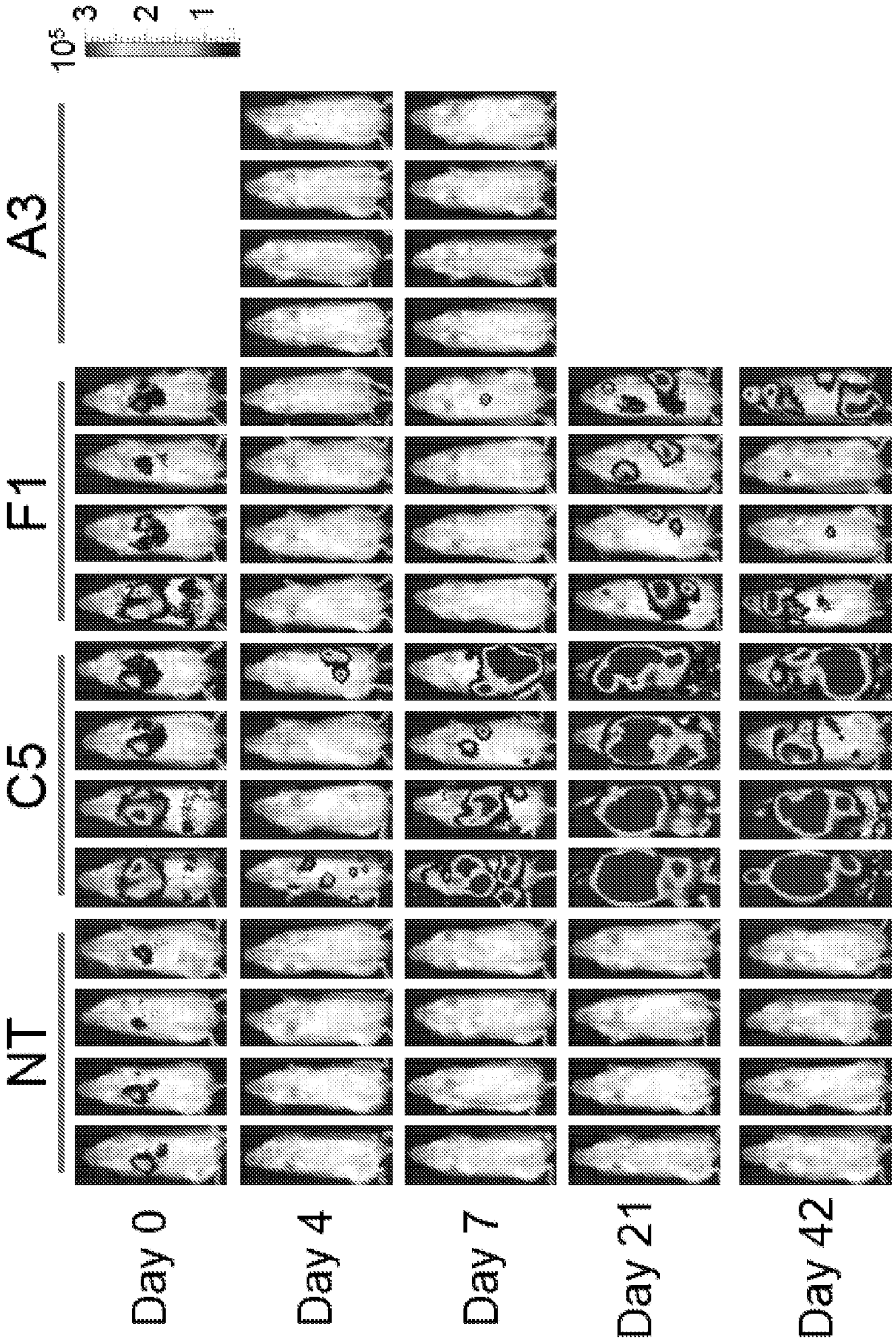
FIGS. 16A to 16C. Images and graphs showing the results of in vivo analysis of adoptively-transferred T cells in NSG mice.
Figure 16B:
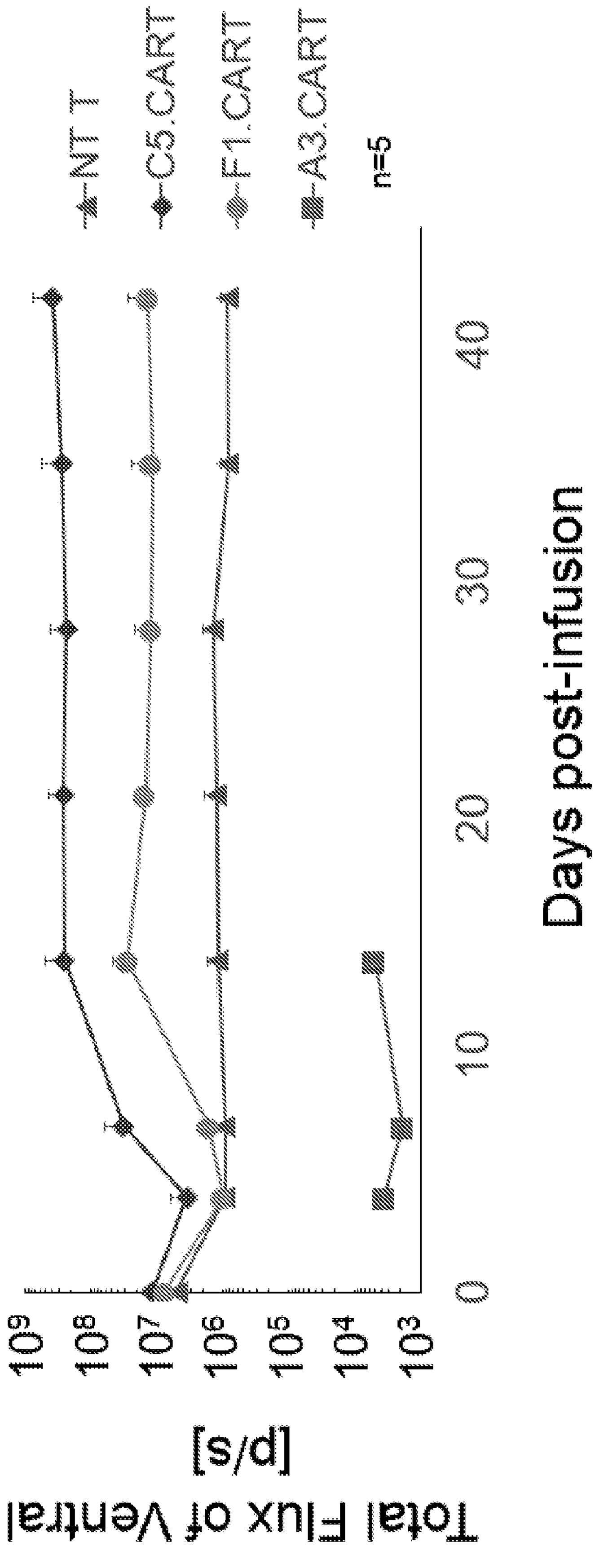
Figure 16C:
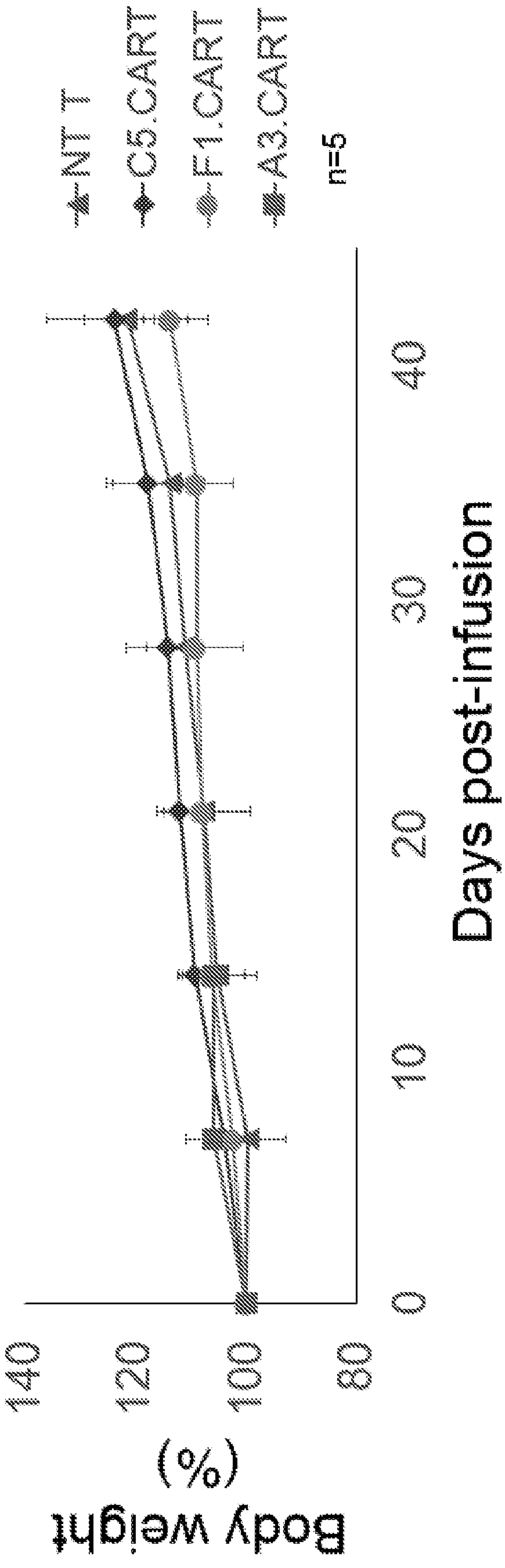

The results of the experiment are shown in FIGS. 16A to 16C. The C5 CAR-T cells were found to expand non-specifically in NSG mice (FIG. 16A). No significant weight loss was observed in NSG mice administered with the HER2-specific CAR-T cells (FIG. 16C).

Example 6: Analysis of the Anti-Cancer Activity of the Combination of Oncolytic Virus. HDAd Virus and HER2-Specific CAR-T Cells In Vivo The anti-cancer activity of a combination of oncolytic virus. HdAd and HER-specific CAR-T cell therapy was investigated in vivo in a FaDu cell-derived xenograft model of squamous cell head and neck cancer.

Briefly, $0.5\times10^6$ FaDu cells were injected orthotopically into NSG male mice. After 6 days, one group of mice was then injected intratumorally with a combination of Onc5/3Ad2E1Δ24 (described in Example 2.1) and HDAdIL-12_TK_PD-L1 described in Example 3.1 (this combination of OncAd and HdAd is referred to herein as "CAdtrio"). A total of $1\times10^7$ viral particles were administered, at a 1:10 ratio of Onc5/3Ad2E1Δ24:HDAdIL-12 TK_PD-L1.

Three days later, mice were injected via the tail vein with $1\times10^6$ T cells engineered to express firefly luciferase, which had been transduced with the HER2-specific CAR construct corresponding to clone F1. A control group of mice which had not been administered with CAdtrio was injected via the tail vein with $1\times10^6$ firefly luciferase-expressing T cells which had not been transduced with a HER2-CAR construct, and a further control group of mice was not administered with CAdtrio nor injected with T cells. Luciferase activity, body weight and survival of the mice was monitored over time.

Figure 17A:
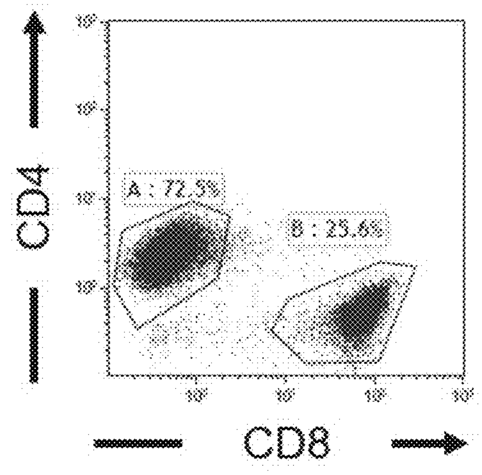
FIGS. 17A to 17C. Scatterplots and histograms showing the results of characterisation by flow cytometry of F1 HER2-specific CAR T cells used in experiments for in vivo analysis of the anti-cancer activity of the combination of CAdtrio and adoptively-transferred T cells.
Figure 17B:
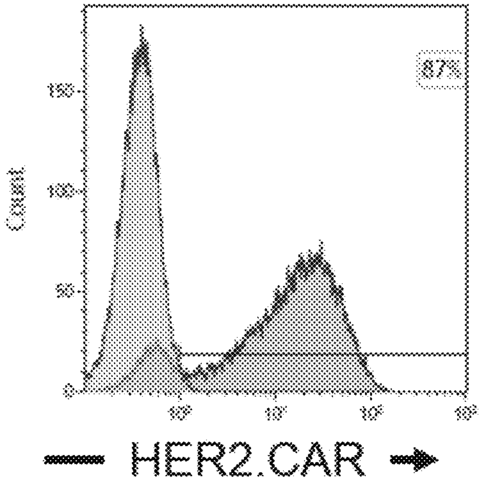
Figure 17C:
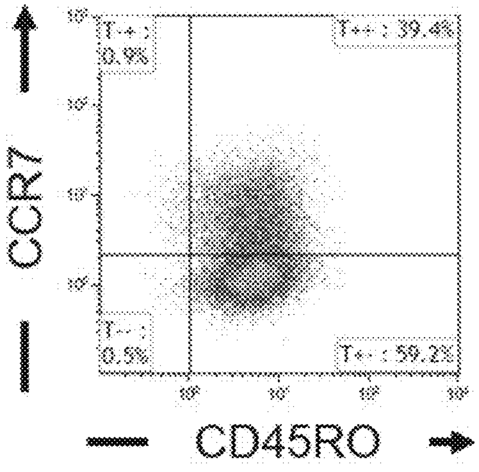
Figure 18A:
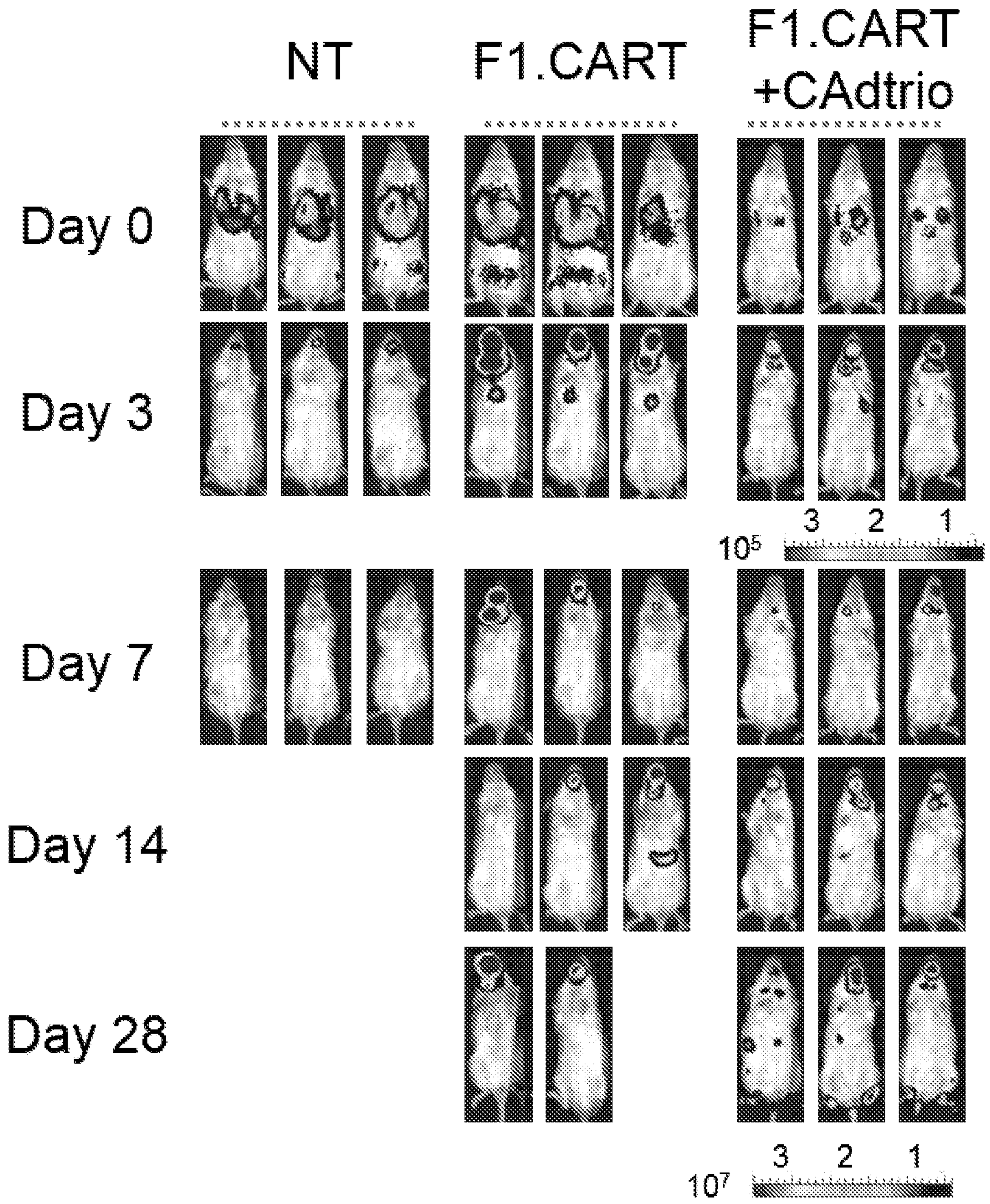
FIGS. 18A to 18D. Images and graphs showing the results of in vivo analysis of the anti-cancer activity of the combination of CAdtrio and adoptively-transferred T cells, in an orthotopic FaDu cell-derived model of squamous cell head and neck carcinoma.
Figure 18B:
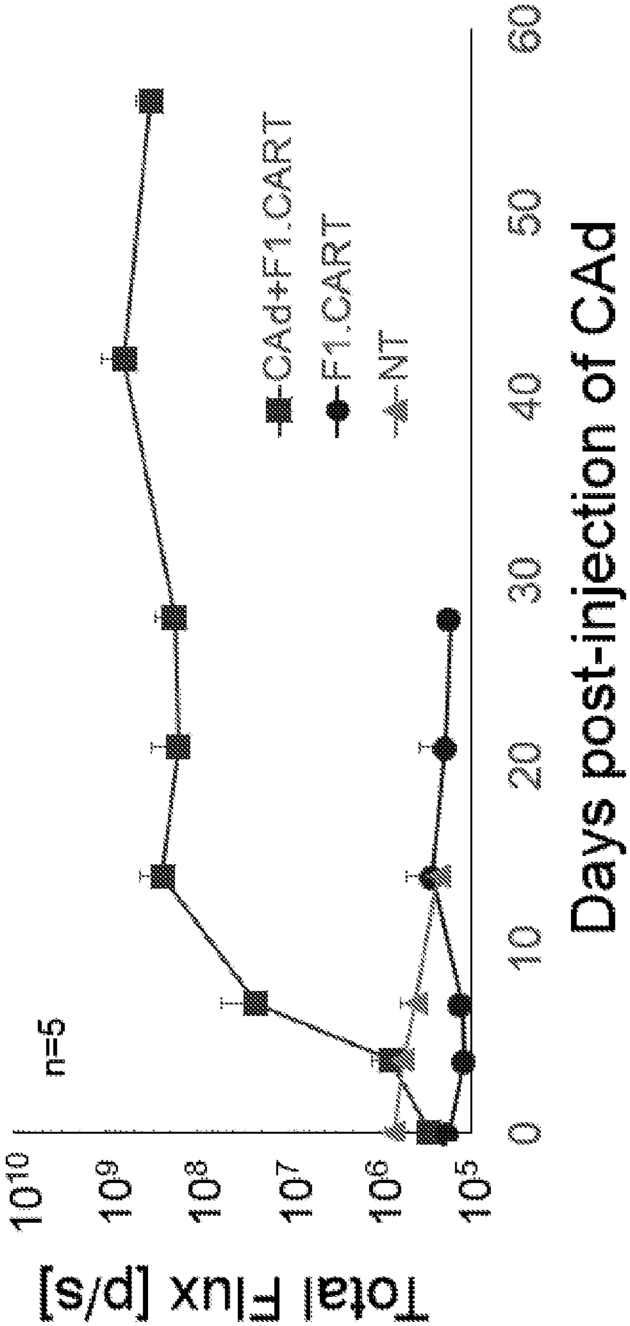
Figure 18C:
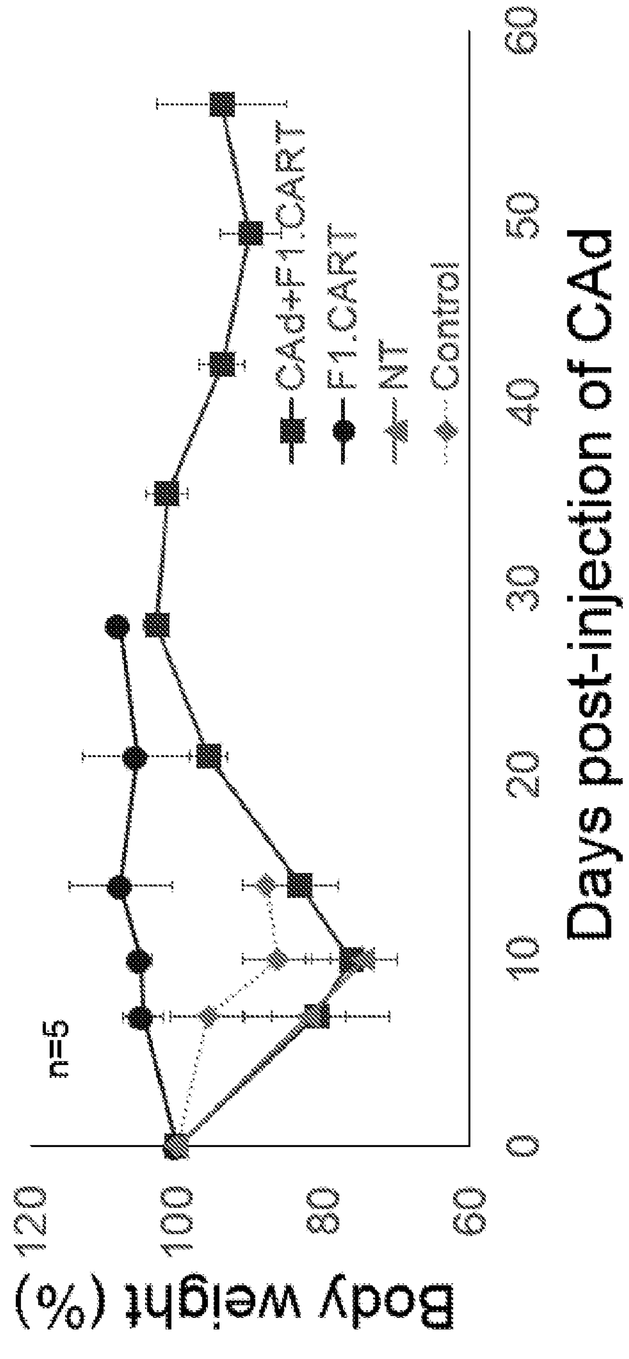
Figure 18D:
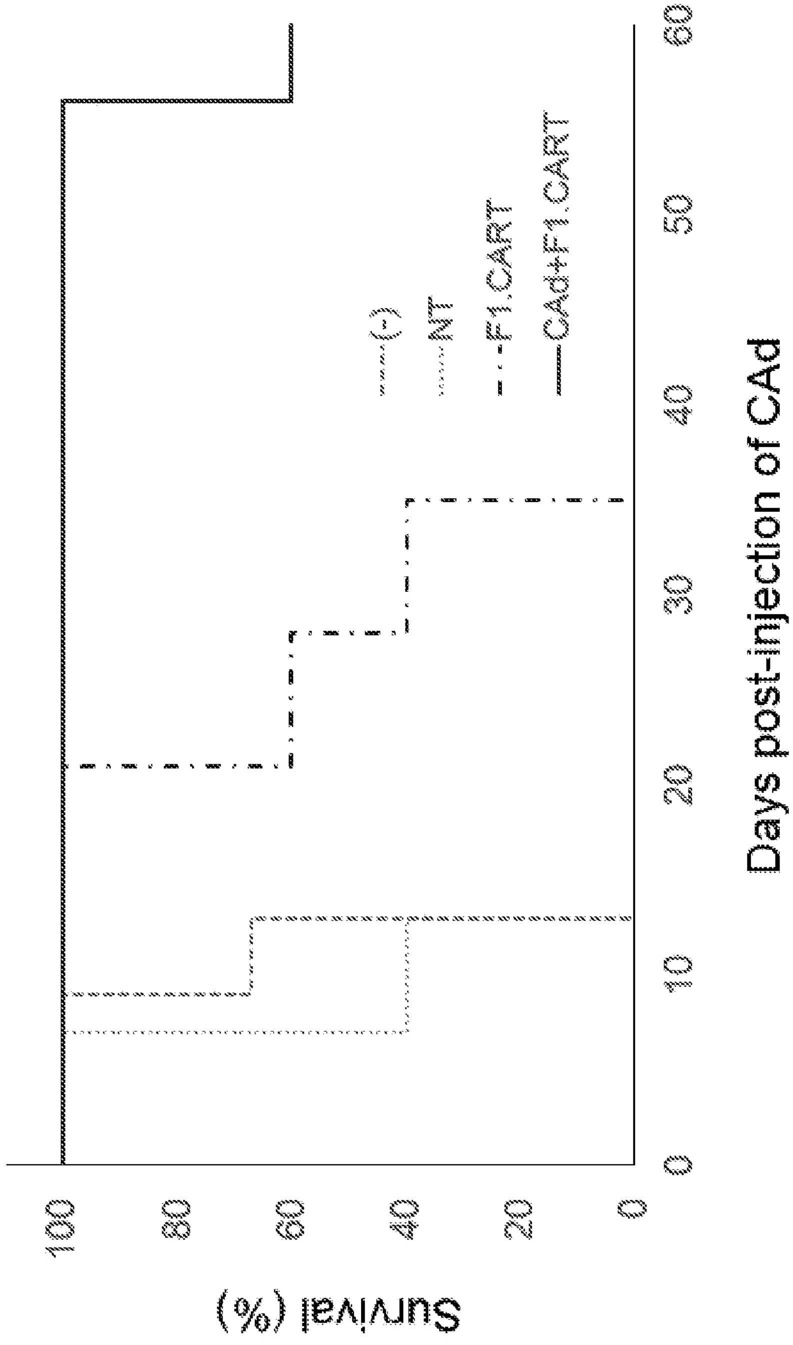

Prior to their use in the experiment the F1.CART cells were characterised flow cytometry, and the results are shown in FIGS. 17A to 17C. The cells were found to comprise 72.5% CD4+ cells and CD8+ cells. 87% of the cells were determined to express HER2 CAR at the cell surface. 39% of the cells were CCDR7+CD45RO+, and 59.2% of the cells were CCR7-CD45RO+.

The results of the experiments analysing the therapeutic efficacy of the combination of oncolytic virus, HDAd virus and HER2-specific CAR-T cells to treat cancer in vivo are shown in FIGS. 18A to 18D. The combination of Onc5/3Ad2E1Δ24. HDAdIL-12_TK_PD-L1 and F1.CART was found to improve survival over treatment with F1.CART cells alone.

In further experiments two different ratios of Onc5/3Ad2E1Δ24 to HDAdIL-12_TK_PD-L1 were investigated.

Briefly, $0.5\times10^6$ FaDu cells modified to express firefly luciferase were injected orthotopically into NSG male mice. After 6 days, mice were injected intratumorally with:

(i) $1\times10^7$ viral particles of CAdtrio, at a ratio of Onc5/3Ad2E1Δ24:HDAdIL-12_TK_PD-L1 of 1:10;

(ii) $1\times10^7$ viral particles of CAdtrio, at a ratio of Onc5/3Ad2E1Δ24:HDAdIL-12_TK_PD-L1 of 1:20;

(iii) $1\times10^6$ viral particles of CAdtrio, at a ratio of Onc5/3Ad2E1Δ24:HDAdIL-12_TK_PD-L1 of 1:10; or (iv) $1\times10^6$ viral particles of CAdtrio, at a ratio of Onc5/3Ad2E1Δ24:HDAdIL-12_TK_PD-L1 of 1:20.

Three days later, mice were injected via the tail vein with $1\times10^6$ T cells which had been transduced with the F1 CAR construct (not expressing firefly luciferase). The cancer was monitored over time by analysis of luciferase activity as described above, and the body weight of the mice was also monitored.

Figure 19A:
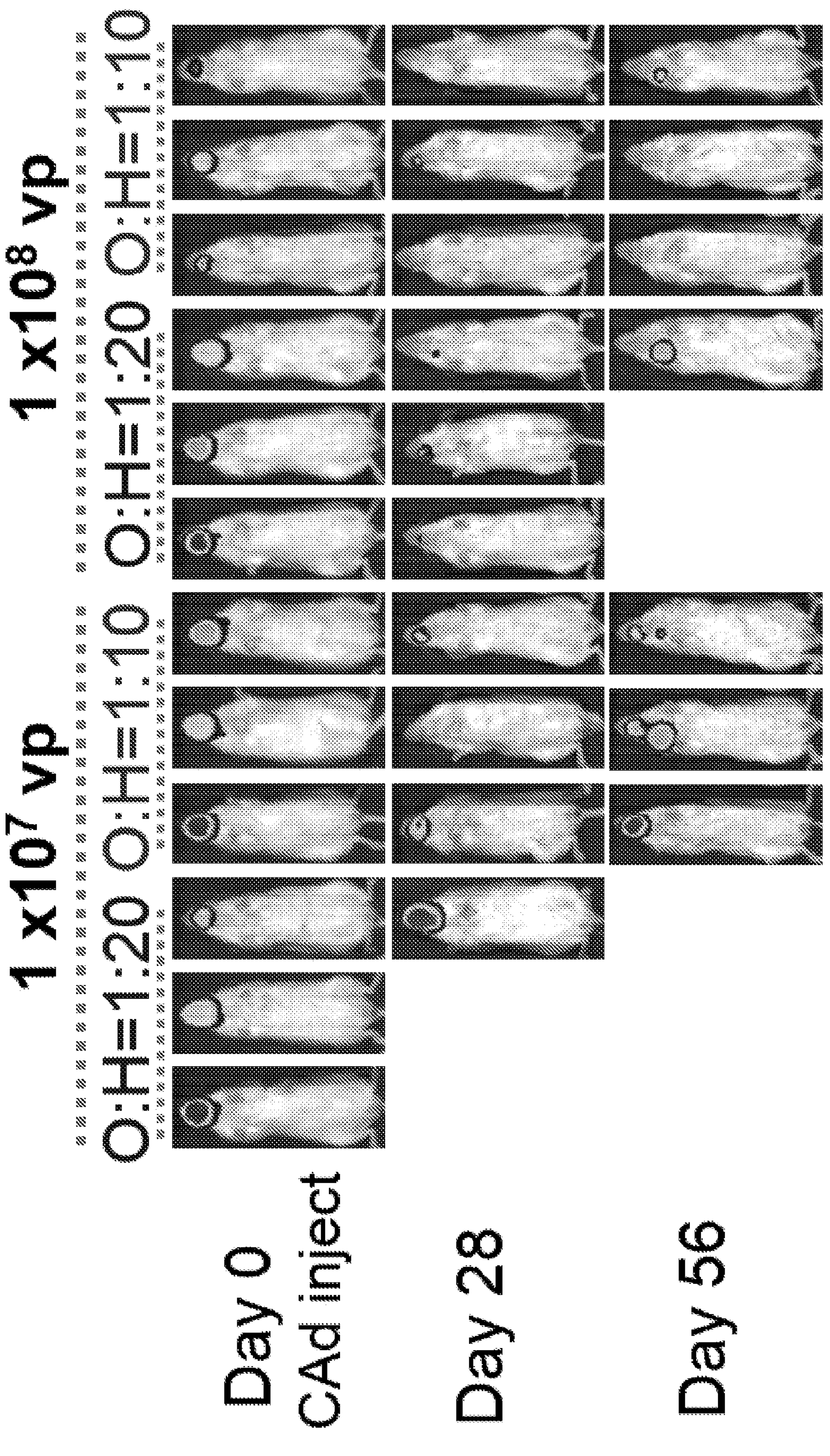
FIGS. 19A to 19C. Images and graphs showing the results of in vivo analysis of the anti-cancer activity of the combination of different ratios of Onc5/3Ad2E1Δ24:HDAdIL-12_TK_PD-L1 and adoptively-transferred HER2-specific CAR T cells, in an orthotopic FaDu cell-derived model of squamous cell head and neck carcinoma.
Figure 19B:
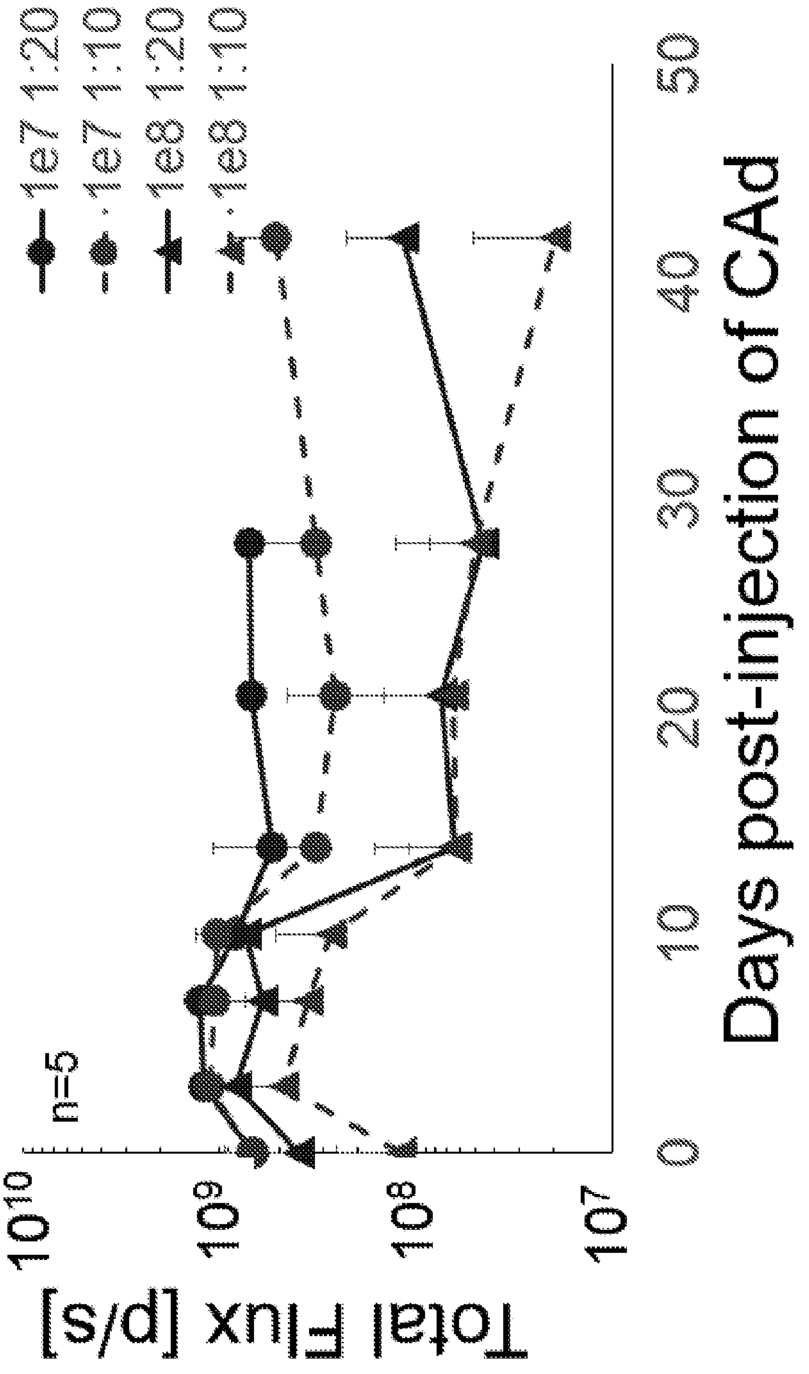
Figure 19C:
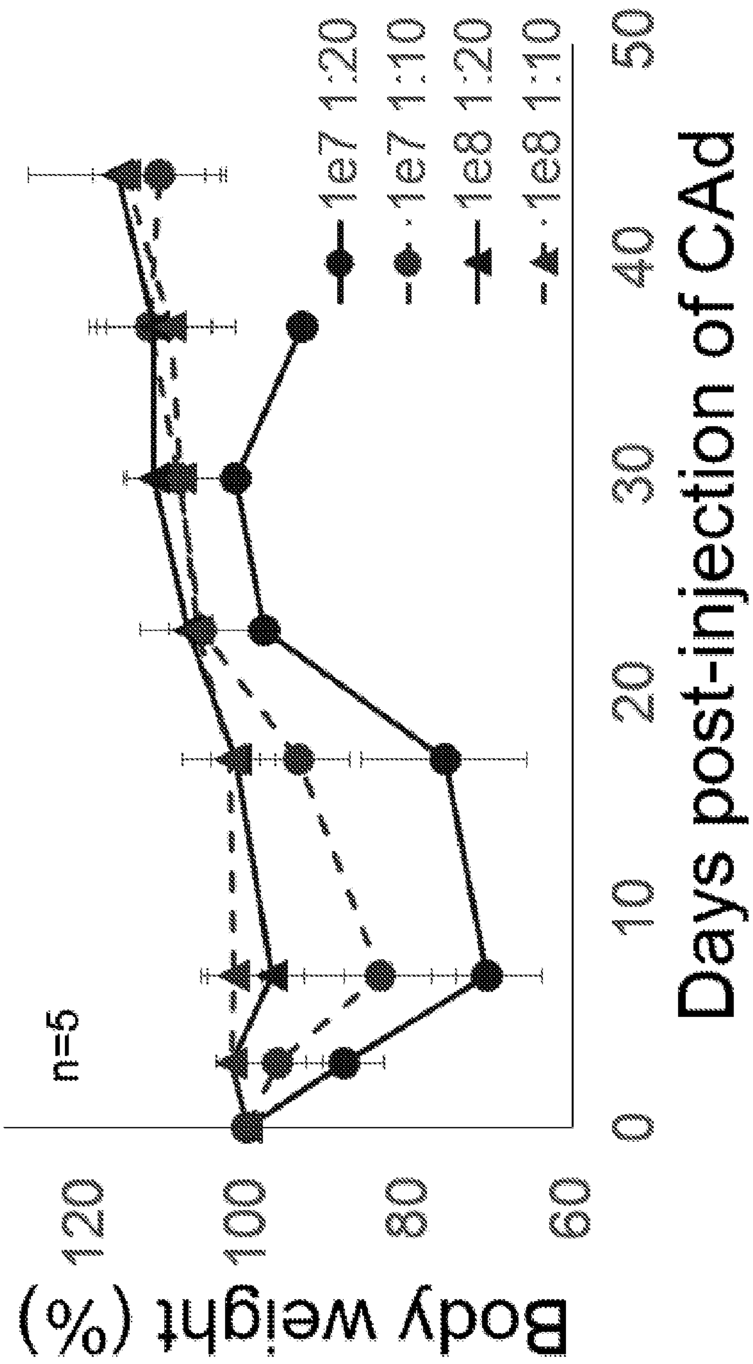

The results of the experiments are shown in FIGS. 19A to 19C. Mice administered with a 1:10 ratio of Onc5/3Ad2E1Δ24:HDAdIL-12_TK_PD-L1 generally had fewer luciferase-expressing FaDu cells than those administered with a 1:20 ratio of Onc5/3Ad2E1Δ24:HDAdIL-12_TK_PD-L1, and mice administered with $1\times10^6$ viral particles of CAdtrio generally had fewer luciferase-expressing FaDu cells than those administered with $1\times10^7$ viral particles of CAdtrio (FIG. 19B).

Example 7: Analysis of the Anti-Cancer Activity of the Combination of Oncolytic Virus, HDAd Virus and Ganciclovir (GCV) In Vivo The anti-cancer activity of a combination of oncolytic virus and HdAd (encoding thymidine kinase) (I,e, CAdtrio) in conjunction with ganciclovir (GCV) was investigated in vivo in a FaDu cell-derived xenograft model of squamous cell head and neck cancer.

Ectopic FaDu tumors were established by subcutaneous injection of FaDu cells into the flanks of mice. The mice were subsequently injected intratumorally with $1\times10^6$ viral particles of CAdtrio, at a ratio of Onc5/3Ad2E1Δ24:HDAdIL-12_TK_PD-L1 of 1:10. One group of mice (n=5) was then injected intraperitoneally on days 2, 3, 4, 5, 7, 10, 14, 17 and 21 days after CAdtrio injection with 10 mg/kg of ganciclovir.

Blood samples were collected from the mice on days 2, 7, 14 and 21 and analysed by ELISA for IL-12 expression. Tumor volumes were monitored throughout the experiment. At day 22 Onc.Ad and HDAd vector copy numbers were determined in DNA extracted from the tumors by quantitative real-time PCR analysis, and normalised using the copy number detected for GAPDH.

Figure 20A:
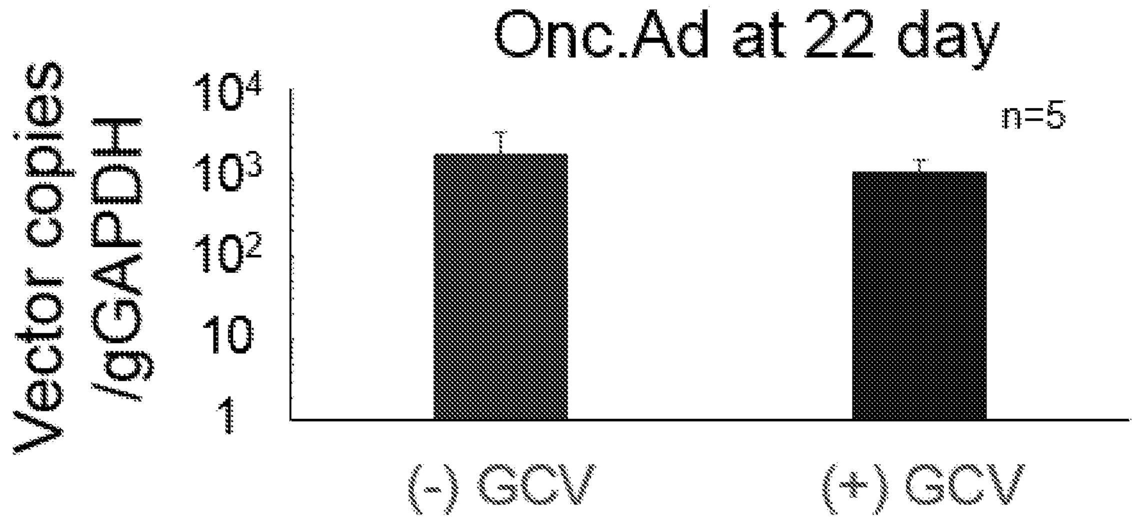
FIGS. 20A to 20D. Bar charts and graphs showing the results of in vivo analysis of the combination of Onc5/3Ad2E1Δ24 and HDAdIL-12_TK_PD-L1 and ganciclovir (GCV), in an ectoptic FaDu cell-derived model of squamous cell head and neck carcinoma.
Figure 20B:
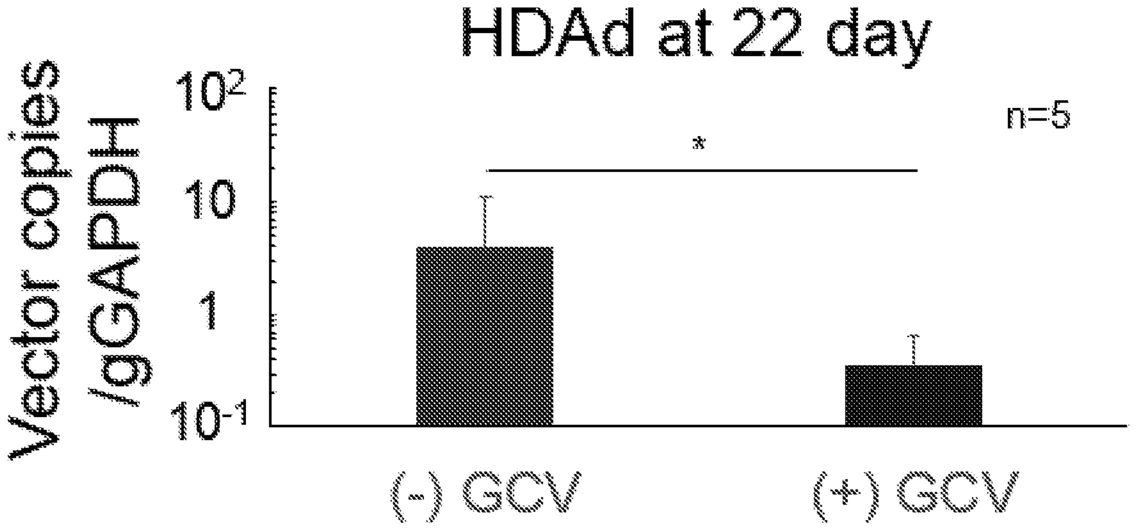
Figure 20C:
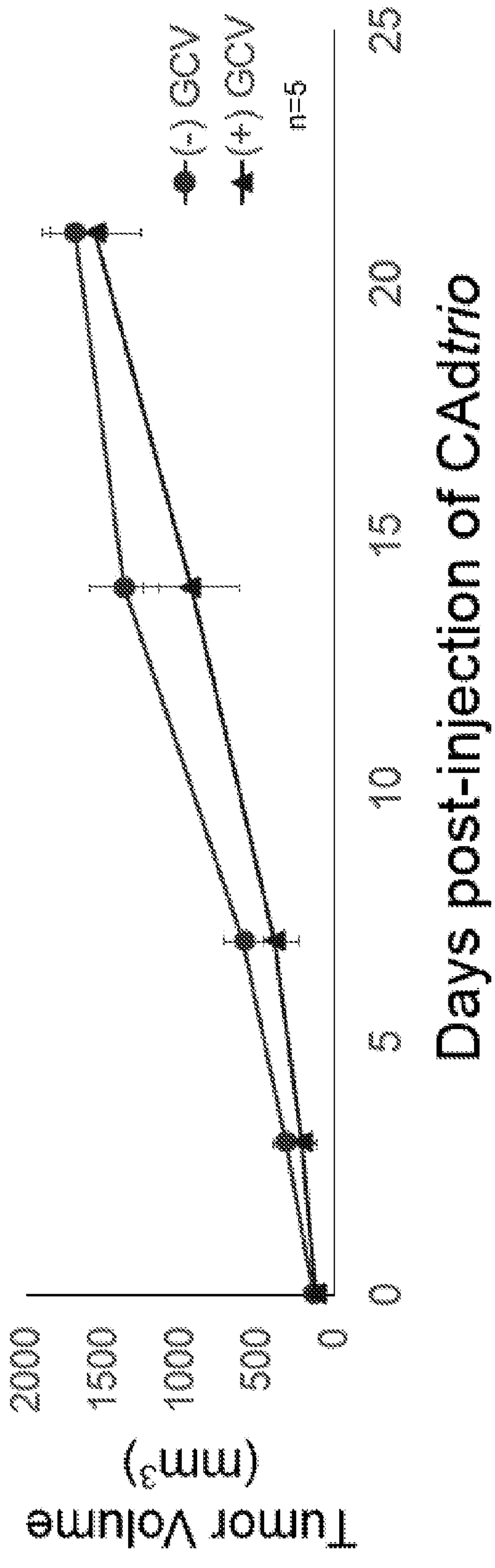
Figure 20D:
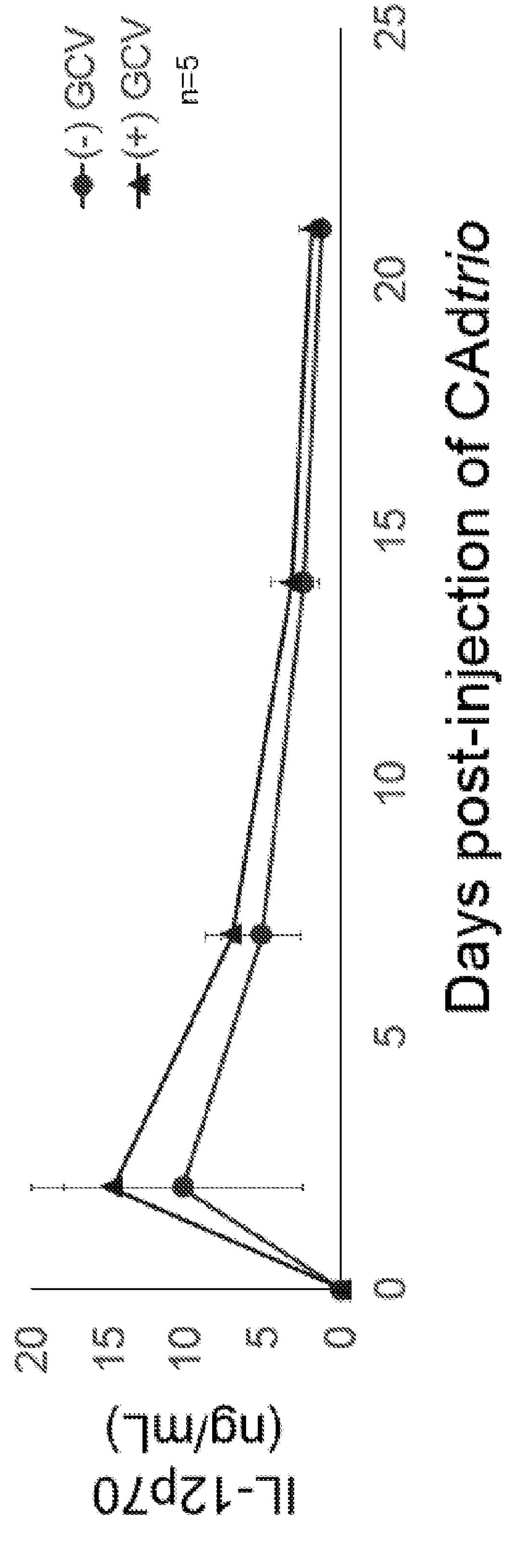

The results of the experiments are shown in FIGS. 20A to 20D. Ganciclovir (GCV) treatment did not significantly influence Onc.Ad vector copy number at day 22 (FIG. 20A), but significantly decreased HDAd vector copy number (FIG. 20B). GCV treatment was also found to improve tumor control (FIG. 20C), but did not significantly influence the levels of IL-12 in the blood (FIG. 20D).

Example 8: Generation of Oncolytic Virus-Specific T Cells and HER-Specific CAR-Expressing Oncolytic Virus-Specific T Cells 8.1 Generation and Characterisation of Oncolytic Virus-Specific T Cells Adenovirus-specific T cells (AdVSTs) and activated T cells (ATCs) were prepared as follows.

Anti-CD3 (clone OKT3) and anti-CD28 agonist antibodies were coated onto wells of tissue culture plates by addition of 0.5 ml of 1:1000 dilution of 1 mg/ml antibodies, and incubation for 2-4 hr at 37° C., or at 4° C. overnight.

PBMCs were isolated from blood samples obtained from healthy donors according to the standard Ficoll-Paque method.

ATCs:

$1\times10^6$ PBMCs (in 2 ml of cell culture medium) were stimulated by culture on the anti-CD3/CD28 agonist antibody-coated plates in CTL cell culture medium (containing 50% Advanced RPMI, 50% Click's medium, 10% FBS, 1% GlutaMax, 1% Pen/Strep) supplemented with 10 ng/ml IL-7 and 5 ng/ml IL-15. The cells were maintained at 37° C. in a 5% $CO_2$ atmosphere. The next day, 1 ml of the cell culture medium was replaced with fresh CTL medium containing 20 ng/ml IL-7 and 10 ng/ml IL-15.

ATCs were maintained in culture, and subsequently harvested and used in experiments or cryopreserved between days 5-7.

AdVSTs:

$1\times10^6$ PBMCs (in 2 ml of cell culture medium) were stimulated by culture on the anti-CD3/CD28 agonist antibody-coated plates in CTL cell culture medium supplemented with 10 ng/ml IL-7 and 100 ng/ml IL-15.

20 μl of a 200-fold dilution of Adenovirus-specific Hexon PEPMIX™ (JPT Cat # PM-HAdV3) or Penton PEPMIX™ (JPT Cat # PM-HAdV5) was added to the wells. The cells were maintained at 37° C. in a 5% $CO_2$ atmosphere. After 48 hours cells were fed with CTL medium, with added IL-7 and IL-15 to a final concentration of 10 ng/ml IL-7 and 100 ng/ml IL-15.

8.2 Generation of CAR-Expressing, Oncolytic Virus-Specific T Cells

On day 3, AdVSTs were resuspended at a concentration of $0.125\times10^6$ cells/ml in CTL cell culture medium containing 10 ng/ml IL-7 and 100 ng/ml IL-15.

Retronectin coated plates were prepared by incubation of RETRONECTIN® (Recombinant Human Fibronectin Fragment) (Clontech) diluted 1:100 in PBS for 2-4 hr at 37° C., or at 4° C. overnight. The wells were washed with CTL medium, 1 ml of retroviral supernatant of HER2-specific CAR retrovirus was added to wells, and plates were centrifuged at 2000 g for 1.5 hr. At the end of the centrifugation step retroviral supernatant was aspirated, and 2 ml of AdVST suspension (i.e. $0.25\times10^6$ cells) was added to wells of the plate. Plates were centrifuged at 400 g for 5 min, and incubated at 37° C. in a 5% $CO_2$ atmosphere.

After 48 hrs (i.e. on day 6) the cell culture medium was aspirated and replaced with CTL cell culture medium containing 10 ng/ml IL-7 and 100 ng/ml IL-15.

On day 9 cells were harvested and used in experiments or cryopreserved, or subjected to a second stimulation to expand CAR-expressing AdVSTs (see Example 8.3).

8.3 Expansion of AdVSTs and CAR-AdVSTs

AdVSTs and CAR-expressing AdVSTs were expanded by further stimulations as desired, as follows.

Pepmix-pulsed autologous ATCs were used as APCs, and K562cs cells (see e.g. Ngo et al., J Immunother. (2014) 37(4):193-203) were used as costimulatory cells. The final ratio of AdVSTs or CAR-AdVSTs-ATCs:K562cs cells in the stimulation cultures was 1:1:3-5.

AdVSTs or CAR-AdVSTs were resuspended to a concentration of $0.2\times10^6$ cells/ml in CTL medium.

$1\times10^6$ ATCs were incubated with 10 μl of 200-fold dilution of Adenovirus-specific Hexon Pepmix (JPT Cat # PM-HAdV3) or Penton PepMix (JPT Cat # PM-HAdV5) at 37° C. for 30 min. The ATCs were subsequently irradiated at 30 Gy and harvested. $3\text{-}5\times10^6$ K562cs cells were irradiated at 100 Gy.

The ATCs and K562cs cells were then mixed in a total volume of 5 ml CTL medium, and 20 ng/ml IL-7 and 200 ng/ml IL-15 was added, 1 ml of this mixture was added to wells of a 24 well plate, and 1 ml of AdVST suspension or CAR-AdVST suspension was added to the wells.

Cells were maintained at 37° C. in a 5% $CO_2$ atmosphere. After 3-4 days cell culture medium was added as necessary, and after 6-7 days cells the expanded AdVSTs or CAR-AdVSTs were harvested for use in experiments.

Example 9: Analysis of the Anti-Cancer Activity of Combinations of Oncolytic Virus, HDAd, Oncolytic Virus-Specific T Cells and CAR-Expressing Oncolytic Virus-Specific T Cells In Vivo The anti-cancer activity of different combinations of oncolytic virus, HDAd, oncolytic virus-specific T cells and CAR-expressing oncolytic virus-specific T cells was investigated in vivo in a FaDu cell-derived xenograft model of squamous cell head and neck cancer.

Briefly, $0.5\times10^6$ FaDu cells engineered to express firefly luciferase were injected orthotopically into NSG male mice. After 6 days groups of mice were injected intratumorally with:

(i) $1\times10^7$ viral particles of CAdtrio, at a ratio of Onc5/3Ad2E1Δ24:HDAdIL-12_TK_PD-L1 of 1:10; or (ii) $1\times10^7$ viral particles of Onc5/3Ad2E1Δ24.

Three days later, mice were injected via the tail vein with:

(a) $1\times10^6$ AdVSTs, or (b) $1\times10^6$ AdVSTs transduced with anti-HER2 CAR clone F1 (prepared as described in Example 8).

Prior to their use in the experiment the AdVSTs and F1.CAR-AdVSTs were characterised by flow cytometry, and the results of the analysis are shown in FIGS. 22A and 22B, and FIGS. 23A to 23C.

The cancer was monitored over time by analysis of luciferase activity as described above, and the body weight of the mice was also monitored.

The results of the experiments are shown in FIGS. 24A to 24D. The greatest level of tumor control was observed in mice treated with a combination of CAdtrio+HER2-specific CAR-expressing AdVSTs (i.e. treatment group (i)(b)).

The invention claimed is:

1. A method of treating a cancer, comprising administering to a subject:

(i) an oncolytic adenovirus comprising a recombinant adenoviral nucleic acid comprising a nucleic sequence encoding an E1A protein that contains a deletion in its retinoblastoma (Rb) protein-binding region;

(ii) a helper-dependent adenovirus comprising a recombinant adenoviral nucleic acid encoding IL-12, an antagonist anti-PD-L1 antibody, and an enzyme that catalyzes conversion of a non-toxic prodrug to an active cytotoxic form; and (iii) at least one T cell comprising a chimeric antigen receptor (CAR), wherein the CAR comprises an antigen binding domain capable of specific binding to HER2;

wherein the cancer comprises cells expressing HER2.

2. The method according to claim 1, wherein the oncolytic virus encodes an E1A protein which displays reduced binding to Rb protein as compared to E1A protein encoded by Ad5.

3. The method according to claim 1, wherein the deletion comprises deletion of the amino acid sequence LTCHEACF (SEQ ID NO:52).

4. The method according to claim 1, wherein the oncolytic virus encodes an E1A protein comprising, or consisting of, the amino acid sequence SEQ ID NO:34.

5. The method according to claim 1, wherein the CAR comprises an antigen-binding domain comprising:

a VL domain comprising:
LC-CRD1: SEQ ID NO:10;
LC-CRD2: SEQ ID NO:11;
LC-CRD3: SEQ ID NO:12;
and a VH domain comprising:
HC-CRD1: SEQ ID NO:13;
HC-CRD2: SEQ ID NO:14;
HC-CRD3: SEQ ID NO:15;
or
a VL domain comprising:
LC-CRD1: SEQ ID NO:18;
LC-CRD2: SEQ ID NO:19;
LC-CRD3: SEQ ID NO:20;
and a VH domain comprising:
HC-CRD1: SEQ ID NO:21;
HC-CRD2: SEQ ID NO:22;
HC-CRD3: SEQ ID NO:23;

or a VL domain comprising:
LC-CRD1: SEQ ID NO:26;
LC-CRD2: SEQ ID NO:27;
LC-CRD3: SEQ ID NO:28;
and a VH domain comprising:
HC-CRD1: SEQ ID NO:29;
HC-CRD2: SEQ ID NO:30;
HC-CRD3: SEQ ID NO:31;

or a VL domain comprising:
LC-CRD1: SEQ ID NO:57;
LC-CRD2: SEQ ID NO:58;
LC-CRD3: SEQ ID NO:59;
and a VH domain comprising:
HC-CRD1: SEQ ID NO:60;
HC-CRD2: SEQ ID NO:61;
HC-CRD3: SEQ ID NO:62.

6. The method according to claim 1, wherein the CAR comprises an antigen binding domain comprising:

a VL comprising, or consisting of, an amino acid sequence having at least 90% sequence identity to SEQ ID NO:16 and a VH comprising, or consisting of, an amino acid sequence having at least 90% sequence identity to SEQ ID NO:17;

or a VL comprising, or consisting of, an amino acid sequence having at least 90% sequence identity to SEQ ID NO:24 and a VH comprising, or consisting of, an amino acid sequence having at least 90% sequence identity to SEQ ID NO:25;

or a VL comprising, or consisting of, an amino acid sequence having at least 90% sequence identity to SEQ ID NO:32 and a VH comprising, or consisting of, an amino acid sequence having at least 90% sequence identity to SEQ ID NO:33;

or a VL comprising, or consisting of, an amino acid sequence having at least 90% sequence identity to SEQ ID NO:63 and a VH comprising, or consisting of, an amino acid sequence having at least 90% sequence identity to SEQ ID NO:64.

7. The method according to claim 1, wherein the enzyme is selected from: thymidine kinase, cytosine deaminase, nitroreductase, cytochrome P450, carboxypeptidase G2, purine nucleoside phosphorylase, horseradish peroxidase and carboxylesterase.

8. The method according to claim 1, wherein the enzyme is HSV-1 thymidine kinase.

9. The method according to claim 1, wherein the method of treating a cancer comprises:

(a) isolating at least one cell from a subject;

(b) modifying the at least one cell to express or comprise a CAR specific for a cancer cell antigen, or a nucleic acid encoding a CAR specific for a cancer cell antigen, (c) optionally expanding the modified at least one cell, and;

(d) administering the modified at least one cell to a subject.

10. The method according to claim 1, wherein the cancer is selected from head and neck cancer, nasopharyngeal carcinoma (NPC), cervical carcinoma (CC), oropharyngeal carcinoma (OPC), gastric carcinoma (GC), hepatocellular carcinoma (HCC) and lung cancer.

* * * * *